(12) United States Patent
Traverso et al.

(10) Patent No.: US 11,179,341 B2
(45) Date of Patent: Nov. 23, 2021

(54) SELF-RIGHTING ARTICLES

(71) Applicants: Massachusetts Institute of Technology, Cambridge, MA (US); The Brigham and Women's Hospital, Inc., Boston, MA (US)

(72) Inventors: Carlo Giovanni Traverso, Newton, MA (US); Alex G. Abramson, St. Louis, MO (US); Ester Caffarel Salvador, Cambridge, MA (US); Niclas Roxhed, Cambridge, MA (US); Minsoo Khang, Boston, MA (US); Taylor Bensel, Walpole, MA (US); Robert S. Langer, Newton, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/614,083

(22) PCT Filed: May 17, 2018

(86) PCT No.: PCT/US2018/033183
§ 371 (c)(1),
(2) Date: Nov. 15, 2019

(87) PCT Pub. No.: WO2018/213576
PCT Pub. Date: Nov. 22, 2018

(65) Prior Publication Data
US 2021/0154396 A1    May 27, 2021

Related U.S. Application Data

(60) Provisional application No. 62/507,647, filed on May 17, 2017, provisional application No. 62/507,653, (Continued)

(51) Int. Cl.
*A61M 5/142* (2006.01)
*A61M 5/158* (2006.01)
(Continued)

(52) U.S. Cl.
CPC ........ *A61K 9/4808* (2013.01); *A61B 5/14503* (2013.01); *A61B 5/14539* (2013.01);
(Continued)

(58) Field of Classification Search
CPC ........ A61M 2205/21; A61M 2210/106; A61M 31/002; A61K 9/0068; A61K 9/4808;
(Continued)

(56) References Cited

U.S. PATENT DOCUMENTS 2,601,767 A    7/1952  Wall
3,386,409 A    6/1968  Dawson
(Continued)

FOREIGN PATENT DOCUMENTS

CN    1820798 A    8/2006
CN    1887373 A    1/2007
(Continued)

OTHER PUBLICATIONS

International Search Report and Written Opinion dated Jul. 30, 2018 for Application No. PCT/US2018/033183.
(Continued)

*Primary Examiner* — Nathan R Price
*Assistant Examiner* — Justin L Zamory
(74) *Attorney, Agent, or Firm* — Wolf, Greenfield & Sacks, P.C.

(57) ABSTRACT

Self-righting articles, such as self-righting capsules for administration to a subject, are generally provided. In some embodiments, the self-righting article may be configured
(Continued)

such that the article may orient itself relative to a surface (e.g., a surface of a tissue of a subject). The self-righting articles described herein may comprise one or more tissue engaging surfaces configured to engage (e.g., interface with, inject into, anchor) with a surface (e.g., a surface of a tissue of a subject). In some embodiments, the self-righting article may have a particular shape and/or distribution of density (or mass) which, for example, enables the self-righting behavior of the article. In some embodiments, the self-righting article may comprise a tissue interfacing component and/or a pharmaceutical agent (e.g., for delivery of the active pharmaceutical agent to a location internal of the subject). In some cases, upon contact of the tissue with the tissue engaging surface of the article, the self-righting article may be configured to release one or more tissue interfacing components. In some cases, the tissue interfacing component is associated with a self-actuating component. For example, the self-righting article may comprise a self-actuating component configured, upon exposure to a fluid, to release the tissue interfacing component from the self-righting article. In some cases, the tissue interfacing component may comprise and/or be associated with the pharmaceutical agent (e.g., for delivery to a location internal to a subject).

66 Claims, 95 Drawing Sheets

Related U.S. Application Data filed on May 17, 2017, provisional application No. 62/507,665, filed on May 17, 2017.

(51) Int. Cl.

| | | |
|---|---|---|
| *A61K 9/48* | (2006.01) | |
| *A61J 3/07* | (2006.01) | |
| *A61K 9/00* | (2006.01) | |
| *A61B 5/145* | (2006.01) | |
| *A61B 10/02* | (2006.01) | |
| *A61M 37/00* | (2006.01) | |
| *A61N 1/32* | (2006.01) | |
| *A61N 1/36* | (2006.01) | |
| *A61M 5/20* | (2006.01) | |
| *A61M 5/32* | (2006.01) | |
| *A61M 31/00* | (2006.01) | |
| *A61K 38/28* | (2006.01) | |
| *A61N 1/05* | (2006.01) | |

(52) U.S. Cl.
CPC ............... *A61B 10/02* (2013.01); *A61J 3/07* (2013.01); *A61K 9/0002* (2013.01); *A61K 9/0012* (2013.01); *A61K 9/0021* (2013.01); *A61K 9/0065* (2013.01); *A61K 9/0092* (2013.01); *A61K 9/4866* (2013.01); *A61K 38/28* (2013.01); *A61M 5/14276* (2013.01); *A61M 5/158* (2013.01); *A61M 5/2033* (2013.01); *A61M 5/329* (2013.01); *A61M 5/3295* (2013.01); *A61M 31/002* (2013.01); *A61M 37/0015* (2013.01); *A61N 1/325* (2013.01); *A61N 1/36007* (2013.01); *A61B 10/0233* (2013.01); *A61B 2010/0208* (2013.01); *A61M 2005/14284* (2013.01); *A61M 2005/1585* (2013.01); *A61M 2037/0023* (2013.01); *A61M 2037/0053* (2013.01); *A61M 2205/0238* (2013.01); *A61M 2205/21* (2013.01); *A61M 2210/106* (2013.01); *A61N 1/0509* (2013.01)

(58) Field of Classification Search
CPC .. A61K 9/0002; A61K 9/0012; A61K 9/4866; A61K 51/1262; A61J 3/07; A61J 1/00; A61J 7/00; A61J 7/04; A61B 34/30; A61B 1/041; A61B 10/04; A61L 27/50; A63H 15/06
See application file for complete search history.

(56) References Cited

U.S. PATENT DOCUMENTS

| | | |
|---|---|---|
| 3,442,045 A | 5/1969 | Green |
| 3,797,492 A | 3/1974 | Place |
| 3,826,220 A | 7/1974 | Jacobson |
| 4,236,525 A | 12/1980 | Sluetz et al. |
| 4,239,040 A | 12/1980 | Hosoya et al. |
| 4,407,283 A | 10/1983 | Reynolds |
| 4,425,117 A | 1/1984 | Hugemann et al. |
| 4,481,952 A | 11/1984 | Pawelec |
| 5,017,187 A | 5/1991 | Sullivan |
| 5,217,449 A | 6/1993 | Yuda et al. |
| 5,279,607 A | 1/1994 | Schentag et al. |
| 5,318,557 A | 6/1994 | Gross |
| 5,443,843 A | 8/1995 | Curatolo et al. |
| 5,474,785 A | 12/1995 | Wright et al. |
| 5,690,691 A | 11/1997 | Chen et al. |
| 6,030,641 A | 2/2000 | Yamashita et al. |
| 6,041,258 A | 3/2000 | Cigaina et al. |
| 6,099,504 A | 8/2000 | Gross et al. |
| 6,120,803 A | 9/2000 | Wong et al. |
| 6,334,856 B1 | 1/2002 | Allen et al. |
| 6,346,519 B1 | 2/2002 | Petrus |
| 6,449,511 B1 | 9/2002 | Mintchev et al. |
| 6,472,423 B1 | 10/2002 | Ross et al. |
| 6,488,962 B1 | 12/2002 | Berner et al. |
| 6,503,231 B1 | 1/2003 | Prausnitz et al. |
| 6,615,084 B1 | 9/2003 | Cigaina |
| 6,660,197 B1 | 12/2003 | Buch-Rasmussen et al. |
| 6,684,104 B2 | 1/2004 | Gordon et al. |
| 6,945,952 B2 | 9/2005 | Kwon |
| 7,076,305 B2 | 7/2006 | Imran et al. |
| 7,076,307 B2 | 7/2006 | Boveja et al. |
| 7,177,693 B2 | 2/2007 | Starkebaum |
| 7,211,062 B2 | 5/2007 | Kwon |
| 7,569,032 B2 | 8/2009 | Naimark et al. |
| 7,620,454 B2 | 11/2009 | Dinsmoor et al. |
| 7,666,844 B2 | 2/2010 | Buch-Rasmussen et al. |
| 7,678,135 B2 | 3/2010 | Maahs et al. |
| 7,704,264 B2 | 4/2010 | Ewers et al. |
| 7,742,818 B2 | 6/2010 | Dinsmoor et al. |
| 8,084,053 B2 | 12/2011 | Buch-Rasmussen et al. |
| 8,241,308 B2 | 8/2012 | Kortenbach et al. |
| 8,252,329 B2 | 8/2012 | Tzannis et al. |
| 8,454,997 B2 | 6/2013 | Hansen et al. |
| 8,518,308 B2 | 8/2013 | Khoshnevis |
| 8,518,430 B2 | 8/2013 | Buch-Rasmussen et al. |
| 8,562,589 B2 | 10/2013 | Imran |
| 8,682,440 B2 | 3/2014 | Imran et al. |
| 8,721,620 B2 | 5/2014 | Imran |
| 8,734,429 B2 | 5/2014 | Imran et al. |
| 8,755,888 B2 | 6/2014 | Voznesensky et al. |
| 8,759,284 B2 | 6/2014 | Imran |
| 8,764,733 B2 | 7/2014 | Imran |
| 8,781,591 B2 | 7/2014 | Imran et al. |
| 8,809,269 B2 | 8/2014 | Imran |
| 8,809,271 B2 | 8/2014 | Imran |
| 8,846,040 B2 | 9/2014 | Imran |
| 8,852,083 B2 | 10/2014 | Mintchev et al. |
| 8,852,151 B2 | 10/2014 | Imran |
| 8,958,879 B2 | 2/2015 | Imran et al. |
| 8,969,293 B2 | 3/2015 | Imran |
| 8,980,822 B2 | 3/2015 | Imran |
| 9,149,617 B2 | 10/2015 | Imran |

(56) References Cited

U.S. PATENT DOCUMENTS

| | | |
|---|---|---|
| 9,186,233 B2 | 11/2015 | Goebel et al. |
| 9,205,127 B2 | 12/2015 | Imran |
| 9,259,386 B2 | 2/2016 | Imran |
| 9,283,179 B2 | 3/2016 | Imran |
| 9,284,367 B2 | 3/2016 | Imran et al. |
| 9,314,228 B2 | 4/2016 | Miller |
| 9,402,806 B2 | 8/2016 | Imran |
| 9,402,807 B2 | 8/2016 | Imran |
| 9,403,002 B2 | 8/2016 | Imran et al. |
| 9,415,004 B2 | 8/2016 | Imran |
| 9,456,988 B2 | 10/2016 | Imran |
| 9,457,065 B2 | 10/2016 | Imran |
| 9,486,414 B2 | 11/2016 | Imran |
| 9,492,378 B2 | 11/2016 | Imran |
| 9,511,121 B2 | 12/2016 | Imran |
| 9,539,207 B2 | 1/2017 | Imran |
| 9,629,799 B2 | 4/2017 | Imran |
| 9,643,005 B2 | 5/2017 | Imran et al. |
| 9,757,514 B2 | 9/2017 | Imran et al. |
| 9,757,548 B2 | 9/2017 | Imran |
| 9,808,510 B2 | 11/2017 | Imran |
| 9,814,763 B2 | 11/2017 | Imran |
| 9,844,505 B2 | 12/2017 | Imran |
| 9,844,655 B2 | 12/2017 | Imran |
| 9,861,683 B2 | 1/2018 | Imran |
| 9,907,747 B2 | 3/2018 | Imran |
| 10,300,259 B2 | 5/2019 | Ziaie et al. |
| 10,632,251 B2 | 4/2020 | Imran et al. |
| 10,667,936 B2 | 6/2020 | Goebel |
| 2002/0055734 A1 | 5/2002 | Houzego et al. |
| 2002/0082543 A1 | 6/2002 | Park et al. |
| 2002/0138049 A1 | 9/2002 | Allen et al. |
| 2002/0198470 A1 | 12/2002 | Imran et al. |
| 2003/0060734 A1 | 3/2003 | Yokoi et al. |
| 2003/0161881 A1 | 8/2003 | Hansen et al. |
| 2003/0167000 A1* | 9/2003 | Mullick ............ A61B 1/00087 600/424 |
| 2003/0181788 A1 | 9/2003 | Yokoi et al. |
| 2004/0025330 A1 | 2/2004 | Sylvia et al. |
| 2004/0044308 A1 | 3/2004 | Naimark et al. |
| 2004/0044364 A1 | 3/2004 | DeVries et al. |
| 2004/0087893 A1 | 5/2004 | Kwon et al. |
| 2004/0111011 A1 | 6/2004 | Uchiyama et al. |
| 2004/0122315 A1 | 6/2004 | Krill |
| 2004/0193229 A1 | 9/2004 | Starkebaum et al. |
| 2004/0215171 A1 | 10/2004 | Houzego et al. |
| 2004/0253304 A1 | 12/2004 | Gross et al. |
| 2005/0055014 A1 | 3/2005 | Coppeta et al. |
| 2005/0055039 A1 | 3/2005 | Burnett et al. |
| 2005/0065463 A1 | 3/2005 | Tobinaga et al. |
| 2005/0065571 A1 | 3/2005 | Imran |
| 2005/0075654 A1 | 4/2005 | Kelleher |
| 2005/0079214 A1 | 4/2005 | Cooker |
| 2005/0124875 A1 | 6/2005 | Kawano et al. |
| 2005/0131345 A1 | 6/2005 | Miller |
| 2005/0147559 A1 | 7/2005 | von Alten |
| 2005/0148847 A1 | 7/2005 | Uchiyama et al. |
| 2005/0149142 A1 | 7/2005 | Starkebaum |
| 2005/0171398 A1 | 8/2005 | Khait et al. |
| 2005/0183733 A1 | 8/2005 | Kawano et al. |
| 2005/0240239 A1 | 10/2005 | Boveja et al. |
| 2005/0245986 A1 | 11/2005 | Starkebaum |
| 2005/0250988 A1 | 11/2005 | Ewers et al. |
| 2005/0267414 A1 | 12/2005 | Abraham-Fuchs et al. |
| 2006/0004255 A1 | 1/2006 | Iddan et al. |
| 2006/0020929 A1 | 1/2006 | Liu |
| 2006/0030752 A1 | 2/2006 | Orihara |
| 2006/0047309 A1 | 3/2006 | Cichocki, Jr. |
| 2006/0058829 A1 | 3/2006 | Sampson et al. |
| 2006/0167339 A1 | 7/2006 | Gilad et al. |
| 2006/0259074 A1 | 11/2006 | Kelleher et al. |
| 2006/0271073 A1 | 11/2006 | Lam et al. |
| 2007/0021760 A1 | 1/2007 | Kelleher |
| 2007/0033682 A1 | 2/2007 | Sretavan et al. |
| 2007/0038181 A1 | 2/2007 | Melamud et al. |
| 2007/0106175 A1 | 5/2007 | Uchiyama et al. |
| 2007/0123809 A1 | 5/2007 | Weiss et al. |
| 2007/0135825 A1 | 6/2007 | Binmoeller |
| 2007/0156211 A1 | 7/2007 | Ferren et al. |
| 2007/0156248 A1 | 7/2007 | Marco et al. |
| 2007/0213659 A1 | 9/2007 | Trovato et al. |
| 2008/0065168 A1 | 3/2008 | Bitton et al. |
| 2008/0121825 A1 | 5/2008 | Trovato |
| 2008/0188837 A1 | 8/2008 | Belsky et al. |
| 2008/0214894 A1 | 9/2008 | Wedel |
| 2008/0255543 A1 | 10/2008 | Tanaka et al. |
| 2008/0257845 A1* | 10/2008 | Rossi .................. B65D 23/104 215/11.1 |
| 2008/0262478 A1 | 10/2008 | Krijnsen et al. |
| 2008/0269664 A1 | 10/2008 | Trovato et al. |
| 2008/0294101 A1 | 11/2008 | Kawano |
| 2008/0294143 A1 | 11/2008 | Tanaka et al. |
| 2009/0005639 A1 | 1/2009 | Kawano et al. |
| 2009/0030473 A1 | 1/2009 | Khawaled et al. |
| 2009/0043278 A1 | 2/2009 | Tanaka et al. |
| 2009/0104250 A1 | 4/2009 | Boyden et al. |
| 2009/0112191 A1 | 4/2009 | Boyden et al. |
| 2009/0137866 A1 | 5/2009 | Boyden et al. |
| 2009/0234331 A1 | 9/2009 | Langereis et al. |
| 2009/0253954 A1 | 10/2009 | Katayama |
| 2009/0253999 A1 | 10/2009 | Aoki et al. |
| 2009/0275923 A1 | 11/2009 | Shimizu et al. |
| 2009/0281557 A1 | 11/2009 | Sander et al. |
| 2009/0299144 A1 | 12/2009 | Shigemori et al. |
| 2009/0306473 A1 | 12/2009 | Tanaka et al. |
| 2009/0306632 A1 | 12/2009 | Trovato et al. |
| 2009/0306633 A1 | 12/2009 | Trovato et al. |
| 2010/0021536 A1 | 1/2010 | Gross |
| 2010/0033324 A1 | 2/2010 | Shimizu et al. |
| 2010/0049120 A1 | 2/2010 | Dijksman et al. |
| 2010/0056874 A1 | 3/2010 | Dijksman et al. |
| 2010/0063486 A1 | 3/2010 | Dijksman et al. |
| 2010/0179381 A1 | 7/2010 | Kawano et al. |
| 2010/0204678 A1 | 8/2010 | Imran |
| 2010/0228313 A1 | 9/2010 | Starkebaum et al. |
| 2010/0247453 A1 | 9/2010 | Jones |
| 2010/0286628 A1 | 11/2010 | Gross |
| 2010/0286668 A1 | 11/2010 | Tanaka et al. |
| 2010/0305656 A1 | 12/2010 | Imran et al. |
| 2010/0331827 A1 | 12/2010 | Shimizu |
| 2011/0017612 A1 | 1/2011 | Dijksman et al. |
| 2011/0034766 A1 | 2/2011 | Tanaka |
| 2011/0071589 A1 | 3/2011 | Starkebaum et al. |
| 2011/0087195 A1 | 4/2011 | Uhland et al. |
| 2011/0098651 A1 | 4/2011 | Falo, Jr. et al. |
| 2011/0106063 A1 | 5/2011 | Dijksman et al. |
| 2011/0106064 A1 | 5/2011 | Zou et al. |
| 2011/0152792 A1 | 6/2011 | Takada |
| 2011/0160129 A1 | 6/2011 | Imran |
| 2011/0160699 A1 | 6/2011 | Imran |
| 2011/0207998 A1 | 8/2011 | Katayama |
| 2011/0208270 A1 | 8/2011 | Imran et al. |
| 2012/0010590 A1 | 1/2012 | Imran |
| 2012/0095290 A1 | 4/2012 | Kawano |
| 2012/0116358 A1 | 5/2012 | Dijksman et al. |
| 2012/0143171 A1 | 6/2012 | Shimizu et al. |
| 2012/0305573 A1 | 12/2012 | Shi et al. |
| 2013/0108695 A1 | 5/2013 | Grenier et al. |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverse et al. |
| 2013/0165859 A1 | 6/2013 | Imran |
| 2013/0171244 A1 | 7/2013 | Imran |
| 2013/0171245 A1 | 7/2013 | Imran |
| 2013/0171246 A1 | 7/2013 | Imran |
| 2013/0171247 A1 | 7/2013 | Imran |
| 2013/0172257 A1 | 7/2013 | Imran |
| 2013/0172672 A1 | 7/2013 | Iddan et al. |
| 2013/0172694 A1 | 7/2013 | Zou et al. |
| 2013/0177527 A1 | 7/2013 | Imran |
| 2013/0177550 A1 | 7/2013 | Imran |

(56) References Cited

U.S. PATENT DOCUMENTS

| | | |
|---|---|---|
| 2013/0189353 A1 | 7/2013 | Imran |
| 2013/0195970 A1 | 8/2013 | Imran |
| 2013/0197440 A1 | 8/2013 | Zou et al. |
| 2013/0204233 A1 | 8/2013 | Zou et al. |
| 2013/0274659 A1 | 10/2013 | Imran et al. |
| 2013/0338583 A1 | 12/2013 | Imran |
| 2014/0135698 A1 | 5/2014 | Zou et al. |
| 2014/0163637 A1 | 6/2014 | Imran et al. |
| 2014/0221912 A1 | 8/2014 | Imran |
| 2014/0221927 A1 | 8/2014 | Imran et al. |
| 2014/0234418 A1 | 8/2014 | Coulter et al. |
| 2014/0243921 A1 | 8/2014 | Imran et al. |
| 2014/0256631 A1 | 9/2014 | Imran |
| 2014/0257238 A1 | 9/2014 | Imran |
| 2014/0276595 A1 | 9/2014 | Imran |
| 2014/0335168 A1 | 11/2014 | Imran |
| 2014/0336112 A1 | 11/2014 | Imran |
| 2014/0378764 A1 | 12/2014 | Mintchev et al. |
| 2015/0011874 A1 | 1/2015 | Amoako-Tuffour et al. |
| 2015/0023962 A1 | 1/2015 | Imran |
| 2015/0025496 A1 | 1/2015 | Imran |
| 2015/0051589 A1 | 2/2015 | Sako et al. |
| 2015/0064241 A1 | 3/2015 | Conrad |
| 2015/0141967 A1 | 5/2015 | Pardoel et al. |
| 2015/0147390 A1 | 5/2015 | Imran |
| 2015/0174076 A1 | 6/2015 | Harris et al. |
| 2015/0174400 A1 | 6/2015 | Imran et al. |
| 2015/0238571 A1 | 8/2015 | Imran |
| 2015/0328287 A1 | 11/2015 | Morales et al. |
| 2015/0329630 A1 | 11/2015 | Morales et al. |
| 2015/0329631 A1 | 11/2015 | Morales et al. |
| 2015/0329633 A1 | 11/2015 | Morales et al. |
| 2016/0015648 A1 | 1/2016 | Gross et al. |
| 2016/0022873 A1 | 1/2016 | Besner et al. |
| 2016/0144000 A1 | 5/2016 | Imran |
| 2016/0158516 A1 | 6/2016 | Imran |
| 2016/0166650 A1 | 6/2016 | Imran |
| 2016/0220759 A1 | 8/2016 | Enggaard et al. |
| 2016/0235663 A1 | 8/2016 | Zou et al. |
| 2016/0263045 A1 | 9/2016 | Grenier et al. |
| 2017/0027520 A1 | 2/2017 | Terry et al. |
| 2017/0027862 A1 | 2/2017 | Imran |
| 2017/0028195 A1 | 2/2017 | Imran et al. |
| 2017/0043144 A1 | 2/2017 | Imran |
| 2017/0049708 A1 | 2/2017 | Imran |
| 2017/0050005 A1 | 2/2017 | Imran |
| 2017/0050010 A1 | 2/2017 | McAllister et al. |
| 2017/0051051 A1 | 2/2017 | Imran et al. |
| 2017/0066824 A1 | 3/2017 | Imran et al. |
| 2017/0066841 A1 | 3/2017 | Imran et al. |
| 2017/0081399 A1 | 3/2017 | Imran |
| 2017/0087299 A1 | 3/2017 | Anderson |
| 2017/0100459 A1 | 4/2017 | Imran |
| 2017/0106099 A1 | 4/2017 | Bellinger et al. |
| 2017/0174758 A1 | 6/2017 | Imran |
| 2017/0189269 A1 | 7/2017 | Fischer et al. |
| 2017/0189659 A1 | 7/2017 | Imran |
| 2017/0216589 A1 | 8/2017 | Imran et al. |
| 2017/0231902 A1 | 8/2017 | Imran |
| 2017/0258732 A1 | 9/2017 | Imran et al. |
| 2017/0258833 A1 | 9/2017 | Imran et al. |
| 2017/0296092 A1 | 10/2017 | Jones et al. |
| 2018/0008771 A1 | 1/2018 | Imran et al. |
| 2018/0015146 A1 | 1/2018 | Imran et al. |
| 2018/0037643 A9 | 2/2018 | Imran et al. |
| 2018/0049725 A1 | 2/2018 | Jones et al. |
| 2018/0064366 A1 | 3/2018 | Sweeney et al. |
| 2018/0168488 A1 | 6/2018 | Jones et al. |
| 2018/0193621 A1 | 7/2018 | Bonner et al. |
| 2018/0296814 A1 | 10/2018 | Shimizu |
| 2018/0311154 A1 | 11/2018 | Kanasty et al. |
| 2019/0046721 A1 | 2/2019 | Iordanov et al. |
| 2019/0133937 A1 | 5/2019 | Imran et al. |
| 2019/0223846 A1 | 7/2019 | Kerkhof et al. |
| 2019/0254966 A1 | 8/2019 | Bellinger et al. |
| 2019/0262265 A1 | 8/2019 | Bellinger et al. |
| 2019/0282791 A1 | 9/2019 | Jones et al. |
| 2019/0321613 A1 | 10/2019 | Jones et al. |
| 2020/0009371 A1 | 1/2020 | Langer et al. |
| 2020/0129441 A1 | 4/2020 | Abramson et al. |
| 2020/0147298 A1 | 5/2020 | Traverso et al. |
| 2020/0205729 A1 | 7/2020 | Jones et al. |
| 2020/0246545 A1 | 8/2020 | Langer et al. |
| 2020/0306515 A1 | 10/2020 | Traverso et al. |
| 2020/0324095 A1 | 10/2020 | Traverso et al. |

FOREIGN PATENT DOCUMENTS

| | | |
|---|---|---|
| CN | 100998904 A | 7/2007 |
| CN | 100376299 C | 3/2008 |
| CN | 104344272 A | 12/2015 |
| CN | 106137099 A | 11/2016 |
| CN | 106730284 A | 5/2017 |
| DE | 102005032290 A1 | 1/2007 |
| DE | 102014015919 A1 | 12/2015 |
| EP | 0 197 697 A2 | 10/1986 |
| EP | 0415671 A2 | 3/1991 |
| EP | 1 784 140 A1 | 5/2007 |
| EP | 1 923 083 A1 | 5/2008 |
| EP | 1 980 290 A1 | 10/2008 |
| EP | 2 196 131 A1 | 6/2010 |
| EP | 2201938 A1 | 6/2010 |
| EP | 2 308 546 A1 | 4/2011 |
| FR | 2 794 654 A1 | 2/2000 |
| FR | 2794654 A1 | 12/2000 |
| JP | 855166142 A | 12/1980 |
| JP | S55-166142 A | 12/1980 |
| JP | S58019232 A | 2/1983 |
| JP | 2003-093332 A | 4/2003 |
| JP | 2003093332 A | 4/2003 |
| JP | 2003-325438 A | 11/2003 |
| JP | 2003325438 A | 11/2003 |
| JP | 2004-222998 A | 8/2004 |
| JP | 2004222998 A | 8/2004 |
| JP | 2013-022291 A | 2/2013 |
| JP | 2013022291 A | 2/2013 |
| KR | 20180053852 A | 5/2018 |
| WO | WO 97/27840 A1 | 8/1997 |
| WO | WO 0062759 A1 | 10/2000 |
| WO | WO 01/026602 A1 | 4/2001 |
| WO | WO 01/058424 A1 | 8/2001 |
| WO | WO 2005/105053 A2 | 11/2005 |
| WO | WO 2006/020929 A2 | 2/2006 |
| WO | WO 2006/084164 A2 | 8/2006 |
| WO | WO 2006/125074 A1 | 11/2006 |
| WO | WO 06131522 A1 | 12/2006 |
| WO | WO 2007093806 A1 | 8/2007 |
| WO | WO 2007/127976 A2 | 11/2007 |
| WO | WO 2008/111078 A2 | 9/2008 |
| WO | WO 09063375 A1 | 5/2009 |
| WO | WO 09063376 A1 | 5/2009 |
| WO | WO 09063377 A1 | 5/2009 |
| WO | WO 2010/140401 A1 | 12/2010 |
| WO | WO 11141372 A1 | 11/2011 |
| WO | WO 2012/004231 A1 | 1/2012 |
| WO | WO 2013/101908 A1 | 7/2013 |
| WO | Wo 2016/039418 A1 | 3/2016 |
| WO | WO 2016/067087 A2 | 5/2016 |
| WO | WO 2016/102526 A1 | 6/2016 |
| WO | WO 16155671 A1 | 10/2016 |
| WO | WO 2016/179120 A1 | 11/2016 |
| WO | WO 2016/193375 A1 | 12/2016 |
| WO | WO 17004623 A1 | 1/2017 |
| WO | WO 2017/019526 A2 | 2/2017 |
| WO | WO 2017/044665 A1 | 3/2017 |
| WO | WO 18112235 A1 | 6/2018 |
| WO | WO 18112245 A1 | 6/2018 |
| WO | WO 18182612 A1 | 10/2018 |
| WO | WO 18182623 A1 | 10/2018 |
| WO | WO 18182641 A1 | 10/2018 |
| WO | WO 18183932 A1 | 10/2018 |
| WO | WO 18183934 A1 | 10/2018 |
| WO | WO 18183941 A2 | 10/2018 |
| WO | WO 2018/213576 A1 | 11/2018 |

(56) References Cited

FOREIGN PATENT DOCUMENTS

| | | |
|---|---|---|
| WO | WO 2018/213579 A1 | 11/2018 |
| WO | WO 2018/213582 A1 | 11/2018 |
| WO | WO 2018/213588 A1 | 11/2018 |
| WO | WO 2018/213593 A1 | 11/2018 |
| WO | WO 2018/213600 A1 | 11/2018 |
| WO | WO 2019/036363 A2 | 2/2019 |
| WO | WO 2019/036382 A1 | 2/2019 |
| WO | WO 19036363 A2 | 2/2019 |
| WO | WO 19036382 A1 | 2/2019 |
| WO | WO 2019/121686 A1 | 6/2019 |
| WO | WO 19121686 A1 | 6/2019 |
| WO | WO 2019/147824 A1 | 8/2019 |
| WO | WO 19147824 A1 | 8/2019 |
| WO | WO 2020/157324 A1 | 8/2020 |
| WO | WO 2020/160399 A1 | 8/2020 |

OTHER PUBLICATIONS

International Preliminary Report on Patentability dated Nov. 28, 2019 for Application No. PCT/US2018/033183.
U.S. Appl. No. 16/614,177, filed Nov. 15, 2019, Traverso et al.
U.S. Appl. No. 16/614,172, filed Nov. 15, 2019, Traverso et al.
U.S. Appl. No. 16/614,229, filed Nov. 15, 2019, Traverso et al.
U.S. Appl. No. 16/613,766, filed Nov. 14, 2019, Traverso et al.
U.S. Appl. No. 16/614,299, filed Nov. 15, 2019, Traverso et al.
U.S. Appl. No. 16/415,417, filed May 17, 2019, Langer et al.
U.S. Appl. No. 16/778,152, filed Jan. 31, 2020, Langer et al.
U.S. Appl. No. 16/691,579, filed Nov. 21, 2019, Abramson et al.
EP18802599.3, Feb. 9, 2021, Extended European Search Report.
Extended European Search Report dated Feb. 9, 2021 for Application No. EP18802599.3.
[No Author Listed] Non-Insulin Therapies for Diabetes: GLP-1 Agonists, DPP4 Inhibitors and SGLT2 Inhibitors, 2016-2026. Cision PR Newswire. Retrieved from www.prnewswire.com/news-releases/non-insulin-therapies-for-diabetes-glp-1-agonists-dpp4-inhibitors-and-sglt2-inhibitors-2016---2026-300317435.html. Aug. 23, 2016. 11 pages.
[No Author Listed], Effect of intensive diabetes treatment on the development and progression of long-term complications in adolescents with insulin-dependent diabetes mellitus: Diabetes Control and Complications Trial. N. Engl. J. Med. 1993;329:977-986.
[No Author Listed], Understanding and Improving Performance of New Manufactured Homes During High-Wind Events. FEMA. Feb. 2007. 8 pages.
Abell et al., Gastric Electrical Stimulation for Medically Refractory Gastroparesis. Gastroenterology. Aug. 2003;2(125):421-8.doi:10.1016/S0016-5085(03)00878-3.
Abrahamsson et al., A novel in vitro and numerical analysis of shear-induced drug release from extended-release tablets in the fed stomach. Pharm Res. Aug. 2005;22(8):1215-26. doi: 10.1007/S11095-005-5272-x. Epub Aug. 3, 2005.
Abramson et al., An ingestible self-orienting system for oral delivery of macromolecules. Science. Feb. 2019;363(6427):611-5. Supplementary Materials included. 38 pages total.
Aguirre et al., Current status of selected oral peptide technologies in advanced preclinical development and in clinical trials. Adv Drug Deliv Rev. Nov. 15, 2016;106(Pt B):223-241. doi: 10.1016/j.addr.2016.02.004. Epub Feb. 24, 2016.
Ahmad et al., Enhancement of oral insulin bioavailability: in vitro and in vivo assessment of nanoporous stimuli-responsive hydrogel microparticles. Expert Opin Drug Deliv. 2016;13(5):621-32. doi: 10.1517/17425247.2016.1160889. Epub Mar. 24, 2016.
Alcock et al., Long-term thermostabilization of live poxviral and adenoviral vaccine vectors at supraphysiological temperatures in carbohydrate glass. Sci Transl Med. Feb. 17, 2010;2(19):19ra12. doi: 10.1126/scitranslmed.3000490. 8 pages.
Anderloni et al., Advances, problems, and complications of polypectomy. Clin Exp Gastroenterol. Aug. 30, 2014;7:285-96. doi: 10.2147/CEG.S43084.

Andrews et al., Mucoadhesive polymeric platforms for controlled drug delivery. Eur J Pharm Biopharm. Mar. 2009;71(3):505-18. doi: 10.1016/j.ejpb.2008.09.028. Epub Oct. 18, 2008.
Aran et al., An oral microjet vaccination system elicits antibody production in rabbits. Sci Transl Med. Mar. 8, 2017;9(380):eaaf6413. doi: 10.1126/scitranslmed.aaf6413. 9 pages.
Banerjee et al., Intestinal micropatches for oral insulin delivery. J. Drug Target. 2017;25:608-615. Epub Mar. 19, 2017.
Banerjee et al., Intestinal mucoadhesive devices for oral delivery of insulin. Bioengineering & Translational Medicine. 2016;1:338-46.
Bass et al., Gastrointestinal safety of an extended-release, nondeformable, oral dosage form (OROS): a retrospective study. Drug Saf. 2002;25(14):1021-33. doi: 10.2165/00002018-200225140-00004.
Becker et al., Novel orally swallowable IntelliCap(®) device to quantify regional drug absorption in human GI tract using diltiazem as model drug. AAPS PharmSciTech. Dec. 2014; 15(6):1490-7. doi: 10.1208/s12249-014-0172-1. Epub Jul. 15, 2014.
Boddupalli et al., Mucoadhesive drug delivery system: An overview. J Adv Pharm Technol Res. Oct. 2010;1(4):381-7. doi: 10.4103/0110-5558.76436.
Bolondi et al., Measurement of gastric emptying time by real-time ultrasonography. Gastroenterology. Oct. 1985;89(4):752-9. doi: 10.1016/0016-5085(85)90569-4.
Brayden et al., Oral delivery of peptides: opportunities and issues for translation. Adv Drug Deliv Rev. Nov. 15, 2016;106(PtB):193-195. doi: 10.1016/j.addr.2016.10.005.
Brunton, GLP-1 receptor agonists vs. DPP-4 inhibitors for type 2 diabetes: is one approach more successful or preferable than the other? Int J Clin Pract. May 2014;68(5):557-67. doi: 10.1111/ijcp.12361. Epub Feb. 6, 2014.
Bui et al., Prediction of viscosity of glucose and calcium chloride solutions. J. Food Eng. 2004;62:345-349.
Buse et al., Liraglutide once a day versus exenatide twice a day for type 2 diabetes: a 26-week randomised, parallel-group, multinational, open-label trial (LEAD-6). Lancet. Jul. 4, 2009;374(9683):39-47. doi: 10.1016/80140-6736(09)60659-0.
Caffarel-Salvador et al., Oral delivery of biologies using drug-device combinations. Curr Opin Pharmacol. Oct. 2017;36:8-13. doi: 10.1016/j.coph.2017.07.003. Epub Aug. 2, 2017.
Calvert et al., Management of type 2 diabetes with multiple oral hypoglycaemic agents or insulin in primary care: retrospective cohort study. Br. J. Gen. Pract. 2007;57. 6 pages.
Camilleri et al., Axial forces during gastric emptying in health and models of disease. Dig. Dis. Sci. 1994;39:14S-17S.
Carino et al., Oral insulin delivery. Adv Drug Deliv Rev. Feb. 1, 1999;35(2-3):249-257. doi: 10.1016/s0169-409x(98)00075-1.
Carlson, Ousting the "ouch factor" in drug delivery. Biotechnol Healthc. Dec. 2007;4(6):15-6.
Chaddock et al., Novel MRI tests of orocecal transit time and whole gut transit time: studies in normal subjects. Neurogastroenterol Motil. Feb. 2014;26(2):205-14. doi: 10.1111/nmo.12249. Epub Oct. 25, 2013.
Cui et al., The study of a remote-controlled gastrointestinal drug delivery and sampling system. Telemed J E Health. Sep. 2008;14(7):715-9. doi: 10.1089/tmj.2007.0118.
Dallel et al., Disposal of insulin syringes by diabetic patients. Report of 100 patients. Tunis Med. Jul. 2005;83(7):390-2.
Defronzo et al., Effects of exenatide versus sitagliptin on postprandial glucose, insulin and glucagon secretion, gastric emptying, and caloric intake: a randomized, cross-over study. Curr Med Res Opin. Oct. 2008;24(10):2943-52. doi: 10.1185/03007990802418851. Epub Sep. 10, 2008.
Degen et al., Variability of gastrointestinal transit in healthy women and men. Gut. Aug. 1996;39(2):299-305. doi: 10.1136/gut.39.2.299.
Delvaux et al., Clinical evaluation of the use of the M2A patency capsule system before a capsule endoscopy procedure, in patients with known or suspected intestinal stenosis. Endoscopy. Sep. 2005;37(9):801-7. doi: 10.1055/s-2005-870241.
Des Rieux et al., Nanoparticles as potential oral delivery systems of proteins and vaccines: a mechanistic approach. J Control Release. Nov. 2006;116(1):1-27. doi: 10.1016/j.jconrel.2006.08.013. Epub Aug. 23, 2006.

(56) References Cited

OTHER PUBLICATIONS

Diamond et al., Experience with a pill-swallowing enhancement aid. Clin Pediatr (Phila). Apr. 2010;49(4):391-3. doi: 10.1177/0009922809355313. Epub Jan. 28, 2010.
Domokos et al., Geometry and self-righting of turtles. Proc Biol Sci. Jan. 7, 2008;275(1630):11-7. doi: 10.1098/rspb.2007.1188.
Eisen et al., Complications of upper GI endoscopy. Gastrointest Endosc. Jun. 2002;55(7):784-93. doi: 10.1016/s0016-5107(02)70404-5.
Eldor et al., Glucose-reducing effect of the ORMD-0801 oral insulin preparation in patients with uncontrolled type 1 diabetes: a pilot study. PLoS One. Apr. 9, 2013;8(4):e59524. doi: 10.1371/journal.pone.0059524. 4 pages.
Ensign et al., Oral drug delivery with polymeric nanoparticles: the gastrointestinal mucus barriers. Adv Drug Deliv Rev. May 1, 2012;64(6):557-70. doi: 10.1016/j.addr.2011.12.009. Epub Dec. 24, 2011.
Fallowfield et al., Patients' preference for administration of endocrine treatments by injection or tablets: results from a study of women with breast cancer. Ann Oncol. Feb. 2006;17(2):205-10. doi: 10.1093/annonc/mdj044. Epub Oct. 20, 2005.
FDA Guidance for Industry. Food-effect bioavailability and Fed Bioequivalence Studies. U.S. Department of Health and Human Services. Food and Drug Administration. Center for Drug Evaluation and Research. Dec. 2002:12 pages.
Ferrua et al., Modeling the fluid dynamics in a human stomach to gain insight of food digestion. J Food Sci. Sep. 2010;75(7):R151-62. doi: 10.1111/j.1750-3841.2010.01748.x.
Finkelstone et al., Etiology of small bowel thickening on computed tomography. Can J Gastroenterol. Dec. 2012;26(12):897-901. doi: 10.1155/2012/282603.
Foster et al., Effect of Texture of Plastic and Elastic Model Foods on the Parameters of Mastication. J Neurophysiol. Jun. 2006;95:3469-79.
Fox et al., Fabrication of Sealed Nanostraw Microdevices for Oral Drug Delivery. CS Nano. Jun. 28, 2016;10(6):5873-81. doi: 10.1021/acsnano.6b00809. Epub Jun. 13, 2016.
Fox et al., Micro/nanofabricated Platforms for Oral Drug Delivery. J Control Release. Dec. 10, 2015; 219: 431-444. Epub Aug. 2, 2015. doi: 10.1016/j.jconrel.2015.07.033.
Gao et al., Biodegradable, pH-responsive carboxymethyl cellulose/poly(acrylic acid) hydrogels for oral insulin delivery. Macromol Biosci. Apr. 2014;14(4):565-75. doi: 10.1002/mabi.201300384. Epub Dec. 19, 2013.
Gilroy et al., Controlled release of biologies for the treatment of type 2 diabetes. J Control Release. Oct. 28, 2016;240:151-164. doi: 10.1016/j.jconrel.2015.12.002. Epub Dec. 2, 2015.
Giudice et al., Needle-free vaccine delivery. Adv Drug Deliv Rev. Apr. 20, 2006;58(1):68-89. doi: 10.1016/j.addr.2005.12.003. Epub Mar. 24, 2006.
Glendorf et al., Importance of the Solvent-Exposed Residues of the Insulin B Chain α-Helix for Receptor Binding. Biochemistry. 2008;47:4743-4751. Epub Apr. 1, 2008.
Goffredo et al., A smart pill for drug delivery with sensing capabilities. 2015 37th Annual International Conference of the IEEE Engineering in Medicine and Biology Society (EMBC), Milan, Aug. 2015, pp. 1361-1364.
Gregory et al., Pattern of gastric emptying the pig: relation to feeding. Br J Nutr. Jul. 1990;64:45-58.
Guilloteau et al., Nutritional programming of gastrointestinal tract development. Is the pig a good model for man? Nutr Res Rev. Jun. 2010;23(1):4-22. doi: 10.1017/S0954422410000077. Epub May 26, 2010.
Gupta et al., A permeation enhancer for increasing transport of therapeutic macromolecules across the intestine. J Control Release. Dec. 10, 2013;172(2):541-9. doi: 10.1016/j.jconrel.2013.05.002. Epub May 14, 2013.
Han et al. A Neural Circuit for Gut-Induced Reward. Cell. Oct. 18, 2018;175(3):665-678.e23. doi: 10.1016/j.cell.2018.08.049. Epub Sep. 20, 2018. Erratum in: Cell. Oct. 18, 2018; 175(3):887-888.
Harding et al., The crystal structure of insulin. II. An investigation of rhombohedral zinc insulin crystals and a report of other crystalline forms. J Mol Biol. Mar. 1966;16(1):212-26. doi: 10.1016/s0022-2836(66)80274-7.
Harrison, Insulin in Alcoholic Solution By the Mouth. Br Med J. Dec. 22, 1923;2(3286):1204-5. doi: 10.1136/bmj.2.3286.1204.
Hay, Can 'Robotic' Pills Replace Injections? The Wall Street Journal. Feb. 17, 2014. Retrieved from www.wsj.com/articles/can-8216robotic8217-pills-replace-injections-1392681501?tesla=y. 4 pages.
He et al., Scalable fabrication of size-controlled chitosan nanoparticles for oral delivery of insulin. Biomaterials. Jun. 2017;130:28-41. doi: 10.1016/j.biomaterials.2017.03.028. Epub Mar. 22, 2017.
Hoebler et al., Particle size of solid food after human mastication and in vitro simulation of oral breakdown. Int J Food Sci Nutr. Sep. 2000;51:353-66.
Höög et al., Capsule retentions and incomplete capsule endoscopy examinations: an analysis of 2300 examinations. Gastroenterol Res Pract. 2012;2012:518718. doi: 10.1155/2012/518718. Epub Sep. 29, 2011. 7 pages.
Hvid et al., In situ phosphorylation of Akt and ERK1/2 in rat mammary gland, colon, and liver following treatment with human insulin and IGF-1. Toxicol Pathol. Jun. 2011;39(4):623-40. doi: 10.1177/0192623311406936. Epub May 10, 2011.
Ingersoll et al., The impact of medication regimen factors on adherence to chronic treatment: a review of literature. J Behav Med. Jun. 2008;31(3):213-24. doi: 10.1007/sl0865-007-9147-y. Epub Jan. 19, 2008.
Jalabert-Malbos et al., Particle size distribution in the food bolus after mastication of natural foods. Food Qual Prefer. 2007;18:803-12. Epub Feb. 13, 2007.
Kaelberer et al., A gut-brain neural circuit for nutrient sensory transduction. Science. Sep. 21, 2018;361(6408):eaat5236, 10 pages. doi: 10.1126/science.aat5236.
Kalantzi et al., Characterization of the human upper gastrointestinal contents under conditions simulating bioavailability/bioequivalence studies. Pharm Res. Jan. 2006;23(1):165-76. doi: 10.1007/s11095-005-8476-1. Epub Dec. 1, 2006.
Kim et al., Droplet-born air blowing: Novel dissolving microneedle fabrication, J. Control. Release. 2013;170:430-436. doi:10.1016/j.jconrel.2013.05.026.
Kim et al., Microneedles for drug and vaccine delivery, Adv. Drug Deliv. Rev. 2012;64:1547-1568. doi:10.1016/j.addr.2012.04.005.
Koetting et al., pH-responsive and enzymatically-responsive hydrogel microparticles for the oral delivery of therapeutic proteins: Effects of protein size, crosslinking density, and hydrogel degradation on protein delivery. J. Control. Release 2016;221:18-25.
Kong et al., Disintegration of solid foods in human stomach. J Food Sci. Jun. 2008;73(5):R67-80. doi: 10.1111/j.1750-3841.2008.00766.x.
Lahiji et al., A patchless dissolving microneedle delivery system enabling rapid and efficient transdermal drug delivery. Sci Rep. Jan. 21, 2015;5:7914. doi: 10.1038/srep07914. 7 pages.
Lee et al., Bioadhesive-based dosage forms: The next generation. J Pharm Sci. 2000;89(7):850-866. doi:10.1002/1520-6017(200007)89:7<850::AID-JPS2>3.0.CO;2-G.
Lee et al., Formulation of two-layer dissolving polymeric microneedle patches for insulin transdermal delivery in diabetic mice. J Biomed Mater Res. Part A. Jan. 2017;105(1):84-93. doi:10.1002/jbm.a.35869.
Ling et al., Dissolving polymer microneedle patches for rapid and efficient transdermal delivery of insulin to diabetic rats. Acta Biomater. Nov. 2013;9(11):8952-61. doi: 10.1016/j.actbio.2013.06.029. Epub Jun. 29, 2013.
Marasini et al., Oral delivery of nanoparticle-based vaccines. Expert Rev Vaccines. Nov. 2014;13(11):1361-76. doi: 10.1586/14760584.2014.936852. Epub Aug. 26, 2014.
Mathiowitz et al., Biologically erodable microspheres as potential oral drug delivery systems. Nature. Mar. 27, 1997;386(6623):410-4. doi: 10.1038/386410a0.
Metcalf et al., Simplified assessment of segmental colonic transit. Gastroenterology. Jan. 1987;92(1):40-7. doi: 10.1016/0016-5085(87)90837-7.

(56) References Cited

OTHER PUBLICATIONS

Mikiewicz et al., Soluble insulin analogs combining rapid- and long-acting hypoglycemic properties—From an efficient E. coli expression system to a pharmaceutical formulation. PLoS One. Mar. 15, 2017;12(3):e0172600. doi: 10.1371/journal.pone.0172600. 19 pages.

Miller et al., The cost of unsafe injections. Bull World Health Organ. 1999;77(10):808-11.

Morishita et al., Novel oral insulin delivery systems based on complexation polymer hydrogels: single and multiple administration studies in type 1 and 2 diabetic rats. J Control Release. Feb. 21, 2006;110(3):587-94. doi: 10.1016/j.jconrel.2005.10.029. Epub Dec. 2, 2005.

Moroz et al., Oral delivery of macromolecular drugs: Where we are after almost 100years of attempts. Adv Drug Deliv Rev. Jun. 1, 2016; 101:108-121. doi: 10.1016/j.addr.2016.01.010. Epub Jan. 27, 2016.

Nahata et al., Extemporaneous drug formulations. Clin Ther. Nov. 2008;30(11):2112-9. doi: 10.1016/j.clinthera.2008.11.020.

Nakamura et al., Oral insulin delivery using P(MAA-g-EG) hydrogels: effects of network morphology on insulin delivery characteristics. J Control Release. Mar. 24, 2004;95(3):589-99. doi: 10.1016/j.jconrel. 2003.12.022.

Nordquist et al., Novel microneedle patches for active insulin delivery are efficient in maintaining glycaemic control: an initial comparison with subcutaneous administration. Pharm Res. Jul. 2007;24(7):1381-8. doi: 10.1007/s11095-007-9256-x. Epub Mar. 27, 2007.

Omre, Bluetooth low energy: wireless connectivity for medical monitoring. J Diabetes Sci Technol. Mar. 1, 2010;4(2):457-63.

Ortiz et al., Identification of insulin variants using Raman spectroscopy. Anal Biochem. Sep. 15, 2004;332(2):245-52. doi: 10.1016/j.ab.2004.06.013.

Ortiz et al., Metallic ions released from stainless steel, nickel-free, and titanium orthodontic alloys: toxicity and DNA damage. Am J Orthod Dentofacial Orthop. Sep. 2011;140(3):e115-22. doi: 10.1016/j.ajodo.2011.02.021. Erratum in: Am J Orthod Dentofacial Orthop. Jun. 2018;153(6):765.

Osterberg et al., Adherence to medication. N Engl J Med. Aug. 4, 2005;353(5):487-97. doi: 10.1056/NEJMra050100.

Outlander Anatomy, Anatomy Lesson #44: "Terrific Tunnel—GI System, Part 1". Retrieved from www.outlanderanatomy.com/anatomy-lesson-44-terrific-tunnel-gi-system-part-1/. Oct. 18, 2016. 43 pages.

Pawar et al., Targeting of gastrointestinal tract for amended delivery of protein/peptide therapeutics: strategies and industrial perspectives. J Control Release. Dec. 28, 2014; 196:168-83. doi: 10.1016/j.jconrel.2014.09.031. Epub Oct. 14, 2014.

Peyron et al., Particle Size Distribution of Food Boluses after Mastication of Six Natural Foods. J Dent Res. Jul. 2004;83:578-82.

Podolsky, Healing the epithelium: Solving the problem from two sides, J Gastroenterol. Jan. 1997;32:122-126.

Pratley et al., Liraglutide versus sitagliptin for patients with type 2 diabetes who did not have adequate glycaemic control with metformin: a 26-week, randomised, parallel-group, open-label trial. Lancet. Apr. 24, 2010;375(9724):1447-56. doi: 10.1016/S0140-6736(10)60307-8. Erratum in: Lancet. Jul. 24, 2010;376(9737):234.

Prego et al., The potential of chitosan for the oral administration of peptides. Expert Opin Drug Deliv. Sep. 2005;2(5):843-54. doi: 10.1517/17425247.2.5.843.

Rao, Rheology of Fluid and Semisolid Foods. Springer US. 2007. doi: 10.1007/978-0-387-70930-7. 491 pages.

Rapaccini et al., Gastric wall thickness in normal and neoplastic subjects: a prospective study performed by abdominal ultrasound. Gastrointest Radiol. Jul. 1988;13(3):197-9. doi: 10.1007/BF01889058.

Ravi et al., Needle free injection technology: A complete insight. Int J Pharm Investig. Oct.-Dec. 2015;5(4):192-9. doi: 10.4103/2230-973X.167662.

Römgens et al., Monitoring the penetration process of single microneedles with varying tip diameters. J Mech Behav Biomed Mater. Dec. 2014;40:397-405. doi: 10.1016/j.jmbbm.2014.09.015. Epub Oct. 8, 2014.

Saniocki, New insights into tablet sticking: characterization and quantification of sticking to punch surfaces during tablet manufacture by direct compaction. PhD Thesis. University Hamburg. 2014. 159 pages.

Santonen et al., Review on toxicity of stainless steel. Finnish Institute of Occupational Health. Helsinki. 2010. Retrieved from: www.bssa.org.uk/cms/File/Review on Toxicity of Stainless Steel Finnish Health Institute.pdf. 87 pages.

Schmidt et al., Viscosity and electrolyte concentrations in gastric juice from cystic fibrosis children compared to healthy children. Eur J Pediatr. May 1981;136(2):193-7. doi: 10.1007/BF00441923.

Schoellhammer et al., Of microneedles and ultrasound: Physical modes of gastrointestinal macromolecule delivery. Tissue Barriers. Feb. 11, 2016;4(2):e1150235. doi: 10.1080/21688370.2016. 1150235. 5 pages.

Schoellhammer et al., Ultrasound-Mediated Delivery of RNA to Colonic Mucosa of Live Mice. Gastroenterology. Apr. 2017;152(5):1151-1160. doi: 10.1053/j.gastro.2017.01.002. Epub Jan. 11, 2017.

Schoellhammer et al., Ultrasound-mediated gastrointestinal drug delivery. Sci Transl Med. Oct. 21, 2015;7(310):310ra168. doi: 10.1126/scitranslmed.aaa5937. 22 pages.

Schwartz et al., Electrical stimulation of the isolated rat intestine in the presence of nutrient stimulus enhances glucagon-like peptide-1 release. Physiol Meas. Sep. 2010;31(9):1147-59. doi: 10.1088/0967-3334/31/9/006. Epub Jul. 28, 2010.

Sharma et al., Development of enteric submicron particle formulation of papain for oral delivery. Int J Nanomedicine. 2011; 6: 2097-2111. Epub Sep. 23, 2011. doi: 10.2147/IJN.S23985.

Sher Akbar et al., Simulation of peristaltic flow of chyme in small intestine for couple stress fluid. Meccanica 2014;49:325-334. Epub Aug. 28, 2013.

Sokolowski et al., Needle phobia: etiology, adverse consequences, and patient management. Dent Clin North Am. Oct. 2010;54(4):731-44. doi: 10.1016/j.cden.2010.06.012.

Steffe, Rheological Methods in Food Process Engineering. Freeman Press. East Lansing, MI. 1996. 428 pages.

Stewart et al., In vitro and ex vivo strategies for intracellular delivery. Nature. Oct. 13, 2016;538(7624):183-192. doi: 10.1038/nature19764.

Tang et al., Biodegradable polymer nanoparticles that rapidly penetrate the human mucus barrier. Proc Natl Acad Sci U S A. Nov. 17, 2009;106(46):19268-73. doi: 10.1073/pnas.0905998106. Epub Nov. 9, 2009.

Taverner et al., Enhanced paracellular transport of insulin can be achieved via transient induction of myosin light chain phosphorylation. J Control Release. Jul. 28, 2015;210:189-97. doi: 10.1016/j.jconrel. 2015.05.270. Epub May 14, 2015.

Thomas, Gut motility, sphincters and reflex control. Anaesth Intensive Care Med. Feb. 2006;7:57-8.

Traverso et al., Microneedles for drug delivery via the gastrointestinal tract., J. Pharm. Sci. 2015;104:362-7. doi:10.1002/jps.24182.

Várkonyi et al., Mono-monostatic Bodies: The Answer to Arnold's Question, Math. Intell. Dec. 2006;28:34-38. doi:10.1.1.132.3141.

Várkonyi et al., Static Equilibria of Rigid Bodies: Dice, Pebbles, and the Poincaré-Hopf Theorem. J. Nonlinear Sci. 2006;16:255-281. Epub May 22, 2006.

Vassallo et al., Measurement of axial forces during emptying from the human stomach. Am J Physiol. Aug. 1992;263(2 Pt 1):G230-9. doi: 10.1152/ajpgi.1992.263.2.G230.

Vazharov, Perforation as a complication of the diagnostic upper and lower endoscopy of the gastrointestinal tract, J. IMAB—Annual Proceeding. 2012; Scientific Paper 18:273-5. doi:10.5272/jimab. 2012183.273. Epub Aug. 2, 2012.

Vinther et al., Insulin analog with additional disulfide bond has increased stability and preserved activity. Protein Sci. Mar. 2013;22(3):296-305. doi: 10.1002/pro.2211. Epub Jan. 17, 2013.

Wallace et al., The cellular and molecular basis of gastric mucosal defense. FASEB J. May 1996;10(7):731-40. doi: 10.1096/fasebj.10. 7.8635690.

(56) References Cited

OTHER PUBLICATIONS

Wang et al., Recent advances in the design of polymeric microneedles for transdermal drug delivery and biosensing. Lab Chip. Apr. 11, 2017;17(8):1373-1387. doi: 10.1039/c7lc00016b.

Wiesner et al., Normal colonic wall thickness at CT and its relation to colonic distension. J Comput Assist Tomogr. Jan.-Feb. 2002;26(1):102-6. doi: 10.1097/00004728-200201000-00015.

Yoshida et al., Complexation hydrogels as potential carriers in oral vaccine delivery systems. Eur J Pharm Biopharm. Mar. 2017;112:138-142. doi: 10.1016/j.ejpb.2016.11.029.

Zhang et al., Systematic review: applications and future of gastric electrical stimulation. Aliment Pharmacol Ther. Oct. 1, 2006;24(7):991-1002.

\* cited by examiner

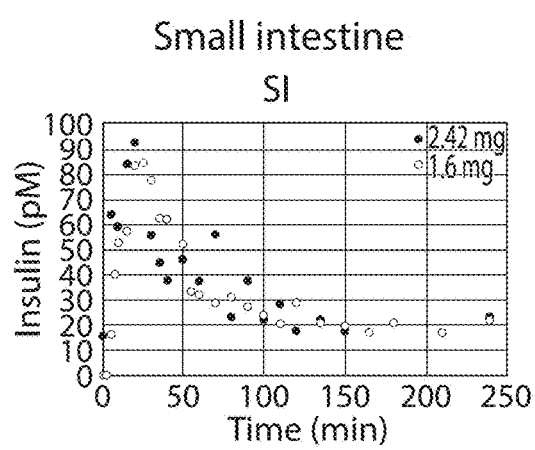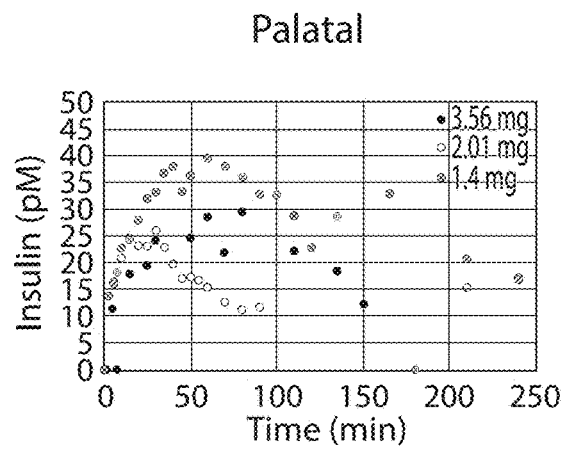
FIG. 45
FIG. 46

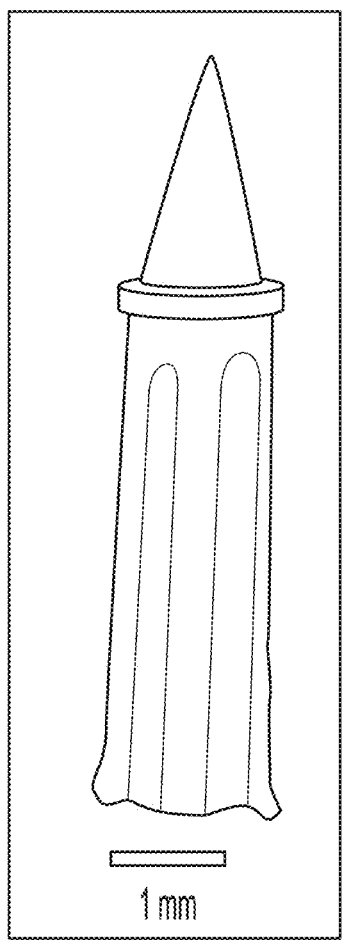
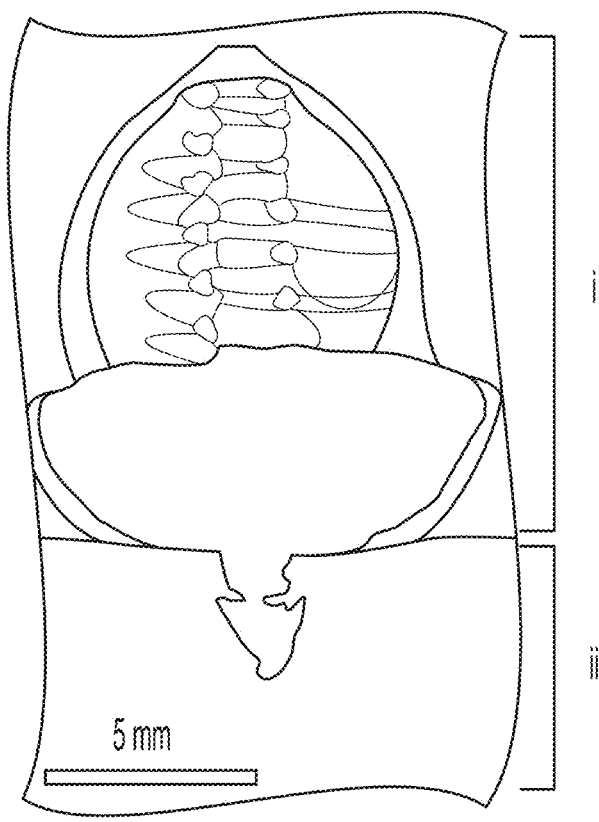
FIG. 73B
FIG. 73C

S.C. Implant

I.G. Surgical Implant

SELF-RIGHTING ARTICLES

RELATED APPLICATIONS

This Application is a national stage filing under 35 U.S.C. § 371 of International PCT application, PCT/US2018/033183, filed May 17, 2018, which claims priority under 35 U.S.C. § 119(e) to U.S. Provisional Application Ser. No. 62/507,647, entitled "SELF-RIGHTING ARTICLES" filed on May 17, 2017, to U.S. Provisional Application Ser. No. 62/507,653, entitled "SELF-ACTUATING ARTICLES" filed on May 17, 2017, and to U.S. Provisional Application Ser. No. 62/507,665, entitled "COMPONENTS WITH HIGH API LOADING" filed on May 17, 2017, each of which is herein incorporated by reference in its entirety.

STATEMENT OF GOVERNMENT SUPPORT

This invention was made with Government support under Grant No. R37 EB000244 awarded by the National Institutes of Health (NIH). The Government has certain rights in the invention.

FIELD

The present invention generally relates to self-righting systems and related components such as self-righting articles, self-actuating articles including, for example, self-actuating needles and/or self-actuating biopsy punches, as well as components with relatively high loading of active pharmaceutical ingredients (API).

BACKGROUND

The GI tract offers an incredible opportunity for diagnosing and treating patients. The development of smart dosage systems and articles to enable this has witnessed significant growth over the preceding decade. One of the most significant challenges in maximizing delivery and interaction with the mucosa is ensuring juxtaposition between an article and/or dosing system and the GI mucosa. Prior attempts at doing this have included the introduction of mucoadhesives as well as texturing of one side of a 2 sided system. Orally ingested drugs generally diffuse through the GI tract tissue walls in order to enter the blood stream. Typical ingested pills or articles release their cargo into the GI tract randomly and allow it move via convection and diffusion to the tissue wall. However, many biologic drugs such as insulin cannot move through the liquid in the GI tract because they will be, for example, degraded by enzymes, even if housed in a solid formulation.

Additionally, many pharmaceutical drug formulations on the market require administration via in injection, including numerous vaccines, RNA, and peptides. Injections traditionally involve the use of a liquid formulation passing through a hollow needle and entering into the body intravenously or intramuscularly. However, these liquid formulations can cause the active pharmaceutical ingredient (API) to become unstable and thus may require refrigeration and/or increase the bulk of the dose significantly because of the required dilution.

Accordingly, improved systems, articles and methods are needed.

SUMMARY

The present invention generally relates to self-righting articles, such as self-righting capsules.

In one aspect, self-righting articles are provided. In some embodiments, the self-righting article comprises a first portion, a second portion adjacent the first portion having a different average density than the first portion, and a hollow portion, wherein the self-righting article is configured and arranged to be encapsulated in a 000 capsule, or smaller.

In some embodiments, although the self-righting article is configured for potential encapsulation in a 000 capsule, or smaller, the self-righting article does not necessarily need to be encapsulated in such capsule. In embodiments wherein the self-righting article is to be administered, such as by ingesting the self-righting article, the self-righting article may thus be administered without encapsulation.

In some embodiments, the self-righting article comprises a first portion, a second portion adjacent the first portion having a different average density than the first portion, and a tissue-interfacing component associated with the self-righting article, wherein a ratio of an average density of the first material to an average density of the second material is greater than or equal to 2.5:1. In some embodiments, the ratio of an average density of the second material to an average density of the first material is greater than or equal to 2.5:1. In some embodiments, the self-righting article is configured to anchor at a location internal to a subject and comprises at least a first portion having an average density greater than 1 g/cm$^3$ wherein a longitudinal axis perpendicular to a tissue-engaging surface of the article is configured to maintain an orientation of 20 degrees or less from vertical when acted on by 0.09*10^-4 Nm or less externally applied torque and at least one anchoring mechanism associated with the self-righting article.

In some embodiments, the self-righting article is configured for administration to a location internal to a subject and comprises at least a first portion having an average density greater than 1 g/cm$^3$, the self-righting article has a self-righting time from 90 degrees in water of less than or equal to 0.05 second, at least two tissue interfacing components comprising a tissue-contacting portion configured for contacting tissue, each tissue-contacting portion comprising an electrically-conductive portion configured for electrical communication with tissue and an insulative portion configured to not be in electrical communication with tissue, and a power source in electric communication with the at least two tissue interfacing components.

In another aspect, self-actuating articles are provided. In some embodiments, the article comprises an outer shell, a spring at least partially encapsulated within the outer shell, a support material associated with the spring such that the support material maintains at least a portion of the spring under at least 5% compressive strain under ambient conditions and a tissue interfacing component associated with the spring.

In some embodiments, the article is configured to anchor at a location internal to a subject and comprises an outer shell, a spring at least partially encapsulated with the outer shell, the spring maintained in an at least partially compressed state by a support material under at least 5% compressive strain, and at least one anchoring mechanism operably linked to the spring.

In some embodiments, the article is configured for administration to at a location internal to a subject and comprises an outer shell, a spring at least partially encapsulated with the outer shell, the spring maintained in an at least partially compressed state by a support material under at least 5% compressive strain, at least two tissue interfacing components comprising a tissue-contacting portion configured for contacting tissue, each tissue-contacting portion comprising an electrically-conductive portion configured for electrical communication with tissue and an insulative portion configured to not be in electrical communication with tissue, and a power source in electric communication with the at least two tissue interfacing components.

In another aspect, tissue-interfacing components are provided. In some embodiments, the component comprises a solid therapeutic agent and a support material, wherein the solid therapeutic agent is present in the tissue interfacing component in an amount of greater than or equal to 10 wt % as a function of the total weight of the tissue interfacing component, wherein the solid therapeutic agent and support material are distributed substantially homogeneously, and wherein the tissue interfacing component is configured to penetrate tissue.

In some embodiments, the component has a tip and comprises a solid therapeutic agent and a support material associated with the solid therapeutic agent, wherein at least a portion of the solid therapeutic agent is associated with one or more tips of the tissue interfacing component, and wherein the solid therapeutic agent is present in the tissue interfacing component in an amount of greater than or equal to 10 wt % as a function of the total weight of the tissue interfacing component.

In another aspect, methods are provided. In some embodiments, the method comprises administering, to a subject, a capsule comprising an outer shell and a self-righting article, the self-righting article comprising, a first portion, and a second portion adjacent the first portion and having an average density different than the first portion.

In some embodiments, the method comprises administering, to the subject, a capsule comprising an outer shell and a self-righting article, the self-righting article comprising, a first portion comprising a first material, a second portion adjacent the first portion and comprising a second material, different than the first material, and a needle associated with an active pharmaceutical agent, wherein a ratio of an average density of the first material to an average density of the second material is greater than or equal to 2.5:1, orienting the self-righting article at the location internal of a subject such that the needle punctures a tissue proximate the location internal of the subject, and releasing at least a portion of the active pharmaceutical agent into the tissue.

In some embodiments, the method comprises administering, to a subject, an article, the article comprising an outer shell, a spring at least partially encapsulated with the outer shell, a support material associated with the spring such that the support material maintains at least a portion of the spring under at least 5% compressive strain under ambient conditions and a tissue interfacing component associated with the spring.

In some embodiments, the method comprises administering, to a subject, an article, the article comprising an outer shell, a spring at least partially encapsulated with the outer shell, a support material associated with the spring such that the support material maintains at least a portion of the spring under at least 5% compressive strain under ambient conditions; and a tissue interfacing component associated with the spring, and degrading at least a portion of the support material such that the spring extends and/or the tissue interfacing component penetrates a tissue located internal to the subject.

In some embodiments, the method comprises administering, to the subject, the article, wherein the article comprises at least a first portion having an average density greater than 1 g/cm³ and at least one anchoring mechanism, the article configured to be retained at the location under greater than or equal to 0.6 N of force and/or a change in orientation of greater than or equal to 30 degrees.

In some embodiments, the method comprises administering, to the subject, an article comprising at least one tissue interfacing component disposed within the article, each tissue interfacing component comprising a conductive material, releasing the at least one interfacing component from the article, inserting the at least one interfacing component into a tissue at the location internal to the subject, applying a current generated by a power source in electrical communication with the tissue interfacing components across the two or more tissue interfacing components, wherein the article comprises a spring maintained in an at least partially compressed state by a support material under at least 5% compressive strain, each tissue interfacing component operably linked to the spring.

In another aspect, methods of forming tissue interfacing components are provided. In some embodiments, the method comprises providing a solid therapeutic agent and a support material and compressing, using at least 1 MPa of pressure, and/or heating the solid therapeutic agent and a support material together to form the tissue interfacing component, wherein the tissue interfacing component is configured to penetrate tissue.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 45 is a plot of blood concentration of insulin versus time after application of a tissue interfacing component comprising a plurality of microneedles and a relatively high loading of insulin to the small intestine of swine, according to one set of embodiments;

FIG. 46 is a plot of blood concentration of insulin versus time after application of a tissue interfacing component comprising a plurality of microneedles and a relatively high loading of insulin to the palatal tissue of swine, according to one set of embodiments;

(FIG. 71A) The exemplary system localizes to the stomach lining and utilizes a unique shape to quickly orient its injection mechanism towards the tissue wall. Within one minute the device actuates and injects a drug payload into the mucosa and submucosa. The drug loaded micropost then slowly dissolves, and the rest of the device passes out of the body. (FIG. 71B) A fabricated exemplary device. (FIG. 71C) A comparison between the Leopard tortoise (*Stigmochelys pardalis*) and the computationally optimized shape for self-orientation and stability in the stomach. The optimized shape possess a more narrow build to allow for quicker orientation times while still maintaining the stability desired for the stomach environment. (FIG. 71D) The exemplary device utilizes a compressed spring fixed in caramelized sucrose to provide a force for micropost insertion, according to one set of embodiments;

(FIG. 72A) High speed imaging at 1000 FPS reveals that the SOMA device, made from a mixture of PCL and stainless steel, self-orients from a 90° angle in 64 ms. (FIG. 72B) Theoretical orientation times from a given initial angle of ellipsoids, spheres, and exemplary system shapes. All are made from the same mass of PCL and stainless steel. (FIG. 72C) Experimentally measured relative righting times of weighted shapes in different fluids from a 90° starting angle when normalized to their righting times in water (n=6 Error Bars=SEM). (FIG. 72D) The experimentally determined maximum tilting angle of weighted 3D shapes when exposed to a rocking motion of 15° at 0.25 rad/s (n=3, Error Bars=SEM). (E) Two exemplary systems made from PCL and stainless steel orient in a porcine stomach in vivo after being dropped from a height of 5 cm, while three exemplary devices made with only PCL failed to orient appropriately, according to one set of embodiments;

FIGS. 73A-73I shows micropost fabrication and insertion force characterization for an exemplary system. (FIG. 73A) (i) micropost five part stainless steel mold. (ii) API mixture is screen printed into tip section. (iii) Vibrations ensure powder fills the cavity. (iv) Top section is filled with biodegradable polymer. (v) Material is compressed at 550 MPa. (FIG. 73B) An insulin micropost. (FIG. 73C) MicroCT imaging shows (i) exemplary system delivering a barium sulfate micropost into (ii) porcine stomach tissue. Bottom is larger to ensure micropost stability during imaging. (FIG. 73D) In vivo insertion force profile measured in swine stomach using insulin microposts propelled at 0.2 mm/s (n=2 stomachs, n=8 insertions, Error Bars=SEM). (FIG. 73E) In vivo H&E stained histology results from Carr-Locke needle insertion into swine stomach tissue. (FIG. 73F) H&E and insulin stained and (FIG. 73H) smooth muscle stained histology from insulin micropost injected into in situ swine via a 5 N spring in exemplary system. (FIG. 73G) H&E stained and (FIG. 73I) smooth muscle stained histology of a steel micropost inserted into ex vivo swine stomach with a 9 N spring, according to one set of embodiments;

DETAILED DESCRIPTION

Overview

Figure 1:
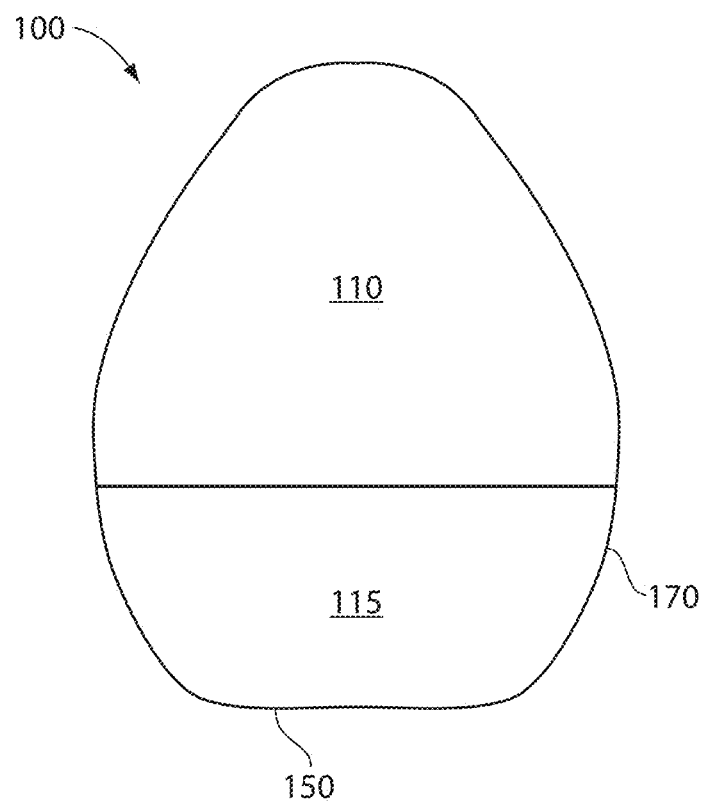
FIG. 1 is a schematic diagram of a self-righting system, according to one set of embodiments.

Self-righting articles, such as self-righting capsules for administration to a subject, are generally provided. In some embodiments, the self-righting article may be configured such that the article may orient itself relative to a surface (e.g., a surface of a tissue of a subject). The self-righting articles described herein may comprise one or more tissue engaging surfaces configured to engage (e.g., interface with, inject into, anchor) with a surface (e.g., a surface of a tissue of a subject). For example, the self-righting article may be placed at any orientation proximate a surface and the self-righting article will (re)-orient itself such that the tissue engaging surface is in contact (e.g., direct contact) with the surface. In some embodiments, the self-righting article may have a particular shape and/or distribution of density (or mass) which, for example, enables the self-righting behavior of the article. In some such embodiments, the capsule containing the self-righting article may be administered to a subject (e.g., for delivery of the self-righting article to a location internal of the subject such as the gastrointestinal tract). In some embodiments, the self-righting may comprise a tissue interfacing component and/or a pharmaceutical agent (e.g., for delivery of the active pharmaceutical agent to a location internal of the subject). In some cases, upon contact of the tissue with the tissue engaging surface of the article, the self-righting article may be configured to release one or more tissue interfacing components. In some cases, the tissue interfacing component is associated with a self-actuating component. For example, the self-righting article may comprise a self-actuating component configured, upon exposure to a fluid, to release the tissue interfacing component from the self-righting article. In some cases, the tissue interfacing component may comprise and/or be associated with the pharmaceutical agent (e.g., for delivery to a location internal to a subject).

The self-righting articles described herein may be useful, for example, as a general platform for delivery of a wide variety of pharmaceutical agents that otherwise are generally delivered via injection directly into tissue due to degradation in the GI tract. In some cases, the self-righting article may be configured to deliver pharmaceutical agents at a desired location and/or at a desired time and/or over a desired duration to a subject. In some embodiments, the self-righting articles described herein may be used to deliver sensors and/or take biopsies, for example, without the need for an endoscopy. In certain embodiments, the self-righting articles described herein may be used to anchor one or more articles to a surface of tissue e.g., in the GI tract. In some cases, the self-righting articles described herein may be used to provide electrical stimulation directly into tissue.

Advantageously, in some embodiments, the self-righting articles and/or self-actuating components described herein may be useful as a general platform for delivery of a wide variety of pharmaceutical agents (e.g., APIs) that are typically delivered via injection directly into tissue due to degradation in the GI tract. For example, the self-righting article may be capable of localizing itself to the tissue wall in a specified direction (e.g., allowing loaded drugs to avoid long passages through the GI tract fluid before diffusing into the blood stream). This article, in some cases, may serve as a platform to allow drugs that are currently degraded by the enzymes in the GI tract to be absorbed with higher bioavailability. Additionally, the article may enable mechanical and electrical mechanisms such as needle plungers, anchors, sensors, etc., to actuate directly at and/or into the tissue wall. In this way, in certain embodiments, the article may serve as a vehicle to deliver electronics or other articles into the GI tract.

In some embodiments, the tissue interfacing component (e.g., associated with a self-actuating component) may comprise a relatively high loading of active pharmaceutical ingredients (e.g., drugs). For example, in certain embodiments, the tissue interfacing component comprises a solid therapeutic agent (e.g., a solid API) and, optionally, a support material (e.g., a binder such as a polymer) such that the solid therapeutic agent is present in the component in a relatively high amount (e.g., greater than or equal to 80 wt %) versus the total weight of the tissue interfacing component. Such tissue-interfacing components may be useful for delivery of API doses (e.g., to a subject). Advantageously, in some embodiments, the reduction of volume required to deliver the required API dose as compared to a liquid formulation permits the creation of solid needle delivery systems for a wide variety of drugs in a variety of places/tissues (e.g., tongue, GI mucosal tissue, skin) and/or reduces and/or eliminates the application of an external force in order to inject a drug solution through the small opening in the needle. In some cases, a physiologically relevant dose may be present in a single tissue interfacing component (e.g., having a relatively high API loading).

In an exemplary embodiment, the self-righting article may comprise a tissue interfacing component and a self-actuating component (e.g., comprising a spring and/or a support material) associated with the tissue interfacing component.

As illustrated in FIG. 1, in some embodiments, system 100 (e.g., a self-righting article) comprises a tissue-engaging surface 150. While embodiments described herein refer to a single tissue interfacing surface, in some embodiments, two or more tissue interfacing surfaces may be present. In certain embodiments, the self-righting article may be designed and configured such that the tissue-engaging surface contacts a surface (e.g., a surface of a tissue at a location internal to a subject such as a surface of a stomach of the subject). In some embodiments, system 100 will self-right (e.g., will orient without the need or use of external forces applied to the self-righting article) such that tissue-engaging surface 150 contacts the surface. In certain embodiments, the self-righting article is configured such that an axis essentially perpendicular to the tissue-engaging surface preferentially aligns parallel to the direction of gravity. As described in more detail herein, the self-righting article may be configured such that the axis essentially perpendicular to the tissue-engaging surface is able to maintain an orientation of 20 degrees or less from vertical under externally applied torque. In some embodiments, the self-righting article is configured such that the tissue interfacing component has a longest longitudinal axis oriented within 15 degrees of vertical upon self-righting.

Without wishing to be bound by theory, the self-righting article may be designed to self-right as a result of a distribution of densities (and/or masses) within the self-righting article. For example, in some embodiments, system 100 (e.g., a self-righting article) comprises a first portion 110 and a second portion 115, the first portion and the second portion having different densities and/or different masses. Different densities/masses of the self-righting article are described in more detail herein. In certain embodiments, the self-righting article may have a particular shape which enables the self-righting behavior. For example, as illustrated in FIG. 1, system 100 comprises a monostatic shape (e.g., a mono-monostatic shape, a gomboc-type shape) as indicated by external surface 170 of system 100. The term "monostatic" as used herein is given its ordinary meaning in the art and generally refers to a three-dimensional shape which has a single stable resting position (e.g., a point of balance). The term "mono-monostatic" as used herein is given its ordinary meaning in the art and generally refers to a three-dimensional shape having a single stable resting position and a single unstable resting positon. By way of example, and without wishing to be bound by theory, a sphere with a center of mass shifted from the geometrical center is general considered a mono-monostatic shape. The term "gomboc" as used herein is given its ordinary meaning in the art and generally refers to a convex three-dimensional shape which, when placed on a flat surface, has a single stable point of equilibrium (or orientation) and a single unstable point of equilibrium (or orientation). For example, and without wishing to be bound by theory, a gomboc-type shape when placed on a surface at any orientation other than the single stable orientation of the shape, then the shape will tend to re-orient to its single stable orientation. Such shapes are described in more detail below.

Figure 2:
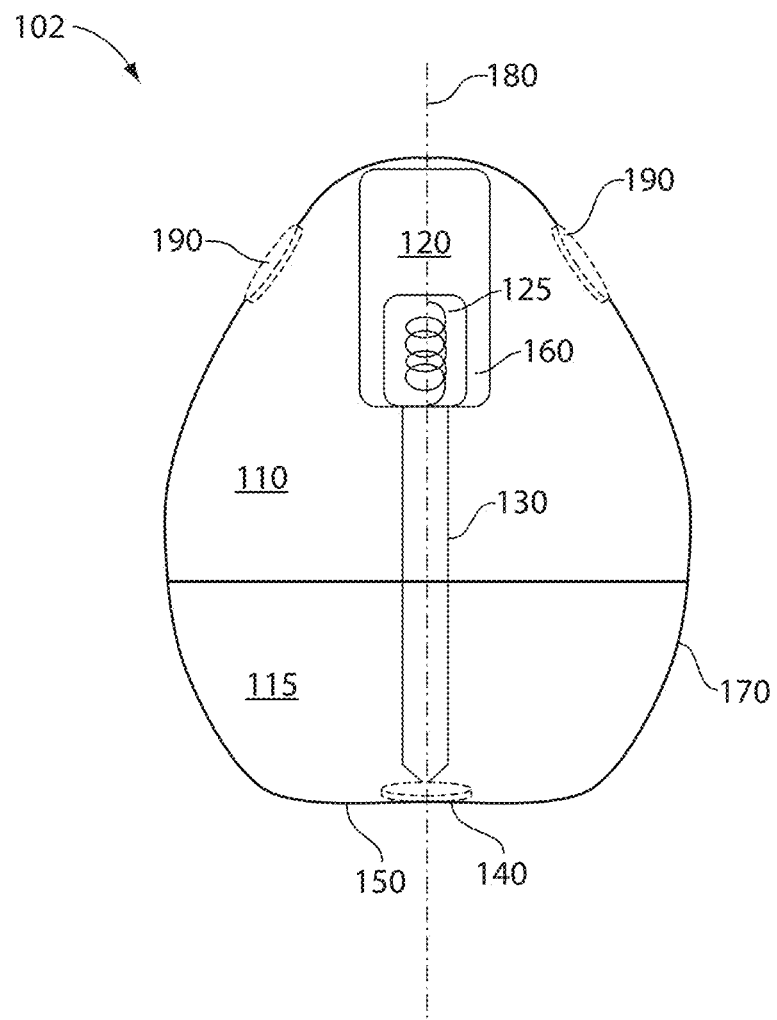
FIG. 2 is a cross-sectional schematic diagram of an exemplary self-righting system, according to one set of embodiments.

FIG. 2 shows a cross-sectional illustration of exemplary system 102. In some embodiments, system 102 comprises a self-actuating component 120. Self-actuating component 120 may be configured, e.g., upon exposure to a particular fluid, to release tissue interfacing component 130 associated with self-actuating component 120, from system 102. For example, in some cases, self-actuating component 120 comprises a spring 125 such that, upon actuation of the self-actuating component, spring 125 expands pushing tissue interfacing component 130 out of system 102 through hole 140 (associated with tissue engaging surface 150). In some cases, spring 125 comprises a support material 160 which maintains spring 125 under compression (e.g., under at least 5% compressive strain). In some cases, upon exposure of support material 160 and/or spring 125 to a fluid, the spring may be configured to release at least 10% (e.g., at least 20%, at least 30%, at least 40%, at least 50%, at least 60%, at least 70%, at least 80%, at least 90%, including any percentage therein) of a stored compressive energy of the spring (e.g., such that tissue interfacing component 130 is released). In some embodiments, the spring is associated with the support material (e.g., at least partially encapsulated by the support material, in direct contact with the support material).

In certain embodiments, tissue interfacing component 130 comprises an active pharmaceutical agent. In some embodiments, the active pharmaceutical agent may be present in the tissue interfacing component at relatively high amounts (e.g., greater than or equal to 10 wt %, greater than or equal to 80 wt %, or greater than or equal to 90 wt % API versus the total weight of the tissue interfacing component). The self-righting articles described herein may, in some cases, be administered to a subject e.g., such that the pharmaceutical agent is delivered to the subject. For example, in some cases, the article may be administered to the subject and a pharmaceutical agent is released from the article at a location internal to the subject. Administration of the articles and release of pharmaceutical agents are described in more detail herein.

In some embodiments, the system is administered to a subject (e.g., orally). In certain embodiments, the system may be administered orally, rectally, vaginally, nasally, or uretherally. In certain embodiments, upon reaching a location internal to the subject (e.g., the gastrointestinal tract), at least a portion of a support material degrades such that a spring extends and/or a tissue interfacing component interfaces (e.g., contacts, penetrates) with a tissue located internal to the subject. In some embodiments, the location internally of the subject is the colon, the duodenum, the ileum, the jejunum, the stomach, or the esophagus. As described above and herein, in some embodiments, an active pharmaceutical ingredient may be released during and/or after penetrate of the tissue located internal to the subject.

Figure 3:
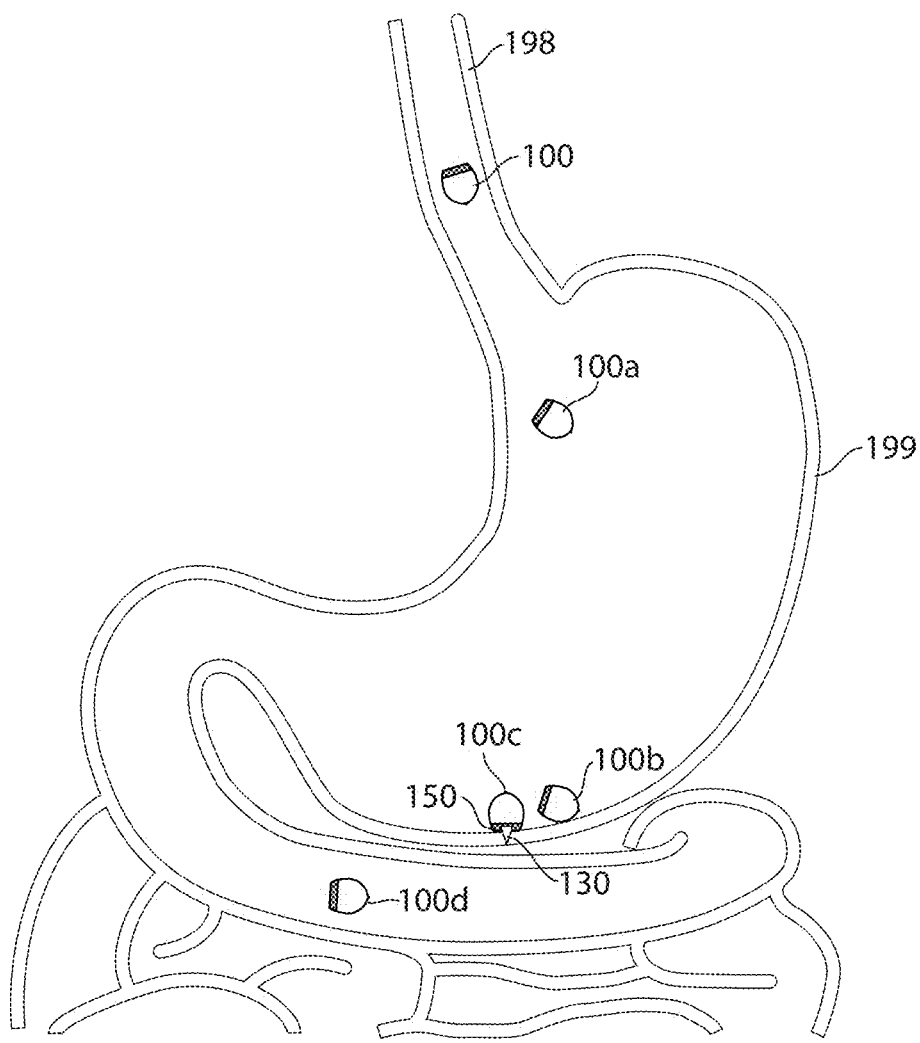
FIG. 3 is a schematic illustration of administration of a self-righting system, according to one set of embodiments.

By way of example, and without wishing to be limited by such an exemplary set of embodiments, the system may be administered to a subject orally where it, in some cases, travels to the stomach of the subject, sinks to the bottom of the subject's stomach, and the system self-rights such that a tissue-engaging surface of the system contacts the stomach tissue (e.g., the system is at least partly supported by the stomach tissue). For example, as illustrated schematically in FIG. 3, exemplary system 100 may be administered to a subject (e.g., orally) such that system 100 enters gastrointestinal system 198 of the subject. System 100 may travel through gastrointestinal system 198 until reaching stomach 199 of the subject (system 100a). In some embodiments, system 100 may sink to the bottom of stomach 199 (system 100b) such that it contacts a surface of stomach 199. In certain embodiments, system 100 self-rights (system 100c) such that tissue engaging surface 150 of system 100 contacts the surface of stomach 199 and system 100 self-actuates such that tissue interfacing component 130 interfaces with a tissue at a location internal to a subject (e.g., the surface of stomach 199). While FIG. 3 illustrates interfacing of the tissue interfacing component with surface of the stomach 199, those of ordinary skill in the art would understand, based upon the teachings of this specification, that the tissue interfacing component may contact one or more layers underlying the surface of the stomach (or other location internal to the subject) including e.g., mucosal, sub-mucosal, and/or muscular tissue layer(s).

In some cases, as described herein, self-righting of system 100 may be driven by gravitational forces (e.g., acting on a center of mass of system 100). After a desired period of time, in some embodiments, system 100 disengages (e.g., tissue interfacing component 130 dissolves and/or is released) and exits stomach 1999 (system 100d). The description above is not meant to be limiting and those of ordinary skill in the art would understand that other interactions between the system and the gastrointestinal system of a subject are also possible, as described herein. In some embodiments, system 100 is a monostatic body, as described in more detail below.

The following description provides various embodiments for the self-righting, self-actuating, and relatively high API loaded components of the systems described herein.

Self-Righting

As described above, in some embodiments, the self-righting article may comprise two or more portions having different average densities such that, for example, the self-righting article may orient itself substantially perpendicular to the surface (e.g., a surface substantially orthogonal to the force of gravity, a surface of a tissue such as the wall of the gastrointestinal tract). In some cases, the self-righting article may have a particular shape which, for example, enables the self-righting behavior of the article. In some embodiments, the self-righting article may be disposed (e.g., encapsulated) in a capsule. In certain embodiments, the self-righting article is not provided in a capsule. In some embodiments, the capsule containing the self-righting article may be administered to a subject (e.g., for delivery of the self-righting article to a location internal of the subject such as the gastrointestinal tract). In some embodiments, the self-righting article and/or the capsule may comprise a pharmaceutical agent (e.g., for delivery of the active pharmaceutical agent to a location internal of the subject).

The self-righting articles described herein may be useful, for example, as a general platform for delivery of a wide variety of pharmaceutical ingredients that otherwise are generally delivered via injection directly into tissue due to degradation in the GI tract. In some embodiments, the self-righting articles described herein may be used to deliver sensors and/or take biopsies, for example, without the need for an endoscopy.

Advantageously, the self-righting article may be capable of localizing itself to the tissue wall in a specified direction (e.g., allowing loaded drugs to avoid long passages through the GI tract fluid before diffusing into the blood stream). As described herein, this article, in some cases, may serve as a platform to allow drugs that are currently degraded by the enzymes in the GI tract to be absorbed with higher bioavailability. Additionally, the article may enable mechanical and electrical mechanisms such as needle plungers, anchors, sensors, etc., to actuate directly at and/or into the tissue wall. In this way, in certain embodiments, the article may serve as a vehicle to deliver electronics or other articles into the GI tract.

In some embodiments, the self-righting article may have a particular cross-sectional shape. In certain embodiments, the shape may be any suitable cross-sectional shape including circular, oval, triangular, irregular, trapezoidal, square or rectangular, or the like. In certain embodiments, the self-righting article may be non-spherical. In some embodiments, the self-righting article may be a monostatic body and/or has only one stable point (e.g., the self-righting article may stably maintain a particular orientation in only one given orientation). In an exemplary embodiment, the self-righting article has a gomboc shape and/or comprises a gomboc shaped component. Self-righting articles having a gomboc shape may self-right to a particular orientation upon displacement from that orientation, without additional forces. In some cases, the self-righting article may self-right in a fluid (e.g., a liquid having a relatively low viscosity, a liquid having a relatively high viscosity). Advantageously, the shape is such that the self-righting article orients the self-righting article predictably and quickly while minimizing the motion caused from forces inside of the GI tract is described. In some cases, at least a surface of the self-righting article comprises a flat surface. For example, as illustrated in FIG. 1 and FIG. 2, in some embodiments, tissue engaging surface 150 may be flat.

Referring again to FIG. 1, in some embodiments, self-righting article comprises a first portion 110 and a second portion 115 adjacent first portion 110, having a different average density than the first portion and/or a different mass than the first portion. For example, in some embodiments, the self-righting article comprises a first portion and a second portion adjacent the first portion having a different average density in the first portion. For example, the first portion may have a first average density and a second portion may have a second average density, different than the first average density. In some embodiments, a ratio of an average density of the first portion to an average density of the second portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than equal to 8:1, greater than or equal to 9:1, or greater than or equal to 10:1. In certain embodiments, a ratio of an average density of the first portion to an average density of the second portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible. Without wishing to be bound by theory, the self-righting article having a first portion and a second portion having different average densities may result in the self-righting article substantially maintaining a particular orientation(s) relative to the surface (e.g. a wall of the gastrointestinal track).

In some embodiments, a ratio of an average density of the second portion to an average density of the first portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than equal to 8:1, greater than equal to 9:1, or greater than or equal to 10:1. In certain embodiments, a ratio of an average density of the second portion to an average density of the first portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible.

In certain embodiments, the self-righting article comprises a first portion and a second portion adjacent the first portion having a different mass than the first portion. For example, the first portion may have a first mass and a second portion may have a second mass, different than the first mass. In some embodiments, a ratio of a mass of the first portion to a mass of the second portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than equal to 8:1, greater than or equal to 9:1, or greater than or equal to 10:1. In certain embodiments, a ratio of a mass of the first portion to a mass of the second portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible. Without wishing to be bound by theory, the self-righting article having a first portion and a second portion having different masses may result in the self-righting article substantially maintaining a particular orientation(s) relative to the surface (e.g. a wall of the guest intestinal track).

In some embodiments, a ratio of a mass of the second portion to a mass of the first portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than equal to 8:1, greater than or equal to 9:1, or greater than or equal to 10:1. In certain embodiments, a ratio of a mass of the second portion to a mass of the first portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible.

Figure 4:
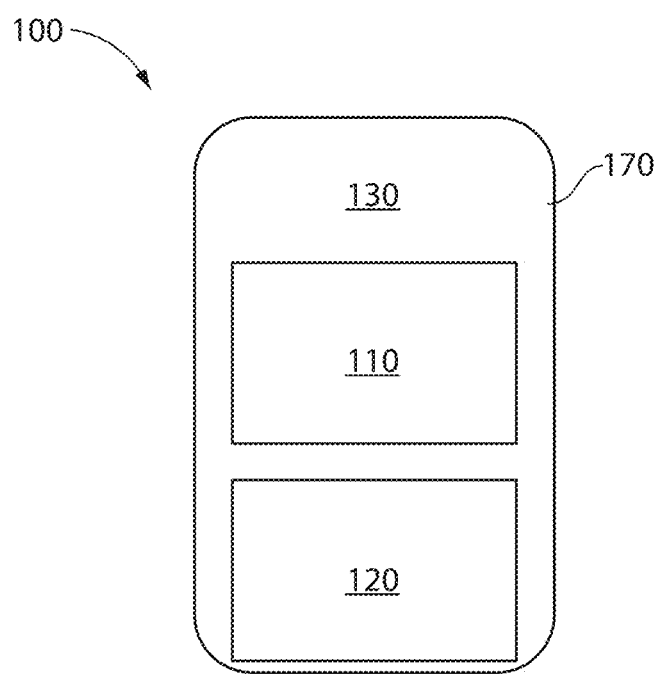
FIG. 4 is a schematic diagram of an exemplary self-righting article, according to one set of embodiments.

As illustrated in FIG. 4, system 100 may comprise a first portion 110 and a second portion 120 adjacent first portion 110. As used herein, when a portion is referred to as being "adjacent" another portion, it can be directly adjacent to (e.g., in contact with) the portion, or one or more intervening components (e.g., a liquid, a hollow portion) also may be present. A portion that is "directly adjacent" another portion means that no intervening component(s) is present.

For example, referring again to FIG. 1, first portion 110 may occupy a first volume of the self-righting article having a first average density and/or mass and second portion 115 may occupy a remaining volume of the self-righting article having a second average density and/or mass. In certain embodiments, referring back to FIG. 4, first portion 110 may occupy a first volume of the self-righting article, second portion 115 may occupy a second volume of the self-righting article, and a third portion 130 may be hollow and/or may contain one or more (additional) components.

In some embodiments, the first portion occupies greater than or equal to 1 vol %, greater than or equal to 5 vol %, greater than or equal to 10 vol %, greater than or equal to 20 vol %, greater than or equal to 25 vol %, greater than or equal to 30 vol %, greater than or equal to 40 vol %, greater than or equal to 45 vol %, greater than or equal to 50 vol %, greater than or equal to 55 vol %, greater than or equal to 60 vol %, greater than or equal to 65 vol %, greater than or equal to 70 vol %, greater than or equal to 75 vol %, greater than or equal to 80 vol %, greater than or equal to 90 vol %, or greater than or equal to 95 vol %, versus the total volume of the self-righting article. In certain embodiments, the first portion occupies less than or equal to 99 vol %, less than or equal to 95 vol %, less than or equal to 90 vol %, less than or equal to 80 vol %, less than or equal to 75 vol %, less than or equal to 70 vol %, less than or equal to 60 vol %, less than or equal to 55 vol %, less than or equal to 50 vol %, less than or equal to 45 vol %, less than or equal to 40 vol %, less than or equal to 30 vol %, less than or equal to 25 vol %, less than or equal to 20 vol %, less than or equal to 10 vol %, or less than or equal to 5 vol %, versus the total volume of the self-righting article. Combinations of the above-referenced ranges are also possible (e.g., greater than or equal to 1 vol % and less than or equal to 99 vol %, greater than or equal to 40 vol % and less than or equal to 60 vol % 0. Other ranges are also possible.

In certain embodiments, the second portion occupies greater than or equal to 1 vol %, greater than or equal to 5 vol %, greater than or equal to 10 vol %, greater than or equal to 20 vol %, greater than or equal to 25 vol %, greater than or equal to 30 vol %, greater than or equal to 40 vol %, greater than or equal to 45 vol %, greater than or equal to 50 vol %, greater than or equal to 55 vol %, greater than or equal to 60 vol %, greater than or equal to 65 vol %, greater than or equal to 70 vol %, greater than or equal to 75 vol %, greater than or equal to 80 vol %, greater than or equal to 90 vol %, or greater than or equal to 95 vol %, versus the total volume of the self-righting article. In some embodiments, the second portion occupies less than or equal to 99 vol %, less than or equal to 95 vol %, less than or equal to 90 vol %, less than or equal to 80 vol %, less than or equal to 75 vol %, less than or equal to 70 vol %, less than or equal to 60 vol %, less than or equal to 55 vol %, less than or equal to 50 vol %, less than or equal to 45 vol %, less than or equal to 40 vol %, less than or equal to 30 vol %, less than or equal to 25 vol %, less than or equal to 20 vol %, less than or equal to 10 vol %, or less than or equal to 5 vol %, versus the total volume of the self-righting article. Combinations of the above-referenced ranges are also possible (e.g., greater than or equal to 1 vol % and less than or equal to 99 vol %, greater than or equal to 40 vol % and less than or equal to 60 vol % 0. Other ranges are also possible.

In some embodiments, the third portion (e.g., the hollow portion) occupies greater than or equal to 1 vol %, greater than or equal to 5 vol %, greater than or equal to 10 vol %, greater than or equal to 20 vol %, greater than or equal to 25 vol %, greater than or equal to 30 vol %, greater than or equal to 40 vol %, greater than or equal to 45 vol %, greater than or equal to 50 vol %, greater than or equal to 55 vol %, greater than or equal to 60 vol %, greater than or equal to 65 vol %, greater than or equal to 70 vol %, greater than or equal to 75 vol %, greater than or equal to 80 vol %, greater than or equal to 90 vol %, or greater than or equal to 95 vol %, versus the total volume of the self-righting article. In certain embodiments, the third portion occupies less than or equal to 99 vol %, less than or equal to 95 vol %, less than or equal to 90 vol %, less than or equal to 80 vol %, less than or equal to 75 vol %, less than or equal to 70 vol %, less than or equal to 60 vol %, less than or equal to 55 vol %, less than or equal to 50 vol %, less than or equal to 45 vol %, less than or equal to 40 vol %, less than or equal to 30 vol %, less than or equal to 25 vol %, less than or equal to 20 vol %, less than or equal to 10 vol %, or less than or equal to 5 vol %, versus the total volume of the self-righting article. Combinations of the above-referenced ranges are also possible (e.g., greater than or equal to 1 vol % and less than or equal to 99 vol %, greater than or equal to 40 vol % and less than or equal to 60 vol % 0. Other ranges are also possible.

In some embodiments, the self-righting article may comprise any suitable ratio of a first volume occupied by the first portion versus a second volume occupied by the second portion. In certain embodiments, the ratio of the first volume to the second volume is greater than or equal to 1:100, greater than or equal to 1:50, greater than or equal to 1:25, greater than or equal to 1:10, greater than or equal to 1:8, greater than or equal to 1:6, greater than or equal to 1:4, greater than or equal to 1:3, greater than or equal to 1:2, greater than or equal to 1:1.5, greater than or equal to 1:1.1, greater than or equal to 1:1, greater than or equal to 1.1:1, greater than or equal to 1.5:1, greater than or equal to 2:1, greater than or equal to 3:1, greater than or equal to 4:1, greater than or equal to 6:1, greater than or equal to 8:1, greater than or equal to 10:1, greater than or equal to 25:1, or greater than or equal to 50:1. In certain embodiments, the ratio of the first volume to the second volume is less than or equal to 100:1, less than or equal to 50:1, less than or equal to 25:1, less than or equal to 10:1, less than or equal to 8:1, less than or equal to 6:1, less than or equal to 4:1, less than or equal to 2:1, less than or equal to 1.5:1, less than or equal to 1.1:1, less than or equal to 1:1, less than or equal to 1:1.1, less than or equal to 1:1.5, less than or equal to 1:2, less than or equal to 1:4, less than or equal to 1:6, less than or equal to 1:8, less than or equal to 1:10, less than or equal to 1:25, or less than or equal to 1:50. Combinations of the above-referenced ranges are also possible (e.g., greater than or equal to 1:100 and less than or equal to 100:1, greater than or equal to 1:10 and less than or equal to 10:1, greater than or equal to 1:2 and less than or equal to 2:1). Other ranges are also possible. Other volume ratios are also possible. Without wishing to be bound by theory, in some embodiments, the ratio of the first volume occupied by the first portion versus the second volume occupied by the second portion may be selected such that the center of mass of the self-righting article has one local minimum.

In some embodiments, the self-righting article is configured to be administered directly to a subject (e.g., without encapsulation in a capsule). In certain embodiments, the self-righting article is configured and arranged to be encapsulated in a capsule having a shell (e.g., outer surface 170 of FIG. 4 comprises a shell). In some such embodiments, referring now to FIG. 4, the self-righting article may comprise a third portion 130 (e.g., a hollow portion). In certain embodiments, a tissue interfacing component and/or an active pharmaceutical ingredient may be disposed within the hollow portion.

In some embodiments, the capsule is a 000 capsule or smaller (e.g., the capsule has a shape or size as described in the USP including, but not limited to, 000 capsule, 00 capsule, 0 capsule, 1 capsule, 2 capsule, 3 capsule, 4 capsule, or 5 capsule.) In certain embodiments, the capsule at least partially encapsulates the first portion and the second portion of the self-righting article. In some embodiments, multiple devices can be placed inside of a capsule.

In some embodiments, although the self-righting article may be configured for potential encapsulation in a 000 capsule, or smaller, the self-righting article does not necessarily need to be encapsulated in such capsule. In embodiments wherein the self-righting article is to be administered, such as by ingesting the self-righting article, the self-righting article may thus be administered without encapsulation.

In certain embodiments, the self-righting article may comprise a coating on at least a portion of an outer surface of the self-righting article. In certain embodiments, the system (e.g., the system comprising the self-righting article) comprises a coating (e.g., a film disposed on a least a surface of the system). In some embodiments, the coating may be applied as an aqueous or organic solvent-based polymer system, fats and/or wax. In certain embodiments, the coating comprises one or more of a polymer, a plasticizer, a colorant, a solvent, a fat, and a wax. Non-limiting examples of suitable fats and/or waxes include beeswax, carnauba wax, cetyl alcohol, and cetostearyl alcohol.

Non-limiting examples of suitable polymers for the coating include of cellulosic (e.g. hydroxypropylmethylcellulose, hydroxypropylcellulose, hydroxyethylcellulose, hydroxyethylcellulose phthalate, ethylcellulose, cellulose acetate phthalate, cellulose acetate trimellitate), vinyl (e.g. poly(vinyl pyrrolidone), poly(vinyl alcohol), poly(vinyl pyrrolidone)-poly(vinyl acetate)copolymers, poly(vinyl alcohol)-poly(ethylene glycol) co-polymers, poly(vinyl acetate phthalate), glycols (e.g. poly(ethylene glycol)), acrylics (e.g. amino alkyl methacrylate copolymers), other carbohydrates (e.g. maltodextrin, polydextrose), and combinations thereof.

Non-limiting examples of suitable colorants include natural pigments (e.g. riboflavin, beta-carotene, carmine lake), inorganic pigments (e.g. titanium dioxide, iron oxides), water-soluble dyes (FD&C Yellow #5, FD&C blue #2), FD&C lakes (FD&C Yellow #5 Lake, FD&C Blue #2 Lake), and D&C lakes (D&C Yellow #10 Lake, D&C Red #30 Lake).

Non-limiting examples of suitable plasticizers include polyhydric alcohols (e.g. propylene glycol, glycerol, polyethylene glycols), acetate esters (e.g. triacetin, triethyl citrate, acetyl triethyl citrate), phthalate esters (e.g. diethyl phthalate), glycerides (e.g. acylated monoglycerides) and oils (e.g. castor oils, mineral oils).

Polymers, plasticizers, colorants, solvents, fats, and/or waxes may be combined in any suitable amount to form the coating. The coating may be applied in any suitable method including, for example, dip coating and/or spray atomization. Other methods of depositing the coating are also possible.

In some embodiments, a tissue interfacing component is associated with the self-righting article. Non-limiting examples of tissue interfacing components include needles (e.g., stainless steel needles, needles comprising an API), biopsy punches, microneedles (e.g., microneedles comprising an API), projectiles, or the like.

In certain embodiments, the tissue interfacing component comprises a jet injection component (e.g., for liquid jet injection using high velocity stream into a tissue of a subject). In an exemplary embodiment, the jet injection component comprises a chamber comprising a polymeric portion. In certain embodiments, the polymeric portion may comprise an acid (e.g., a weak acid) and/or a base. In some cases, a fluid (e.g., a gastric fluid) may enter the chamber such that it reacts with the acid and/or base to form a gas. In some cases, the chamber may comprise a coating (e.g., such that the fluid does not contact the polymeric portion under the coating dissolves). In another exemplary embodiments, the jet injection component comprises a plunger/piston (e.g., activated by a spring associated with the plunger/piston) such that a material is expelled rapidly from the system.

In some embodiments, the tissue-interfacing component comprises a spring-actuated component. Such tissue interfacing components are generally described in a co-owned U.S. Provisional Application Ser. No. 62/507,653, entitled "SELF-ACTUATING ARTICLES" filed on May 17, 2017 which is incorporated herein by reference in its entirety. For example, a self-righting article comprising a tissue interfacing component (e.g., a needle) may be administered to a subject such that, the self-righting article orients at a location internal of the subject such that the tissue interfacing opponent punctures a tissue proximate the location internal of the subject. In some such amendments, and active pharmaceutical ingredient associated with the self-righting article may be released into and or proximate the tissue. In some embodiments, the tissue-interfacing component may penetrate the tissue. In some embodiments, the tissue is penetrated with a force of greater than or equal to 1 mN and less than or equal to 20,000 mN (e.g., greater than or equal to 10 mN and less than or equal to 20 mN, greater than or equal to 10 mN and less than or equal to 100 mN, greater than or equal to 100 mN and less than or equal to 20,000 mN, greater than or equal to 5,000 mN and less than or equal to 20,000 mN).

In certain embodiments, the tissue interfacing component may be oriented within the self-righting article such that, upon administration to a subject, the tissue interfacing component is aligned substantially orthogonally (e.g., within 15° of orthogonal) with a tissue internal to the subject (e.g., GI mucosal tissue). In some embodiments, the tissue interfacing component may be disposed within a hollow portion of the self-righting device such that the tissue interfacing component releases from the self-righting device along a longitudinal axis of the hollow portion. For example, referring again to FIG. 2, self-righting article may have a longest longitudinal axis 180 aligned within 15 degrees of orthogonal of tissue engaging surface 150. In certain embodiments, longest longitudinal axis 180 is parallel to a major axis of tissue interfacing component 130. In some embodiments, tissue interfacing component 130 is released (e.g., upon activation of self-actuating component 120 and/or spring 125) such that spring 125 expands along longitudinal axis 180 and/or tissue interfacing component travels parallel to the direction of longitudinal axis 180. In some such embodiments, tissue interfacing component may exit hole 140 and enter a tissue of the subject in a direction substantially parallel to longitudinal axis 180. In other embodiments, however, the tissue interfacing component is not aligned substantially orthogonally with a tissue internal to a subject.

In some embodiments, the self-righting article has a longest longitudinal axis oriented within less than or equal to 15 degrees, less than or equal to 10 degrees, less than or equal to 5 degrees, less than or equal to 2 degrees, or less than or equal to 1 degree of vertical upon self-righting. In certain embodiments, the self-righting article has a longest longitudinal axis oriented within greater than or equal to 0.1 degrees, greater than or equal to 1 degree, greater than or equal to 2 degrees, greater than or equal to 5 degrees, or greater than or equal to 10 degrees. Combinations of the above-referenced ranges are also possible (e.g., greater than or equal to 0.1 degrees and less than or equal to 15 degrees). Other ranges are also possible.

In certain embodiments, the tissue-interfacing component has a longest longitudinal axis oriented within less than or equal to 15 degrees, less than or equal to 10 degrees, less than or equal to 5 degrees, less than or equal to 2 degrees, or less than or equal to 1 degree of vertical upon self-righting. In some embodiments, the tissue-interfacing component has a longest longitudinal axis oriented within greater than or equal to 0.1 degrees, greater than or equal to 1 degree, greater than or equal to 2 degrees, greater than or equal to 5 degrees, or greater than or equal to 10 degrees. Combinations of the above-referenced ranges are also possible (e.g., greater than or equal to 0.1 degrees and less than or equal to 15 degrees). Other ranges are also possible.

In some embodiments, the hollow portion may be cylindrical in shape. Other shapes are also possible.

In an exemplary embodiment, the tissue-interfacing component comprises a plurality of microneedles. In another exemplary embodiment, the tissue interfacing component comprises a single needle. In yet another exemplary embodiment, the tissue interfacing component comprises a biopsy component (e.g., a biopsy jaw). In some cases, the tissue interfacing component may comprise an anchoring mechanism (e.g., a hook, a mucoadhesive). Tissue interfacing components are described in more detail, below.

As described above, in some embodiments, the first portion comprises a first material having a first average density. In some embodiments, the first material and/or the second material may be selected to impart a particular mass and/or density to the first portion and/or the second portion.

In some embodiments the average density of the first portion is less than or equal to 2 g/mL, less than or equal to 1.8 g/mL, less than or equal to 1.6 g/mL, less than or equal to 1.4 g/mL, less than or equal to 1.2 g/mL, less than or equal to 1 g/mL, less than or equal to 0.8 g/mL, less than or equal to 0.6 g/mL, less than or equal to 0.4 g/mL, less than or equal to 0.2 g/mL, less than or equal to 0.1 g/mL, less than or equal to 0.05 g/mL, or less than or equal to 0.02 g/mL. In certain monuments, the first portion has an average density of greater than or equal to 0.01 g/mL, greater than or equal to 0.02 g/mL, greater than or equal to 0.05 g/mL, greater than or equal to 0.1 g/mL, greater than or equal to 0.2 g/mL, greater than or equal to 0.4 g/mL, greater than or equal to 0.6 g/mL, greater than or equal to 0.8 g/mL, greater than or equal to 1 g/mL, greater than or equal to 1.2 g/mL, greater than or equal to 1.4 g/mL, greater than or equal to 1.6 g/mL, or greater than or equal to 1.8 g/mL. Combinations of the above referenced ranges are also possible (e.g., greater than or equal to 0.01 g/mL and less than or equal to 2 g/mL, greater than or equal to 0.6 g/mL and less than or equal to 2 g/mL). Other ranges are also possible.

In certain embodiments, the second portion comprises a second material having a second average density (e.g., different than the first average density). In some embodiments, the average density of the second portion (e.g. and/or second material) is less than or equal to 20 g/mL, less than or equal to 18 g/mL, less than or equal to 16 g/mL, less than or equal to 14 g/mL, less than or equal to 12 g/mL, less than or equal to 10 g/mL, less than or equal to 8 g/mL, less than or equal to 6 g/mL, less than or equal to 4 g/mL, or less than or equal to 3 g/L. In certain embodiments, the average density of the second portion is greater than or equal to 2 g/mL, greater than or equal to 3 g/mL, greater than or equal to 4 g/mL, greater than or equal to 6 g/mL, greater than or equal to 8 g/mL, greater than equal to 10 g/mL, greater than equal to 12 g/mL, greater than or equal to 14 g/mL, greater than or equal to 16 g/mL, or greater than or equal to 18 g/mL. Combinations of the above referenced ranges are also possible (e.g., greater than or equal to 2 g/mL and less than or equal to 20 g/mL). Other ranges are also possible. In some embodiments, the second portion may have an average density in one or more ranges described above in the context of the first portion (e.g., greater than or equal to 0.6 g/mL and less than or equal to 2 g/mL) and is different than the average density of the first portion.

The first portion and the second portion may be selected to have any suitable mass. In some embodiments, the first portion may have a total mass (e.g., including all components within the first portion) of greater than or equal to 20 mg, greater than or equal to 50 mg, greater than or equal to 75 mg, greater than or equal to 100 mg, greater than or equal to 200 mg, greater than or equal to 300 mg, greater than or equal to 400 mg, greater than or equal to 500 mg, greater than or equal to 750 mg, greater than or equal to 1 g, greater than or equal to 1.5 g, greater than or equal to 2 g, greater than or equal to 3 g. greater than or equal to 4 g, greater than or equal to 5 g, greater than or equal to 7 g, greater than or equal to 10 g, greater than or equal to 15 g, including any mass in between 20 mg and 15 g. In certain embodiments, the first portion may have a total mass of less than or equal to 15 g, less than or equal to 10 g, less than or equal to 7 g, less than or equal to 5 g, less than or equal to 4 g, less than or equal to 3 g, less than or equal to 2 g, less than or equal to 1.5 g, less than or equal to 1 g, less than or equal to 750 mg, less than or equal to 500 mg, less than or equal to 400 mg, less than or equal to 300 mg, less than or equal to 200 mg, less than or equal to 100 mg, less than or equal to 75 mg, less than or equal to 50 mg, or less than or equal to 20 mg, including any mass in between 15 g and 20 mg. Combinations of the above-referenced ranges are also possible (e.g., greater than or equal to 50 mg and less than or equal to 4 g, greater than or equal to 50 mg and less than or equal to 15 g). In some embodiments, the first portion or second portion has a mass in a range of greater than equal to 20 mg and less than or equal to 15 g. In some embodiments, the first portion or second portion has a mass in a range of greater than equal to 20 mg and less than or equal to 1 g. In some embodiments, the first portion or second portion has a mass in a range of greater than equal to 300 mg and less than or equal to 12 g. In some embodiments, the first portion or second portion has a mass in a range of greater than equal to 100 mg and less than or equal to 250 mg. In some embodiments, the first portion or second portion has a mass in a range of greater than equal to 20 mg and less than or equal to 15 g. In some embodiments, the first portion or second portion has a mass in a range of greater than equal to 1.5 and less than or equal to 6.5 g. Other ranges are also possible.

In certain embodiments, the second portion may have a total mass (e.g., including all components within the second portion) of greater than or equal to 50 mg, greater than or equal to 75 mg, greater than or equal to 100 mg, greater than or equal to 200 mg, greater than or equal to 400 mg, greater than or equal to 500 mg, greater than or equal to 750 mg, greater than or equal to 1 g, greater than or equal to 1.5 g, greater than or equal to 2 g, greater than or equal to 3 g. greater than or equal to 4 g, greater than or equal to 5 g, greater than or equal to 7 g, or greater than or equal to 10 g In certain embodiments, the second portion may have a total mass of less than or equal to 15 g, less than or equal to 10 g, less than or equal to 7 g, less than or equal to 5 g, less than or equal to 4 g, less than or equal to 3 g, less than or equal to 2 g, less than or equal to 1.5 g, less than or equal to 1 g, less than or equal to 750 mg, less than or equal to 500 mg, less than or equal to 400 mg, less than or equal to 200 mg, less than or equal to 100 mg, or less than or equal to 75 mg. Combinations of the above-referenced ranges are also possible (e.g., greater than or equal to 50 mg and less than or equal to 4 g, greater than or equal to 50 mg and less than or equal to 15 g). Other ranges are also possible.

In some embodiments the first material and/or second material is selected from the group consisting of polymers, ceramics, metals, and combinations thereof (e.g., metal filled polymer). In some cases, the first material and/or the second material may be biocompatible. In some cases, the metal may be selected from the group consisting of stainless steel, iron-carbon alloys, Field's metal, wolfram, molybdemum, gold, zinc, iron, and titanium.

In some embodiments, the ceramic may be selected from the group consisting of hydroxyapatite, aluminum oxide, calcium oxide, tricalcium phosphate, silicates, silicon dioxide, and zirconium oxide.

In certain embodiments, the polymer may be selected from the group consisting of polycaprolactone, polylactic acid, polyethylene glycol, polypropylene, polyethylene, polycarbonate, polystyrene, and polyether ether ketone, and polyvinyl alcohol.

In an exemplary embodiment, the first material comprises a metal and the second material comprises a polymer.

The self-righting article generally has a geometric center (e.g., center of the geometric volume). In certain embodiments, the density, mass, and/or volume of the first portion and/or the second portion may be selected such that the self-righting article exhibit self-righting behavior. For example, in some embodiments, a center of mass of the self-righting article may be offset from the geometric center such that the article, suspended via an axis passing through the geometric center, with the center of mass offset laterally from the geometric center, is configured to maintain an orientation of 20 degrees or less from vertical when acted on by $0.09*10^{-4}$ Nm or less externally applied torque.

In some embodiments, the self-righting article maintains an orientation of 20° or less from vertical when acted on by 0.09*10^-4 Nm or less of externally applied torque. In certain embodiments, the self-righting article maintains an orientation of 15° or less, 12° or less, 10° or less, 8° or less, 6° or less, 4° or less, or 2° or less from vertical when acted on by 0.09*10^-4 Nm or less of externally applied torque. In some embodiments, the self-righting article maintains an orientation of greater than or equal to 1°, greater than or equal to 2°, greater than or equal to 4°, greater than or equal to 6°, greater than or equal to 8°, greater than or equal to 10°, greater than or equal to 12°, or greater than or equal to 15° from vertical when acted on by 0.09*10^-4 Nm or less of externally applied torque. Combinations of the above referenced ranges are also possible (e.g., 20° or less and greater than or equal to 1°). Other ranges are also possible.

In some embodiments the self-righting article may be characterized as having a particular self-righting time from 90° in a particular fluid. The self-righting time may be determined by placing the self-righting article in the particular fluid at 90°, and allowing the self-righting article to return to a particular orientation otherwise maintained by the self-righting article in the absence of the fluid (e.g., an orientation corresponding to a stable point of equilibrium (or orientation) of the article).

In certain embodiments, the fluid is oil. In some such embodiments, the self-righting article has a self-righting time from 90° in oil of less than or equal to 0.15 seconds, less than or equal to 0.1 seconds, less than or equal to 0.05 seconds, or less than or equal to 0.02 seconds. In certain embodiments, the self-righting article has a self-righting time from 90° in oil of greater than or equal to 0.01 seconds, greater than or equal to 0.02 seconds, greater than or equal to 0.05 seconds, greater than or equal to 0.1 seconds, or greater than or equal to 0.12 seconds. Combinations of the above referenced ranges are also possible (e.g., less than or equal to 0.15 seconds and greater than or equal to 0.01 seconds). Other ranges are also possible. Self-righting time in oil is determined with the system/article fully submerged.

In some embodiments, the fluid is gastric fluid. In some such embodiments the self-righting article has a self-righting time from 90° in gastric fluid of less than or equal to 0.06 seconds, less than or equal to 0.05 seconds, less than or equal to 0.04 seconds, less than or equal to 0.03 seconds, or less than or equal to 0.02 seconds. In certain embodiments, the self-righting article has a self-righting time from 90° in gastric fluid of greater than or equal to 0.005 seconds greater than or equal to 0.01 seconds, greater than or equal to 0.02 seconds, greater than or equal to 0.03 seconds, greater than or equal to 0.04 seconds, or greater than or equal to 0.05 seconds. Combinations of the above referenced ranges are also possible (e.g., less than or equal to 0.06 seconds and greater than or equal to 0.005 seconds). Other ranges are also possible. Self-righting time in gastric fluid is determined with the system/article fully submerged.

In certain embodiments, the fluid is mucus. In some such embodiments the self-righting article has a self-righting time from 90° in mucus of less than or equal to 0.05 seconds, less than or equal to 0.04 seconds, less than or equal to 0.03 seconds, or less than or equal to 0.02 seconds. In certain embodiments, the self-righting article has a self-righting time from 90° in mucus of greater than or equal to 0.005 seconds greater than or equal to 0.01 seconds, greater than or equal to 0.02 seconds, greater than or equal to 0.03 seconds, greater than or equal to 0.04 seconds, or greater than or equal to 0.045 seconds. Combinations of the above referenced ranges are also possible (e.g., less than or equal to 0.05 seconds and greater than or equal to 0.005 seconds). Other ranges are also possible. Self-righting time in mucus is determined with the system/article fully submerged.

In some embodiments, the fluid is water. In some such embodiments the self-righting article has a self-righting time from 90° in water of less than or equal to 0.05 seconds, less than or equal to 0.04 seconds, less than or equal to 0.03 seconds, or less than or equal to 0.02 seconds. In certain embodiments, the self-righting article has a self-righting time from 90° in water of greater than or equal to 0.005 seconds greater than or equal to 0.01 seconds, greater than or equal to 0.02 seconds, greater than or equal to 0.03 seconds, greater than or equal to 0.04 seconds, or greater than or equal to 0.045 seconds. Combinations of the above referenced ranges are also possible (e.g., less than or equal to 0.05 seconds and greater than or equal to 0.005 seconds). Other ranges are also possible. Self-righting time in water is determined with the system/article fully submerged.

In some embodiments, the self-righting article comprises one or more vents (e.g., to permit the flow of air and/or fluid through the self-righting article). In some embodiments, the self-righting article comprises one or more (e.g., two or more, three or more, four or more) vents associated with at least a portion (e.g., the first portion, the second portion) of the self-righting article. In some such embodiments, the vent may permit a fluid (e.g., gastric fluid) to enter at least a portion of the self-righting article such that e.g., the self-actuating component and/or the spring are exposed to the fluid (e.g., such that the self-actuating component and/or the spring actuate). For example, referring again to FIG. 2, system 102 comprises vents 190 associated with at least a portion of the self-righting article (e.g., first portion 110). In some cases, vent(s) 190 may be in fluidic communication with self-actuating component 120, support material 160, and/or spring 125. While vents are depicted herein as being associated with the first portion of the self-righting article, in some embodiments, one of ordinary skill in the art based upon the teachings of this specification would understand that one or more vents may be associated with the second portion of the self-righting article.

In certain embodiments, the self-righting article does not comprise vents.

In some embodiments, the self-righting article may have a particular larges cross-sectional dimension. In some embodiments, the largest cross-sectional dimension of the self-righting article is less than or equal to 2.0 cm, less than or equal to 1.8 cm, less than or equal to 1.6 cm, less than or equal to 1.4 cm, less than or equal to 1.2 cm, less than or equal to 1.1 cm, less than or equal to 1 cm, less than equal to 0.8 cm, less than or equal to 0.6 cm, less than or equal to 0.4 cm, or less than or equal to 0.2 cm, including any dimension less than 2.0 cm (e.g., 0.1 cm, 0.3 cm, 0.5 cm . . . 1.7 cm, etc.). In certain embodiments, the largest cross-sectional dimension of the self-righting article is greater than or equal to 0.1 cm, greater than or equal to 0.2 cm, greater than or equal to 0.4 cm, greater than or equal to 0.6 cm, greater than or equal to 0.8 cm, greater than or equal to 1 cm, greater than or equal to 1.2 cm, greater than or equal to 1.4 cm, greater than or equal to 1.6 cm, greater than or equal to 1.8 cm, including any dimension greater than 0.1 cm and less than or equal to 2.0 cm (e.g., 0.3 cm, 0.5 cm . . . 1.7 cm, 1.9 cm, etc.). Combinations of the above referenced ranges are also possible (e.g., less than or equal to 2 cm and greater than or equal to 0.1 cm, less than or equal to 1.1 cm and greater than or equal to 0.1 cm). Other ranges are also possible.

In some embodiments, the self-righting article may be administered (e.g., orally) to a subject. In some such embodiments, the self-righting article may comprise one or more active pharmaceutical ingredients. In certain embodiments, the active pharmaceutical ingredient is released at a location internal of the subject (e.g. within the G.I. tract).

In certain embodiments, one or more sensors may be associated with the self-righting article. For example, in some cases, one or more sensors may be used to determine the location of the self-righting article (e.g., a location internal to a subject) and/or to trigger actuation of one or more tissue interfacing components associated with the self-righting article. Non-limiting examples of suitable sensors include pH, gas, light, GPS, Bluetooth, orientation, proximity, thermal, fluid, and others.

In some cases, one or more of the first portion and/or second portion may be magnetic.

In an exemplary embodiment, the self-righting article is ingestible. According to certain embodiments, the ingestible self-righting article comprises a first portion having an average density, a second portion having an average density different from the average density of the first portion, and a payload portion for carrying an agent for release internally of a subject that ingests the article. In certain embodiments, the self-righting article comprises at least a first portion having an average density greater than 1 g/cm$^3$. According to certain embodiments, the ratio of the average density of the first portion to the average density of the second portion is greater than or equal to 2.5:1. In certain exemplary embodiments, the self-righting article comprises a first portion comprising a first material having a first average density, and a second portion comprising a second material having a second average density different from the first average density. In certain embodiments, the self-righting article comprises a first material and a second material different than the first material, and an active pharmaceutical agent associated with the self-righting article. According to some embodiments, the ratio of an average density of the first material to an average density of the second material is greater than or equal to 2.5:1. In some embodiments, the self-righting article has a largest cross-sectional dimension of less than or equal to 2 cm (e.g., less than or equal to 1.1 cm).

In certain embodiments, the article has a geometric center, and a center of mass offset from the geometric center such that the article, suspended via an axis passing through the geometric center, with the center of mass offset laterally from the geometric center, experiences an externally applied torque of 0.09*10^−4 Nm or less due to gravity about the axis. According to some embodiments, the self-righting article is configured to be encapsulated in a 000 or smaller capsule. In other embodiments, the self-righting article is not encapsulated. In certain embodiments, the self-righting article comprises a tissue interfacing component associated with the self-righting article. Some exemplary embodiments are related to an axis essentially perpendicular to the tissue-engaging surface of the self-righting article configured to maintain an orientation of 20 degrees or less from vertical when acted on by 0.09*10^−4 Nm or less externally applied torque. According to some embodiments, the self-righting article has a most stable, lowest-potential-energy physical configuration, and a self-righting time, from 90 degrees offset in any orientation from the most stable configuration, in water of less than or equal to 0.05 seconds. According to certain embodiments, the self-righting article has a rate of obstruction of less than or equal to 1% (e.g., less than or equal to 0.5%, less than or equal to 0.1%).

Certain exemplary embodiments are related to a method of delivering a pharmaceutical agent to a location internal of a subject. According to some embodiments, the method comprises administering, to the subject, a capsule comprising an outer shell and a self-righting article, and orienting the self-righting article at the location internal of a subject such that the tissue interfacing component punctures a tissue proximate the location internal of the subject.

Tissue Anchoring

In some embodiments, the article (e.g., the self-righting article) may be configured to anchor to a location internal to a subject (e.g., a tissue at a location internal to a subject). As described above, in some embodiments, the self-righting article may comprise one or more tissue interfacing components comprising one or more anchoring mechanisms (e.g., a hook, a mucoadhesive). Hooks are described in more detail below. Mucoadhesives are described in more detail below. In an exemplary embodiment, the self-righting article may, in some cases, have a longitudinal axis perpendicular to a tissue-engaging surface of the article configured to maintain an orientation of 20 degrees or less from vertical when acted on by 0.09*10^−4 Nm or less externally applied torque and at least one anchoring mechanism associated with the self-righting article. In another exemplary embodiment, the article may comprise a spring associated with (e.g., at least partially encapsulated with) a support material (e.g., such that the spring is maintained in an at least partially compressed state by a support material under at least 5% compressive strain) and at least one anchoring mechanism operably linked to the spring. Springs and support materials are described in more detail, below. Other embodiments are also possible comprising at least one anchoring mechanism associated with a self-righting article and/or a self-actuating component.

Figure 5:
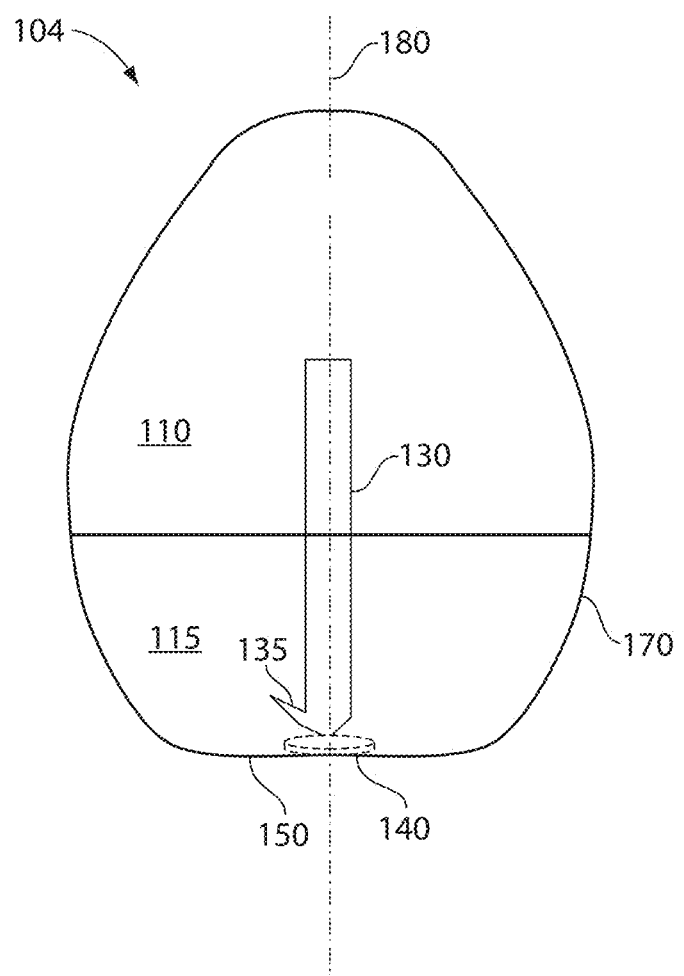
FIG. 5 is a cross-sectional schematic diagram of an exemplary self-righting system, according to one set of embodiments.

In some embodiments, the anchoring mechanism comprises a hook (e.g., a hooked needle). For example, as illustrated in FIG. 5, system 104 comprises a first portion 110 and a second portion 115. In certain embodiments, a tissue-engaging surface 150 is associated with second portion 115. In some cases, system 104 may comprises a tissue interfacing component 130 comprising an anchoring mechanism 135. In some embodiments, anchoring mechanism 135 may be a hook. In certain embodiments, anchoring mechanism 135 may be disposed internally within system 104 and released (e.g., via hole 140) under a desired set of conditions (e.g., at a particular location internal to a subject). In certain embodiments, not depicted in FIG. 5, hook 135 may disposed on an external surface of system 104.

Figure 6:
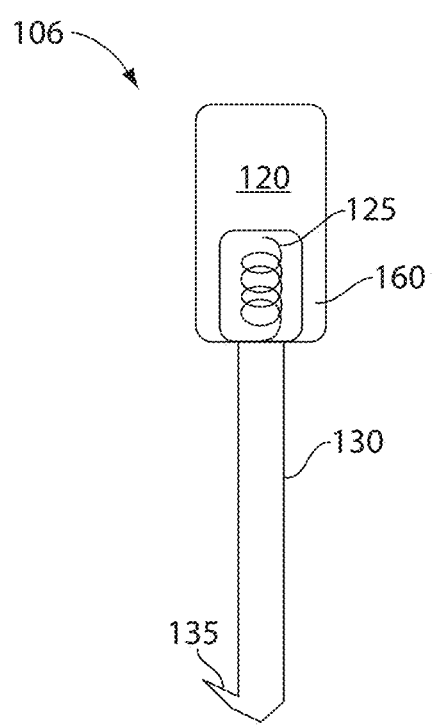
FIG. 6 is a cross-sectional schematic diagram of an exemplary self-actuating component, according to one set of embodiments.

Referring now to FIG. 6, in certain embodiments, system 106 comprises anchoring mechanism 135 associated with self-actuating component 120 (e.g., comprising spring 125 and/or support material 160). In certain embodiments, upon exposure to a fluid (e.g., gastric fluid) and/or under a particular set of conditions (e.g., physiological conditions of the gastrointestinal tract such as in the stomach), the self-actuating component actuates inserting the anchoring mechanism into a tissue located internal to a subject.

In some embodiments, the anchoring mechanism (and/or the article comprising the anchoring mechanism) is configured to be retained at a location internal to a subject. For example, in some embodiments, the anchoring mechanism engages with a surface (e.g., a surface of a tissue) at the location internal to the subject such that it is retained at that location.

Advantageously, the systems comprising one or more anchoring mechanisms described herein may be inserted into a surface of tissue at a location internal to a subject, and may maintain contact with the tissue under relatively high applied forces and/or relatively high change in orientation (e.g., by compressive forces exerted by the gastrointestinal tract and/or under high flow rates within the gastrointestinal tract). In some embodiments, the systems described herein do not substantially block orifices within the gastrointestinal tract (e.g., in the pylorus) e.g., restricting flow and enabling longer contact times. In certain embodiments, natural replenishment of the walls of the gastrointestinal tract may permit desirable detachment and/or expulsion of the systems described herein, without the need for surgical and/or endoscopic retrieval.

For example, in some embodiments, the anchoring mechanism may be inserted into a surface of a tissue at a location internal to a subject and maintains contact with the tissue (e.g., the system remains anchored) under a change of orientation of the system of greater than or equal to 1 degree, greater than or equal to 2 degrees, greater than or equal to 5 degrees, greater than or equal to 10 degrees, greater than or equal to 15 degrees, greater than or equal to 20 degrees, greater than or equal to 25 degrees, greater than or equal to 30 degrees, greater than or equal to 45 degrees, greater than or equal to 60 degrees, greater than or equal to 75 degrees, or greater than or equal to 85 degrees. In certain embodiments, the system may remain anchored under a change of orientation of the system of less than or equal to 90 degrees, less than or equal to 85 degrees, less than or equal to 75 degrees, less than or equal to 60 degrees, less than or equal to 45 degrees, less than or equal to 30 degrees, less than or equal to 25 degrees, less than or equal to 20 degrees, less than or equal to 15 degrees, less than or equal to 10 degrees, less than or equal to 5 degrees, or less than or equal to 2 degrees. Combinations of the above-referenced ranges are also possible (e.g., greater than or equal to 1 degree and less than or equal to 90 degrees, greater than or equal to 1 degree and less than or equal to 45 degrees, greater than or equal to 2 degrees and less than or equal to 30 degrees). Other ranges are also possible.

In certain embodiments, the system (e.g., comprising the anchoring mechanism) is configured to be retained at the location internal to the subject under a normal retention force of greater than or equal to 0.002 N, greater than or equal to 0.004 N, greater than or equal to 0.006 N, greater than or equal to 0.008 N, greater than or equal to 0.01 N, greater than or equal to 0.012 N, greater than or equal to 0.014 N, greater than or equal to 0.016 N, greater than or equal to 0.018 N, greater than or equal to 0.02 N, greater than or equal to 0.025 N, greater than or equal to 0.03 N, greater than or equal to 0.04 N, greater than or equal to 0.05 N, greater than or equal to 0.1 N, greater than or equal to 0.15 N, greater than or equal to 0.2 N, greater than or equal to 0.25 N, greater than or equal to 0.3 N, greater than or equal to 0.35 N, greater than or equal to 0.4 N, greater than or equal to 0.5 N, greater than or equal to 0.6 N, greater than or equal to 0.7 N, greater than or equal to 0.8 N, or greater than or equal to 0.9 N of normally applied force per anchoring mechanism. In some embodiments, the system has a normal retention force of less than or equal to 1 N, less than or equal to 0.9 N, less than or equal to 0.8 N, less than or equal to 0.7 N, less than or equal to 0.6 N, less than or equal to 0.5 N, less than or equal to 0.4 N, less than or equal to 0.35 N, less than or equal to 0.3 N, less than or equal to 0.25 N, less than or equal to 0.2 N, less than or equal to 0.15 N, less than or equal to 0.1 N, less than or equal to 0.05 N, less than or equal to 0.04 N, less than or equal to 0.03 N, less than or equal to 0.025 N, less than or equal to 0.02 N, less than or equal to 0.018 N, less than or equal to 0.016 N, less than or equal to 0.014 N, less than or equal to 0.012 N, less than or equal to 0.01 N, less than or equal to 0.008 N, less than or equal to 0.006, or less than or equal to 0.004 N of normally applied force per anchoring mechanism. Combinations of the above referenced ranges are also possible (e.g., greater than or equal to 0.002 N and less than or equal to 1 N, greater than or equal to 0.02 N and less than or equal to 0.08 N, greater than or equal to 0.1 N and less than or equal to 1 N). Other ranges are also possible. The normal retention force as described herein may be determined by inserting the anchoring mechanism of the system into a surface of tissue (e.g., ex vivo swine stomach) to a penetration depth of at least 0.9 mm and then pulling the system, in a direction orthogonal to the surface of the tissue until the system dislodges from the tissue. The maximum force before dislodging the system is the normal retention force.

In some embodiments, the system (e.g., comprising the anchoring mechanism) is configured to be retained at the location internal to the subject under an orthogonal retention force of greater than or equal to 0.002 N, greater than or equal to 0.004 N, greater than or equal to 0.006 N, greater than or equal to 0.008 N, greater than or equal to 0.01 N, greater than or equal to 0.012 N, greater than or equal to 0.014 N, greater than or equal to 0.016 N, greater than or equal to 0.018 N, greater than or equal to 0.02 N, greater than or equal to 0.025 N, greater than or equal to 0.03 N, greater than or equal to 0.04 N, greater than or equal to 0.05 N, greater than or equal to 0.1 N, greater than or equal to 0.15 N, greater than or equal to 0.2 N, greater than or equal to 0.25 N, greater than or equal to 0.3 N, greater than or equal to 0.35 N, greater than or equal to 0.4 N, greater than or equal to 0.5 N, greater than or equal to 0.6 N, greater than or equal to 0.7 N, greater than or equal to 0.8 N, or greater than or equal to 0.9 N of normally applied force per anchoring mechanism. In some embodiments, the system has an orthogonal retention force of less than or equal to 1 N, less than or equal to 0.9 N, less than or equal to 0.8 N, less than or equal to 0.7 N, less than or equal to 0.6 N, less than or equal to 0.5 N, less than or equal to 0.4 N, less than or equal to 0.35 N, less than or equal to 0.3 N, less than or equal to 0.25 N, less than or equal to 0.2 N, less than or equal to 0.15 N, less than or equal to 0.1 N, less than or equal to 0.05 N, less than or equal to 0.04 N, less than or equal to 0.03 N, less than or equal to 0.025 N, less than or equal to 0.02 N, less than or equal to 0.018 N, less than or equal to 0.016 N, less than or equal to 0.014 N, less than or equal to 0.012 N, less than or equal to 0.01 N, less than or equal to 0.008 N, less than or equal to 0.006, or less than or equal to 0.004 N of normally applied force per anchoring mechanism. Combinations of the above referenced ranges are also possible (e.g., greater than or equal to 0.002 N and less than or equal to 1 N, greater than or equal to 0.02 N and less than or equal to 0.08 N, greater than or equal to 0.1 N and less than or equal to 1 N). Other ranges are also possible. The orthogonal retention force as described herein may be determined by inserting the anchoring mechanism of the system into a surface of tissue (e.g., ex vivo swine stomach) to a penetration depth of at least 0.9 mm and then applying a force to the system (see e.g., FIG. 59), in a direction parallel to the surface of the tissue, until the system dislodges from the tissue. The maximum force before dislodging the system is the orthogonal retention force.

In some embodiments, the system is configured to remain anchored to the surface of the tissue located internal to the subject under less than or equal to 30 degrees change in orientation and less than or equal to 1 N of applied (e.g., normal, orthogonal) force.

In some embodiments, the system comprises two or more anchoring mechanisms. In some cases, the system may comprise a single self-righting article comprising two or more anchoring mechanisms. In certain embodiments, the system comprises two or more self-righting articles each comprising one or more anchoring mechanisms. In certain embodiments, the force required to dislodge the anchoring mechanism (e.g., the normal retention force, the orthogonal retention force) may be increased by increasing the number of anchoring mechanisms associated with the system. Without wishing to be bound by theory, the spacing between anchoring mechanisms may be related to the retention force (e.g., the normal retention force, the orthogonal retention force) of the system.

In some embodiments, the system may have an average spacing between anchoring mechanisms of greater than or equal to 0.1 mm, greater than or equal to 0.2 mm, greater than or equal to 0.3 mm, greater than or equal to 0.4 mm, greater than or equal to 0.5 mm, greater than or equal to 0.6 mm, greater than or equal to 0.7 mm, greater than or equal to 0.8 mm, greater than or equal to 0.9 mm, greater than or equal to 1 mm, greater than or equal to 1.2 mm, greater than or equal to 1.4 mm, greater than or equal to 1.5 mm, greater than or equal to 1.6 mm, greater than or equal to 1.8 mm, or greater than or equal to 2 mm. In certain embodiments, the system may have an average spacing between anchoring mechanisms of less than or equal to 2.5 mm, less than or equal to 2 mm, less than or equal to 1.8 mm, less than or equal to 1.6 mm, less than or equal to 1.4 mm, less than or equal to 1.2 mm, less than or equal to 1 mm, less than or equal to 0.9 mm, less than or equal to 0.8 mm, less than or equal to 0.7 mm, less than or equal to 0.6 mm, less than or equal to 0.5 mm, less than or equal to 0.4 mm, less than or equal to 0.3 mm, or less than or equal to 0.2 mm. Combinations of the above-referenced ranges are also possible (e.g., greater than or equal to 0.1 mm and less than or equal to 2.5 mm, greater than or equal to 1 mm and less than or equal to 1.5 mm). Other ranges are also possible.

The anchoring mechanism may have any suitable dimension and/or shape. For example, in some embodiments, the largest dimension (e.g., the length) of the tissue interfacing component comprising the anchoring mechanism may be less than or equal to 1 cm, less than or equal to 0.8 cm, less than or equal to 0.6 cm, less than or equal to 0.5 cm, less than or equal to 0.4 cm, less than or equal to 0.3 cm, less than or equal to 0.25 cm, less than or equal to 0.23 cm, or less than or equal to 0.2 cm. In certain embodiments, the largest dimension (e.g., the length) of the tissue interfacing component comprising the anchoring mechanism may be greater than or equal to 0.15 cm, greater than or equal to 0.2 cm, greater than or equal to 0.23 cm, greater than or equal to 0.25 cm, greater than or equal to 0.3 cm, greater than or equal to 0.4 cm, greater than or equal to 0.5 cm, greater than or equal to 0.6 cm, or greater than or equal to 0.8 cm. Combinations of the above-referenced ranges are also possible (e.g., greater than or equal to 0.2 cm and less than or equal to 1 cm, greater than or equal to 0.15 cm and less than or equal to 1 cm). Other ranges are also possible.

In some embodiments, the anchoring mechanism has a particular anchor length. By way of example, for an anchoring mechanism comprising a hook, the anchor length corresponds to the largest cross-sectional dimension of a bent length of the hook (e.g., a diameter of the hook, not including any unbent portion). In certain embodiments, the anchor length is greater than or equal to 10 microns, greater than or equal to 20 microns, greater than or equal to 23 microns, greater than or equal to 25 microns, greater than or equal to 30 microns, greater than or equal to 34 microns, greater than or equal to 35 microns, greater than or equal to 40 microns, greater than or equal to 50 microns, greater than or equal to 60 microns, greater than or equal to 70 microns, greater than or equal to 80 microns, greater than or equal to 90 microns, greater than or equal to 100 microns, greater than or equal to 120 microns, greater than or equal to 140 microns, greater than or equal to 160 microns, greater than or equal to 180 microns, greater than or equal to 200 microns, or greater than or equal to 225 microns. In certain embodiments, the anchor length is less than or equal to 250 microns, less than or equal to 225 microns, less than or equal to 200 microns, less than or equal to 180 microns, less than or equal to 160 microns, less than or equal to 140 microns, less than or equal to 120 microns, less than or equal to 100 microns, less than or equal to 90 microns, less than or equal to 80 microns, less than or equal to 70 microns, less than or equal to 60 microns, less than or equal to 50 microns, less than or equal to 40 microns, less than or equal to 30 microns, or less than or equal to 20 microns. Combinations of the above-referenced ranges are also possible (e.g., greater than or equal to 10 microns and less than or equal to 250 microns). Other ranges are also possible.

In some cases, the anchoring mechanism may be configured to have an optimal penetration depth (e.g., the depth at which the anchoring mechanism is disposed beneath the surface of a tissue located internal to a subject). In some embodiments, the anchoring mechanism has a penetration depth of greater than or equal to 0.5 mm, greater than or equal to 0.6 mm, greater than or equal to 0.7 mm, greater than or equal to 0.8 mm, greater than or equal to 0.9 mm, greater than or equal to 1 mm, greater than or equal to 1.2 mm, greater than or equal to 1.4 mm, greater than or equal to 1.5 mm, greater than or equal to 1.7 mm, greater than or equal to 1.9 mm, greater than or equal to 2 mm, greater than or equal to 2.2 mm, greater than or equal to 2.4 mm, greater than or equal to 2.5 mm, greater than or equal to 3 mm, greater than or equal to 3.5 mm, greater than or equal to 4 mm, greater than or equal to 4.5 mm, or greater than or equal to 5 mm. In certain embodiments, the anchoring mechanism has a penetration depth of less than or equal to 6 mm, less than or equal to 5 mm, less than or equal to 4.5 mm, less than or equal to 4 mm, less than or equal to 3.5 mm, less than or equal to 3 mm, less than or equal to 2.5 mm, less than or equal to 2.4 mm, less than or equal to 2.2 mm, less than or equal to 2 mm, less than or equal to 1.9 mm, less than or equal to 1.7 mm, less than or equal to 1.5 mm, less than or equal to 1.4 mm, less than or equal to 1.2 mm, less than or equal to 1 mm, less than or equal to 0.9 mm, less than or equal to 0.8 mm, less than or equal to 0.7 mm, or less than or equal to 0.6 mm. Combinations of the above-referenced ranges are also possible (e.g., greater than or equal to 0.5 mm and less than or equal to 6 mm, greater than or equal to 0.9 mm and less than or equal to 2.5 mm). Other ranges are also possible. Without wishing to be bound by theory, the displacement of the tissue may be greater than or equal to the penetration depth of the anchoring mechanism. By way of example only, and in a particular set of embodiments, the anchoring mechanism may displace tissue up to 14 mm to achieve a penetration depth of e.g., up to 4 mm.

Advantageously, the systems comprising an anchoring mechanism described herein may be retained for a relatively long period of time under physiological conditions and fluid flows (e.g., exposed to a fluid flowing at approximately 0.1 m/s). For example, in some embodiments, the system comprising an anchoring mechanism is retained at a surface of tissue located internal to a subject for greater than or equal to 1 hour, greater than or equal to 2 hours, greater than or equal to 4 hours, greater than or equal to 8 hours, greater than or equal to 12 hours, greater than or equal to 24 hours, greater than or equal to 2 days, greater than or equal to 3 days, greater than or equal to 5 days, greater than or equal to 7 days, or greater than or equal to 10 days. In certain embodiments, the system is retained for less than or equal to 14 days, less than or equal to 10 days, less than or equal to 7 days, less than or equal to 5 days, less than or equal to 3 days, less than or equal to 2 days, less than or equal to 24 hours, less than or equal to 12 hours, less than or equal to 8 hours, less than or equal to 4 hours, or less than or equal to 2 hours. Combinations of the above referenced ranges are also possible (e.g., greater than or equal to 1 hour and less than or equal to 14 days). Other ranges are also possible. In some cases, the anchoring mechanism may be configured to be retained for relative very long periods of time under physiological conditions and fluid flows. For example, in certain embodiments, the anchoring mechanism may be retained at a surface of tissue location internal to a subject for greater than or equal to 1 month, greater than or equal to 2 months, greater than or equal to 3 months, greater than or equal to 6 months, or greater than or equal to 1 year. In some embodiments, the anchoring mechanism may be retained at a surface of tissue location internal to a subject for less than or equal to 2 years, less than or equal to 1 year, less than or equal to 6 months, less than or equal to 3 months, or less than or equal to 2 months. Combinations of the above-referenced ranges are also possible (e.g., greater than or equal to 1 hour and less than or equal to 2 years, greater than or equal to 1 month and less than or equal to 2 years). Other ranges are also possible.

The anchoring mechanisms described herein may comprise any suitable material. In some embodiments, the anchoring mechanism material is relatively non-degradable. In certain embodiments, the anchoring mechanism may be configured to degrade within a certain period of time. In some embodiments, the anchoring mechanism is configured to degrade within one or more ranges of time described above in the context of being retained. For example, in some embodiments, the anchoring mechanism is configured to degrade (e.g., such that the system is no longer retained at the location internal to the subject) in greater than or equal to 1 hour, greater than or equal to 2 hours, greater than or equal to 4 hours, greater than or equal to 8 hours, greater than or equal to 12 hours, greater than or equal to 24 hours, greater than or equal to 2 days, greater than or equal to 3 days, greater than or equal to 5 days, greater than or equal to 7 days, or greater than or equal to 10 days. In certain embodiments, the anchoring mechanism is configured to degrade in less than or equal to 14 days, less than or equal to 10 days, less than or equal to 7 days, less than or equal to 5 days, less than or equal to 3 days, less than or equal to 2 days, less than or equal to 24 hours, less than or equal to 12 hours, less than or equal to 8 hours, less than or equal to 4 hours, or less than or equal to 2 hours. Combinations of the above referenced ranges are also possible (e.g., greater than or equal to 1 hour and less than or equal to 14 days). Other ranges are also possible. In some cases, the anchoring mechanism may be configured to degrade (e.g., such that the system is no longer retained at the location internal to the subject) in greater than or equal to 1 month, greater than or equal to 2 months, greater than or equal to 3 months, greater than or equal to 6 months, or greater than or equal to 1 year. In some embodiments, the anchoring mechanism may degrade in less than or equal to 2 years, less than or equal to 1 year, less than or equal to 6 months, less than or equal to 3 months, or less than or equal to 2 months. Combinations of the above-referenced ranges are also possible (e.g., greater than or equal to 1 hour and less than or equal to 2 years, greater than or equal to 1 month and less than or equal to 2 years). Other ranges are also possible.

In some cases, the anchoring mechanism may comprise a conductive material, as described below.

Electrical Stimulation

In some embodiments, the systems, articles, and methods described herein may be useful for providing electrical stimulation at a location internal to a subject. Advantageously, the systems described herein may be administered orally (e.g., in a capsule) to provide temporary electrical stimulation to the gastrointestinal tract, as compared to traditional methods including e.g., endoscopic placement and/or electrical device installation. In some embodiments, the system comprises one or more anchoring mechanisms, wherein at least one anchoring mechanism comprises a conductive portion (e.g., for electrical communication with the tissue at the location internal to the subject). Such systems may be useful for, for example, iontophoresis (e.g., introducing an API into a tissue internal to a subject during application of a local electric current). In certain embodiments in which the systems described herein are configured for iontophoresis, the system may comprise a first tissue interfacing component (e.g., contained within a first self-righting article) comprising a conductive tip and a second tissue interfacing component (e.g., contained within a second self-righting article) configured to contact but not penetrate tissue (e.g., a blunt cylinder). In some embodiments, one or more electrodes may be in electrical communication with the first and/or second tissue interfacing components.

In some embodiments, the system (e.g., a self-righting system) comprises two or more tissue interfacing components. In certain embodiments, each of the tissue interfacing components comprises a tissue-contacting portion configured to contact tissue. In some cases, the tissue-contacting portion may be electrically conductive. In certain embodiments, the tissue-contacting portion may be electrically insulative.

In some embodiments, the tissue-contacting portion comprises a first electrically-conductive portion and a second insulative portion. In some such embodiments, the electrically conductive portion may be configured for electrical communication with tissue and the insulative portion may be configured to not be in electrical communication with tissue.

Without wishing to be bound by theory, in some embodiments, the length of the insulative portion may be configured to prevent electrical communication with certain layers of tissue (e.g., for muscle stimulation of the stomach the length may correspond to the outer muscular layer (e.g., 2-4 mm), for SI mucosa the length may be e.g., 0.1-1 mm. In some cases, the insulative portion may be configured such that gastrointestinal fluid and/or a mucus coating of the tissue does not contact the electrically conductive portion (e.g., without wishing to be bound by theory, the gastrointestinal fluid and mucus coating are generally electrically conductive, and thus may prevent, in some cases, electrical stimulation from reaching the underlying tissue).

The tissue contacting portion may comprise any suitable ratio of the electrically conductive portion to the insulative portion. For example, in some embodiments, the electrically conductive portion is present in the tissue contacting portion in the amount greater than or equal to 0.1%, greater than or equal to 0.5%, greater than or equal to 1%, greater than or equal to 2%, greater than or equal to 5%, greater than or equal to 10%, greater than equal to 20%, greater than equal to 30%, greater than equal to 40%, greater than equal to 50%, greater than equal to 60%, greater or equal to 70%, greater or equal to 80%, or greater or equal to 90%, of the total surface area of the tissue contacting portion of the tissue interfacing component. In certain embodiments, the electrically conductive portion is present in the tissue contacting portion in an amount less than or equal to 100%, less than equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 2%, less than or equal to 1%, or less than or equal to 0.5% of the total surface area of the tissue contacting portion of the tissue interfacing component. Combinations of the above referenced ranges are also possible (e.g., greater than or equal to 0.1% and less than or equal to 100%, greater than or equal to 10% and less than or equal to 100%, greater than or equal to 30% and less than or equal to 90%). Other ranges are also possible. In some embodiments, the tip of the tissue contacting portion is conductive and the remainder of the tissue contacting portion is insulative.

In certain embodiments, the insulative portion is present in the tissue contacting portion in the amount greater than or equal to 10%, greater than equal to 20%, greater than equal to 30%, greater than equal to 40%, greater than equal to 50%, greater than equal to 60%, greater or equal to 70%, greater or equal to 80%, or greater or equal to 90%, of the total surface area of the tissue contacting portion of the tissue interfacing component. In certain embodiments, the insulative portion is present in the tissue contacting portion in an amount less than or equal to 100%, less than equal to 90%, less than or equal to 80%, less than or equal to 70%, less than or equal to 60%, less than or equal to 50%, less than or equal to 40%, less than or equal to 30%, or less than or equal to 20% of the total surface area of the tissue contacting portion of the tissue interfacing component. Combinations of the above referenced ranges are also possible (e.g., greater than or equal to 10% less than or equal to 100%, greater than or equal to 30% and less than or equal to 90%). Other ranges are also possible.

In some embodiments, the system comprises a self-righting article as described herein and at least one tissue interfacing component each comprising a tissue contacting portion configured for contacting tissue associated with each tissue interfacing opponent. In certain embodiments, the system comprises two or more self-righting articles described herein, each self-righting article comprising at least one tissue interfacing component, each tissue interfacing component comprising a tissue contacting portion configured for contacting tissue. For example, in an exemplary set of embodiments, a single self-righting article may be administered to a subject, the self-righting article comprising two or more tissue interfacing components, where a power source may be placed in electrical communication with the two or more tissue interfacing components, such that a current may be applied to the tissue in direct contact with a tissue contacting portion of the tissue interfacing components. In another exemplary set of embodiments, two (or more) self-righting articles may be administered to the subject, each self-righting article comprising at least one tissue interfacing component, where a power source may be placed electrical communication with the to self-righting articles, such an economy be applied to the tissue in direct contact with the tissue contacting portion of each tissue interfacing component from each self-righting article. Other combinations are also possible. One of ordinary skill in the art would understand how to select combinations of self-righting articles, tissue interfacing components, and tissue contacting portions based upon the teachings of this specification.

As described herein, in some embodiments, a system comprising a self-righting article and/or a self-actuating article may be administered to a subject, where the system comprises at least one tissue interfacing component disposed within the article (e.g., the self-writing article and/or the self-actuating article). The system may be administered such that, at least one interfacing component is released from the article and/or inserted into the tissue at a location internal to the subject. In certain embodiments, a current may be applied (e.g., generated by a power source knowledgeable communication with the tissue interfacing component) such that the current travels across two or more tissue interfacing components. In some such embodiments, the tissue interfacing components are not electrical communication with the tissue.

The electrically conductive portion may comprise any suitably electrically conductive material. Non-limiting examples of suitable electronic conductive materials include electrically conductive polymers, silver, copper, gold, stainless steel, platinum, zinc, and steel. Other conductive materials are also possible.

The insulative portion may comprise any suitably electrically insulating material. Non-limiting examples of suitable to insulative materials include polymers such as parylene, polycaprolactone, and polyethylene. Other insulative materials are also possible.

The electrically conductive material and/or the insulative material may, in some cases, be provided as a coating on the tissue interfacing component. In certain embodiments, the tissue contacting portion may comprise a bulk material comprising the electrically conductive and/or the insulative material.

In some embodiments, the current applied (e.g., across the tissue contacting portions, for electrically stimulating the tissue) may be greater than or equal to 0.001 milliamps, greater than or equal to 0.01 milliamps, greater than or equal to 0.1 milliamps, greater than or equal to 0.5 milliamps, greater than or equal to 1 milliamp, greater than or equal to 5 milliamps, greater than or equal to 10 milliamps, greater than or equal to 50 milliamps, greater than or equal to 100 milliamps, or greater than or equal to 250 milliamps. In certain embodiments, the current applied may be less than or equal to 500 milliamps, less than or equal to 250 milliamps, less than or equal to 100 milliamps, less than or equal to 50 milliamps, less than or equal to 10 milliamps, less than or equal to 5 milliamps, less than or equal to 1 milliamp, less than or equal to 0.5 milliamps, less than or equal to 0.1 milliamps, or less than or equal to 0.01 milliamps. Combinations of the above-referenced ranges are also possible (e.g., greater than or equal to 0.001 milliamps and less than or equal to 500 milliamps, greater than or equal to 0.1 milliamps and less than or equal to 10 milliamps). Other ranges are also possible. Current may be applied using any suitable means including, for example, an external power source (e.g., a battery).

In certain embodiments, the system is configured to be retained at the location internal to subject under greater than or equal to 0.1 N (e.g., greater than or equal to 0.6 N) of force and/or a change in orientation of greater than or equal to 30 degrees, as described above.

Self-Actuating

Self-actuating articles including, for example, self-actuating tissue interfacing components such as self-actuating needles, self-actuating anchoring mechanisms, and/or self-actuating biopsy punches, are generally provided. Advantageously, in some embodiments, the self-actuating articles described herein may be useful as a general platform for delivery of a wide variety of pharmaceutical drugs that are typically delivered via injection directly into tissue due to degradation in the GI tract. The self-actuating articles described herein may also be used to deliver sensors, electrical stimulation, anchor systems described herein to tissue, and/or take biopsies without the need for an endoscopy. In some embodiments, the article comprises a spring (e.g., a coil spring, wave springs, Belleville washers, a beam, a membrane, a material having particular mechanical recovery characteristics). Those of ordinary skill in the art would understand that the term spring is not intended to be limited to coil springs, but generally encompass any reversibly compressible material and/or component which, after releasing an applied compressive force on the material/component, the material/component substantially returns to an uncompressed length of the material/component under ambient conditions (e.g., within 40%, within 50%, within 60%, within 70%, within 80%, within 90%, within 95%, or any percentage in between, of the length of the material/component prior to compression).

In certain embodiments, the term spring of the self-actuating article may be provided as, or further comprise, an expanding component. Those of ordinary skill in the art would understand the term extending component comprises reversibly and irreversibly compressive materials and are components which, upon stimulating and/or releasing a restraint on the expanding component, the expanding component extends in at least one direction (e.g., along its length). In some embodiments, the expanding component comprises a gaseous composition(s) for expanding the gaseous volume expanding component (e.g., a mixture of baking soda and vinegar).

In some embodiments, the spring and/or expanding component may extend in at least one direction via thermal expansion, swelling (e.g., due to fluid absorption), a gas driven process, a pneumatic process, a hydraulic process, an electrical motor, a magnetic mechanism, a torsional spring mechanism, a chemical gas generator, and/or an self-catalyzing reaction. In an exemplary set of embodiments, the spring and/or expanding component may extend in at least one direction upon exposure of the spring and/or expanding component to a fluid (e.g., gastrointestinal fluid).

In some cases, the spring and/or the expanding component may be activated (e.g., extended in at least one direction, returns to an uncompressed length of the component) by any suitable activation mechanism. Non-limiting examples of suitable activation mechanisms include release of a pressure difference, electrical timer, light sensor, color sensor, enzymatic sensor, capacitance, magnetism, activation by applied stress (e.g., shape memory materials), external activation (e.g., applied magnetic field, applied light, reaction with gastrointestinal fluid such as stomach acid), and combinations thereof. In an exemplary set of embodiments, the spring and/or expanding component are activated by interaction (e.g., reaction) with a gastrointestinal fluid.

In some cases, the activation mechanism displaces the tissue interfacing component by a particular distance (e.g., less than or equal to 10 mm, less than or equal to 8 mm, less than or equal to 6 mm, less than or equal to 4 mm, less than or equal to 2 mm) and/or with a particular force (e.g., greater than or equal to 0.1 N, greater than or equal to 0.3 N, greater than or equal to 0.5 N, greater than or equal to 1 N, greater than or equal to 1.5 N).

Figure 21:
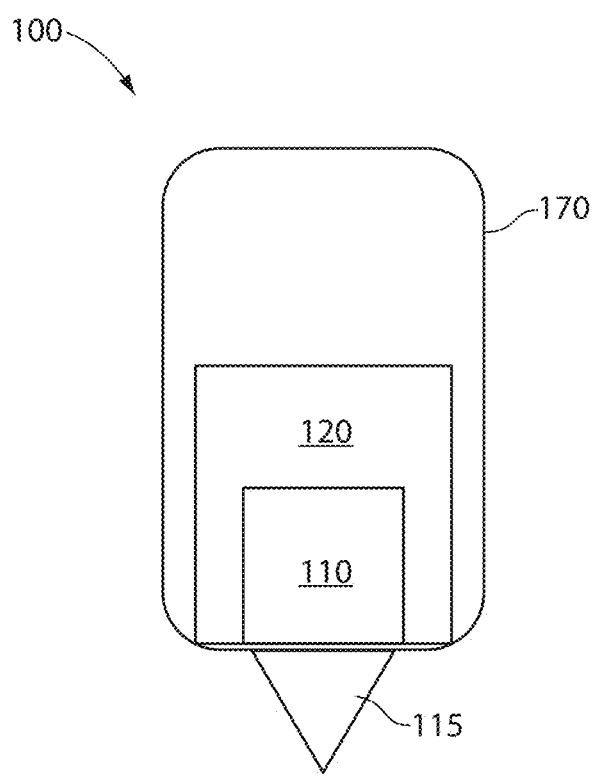
FIG. 21 is a schematic illustration of a self-actuating article, according to one set of embodiments.

As illustrated in FIG. 21, in some embodiments, article 100 comprises a spring 110 and a support material 120 associated with (e.g., operably linked with) spring 110. Support material 120, in certain embodiments, maintains the spring under compressive strain under a first set of conditions (e.g., under ambient conditions (e.g., room temperature, atmospheric pressure and relative humidity)). In some embodiments, the support material at least partially releases (e.g., at least a portion of the support material degrades) the spring from compressive strain under a second set of conditions different than the first set of conditions. For example, in some embodiments, the second set of conditions comprises physiological conditions (e.g., at or about 37° C., in physiologic fluids such as gastric fluid).

In some cases, spring 110 may be adjacent (e.g., directly adjacent) support material 120. As used herein, when a component is referred to as being "adjacent" another component, it can be directly adjacent to (e.g., in contact with) the component, or one or more intervening components also may be present. A component that is "directly adjacent" another component means that no intervening component(s) is present. In some cases, the spring may be at least partially embedded within the support material. In certain embodiments, the spring is coated with the support material.

In certain embodiments, referring again to FIG. 21, article 100 comprises an outer shell 170 (e.g., such that spring 110 is at least partially encapsulated within outer shell 170). In some cases, the support material may be a coating. In some embodiments, the support material is a biodegradable coating. In certain embodiments, the coating may have any suitable thickness. For example, the thickness of the coating may be greater than or equal to 3 mm, greater than or equal to 4 mm, or greater than or equal to 5 mm. In certain embodiments, the thickness of the coating may be less than or equal to 6 mm, less than or equal to 5 mm, or less than or equal to 4 mm. Combinations of the above-referenced ranges are also possible (e.g., greater than or equal to 3 mm and less than or equal to 6 mm). In certain embodiments, the biodegradable coating at least partially degrades under physiological conditions. In some cases, the support material may be a brittle material. Non-limiting examples of suitable support materials include sugars and/or polymers (e.g., polyethylene glycol, polyvinylpyrrolidinone, polyvinylalcohol).

The support material may have any suitable cross-sectional dimension. In some embodiments, the average cross-sectional dimension of the support material is greater than or equal to 0.1 mm, greater than or equal to 0.5 mm, greater than or equal to 1 mm, greater than or equal to 2 mm, greater than or equal to 3 mm, greater than or equal to 4 mm, or greater than or equal to 5 mm. In certain embodiments, the average cross-sectional dimension of the support material is less than or equal to 10 mm, less than or equal to 6 mm, less than or equal to 5 mm, less than or equal to 4 mm, less than or equal to 3 mm, less than or equal to 2 mm, less than or equal to 1 mm, or less than or equal to 0.5 mm. Combinations of the above-referenced ranges are also possible (e.g., greater than or equal to 0.1 mm and less than or equal to 10 mm). Other ranges are also possible.

In some embodiments, the support material, the spring, and/or the expanding component comprise one or more materials configured to dissolve (e.g., in an acidic environment in a pH neutral environment, in water, in a basic environment), melt at physiological temperature (e.g., 37° C.), change in stiffness (e.g., in response to a change in temperature, in response to fluid absorption), thermally expand, and/or change in shape (e.g., in response to fluid absorption, by deflation, by leakage).

Advantageously, the configuration and/or material used for the support material may permit tuning of the dissolution of the support material. In some cases, the dissolution of the support material may be tuned such that the tissue interfacing component is released from the article at a desired location and/or at a desired time.

The support material may comprise any suitable material. Non-limiting examples of suitable materials include sugars and derivatives thereof (e.g., sugar alcohols such as isomalt, sugar mixtures such as toffee), starch, calcium carbonate, zinc, sodium chloride, and/or polymers (e.g., polyethylene glycol, polyvinylpyrrolidinone, polyvinylalcohol, polyethylene oxide, diethyl pyrocarbonate, hydrogels). Other materials are also possible. Without wishing to be bound by theory, the support material may be selected to be relatively brittle (e.g., such that the spring is released upon dissolution of the support material).

In certain embodiments, the support material may be configured to have a particular architecture which provides desirable dissolution profiles. For example, in some embodiments, the support material may be configured to enhance dissolution profiles, have controlled failure modes (e.g., breakage into small pieces at relatively predictable locations) and/or provide structural integrity of the support material.

In some embodiments, the support material has desirable mechanical properties (e.g., such that the spring recovers at least a portion of its uncompressed length relatively quickly). For example, in certain embodiments, the support material may have a critical stress of greater than or equal to 0.01 N, greater than or equal to 0.1 N, greater than or equal to 0.5 N, greater than or equal to 1 N, greater than or equal to 2 N, greater than or equal to 3 N, greater than or equal to 5 N, greater than or equal to 7 N, greater than or equal to 10 N, greater than or equal to 15 N, greater than or equal to 20 N, greater than or equal to 25 N, greater than or equal to 30 N, greater than or equal to 35 N, greater than or equal to 40 N, greater than or equal to 45 N, greater than or equal to 50 N, or greater than or equal to 60 N, including any critical stress value in between. In certain embodiments, the support material may have a critical stress of less than or equal to 70 N, less than or equal to 60 N, less than or equal to 50 N, less than or equal to 45 N, less than or equal to 40 N, less than or equal to 35 N, less than or equal to 30 N, less than or equal to 25 N, less than or equal to 20 N, less than or equal to 15 N, less than or equal to 10 N, less than or equal to 7 N, less than or equal to 5 N, less than or equal to 3 N, less than or equal to 2 N, less than or equal to 1 N, less than or equal to 0.5 N, or less than or equal to 0.1 N including any critical stress value in between. Combinations of the above-referenced ranges are also possible (e.g., greater than or equal to 10 N and less than or equal to 70 N, greater than or equal to 30 N and less than or equal to 45 N). Other ranges are also possible. The critical stress is generally the maximum force the support material can hold (e.g., as applied by the adjacent spring) before cracking and may be determined by calculating the critical stress, where:

$$\sigma_c^2 = \frac{2\gamma E}{\pi a},$$

where $\sigma_c$ is the critical stress applied by the spring, $\gamma$ is the surface energy of the material, E is the Young's modulus of the material, and a is the surface area perpendicular to the applied stress. In some embodiments, the support material may have a characteristic dissolution time. In certain embodiments, the characteristic dissolution time of the support material is less than or equal to 10 minutes, less than or equal to 9 minutes, less than or equal to 8 minutes, less than or equal to 7 minutes, less than or equal to 6 minutes, less than or equal to 5 minutes, less than or equal to 4 minutes, less than or equal to 3 minutes, or less than or equal to 2 minutes. In some embodiments, the characteristic dissolution time of the support material is greater than or equal to 1 minute, greater than or equal to 2 minutes, greater than or equal to 3 minutes, greater than or equal to 4 minutes, greater than or equal to 5 minutes, greater than or equal to 6 minutes, greater than or equal to 7 minutes, greater than or equal to 8 minutes, or greater than or equal to 9 minutes. Combinations of the above-referenced ranges are also possible (e.g., greater than or equal to 1 minute and less than or equal to 10 minutes). Other ranges are also possible. The characteristic dissolution time is determined as the time in which a support material begins to propagate a crack after exposure to gastrointestinal fluid.

Spring

In some embodiments, the support material maintains at least a portion of the spring under at least 5%, at least 10%, at least 15%, at least 20%, at least 25%, at least 30%, at least 40%, at least 50%, at least 60%, at least 70%, or at least 80% compressive strain under the first set of conditions. In certain embodiments, the support material maintains at least a portion of the spring under less than or equal to 90%, less than or equal to 80%, less than or equal to 70%, less than or equal to 60%, less than or equal to 50%, less than or equal to 40%, less than or equal to 30%, less than or equal to 25%, less than or equal to 20%, less than or equal to 15%, or less than or equal to 10% compressive strain under the first set of conditions.

In certain embodiments, the spring recovers (e.g., within less than 10 minutes, less than 5 minutes, less than 1 minute, less than 30 seconds, less than 10 seconds, less than 5 seconds, less than 1 second, less than 0.1 seconds, less than 0.01 seconds) to a length of greater than or equal to 10%, greater than or equal to 20%, greater than or equal to 30%, greater than or equal to 40%, greater than or equal to 50%, greater than or equal to 60%, greater than or equal to 70%, greater than or equal to 80%, greater than or equal to 85%, greater than or equal to 90%, greater than or equal to 95%, greater than or equal to 98%, or greater than or equal to 99% of the length of the spring (e.g., an uncompressed spring length) prior to applying and/or in the absence of the compressive strain (e.g., by the support material), including any percentage in between 10% and 99%. In some embodiments, the spring recovers to a length of less than or equal to 100%, less than or equal to 99%, less than or equal to 98%, less than or equal to 95%, less than or equal to 90%, less than or equal to 85%, less than or equal to 80%, less than or equal to 75%, less than or equal to 70%, less than or equal to 60%, less than or equal to 50%, less than or equal to 40%, less than or equal to 30%, or less than or equal to 20% of the length of the spring prior to applying and/or in the absence of the compressive strain, including any percentage in between 20% and 100%. Advantageously, the use of springs and support materials as described herein may enable, for example, the release of a tissue interfacing component (e.g., a needle) associated with (e.g., operably linked with) the spring such that the tissue interfacing component contacts and/or penetrates tissue proximate the article. In an illustrative example, in some embodiments, a needle associated with the spring is administered to a subject such that, upon degradation of the support material, the spring recovers and the needle is pushed into tissue proximate the article such that the needle penetrates the tissue (e.g., a GI mucosal layer). In some such embodiments, an active pharmaceutical ingredient may be delivered into the tissue by the tissue interfacing components. For example, in some embodiments, the article comprises an active pharmaceutical ingredient such that, upon release of the spring at a location internal of a subject, the active pharmaceutical ingredient is released (e.g., into tissue proximate the location internal of the subject). In other embodiments, a biopsy may be conducted (e.g., by the tissue interfacing component such as a biopsy device) upon release of the spring by the support material. Referring again to FIG. 21, in some embodiments, article 100 comprises tissue interfacing component 115 associated with spring 110. Tissue interfacing components (e.g., needles, hooks, high API loaded components) are described in more detail, herein.

In certain embodiments, the tissue interfacing component comprises a needle, a patch or an array of needles (e.g., microneedles), a biopsy component, a hook, a mucoadhesive patch, or combinations thereof.

In some embodiments, the spring comprises an elastic material. In certain embodiments, the spring comprises a material selected from the group consisting of nitinol, metals, polymers, and combinations thereof.

In certain embodiments, the spring may have a particular spring constant. For example, in some embodiments, the spring constant of the spring may be greater than or equal to 100 N/m, greater than or equal to 150 N/m, greater than or equal to 200 N/m, greater than or equal to 250 N/m, greater than or equal to 300 N/m, greater than or equal to 350 N/m, greater than or equal to 400 N/m, greater than or equal to 450 N/m, greater than or equal to 500 N/m, greater than or equal to 600 N/m, greater than or equal to 700 N/m, greater than or equal to 800 N/m, greater than or equal to 900 N/m, greater than or equal to 1000 N/m, greater than or equal to 1100 N/m, greater than or equal to 1200 N/m, greater than or equal to 1300 N/m, or greater than or equal to 1400 N/m, less than or equal to 1500 N/m, less than or equal to 1800 N/m, or greater than or equal to 2000 N/m, and including any spring constant in between these values. In certain embodiments, the spring constant of the spring may be less than or equal to 2200 N/m, less than or equal to 2000 N/m, less than or equal to 1800 N/m, less than or equal to 1500 N/m, less than or equal to 1400 N/m, less than or equal to 1300 N/m, less than or equal to 1200 N/m, less than or equal to 1100 N/m, less than or equal to 1000 N/m, less than or equal to 900 N/m, less than or equal to 800 N/m, less than or equal to 700 N/m, less than or equal to 600 N/m, less than or equal to 500 N/m, less than or equal to 450 N/m, less than or equal to 400 N/m, less than or equal to 350 N/m, less than or equal to 300 N/m, less than or equal to 250 N/m, less than or equal to 200 N/m, or less than or equal to 150 N/m, including any spring constant in between these values. Combinations of the above-referenced ranges are also possible (e.g., greater than or equal to 100 N/m and less than or equal to 500 N/m, greater than or equal to 100 N/m and less than or equal to 1500 N/m). Other ranges are also possible.

In some embodiments, the spring is compressed (e.g., by the support material) by greater than or equal to 1 mm, greater than or equal to 2 mm, greater than or equal to 3 mm, greater than or equal to 4 mm, greater than or equal to 5 mm, greater than or equal to 6 mm, greater than or equal to 7 mm, greater than or equal to 8 mm, greater than or equal to 9 mm, greater than or equal to 10 mm, greater than or equal to 12 mm, or greater than or equal to 15 mm along a longitudinal axis of the spring as compared to the uncompressed length of the spring. In certain embodiments, the spring is compress by less than or equal to 20 mm, less than or equal to 15 mm, less than or equal to 12 mm, less than or equal to 10 mm, less than or equal to 9 mm, less than or equal to 8 mm, less than or equal to 7 mm, less than or equal to 6 mm, less than or equal to 5 mm, less than or equal to 4 mm, less than or equal to 3 mm, or less than or equal to 2 mm along a longitudinal axis of the spring as compared to the uncompressed length of the spring. Combinations of the above-referenced ranges are also possible (e.g., greater than or equal to 1 mm and less than or equal to 5 mm, greater than or equal to 5 mm and less than or equal to 10 mm). Other ranges are also possible.

In certain embodiments, the spring is configured to release a desirable amount of a stored compressive energy of the spring (e.g., upon exposure of the support material to a fluid such as gastrointestinal fluid). For example, the spring and/or the support material may be exposed to a fluid and, upon at least partial dissolution of the support material, the spring at least partially releases stored compressive energy e.g., to displace the tissue interfacing component operably linked to the spring (e.g., to release it into a tissue located internal to a subject). For example, in some embodiments, the spring is configured to release at least 10%, at least 20%, at least 30%, at least 40%, at least 50%, at least 60%, at least 70%, or at least 80% of the stored compressive energy of the spring, including any percentage in between these values. In certain embodiments, the spring is configured to release at least 90% of the stored compressive energy of the spring, at least 92% of the stored compressive energy of the spring, at least 94% of the stored compressive energy of the spring, at least 96% of the stored compressive energy of the spring, at least 98% of the stored compressive energy of the spring, or at least 99% of the stored compressive energy of the spring (e.g., upon exposure of the support material to a fluid such as gastrointestinal fluid), including any percentage in between these values. In certain embodiments, the spring is configured to release less than or equal to 100% of the stored compressive energy of the spring, less than 99% of the stored compressive energy of the spring, less than 98% of the stored compressive energy of the spring, less than 96% of the stored compressive energy of the spring, less than 94% of the stored compressive energy of the spring, less than 92% of the stored compressive energy of the spring, or less than 91% of the stored compressive energy of the spring. In some embodiments, the spring is configured to release less than or equal to 90%, less than or equal to 80%, less than or equal to 70%, less than or equal to 60%, less than or equal to 50%, less than or equal to 40%, less than or equal to 30%, or less than or equal to 20% of the stored compressive energy of the spring (e.g., upon exposure of the support material to a fluid such as gastrointestinal fluid), including any percentage in between these values. Combinations of the above-referenced ranges are also possible (e.g., at least 92% and less than 98% of the stored compressive energy of the spring, at least 94% and less than 96% of the stored compressive energy of the spring, at least 10% and less than or equal to 99%). Other ranges are also possible.

In some embodiments, the spring is configured to release the stored compressive energy of the spring within any suitable time of exposing the support material to a fluid and/or mechanical failure (e.g., cracking, fracture) of the support material. For example, in some embodiments, the spring is configured to release the stored compressive energy (e.g., at least 10% of the stored compressive energy) of the spring within less than 5 ms, less than 4 ms, less than 3 ms, less than 2 ms, less than 1 ms, less than 0.5 ms, or less than 0.2 ms of mechanical failure of the support material. In certain embodiments, the spring is configured to release the stored compressive energy of the spring within in greater than 0.1 ms, greater than 0.2 ms, greater than 0.5 ms, greater than 1 ms, greater than 2 ms, greater than 3 ms, or greater than 4 ms of mechanical failure of the support material. Combinations of the above-referenced ranges are also possible (e.g., within less than 5 ms and greater than 1 ms, within less than 2 ms and greater than 0.1 ms). Other ranges are also possible.

In certain embodiments, the spring is configured to release the stored compressive energy of the spring (e.g., at least 10% of the stored compressive energy) as described herein within less than 10 min, less than 9 min, less than 7 min, less than 5 min, less than 3 min, or less than 1 min of exposing the support material to a fluid, including any time in between these values. In some embodiments, the spring is configured to release the stored compressive energy of the spring within greater than 30 seconds, greater than 1 min, greater than 3 min, greater than 5 min, greater than 7 min, or greater than 9 min, including any time in between these values. Combinations of the above-referenced ranges (e.g., within less than 10 min and greater than 30 seconds, within less than 7 min and greater than 5 min). Other ranges are also possible.

Any combination of the above-referenced ranges are also possible. For example, in certain embodiments, the spring is configured to release at least 10% (e.g., at least 90%) of the stored compressive energy of the spring within 10 min of exposing the support material to a fluid. In certain embodiments, the spring is configured to release at least 10% (e.g., at least 90%) of a stored compressive energy of the spring within 30 seconds of exposing the support material to a fluid. In some embodiments, the spring is configured to release less than or equal to 100% of a stored compressive energy of the spring within 10 min of exposing the support material to a fluid. In certain embodiments, the spring is configured to release less than or equal to 100% of the stored compressive energy of the spring within 30 seconds of exposing the support material to a fluid.

In certain embodiments, the spring is configured to release at least 10% (e.g., at least 90%) of the stored compressive energy of the spring within 5 ms of mechanical failure of the support material. In certain embodiments, the spring is configured to release at least 10% (e.g., at least 90%) of a stored compressive energy of the spring within 0.1 ms of mechanical failure of the support material. In some embodiments, the spring is configured to release less than or equal to 100% of a stored compressive energy of the spring within 5 ms of mechanical failure of the support material. In certain embodiments, the spring is configured to release less than or equal to 100% of the stored compressive energy of the spring within 0.1 ms of mechanical failure of the support material.

The spring may have any suitable cross-sectional dimension. In some embodiments, the largest cross-sectional dimension of the (uncompressed) spring is greater than or equal to 1 mm, greater than or equal to 2 mm, greater than or equal to 3 mm, greater than or equal to 4 mm, or greater than or equal to 5 mm. In certain embodiments, the largest cross-sectional dimension of the (uncompressed) spring is less than or equal to 10 mm, less than or equal to 6 mm, less than or equal to 5 mm, less than or equal to 4 mm, less than or equal to 3 mm, or less than or equal to 2 mm. Combinations of the above-referenced ranges are also possible (e.g., greater than or equal to 1 mm and less than or equal to 10 mm). Other ranges are also possible.

In some embodiments, the article is administered to a subject (e.g., orally). In certain embodiments, the article may be administered orally, rectally, vaginally, nasally, or uretherally. In certain embodiments, upon reaching a location internal to the subject (e.g., the gastrointestinal tract), at least a portion of the support material degrades such that the spring extends and/or the tissue interfacing component interfaces (e.g., contacts, penetrates) with a tissue located internal to the subject. In some embodiments, the location internally of the subject is the colon, the duodenum, the ileum, the jejunum, the stomach, or the esophagus. In certain embodiments, the location internally of the subject is in the buccal space, in the venous system (e.g., an artery), in the respiratory system (e.g., lung), in the renal system, in the urinary system, or in the gastrointestinal system. As described above and herein, in some embodiments, an active pharmaceutical ingredient is released during and/or after penetrate of the tissue located internal to the subject.

In some embodiments, the tissue interfacing component comprises a needle and the tissue is penetrated with a force of greater than or equal to 1 mN and less than or equal to 100 mN (e.g., greater than or equal to 10 mN and less than or equal to 20 mN). In certain embodiments, the tissue interfacing component comprises a plurality of microneedles and the tissue is penetrated with a force of greater than or equal to 100 mN and less than or equal to 10 N (e.g., greater than or equal to 1 N and less than or equal to 2 N, greater than or equal to 100 mN and less than or equal to 6 N).

In some cases, and as described herein, the article may be oriented such that a longitudinal axis of the tissue interfacing component is orthogonal (e.g., within less than or equal to 10%, less than or equal to 5%, or less than or equal to 1% of 90°) to the tissue located proximate the article. In some embodiments, the self-actuating articles (e.g., comprising a tissue-interfacing component) described herein may be associated with one or more self-righting articles. Non-limiting examples of suitable self-righting articles are generally described in a co-owned U.S. Provisional Application Ser. No. 62/507,647, entitled "SELF-RIGHTING ARTICLES" filed on May 17, 2017, which is incorporated herein by reference in its entirety.

In an exemplary embodiment, the article comprises an outer shell, a spring at least partially encapsulated within the outer shell, a support material associated with the spring such that the support material maintains at least a portion of the spring under at least 5% compressive strain under ambient conditions, and a tissue interfacing component operably linked to the spring. In certain embodiments, the article comprises a tissue interfacing component and a spring associated with the tissue interfacing component, the spring maintained in an at least partially compressed state by a support material under at least 5% compressive strain. According to certain embodiments, the spring is configured to release at least 10% (e.g., at least 90%) of a stored compressive energy of the spring within 0.1 ms of mechanical failure of the support material. According to certain embodiments, the article compresses a pharmaceutical agent associated with the tissue interfacing component. In some embodiments, the article comprises a self-righting article associated with the tissue interfacing component.

High API

In some embodiments, as described above and herein, the system comprises a component (e.g., a tissue interfacing component) comprising a solid therapeutic agent (e.g., a solid API) and a second material (e.g., a support(ing) material for the solid API such as a binder and/or a polymer) such that the solid therapeutic agent is present in the component in an amount of greater than or equal to 10 wt % versus the total weight of the tissue interfacing component. Such tissue-interfacing components may be useful for delivery of API doses (e.g., to a subject). Advantageously, in some embodiments, the reduction of volume required to deliver the required API dose as compared to a liquid formulation permits the creation of solid needle delivery systems for a wide variety of drugs in a variety of places/tissues (e.g., tongue, GI mucosal tissue, skin) and/or reduces and/or eliminates the application of an external force in order to inject a drug solution through the small opening in the needle. In some cases, a physiologically relevant dose may be present in a single tissue interfacing component (e.g., having a relatively high API loading).

In certain embodiments, the API is substantially solid (e.g., a powder, a compressed powder, a crystalline solid, an amorphous solid) i.e. a solid therapeutic agent. In some embodiments, the API may be in liquid form. In certain embodiments, the API may be In some embodiments, the tissue-interfacing component comprises a needle, a biopsy component, a projectile, a plurality of microneedles, a hook, a mucoadhesive patch, or combinations thereof. In certain embodiments, as described herein and above, the tissue interfacing component is configured to penetrate tissue (e.g., skin, tongue, tissue of the GI tract such as GI mucosal tissue). In some embodiments, the tissue in penetrated with a force of greater than or equal to 1 mN and less than or equal to 20 N (e.g., greater than or equal to 10 mN and less than or equal to 20 mN, greater than or equal to 1 mN and less than or equal to 100 mN, greater than or equal to 20 mN and less than or equal to 1 N, greater than or equal to 1 N and less than or equal to 20 N, greater than or equal to 10 N and less than or equal to 20 N).

Advantageously, a tissue-interfacing component comprising a needle and/or a plurality of microneedles comprising a relative high API loading (e.g., greater than or equal to 10 wt % versus the total weight of the component) may significantly reduce the number of needles and/or the overall size of the microneedle array required to deliver a particular API dose, as compared to traditional microneedles (e.g., generally comprising less than 10 wt % loading and/or requiring a plurality of microneedles on the order of thousands to tens of thousands of microneedles to deliver a similar dose).

In some embodiments, the tissue-interfacing component has a particular largest dimension (e.g., length). In certain embodiments, the largest dimension of the tissue interfacing component is greater than or equal to 1 mm, greater than or equal to 2 mm, greater than or equal to 3 mm, greater than or equal to 5 mm, greater than or equal to 7 mm, greater than or equal to 10 mm, greater than or equal to 12 mm, greater than or equal to 15 mm, greater than or equal to 20 mm, greater than or equal to 25 mm, greater than or equal to 30 mm, or greater than or equal to 50 mm. In some embodiments, the largest dimension of the tissue interfacing component is less than or equal to 100 mm, less than or equal to 50 mm, less than or equal to 30 mm, less than or equal to 25 mm, less than or equal to 20 mm, less than or equal to 15 mm, less than or equal to 12 mm, less than or equal to 10 mm, less than or equal to 7 mm, less than or equal to 5 mm, less than or equal to 3 mm, or less than or equal to 2 mm. Combinations of the above-referenced ranges are also possible.

In certain embodiments, the tissue-interfacing component has an average cross-sectional dimension (e.g., diameter) of greater than or equal to 0.25 mm, greater than or equal to 0.5 mm, greater than or equal to 0.6 mm, greater than or equal to 0.7 mm, greater than or equal to 0.8 mm, greater than or equal to 0.9 mm, greater than or equal to 1 mm, greater than or equal to 1.1 mm, greater than or equal to 1.2 mm, greater than or equal to 1.3 mm, greater than or equal to 1.4 mm, greater than or equal to 1.5 mm, greater than or equal to 1.7 mm, mm, greater than or equal to 1.9 mm, greater than or equal to 2.5 mm, greater than or equal to 3.0 mm, greater than or equal to 4.0 mm, or greater than or equal to 5.0 mm. In some embodiments, the tissue-interfacing component has an average cross-sectional dimension of less than or equal to 6.0 mm, less than or equal to 5.0 mm, less than or equal to 4.0 mm, less than or equal to 3.0 mm, less than or equal to 2.5 mm, less than or equal to 1.9 mm, less than or equal to 1.7 mm, less than or equal to 1.5 mm, less than or equal to 1.4 mm, less than or equal to 1.3 mm, less than or equal to 1.2 mm, less than or equal to 1.1 mm, less than or equal to 1 mm, less than or equal to 0.9 mm, less than or equal to 0.8 mm, less than or equal to 0.7 mm, or less than or equal to 0.6, or less than or equal to 0.5 mm. Combinations of the above-referenced ranges are also possible (e.g., greater than or equal to 0.5 mm and less than or equal to 2.0 mm). Other ranges are also possible.

In some embodiments, the tissue interfacing component may comprise a plurality of microneedles. In some such embodiments, the plurality of microneedles may have a particular base largest cross-sectional dimension (e.g., diameter of the base), a particular height, and/or a particular spacing.

In some embodiments, the average diameter of the base of the plurality of microneedles is greater than or equal to 100 microns, greater than or equal to 150 microns, greater than or equal to 200 microns, greater than or equal to 250 microns, greater than or equal to 300 microns, greater than or equal to 350 microns, greater than or equal to 400 microns, or greater than or equal to 450 microns. In certain embodiments, the average diameter of the base of the plurality of microneedles is less than or equal to 500 microns, less than or equal to 450 microns, less than or equal to 400 microns, less than or equal to 350 microns, less than or equal to 300 microns, less than or equal to 250 microns, less than or equal to 200 microns, or less than or equal to 150 microns. Combinations of the above-referenced ranges are also possible (e.g., greater than or equal to 100 microns and less than or equal to 500 microns). Other ranges are also possible.

In certain embodiments, the average height of the plurality of microneedles is greater than or equal to 0.1 mm, greater than or equal to 0.2 mm, greater than or equal to 0.5 mm, greater than or equal to 0.7 mm, greater than or equal to 1 mm, greater than or equal to 1.2 mm, greater than or equal to 1.5 mm, or greater than or equal to 2 mm. In some embodiments, the average height of the plurality of microneedles is less than or equal to 2.5 mm, less than or equal to 2 mm, less than or equal to 1.5 mm, less than or equal to 1.2 mm, less than or equal to 1 mm, less than or equal to 0.7 mm, less than or equal to 0.5 mm, or less than or equal to 0.2 mm. Combinations of the above-referenced ranges are also possible (e.g., greater than or equal to 0.1 mm and less than or equal to 2.5 mm). Other ranges are also possible.

In some cases, the average spacing (e.g., spacing between adjacent microneedles in the plurality of microneedles) of the plurality of microneedles may be greater than or equal to 100 microns, greater than or equal to 200 microns, greater than or equal to 300 microns, greater than or equal to 400 microns, greater than or equal to 500 microns, greater than or equal to 600 microns, greater than or equal to 700 microns, greater than or equal to 800 microns, greater than or equal to 900 microns, greater than or equal to 1000 microns, greater than or equal to 1100 microns, greater than or equal to 1200 microns, greater than or equal to 1300 microns, or greater than or equal to 1400 microns. In certain embodiments, the average spacing of the plurality of microneedles is less than or equal to 1500 microns, less than or equal to 1400 microns, less than or equal to 1300 microns, less than or equal to 1200 microns, less than or equal to 1100 microns, less than or equal to 1000 microns, less than or equal to 900 microns, less than or equal to 800 microns, less than or equal to 700 microns, less than or equal to 600 microns, less than or equal to 500 microns, less than or equal to 400 microns, less than or equal to 300 microns, or less than or equal to 200 microns. Combinations of the above-referenced ranges are also possible (e.g., greater than or equal to 100 microns and less than or equal to 1500 microns). Other ranges are also possible.

Advantageously, in some embodiments, the tissue-interfacing component (e.g., needle), dissolves relatively quickly, reducing and/or eliminating the risk of secondary penetration by the component in undesired locations. In some embodiments, the largest cross-sectional dimension (e.g., length) of the component is designed to be delivered to whichever organ it is targeting to prevent pain and/or undesired perforation of the GI tract.

Figure 28:
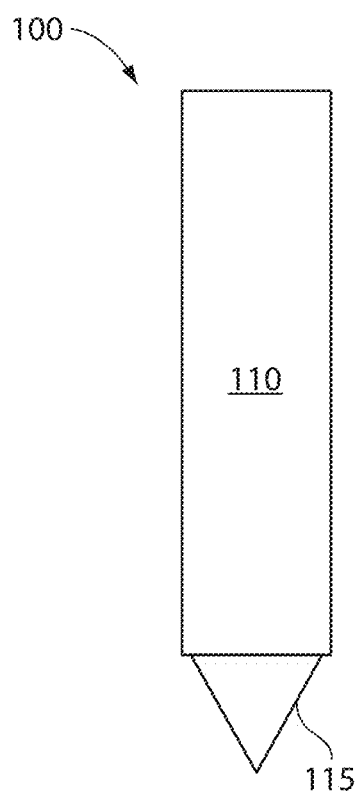
FIG. 28 is a schematic illustration of a tissue interfacing component, according to one set of embodiments.

In some embodiments, the tissue interfacing component comprises a base portion and a tip. For example, as illustrated in FIG. 28, tissue interfacing component 100 comprises base portion 110 and tip 115. In some embodiments, the base portion and/or the tip portion comprises a mucoadhesive material. Non-limiting examples of suitable mucoadhesive materials include polymers such as poly(vinyl alcohol), hydroxylated methacrylate, and poly(methacrylic acid), polyacrylates (e.g., polyacrylic acid, thiolated poly(acrylic acid), Carbopol®), cyanoacrylates, sodium carboxymethylcellulose, hyaluronic acid, hydroxypropylcellulose, polycarbophil, chitosan, mucin, alginate, xanthan gum, gellan, poloxamer, celluloseacetophthalate, methyl cellulose, hydroxy ethyl cellulose, poly(amidoamine) dendrimers, poly(dimethyl siloxane), poly(vinyl pyrrolidone), polycarbophil, combinations thereof, and copolymers thereof.

In some embodiments, the base portion and/or the tip comprises a solid therapeutic agent (e.g., API) and a second material (if present), such that the solid therapeutic agent is present in the tissue interfacing component in an amount of greater than or equal to 10 wt % versus the total weight of the tissue interfacing component. In certain embodiments, the solid therapeutic agent is present in the tissue interfacing component in an amount of greater than or equal to 10 wt %, greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 90 wt %, greater than or equal to 95 wt %, greater than or equal to 98 wt %, or greater than or equal to 99.1 wt % versus the total weight of the tissue interfacing component. In some embodiments, the solid therapeutic agent is present in the tissue interfacing component in an amount of less than or equal to 100 wt %, less than or equal to 99 wt %, less than or equal to 98 wt %, less than or equal to 95 wt %, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, or less than or equal to 20 wt % versus the total weight of the tissue interfacing component. Combinations of the above-referenced ranges are also possible (e.g., greater than or equal to 10 wt % and less than or equal to 100 wt %, greater than or equal to 80 wt % and less than or equal to 100 wt %). Other ranges are also possible. In an exemplary set of embodiments, the solid therapeutic agent is present in the tissue interfacing component in an amount greater than or equal to 80 wt % and less than or equal to 100 wt % versus the total weight of the tissue interfacing component.

In certain embodiments, the solid therapeutic agent is present in the base portion in an amount of greater than or equal to 0 wt %, greater than or equal to 5 wt %, greater than or equal to 10 wt %, greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 90 wt %, greater than or equal to 95 wt %, greater than or equal to 98 wt %, or greater than or equal to 99 wt % versus the total weight of the base portion. In some embodiments, the solid therapeutic agent is present in the base portion in an amount of less than or equal to 100 wt %, less than or equal to 99 wt %, less than or equal to 98 wt %, less than or equal to 95 wt %, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, less than or equal to 20 wt %, less than or equal to 10 wt %, or less than or equal to 5 wt % versus the total weight of the base portion. Combinations of the above-referenced ranges are also possible (e.g., greater than or equal to 10 wt % and less than or equal to 100 wt %, greater than or equal to 80 wt % and less than or equal to 100 wt %). Other ranges are also possible. In an exemplary embodiment, the base portion substantially comprises only the solid therapeutic agent.

In certain embodiments, the solid therapeutic agent is present in the tip in an amount of greater than or equal to 0 wt %, greater than or equal to 5 wt %, greater than or equal to 10 wt %, greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 90 wt %, greater than or equal to 95 wt %, greater than or equal to 98 wt %, or greater than or equal to 99 wt % versus the total weight of the tip. In some embodiments, the solid therapeutic agent is present in the tip in an amount of less than or equal to 100 wt %, less than or equal to 99 wt %, less than or equal to 98 wt %, less than or equal to 95 wt %, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, less than or equal to 20 wt %, less than or equal to 10 wt %, or less than or equal to 5 wt % versus the total weight of the tip. Combinations of the above-referenced ranges are also possible (e.g., greater than or equal to 10 wt % and less than or equal to 100 wt %, greater than or equal to 80 wt % and less than or equal to 100 wt %). Other ranges are also possible. In an exemplary embodiment, the tip substantially comprises only the solid therapeutic agent. In another exemplary embodiment, the tip substantially comprises no solid therapeutic agent.

In certain embodiments, the tissue interfacing component comprises greater than or equal to 10 wt % (e.g., greater than or equal to 80 wt %) solid therapeutic agent, regardless of the makeup of the base portion and/or the tip, versus the total weight of the tissue interfacing component.

In some embodiments, the tissue interfacing component comprises greater than or equal to 0.1 mg, greater than or equal to 0.5 mg, greater than or equal to 0.8 mg, greater than or equal to 1 mg, greater than or equal to 1.5 mg, greater than or equal to 2 mg, greater than or equal to 2.5 mg, greater than or equal to 3 mg, greater than or equal to 4 mg, greater than or equal to 5 mg, greater than or equal to 7 mg, greater than or equal to 9 mg of therapeutic agent (e.g., solid therapeutic agent). In certain embodiments, the tissue interfacing component comprises less than or equal to 10 mg, less than or equal to 9 mg, less than or equal to 7 mg, less than or equal to 5 mg, less than or equal to 4 mg, less than or equal to 3 mg, less than or equal to 2.5 mg, less than or equal to 2 mg, less than or equal to 1.5 mg, less than or equal to 1 mg, less than or equal to 0.8 mg, less than or equal to 0.5 mg, or less than or equal to 0.2 mg of therapeutic agent. Combinations of the above-referenced ranges are also possible (e.g., greater than or equal to 0.1 mg and less than or equal to 10 mg). Other ranges are also possible.

In certain embodiments, at least a portion of the solid therapeutic agent (e.g., API) is associated with a base portion and/or one or more tips of the tissue interfacing component. For example, in some embodiments, the solid therapeutic agent and second material (if present) are distributed substantially homogeneously in the tissue interfacing component (e.g., in the base portion and/or in the tip). In some cases, the solid therapeutic agent may be a coating (e.g., disposed on at least a portion of the tip(s)) such that the tissue interfacing component comprises greater than or equal to 10 wt % solid therapeutic agent versus the total weight of the tissue interfacing component.

In some embodiments, the tissue interfacing component may comprise an additional coating. In some embodiments, the additional coating may comprise a material configured to e.g., slow the dissolution time relative to the dissolution of the tissue interfacing component without said additional coating. Non-limiting examples of suitable additional coating materials including Zn, Al, Mg, polymers (e.g., enteric polymers, polycaprolactone, parylene, hypromellose, polyethylene glycol), and combinations thereof. Other additional coating materials are also possible. In some embodiments, the additional coating may be configured such that the solid therapeutic agent is released over a particular amount of time. For example, in some embodiments, the additional coating is configured such that the solid therapeutic agent is released in less than or equal to 6 months, less than or equal to 3 months, less than or equal to 1 month, less than or equal to 2 weeks, less than or equal to 1 week, less than or equal to 4 days, less than or equal to 2 days, less than or equal to 1 day, less than or equal to 12 hours, less than or equal to 6 hours, less than or equal to 3 hours, less than or equal to 1 hour, less than or equal to 30 minutes, less than or equal to 15 minutes, less than or equal to 10 minutes, less than or equal to 5 minutes, or less than or equal to 2 minutes (e.g., upon exposure of the additional coating to a fluid such as gastric fluid). In certain embodiments, the additional coating is configured such that the solid therapeutic agent is released in greater than or equal to 1 minute, greater than or equal to 2 minutes, greater than or equal to 5 minutes, greater than or equal to 10 minutes, greater than or equal to 15 minutes, greater than or equal to 30 minutes, greater than or equal to 1 hour, greater than or equal to 3 hours, greater than or equal to 6 hours, greater than or equal to 12 hours, greater than or equal to 1 day, greater than or equal to 2 days, greater than or equal to 4 days, greater than or equal to 1 week, greater than or equal to 2 weeks, greater than or equal to 1 month, or greater than or equal to 3 months. Combinations of the above-referenced ranges are also possible (e.g., greater than or equal to 1 minute and less than or equal to 1 day, greater than or equal to 1 day and less than or equal to 2 weeks, greater than or equal to 1 week and less than or equal to 6 months). Other ranges are also possible.

In certain embodiments, the tissue interfacing component comprises a plurality of microneedles comprising the solid therapeutic agent and the second material (if present).

In some embodiments, at least a portion of the solid therapeutic agent is present on at least a surface of the tip. In certain embodiments, at least a portion of the second material is present on at least a surface of the tip.

The tissue-interfacing components described herein may be formed using any suitable method. In some embodiments, the tissue-interfacing component is formed by providing the solid therapeutic agent and the second material (if present) and centrifuging and/or compressing, using at least 1 MPa of pressure, the solid therapeutic agent and a second material together to form the tissue interfacing component. In some embodiments, the second material (if present) and the solid therapeutic agent is heated to form the tissue interfacing component.

In some embodiments, the tissue-interfacing component is formed using at least 1 MPa of pressure, at least 2 MPa of pressure, at least 3 MPa of pressure, at least 5 MPa of pressure, at least 7 MPa of pressure, at least 10 MPa of pressure, at least 12 MPa of pressure, at least 15 MPa of pressure, at least 20 MPa of pressure, at least 25 MPa of pressure, at least 30 MPa of pressure, at least 40 MPa of pressure, at least 50 MPa of pressure, at least 75 MPa of pressure, at least 150 MPa of pressure, at least 300 MPa of pressure, at least 600 MPa of pressure, at least 900 MPa of pressure, at least 1 GPa of pressure, or at least 1.2 GPa of pressure. In some embodiments, the tissue-interfacing component is formed using less than or equal to 1.4 GPa of pressure, less than or equal to 1.2 GPa of pressure, less than or equal to 1 GPa of pressure, less than or equal to 900 MPa of pressure, less than or equal to 600 MPa of pressure, less than or equal to 300 MPa of pressure, less than or equal to 150 MPa of pressure, less than or equal to 100 MPa of pressure, less than or equal to 75 MPa of pressure, less than or equal to 50 MPa of pressure, less than or equal to 40 MPa of pressure, less than or equal to 30 MPa of pressure, less than or equal to 25 MPa of pressure, less than or equal to 20 MPa of pressure, less than or equal to 15 MPa of pressure, less than or equal to 12 MPa of pressure, less than or equal to 10 MPa of pressure, less than or equal to 7 MPa of pressure, less than or equal to 5 MPa pressure, less than or equal to 3 MPa of pressure, or less than or equal to 2 MPa of pressure. Combinations of the above-referenced ranges are also possible (e.g., at least 1 MPa of pressure and less than or equal to 100 MPa of pressure, at least 20 MPa of pressure and less than or equal to 100 MPa of pressure, at least 100 MPa and less than or equal to 1.4 GPa of pressure). Other ranges are also possible.

In certain embodiments, the tissue interfacing component may be formed at a particular temperature. For example, the tissue interfacing component, in some embodiments, is formed at a temperature of greater than or equal to 50° C., greater than or equal to 60° C., greater than or equal to 70° C., greater than or equal to 80° C., greater than or equal to 90° C., greater than or equal to 100° C., or greater than or equal to 120° C. In some embodiments, the tissue interfacing component is formed at a temperature of less than or equal to 150° C., less than or equal to 130° C., less than or equal to 120° C., less than or equal to 110° C., less than or equal to 100° C., less than or equal to 90° C., less than or equal to 80° C., less than or equal to 70° C., or less than or equal to 60° C. Combinations of the above referenced ranges are also possible (e.g., greater than or equal to 50° C. and less than or equal to 130° C.). Other temperatures and ranges are also possible.

Advantageously, the tissue interfacing component may have desirable mechanical properties (e.g., Young's elastic modulus) e.g., such that the tissue interfacing component may suitably puncture tissue of the gastrointestinal tract. In some embodiments, the Young's elastic modulus of the tissue interfacing component is greater than or equal to 100 MPa (e.g., greater than or equal to 125 MPa, greater than or equal to 150 MPa, greater than or equal to 175 MPa, greater than or equal to 200 MPa, greater than or equal to 250 MPa, greater than or equal to 300 MPa, or greater than or equal to 350 MPa). In certain embodiments, the tissue interfacing component has a Young's elastic modulus of less than or equal to 400 MPa, less than or equal to 350 MPa, less than or equal to 300 MPa, less than or equal to 250 MPa, less than or equal to 200 MPa, less than or equal to 175 MPa, less than or equal to 150 MPa, or less than or equal to 125 MPa. Combinations of the above-referenced ranges are also possible (e.g., greater than or equal to 100 MPa and less than or equal to 250 MPa, greater than or equal to 100 MPa and less than or equal to 400 MPa). Other ranges are also possible.

In some cases, the tissue interfacing component may be configured to penetrate a particular depth into human gastrointestinal mucosal tissue at a particular force. For example, the tissue interfacing component may be configured to penetrate greater than or equal to 1 mm (e.g., greater than or equal to 2 mm, greater than or equal to 3 mm, or greater than or equal to 4 mm) with a force of less than or equal to 20 N (e.g., less than or equal to less than or equal to 10 N, less than or equal to 5 N, less than or equal to 1 N, less than or equal to 500 mN, less than or equal to 100 mN, less than or equal to 50 mN, less than or equal to 20 mN, less than or equal to 15 mN, less than or equal to 10 mN, less than or equal to 5 mN).

In some embodiments, the second material comprises a polymerizable monomer and/or a polymer. In certain embodiments, the second material is biodegradable. Non-limiting examples of suitable materials for the second material include polyethylene glycol, polyvinylpyrrolidone, polylactic acid, polysaccharides (e.g., maltose, lactose, starch, cellulose), acacia, methyl cellulose, gelatin, tragacanth, clays, HPMC, stearic acid, sodium stearate, magnesium stearate, talc, polyethylene glycol, mineral oil, preservatives (e.g., phenol, paraben, cetrimide), antioxidants (e.g., gallic acid, tocopherol), derivatives thereof, and combinations thereof.

In some embodiments, the tissue interfacing component comprises a coating having a yield strength of greater than or equal to 50 MPa (e.g., greater than or equal to 60 MPa, greater than or equal to 70 MPa, or greater than or equal to 80 MPa).

In some embodiments, the coating may be comprised of a thin film metal, a ceramic or a Diamond Like Coating (DLC). In some embodiments, the tissue interfacing component does not comprise a coating.

In some embodiments, the coating may be comprised of a corrodible material (e.g. iron, zinc, aluminum or alloys) such that when the coating comes in contact with the physiological environment it will disintegrate and present the therapeutic agent. In certain embodiments, the coating may comprise a polymer such as parylene, as described herein.

In some cases, the tissue interfacing component may be configured to deliver a particular amount of active pharmaceutical agent per square centimeter of tissue of a subject. For example, in some embodiments, the tissue interfacing component is configured to deliver greater than or equal to 0.01 µg, greater than or equal to 0.05 µg, greater than or equal to 0.1 µg, greater than or equal to 0.2 µg, greater than or equal to 0.5 µg, greater than or equal to 0.7 µg, greater than or equal to 1 µg, greater than or equal to 2 µg, greater than or equal to 5 µg, or greater than or equal to 10 µg of pharmaceutical agent per square centimeter of tissue of the subject proximate the penetration location of the tissue interfacing component. In certain embodiments, the tissue interfacing component is configured to deliver less than or equal to 20 µg, less than or equal to 5 µg, less than or equal to 2 µg, less than or equal to 1 µg, less than or equal to 0.7 µg, less than or equal to 0.5 µg, less than or equal to 0.2 µg, less than or equal to 0.1 µg, or less than or equal to 0.05 µg of pharmaceutical agent per square centimeter of tissue. Combinations of the above-referenced ranges are also possible (e.g., greater than or equal to 1 µg and less than or equal to 20 m). In some embodiments, the tissue interfacing component is configured to deliver greater than or equal to 1 µg of pharmaceutical agent per square centimeter of tissue of the subject over any suitable time period (e.g., in greater than or equal to 0.1 seconds, in greater than or equal to 0.5 seconds, in greater than or equal to 1 second, in greater than or equal to 5 seconds, in greater than or equal to 30 seconds, greater than or equal to 1 minute, greater than or equal to 5 minutes, 10 minutes, greater than or equal to 30 minutes, greater than or equal to 1 hour, greater than or equal to 4 hours, greater than or equal to 24 hours, greater than or equal to 48 hours, greater than or equal to 72 hours, greater than or equal to 96 hours, greater than or equal to 120 hours, greater than or equal to 144 hours, greater than or equal to 168 hours).

In certain embodiments, the tissue interfacing component comprises a binder (e.g., in some cases, the second material is a binder). Non-limiting examples of suitable binders include sugar such as sorbitol and sucrose, gelatin, polymers such as polyvinyl alcohol (PVA), polyethylene glycol (PEG), polycaprolactone (PCL), and polyvinylpyrrolidone (PVP), and polymers comprising ethanol or other Class 3 organic solvents (e.g., acetic acid, heptane, acetone, formic acid, isobutyl acetate, etc.).

In an exemplary embodiment, the article comprises greater than or equal to 80 wt % solid active pharmaceutical agent versus the total article weight. In certain embodiments, the article comprises greater than or equal to 1 mg of active pharmaceutical agent. According to some embodiments, the pharmaceutical agent is selected from the group consisting of bacteriophage, DNA, mRNA, insulin, human growth hormone, monoclonal antibodies, adalimumab, epinephrine, and ondansetron. In certain exemplary embodiments, the active pharmaceutical agent is cast into a mold to form the article. In some embodiments, the mold is centrifuged. According to certain embodiments, the article further comprises a binder. In certain embodiments, the binder comprises sugar such as sorbitol or sucrose, gelatin, polymer such as PVA, PEG, PCL, PVA, or PVP, and/or ethanol. According to certain embodiments, the article has a Young's elastic modulus of greater than or equal to 100 MPa. In some embodiments, the article is configured to penetrate at least 1 mm into human gastrointestinal mucosal tissue with a force of less than or equal to 20 mN. According to certain embodiments, the article is configured to deliver at least 1 mg of pharmaceutical agent per square centimeter of a tissue of a subject, and/or the article comprises greater than or equal to 1 mg of active pharmaceutical agent per square centimeter.

Certain exemplary embodiments are related to a method of forming the article, wherein the method comprises introducing, into a mold, a composition comprising greater than 80 wt % solid pharmaceutical agent versus the total weight of the composition, applying greater than or equal to 1 MPa of pressure to the composition, and heating the composition to a temperature of at least 70° C. for at least 1 minute. As used herein, the term "active pharmaceutical ingredient" (also referred to as a "drug" or "therapeutic agent") refers to an agent that is administered to a subject to treat a disease, disorder, or other clinically recognized condition, or for prophylactic purposes, and has a clinically significant effect on the body of the subject to treat and/or prevent the disease, disorder, or condition.

Agents

According to some embodiments, the composition and methods described herein are compatible with one or more therapeutic, diagnostic, and/or enhancement agents, such as drugs, nutrients, microorganisms, in vivo sensors, and tracers. In some embodiments, the active substance, is a therapeutic, nutraceutical, prophylactic or diagnostic agent. While much of the specification describes the use of therapeutic agents, other agents listed herein are also possible.

Agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals, Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, non-steroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, anti(retro)viral agents like entecavir, dolutegravir, rilpivirine, and cabotegravir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In certain embodiments, the active substance is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, anti-epileptics, antipsychotic agents, neuroprotective agents, anti-proliferatives, such as anti-cancer agents, antihistamines, antimigraine drugs, hormones, prostaglandins, anti-microbials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery device. These may be vitamins, supplements such as calcium or biotin, or natural ingredients such as plant extracts or phytohormones.

In some embodiments, the therapeutic agent is one or more antimalarial drugs. Exemplary antimalarial drugs include quinine, lumefantrine, chloroquine, amodiaquine, pyrimethamine, proguanil, chlorproguanil-dapsone, sulfonamides such as sulfadoxine and sulfamethoxypyridazine, mefloquine, atovaquone, primaquine, halofantrine, doxycycline, clindamycin, artemisinin and artemisinin derivatives. In some embodiments, the antimalarial drug is artemisinin or a derivative thereof. Exemplary artemisinin derivatives include artemether, dihydroartemisinin, arteether and artesunate. In certain embodiments, the artemisinin derivative is artesunate.

In another embodiment, the therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell recepotors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In certain embodiments, the therapeutic agent is a hormone or derivative thereof. Non-limiting examples of hormones include insulin, growth hormone (e.g., human growth hormone), vasopres sin, melatonin, thyroxine, thyrotropin-releasing hormone, glycoprotein hormones (e.g., luteinzing hormone, follicle-stimulating hormone, thyroid-stimulating hormone), eicosanoids, estrogen, progestin, testosterone, estradiol, cortisol, adrenaline, and other steroids.

In some embodiments, the therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In some embodiments, the therapeutic agent is selected from the group consisting of active pharmaceutical agents such as insulin, nucleic acids, peptides, bacteriophage, DNA, mRNA, human growth hormone, monoclonal antibodies, adalimumab, epinephrine, GLP-1 Receptor agoinists, semaglutide, liraglutide, dulaglitide, exenatide, factor VIII, small molecule drugs, progrstin, vaccines, subunit vaccines, recombinant vaccines, polysaccharide vaccines, and conjugate vaccines, toxoid vaccines, influenza vaccine, shingles vaccine, prevnar pneumonia vaccine, mmr vaccine, tetanus vaccine, hepatitis vaccine, HIV vaccine Ad4-env Clade C, HIV vaccine Ad4-mGag, dna vaccines, ma vaccines, etanercept, infliximab, filgastrim, glatiramer acetate, rituximab, bevacizumab, any molecule encapsulated in a nanoparticle, epinephrine, lysozyme, glucose-6-phosphate dehydrogenase, other enzymes, certolizumab pegol, ustekinumab, ixekizumab, golimumab, brodalumab, gusellu,ab, secikinumab, omalizumab, tnf-alpha inhibitors, interleukin inhibitors, vedolizumab, octreotide, teriperatide, crispr cas9, insulin glargine, insulin detemir, insulin lispro, insulin aspart, human insulin, antisense oligonucleotides, and ondansetron.

In an exemplary embodiment, the therapeutic agent is insulin.

In some embodiments, the tissue-interfacing component described herein comprises two or more types of therapeutic agents.

In certain embodiments, the therapeutic agent is present in the tissue interfacing component at a concentration such that, upon release from the tissue interfacing component, the therapeutic agent elicits a therapeutic response.

In some cases, the therapeutic agent may be present at a concentration below a minimal concentration generally associated with an active therapeutic agent (e.g., at a microdose concentration). For example, in some embodiments, the tissue interfacing component comprises a first therapeutic agent (e.g., a steroid) at a relatively low dose (e.g., without wishing to be bound by theory, low doses of therapeutic agents such as steroids may mediate a subject's foreign body response(s) (e.g., in response to contact by a tissue interfacing components) at a location internal to a subject). In some embodiments, the concentration of the therapeutic agent is a microdose less than or equal to 100 μg and/or 30 nMol. In other embodiments, however, the therapeutic agent is not provided in a microdose and is present in one or more amounts listed above.

In some embodiments, the tissue-interfacing component comprises a self-actuating component. Such self-actuating tissue interfacing components are generally described in a co-owned U.S. Provisional Application Ser. No. 62/507,653, entitled "SELF-ACTUATING ARTICLES" filed on May 17, 2017 which is incorporated herein by reference in its entirety.

In some embodiments, the tissue-interfacing component is administered to a subject (e.g., orally). In certain embodiments, the article may be administered orally, rectally, vaginally, nasally, or uretherally. In certain embodiments, the tissue-interfacing component (e.g., and/or the API contained therein) is administered by contacting the skin of a subject with the component. In an exemplary embodiment, the tissue-interfacing component (e.g., and/or the API contained therein) is administered by contacting the buccal tissue (e.g., lip, palatal area, cheek, sublingual, tongue) of a subject with the component. In yet another exemplary embodiment, the tissue-interfacing component is administered orally and, upon reaching a location internal the subject (e.g., the GI tract such as the colon, the duodenum, the ileum, the jejunum, the stomach, the buccal space, the esophagus, etc.), the tissue-interfacing component interfaces (e.g., contacts) with the tissue of the subject at the location internal the subject and at least partially penetrates the tissue. In certain embodiments, at least a portion of the tissue-interfacing component penetrates the tissue of the subject and at least a portion of the support material and/or the active pharmaceutical agent dissolves into the tissue of the subject.

Advantageously, administration of a tissue-interfacing component having a relatively high loading of API to the GI tract may permit more effective delivery of the API as compared to traditional methods. For example, without wishing to be bound by theory, delivering a drug via an injection to the GI tract has been shown to have a higher bioavailability compared to other methods.

In some embodiments, the system comprises a self-righting article (e.g., configured to localize to a location internal to a subject at a particular orientation), a self-actuating component (e.g., configured to activate under a particular set of conditions e.g., upon exposure to a fluid such as gastrointestinal fluid), a tissue-interfacing component associated with the self-actuating component, and an API associated with the tissue-interfacing component. In certain embodiments, the system comprises a self-righting article, a self-actuating component, and a tissue interfacing component associated with the self-actuating component. In some embodiments, the system comprises a self-actuating component and a tissue interfacing component associated with the self-actuating component. In certain embodiments, the system comprises a self-righting article and an API associated with the self-righting article. In some embodiments, the system comprises a tissue interfacing component and an API associated with the tissue interfacing component. In some embodiments, the system comprises a self-actuating component, a tissue interfacing component associated with the self-actuating component, and an API associated with the tissue interfacing component. Self-righting articles, self-actuating components, tissue interfacing components, and APIs and related configurations are described above and herein.

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the self-righting article.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

EXAMPLES

The following examples are intended to illustrate certain embodiments described herein, including certain aspects of the present invention, but do not exemplify the full scope of the invention.

Example 1—Self-Righting Article

A self-righting article consisting of a specific shape and/or density distribution, optionally, with the capacity for encapsulation in standard '000,' '00,' or potentially smaller or larger capsules are provided. For example, the distribution of density and/or shape may be such that:
1. The design has only one stable point and one unstable point so that it will always right itself to a single configuration and orientation;
2. The design of the article has a relatively low righting time to its stable configuration from every possible orientation;
3. The design minimizes the destabilizing effects felt from forces in the GI tract such as fluid flow and muscle contractions; and/or
4. The design allows for the loading of articles of various shapes and weights into the system via hollow crevices created in specific locations on the article.

In some cases, the article shape originates from a smooth curve that is drawn within the two right quadrants of a Cartesian plane and rotated about the y axis. The shape has several noticeable characteristics. It possesses a flat bottom perpendicular to the y axis moving into a high curvature corner and then slowly lowers its curvature as the curve continues. The flat bottom section of the curve may help to satisfy the third specification for the article. Because the bottom is flat and is surrounded by steep corners, a larger force is required to push the article onto its side. This is similar to the way that an ellipsoid will wobble when pushed but a cube will not.

The rest of the curve may be is optimized in a way to satisfy the first and second specifications using the equations below. The righting times of the article are calculated from the angular kinematic equation:

$\Delta\theta = \omega t + \frac{1}{2}\alpha t^2$ where $\omega$ is the angular velocity, t is time and $\alpha$ is angular acceleration. The angular acceleration is calculated from the torques generated by the gravitational and buoyant forces acting on the article. $\alpha = \tau/I$ where $\tau$ is torque and I is moment of inertia. Torque is determined from the cross product between the force and distance vectors: $\tau = \|d \otimes F\| = d*F*\sin\theta$) where d is a distance vector from the center of mass (for gravity) or center of volume (for buoyancy) to the edge point of the curve touching the resting surface, F is the force vector in the direction of the force generated, and $\theta$ is the angle between those two vectors.

The article can be made, in some cases, of two different materials: one with a high density and another with a low density. The ratio of the densities is defined so that the center of mass of the shape is located at the origin of the coordinate system. The lower half of the plane consists of the high density material while the upper portion of the plane consists of the low density material. In order to keep the material densities realizable from currently available materials, certain holes and modifications can be made to the original shape which are explained in the examples. These holes and modification are also utilized to house articles within the system, which are then taken into account when determining the densities of the other materials.

Once a 3D shape has been designed, it is possible to test the righting times from a given orientation by using the equations above. The weight and volume of the article determine the acting forces that determine the torque and are set by the densities of the materials as well as the generated curve. The distance and angle measurements used to determine the torque are determined solely by the generated curve. A curve is generated by drawing a smooth curve through a set of points in radial coordinates with the angle coordinate set. The code then varies the distance coordinates of the points until the minimum set of righting times is reached.

Example 2

Figure 7:
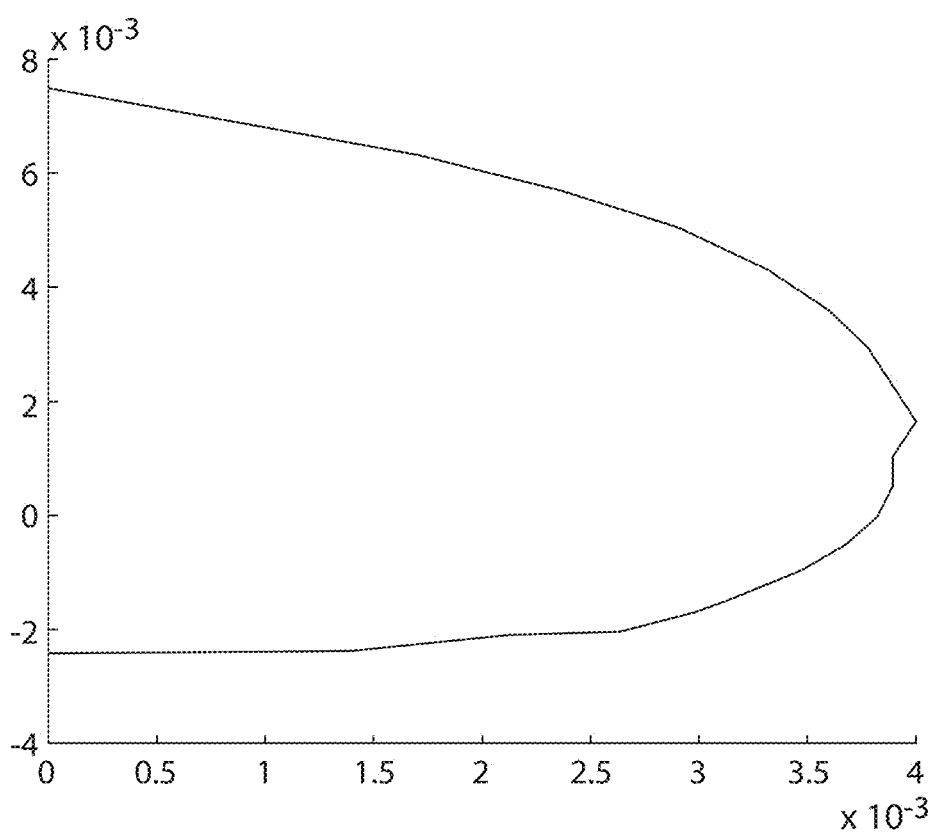
FIG. 7 is a plot of an exemplary self-righting shape graph, according to one set of embodiments.
Figure 8:
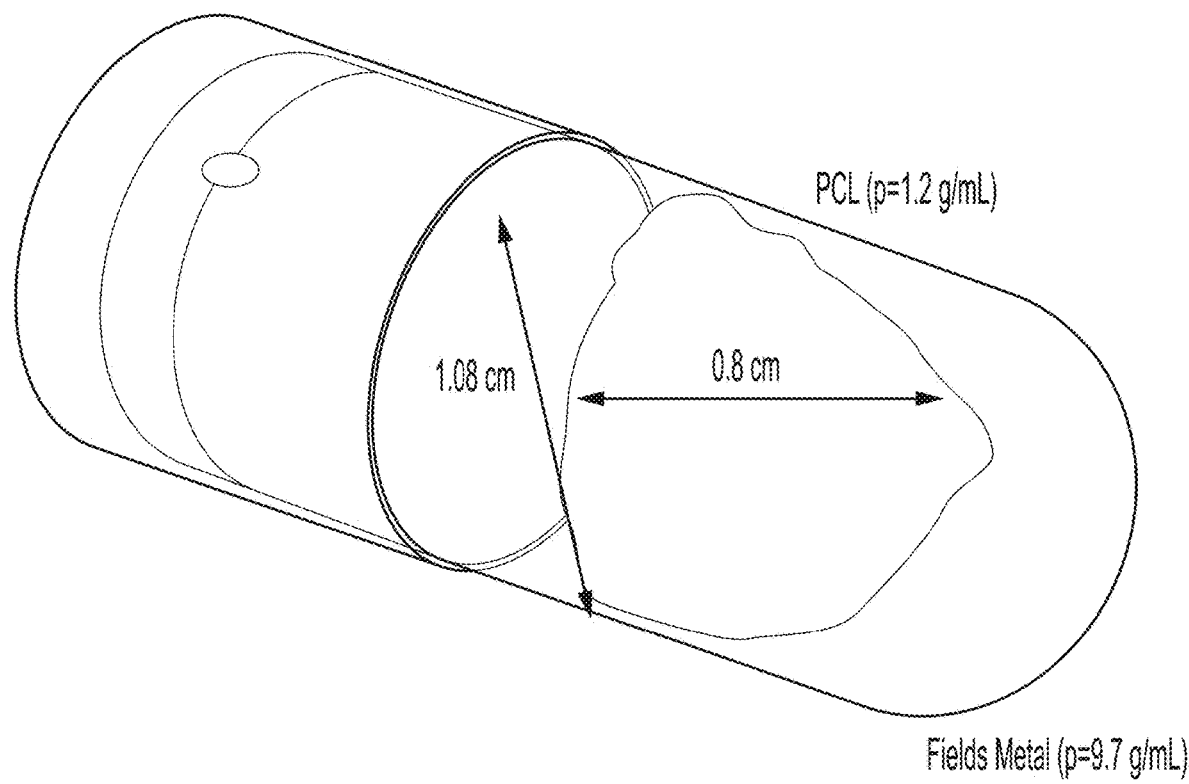
FIG. 8 is a photograph of an exemplary self-righting article inside a 000 capsule, according to one set of embodiments.
Figure 9:
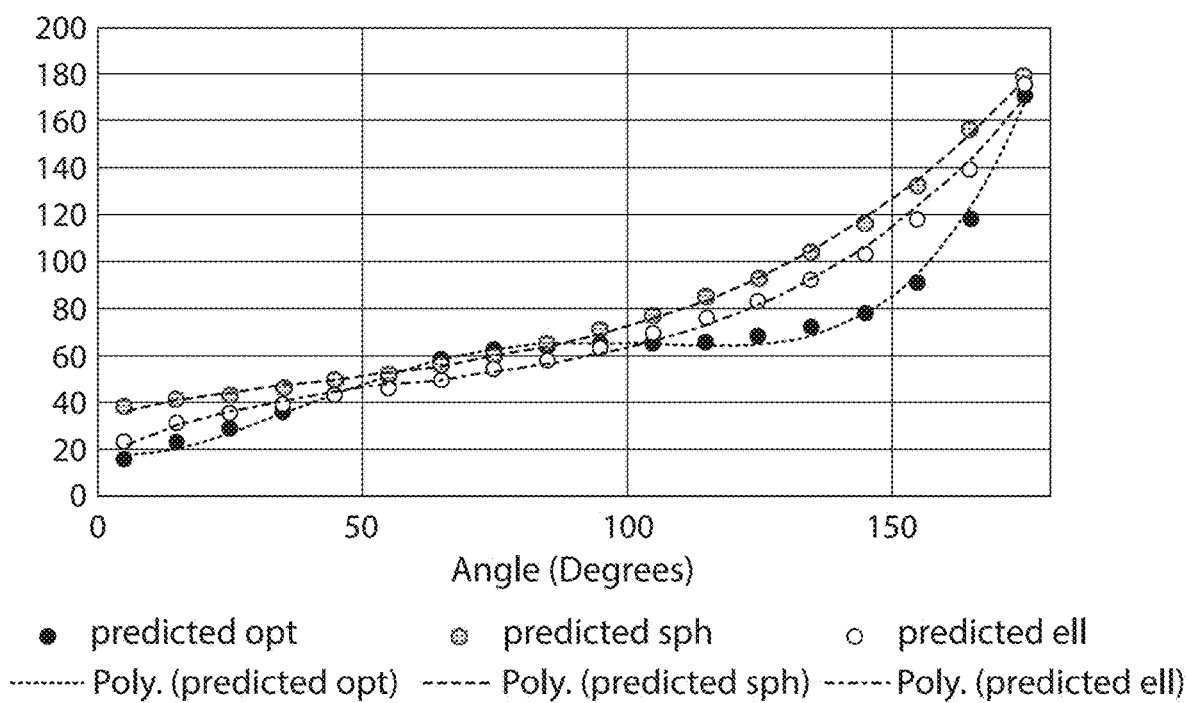
FIG. 9 is a plot of self-righting article speed of righting testing via computer models (predicted), according to one set of embodiments.
Figure 10:
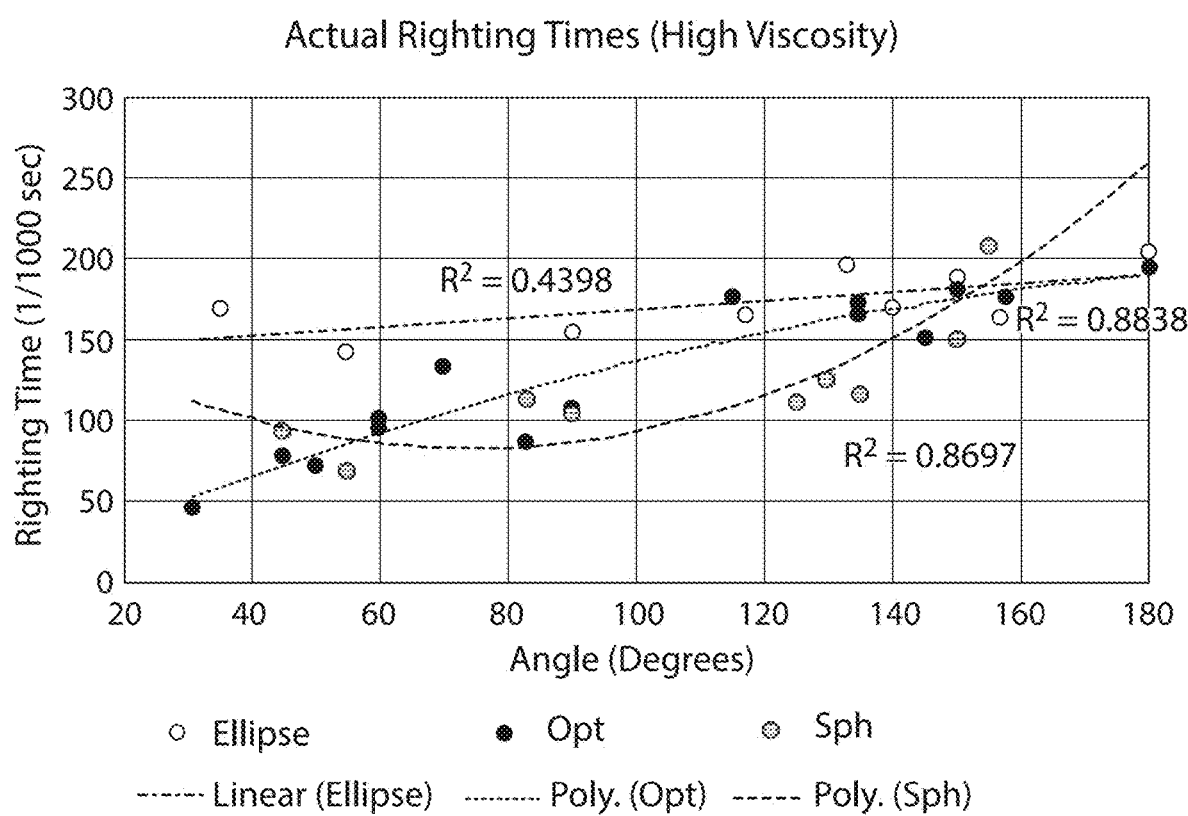
FIG. 10 is a plot of self-righting article speed of righting via high speed camera analysis (poly), according to one set of embodiments.
Figure 11:
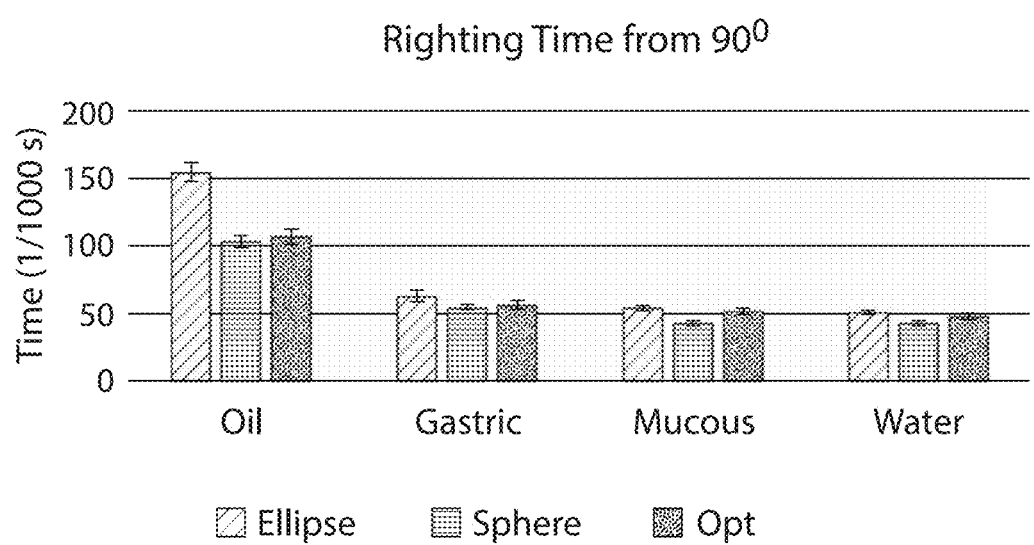
FIG. 11 is a plot of self-righting article speed of righting via high speed camera analysis (poly), according to one set of embodiments.
Figure 12:
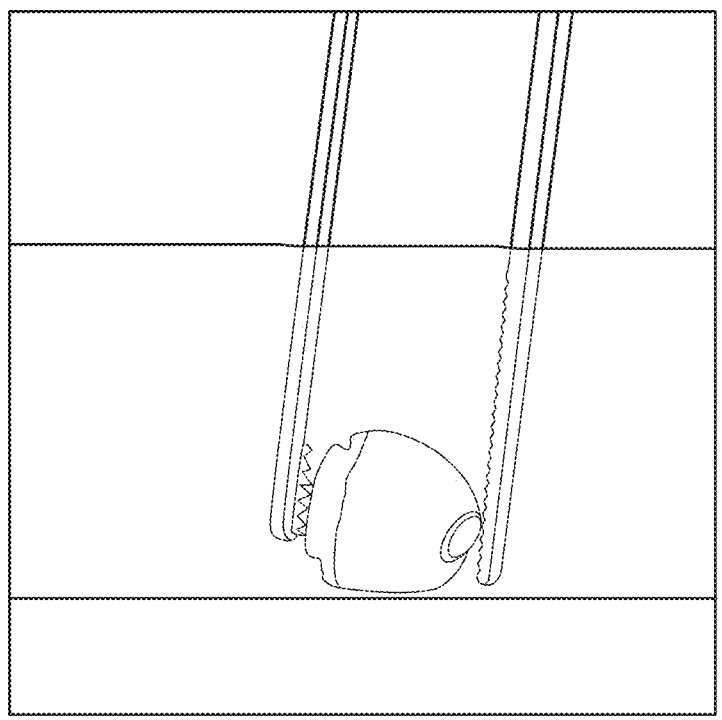
FIG. 12 is a photograph of an exemplary self-righting article, according to one set of embodiments.
Figure 13:
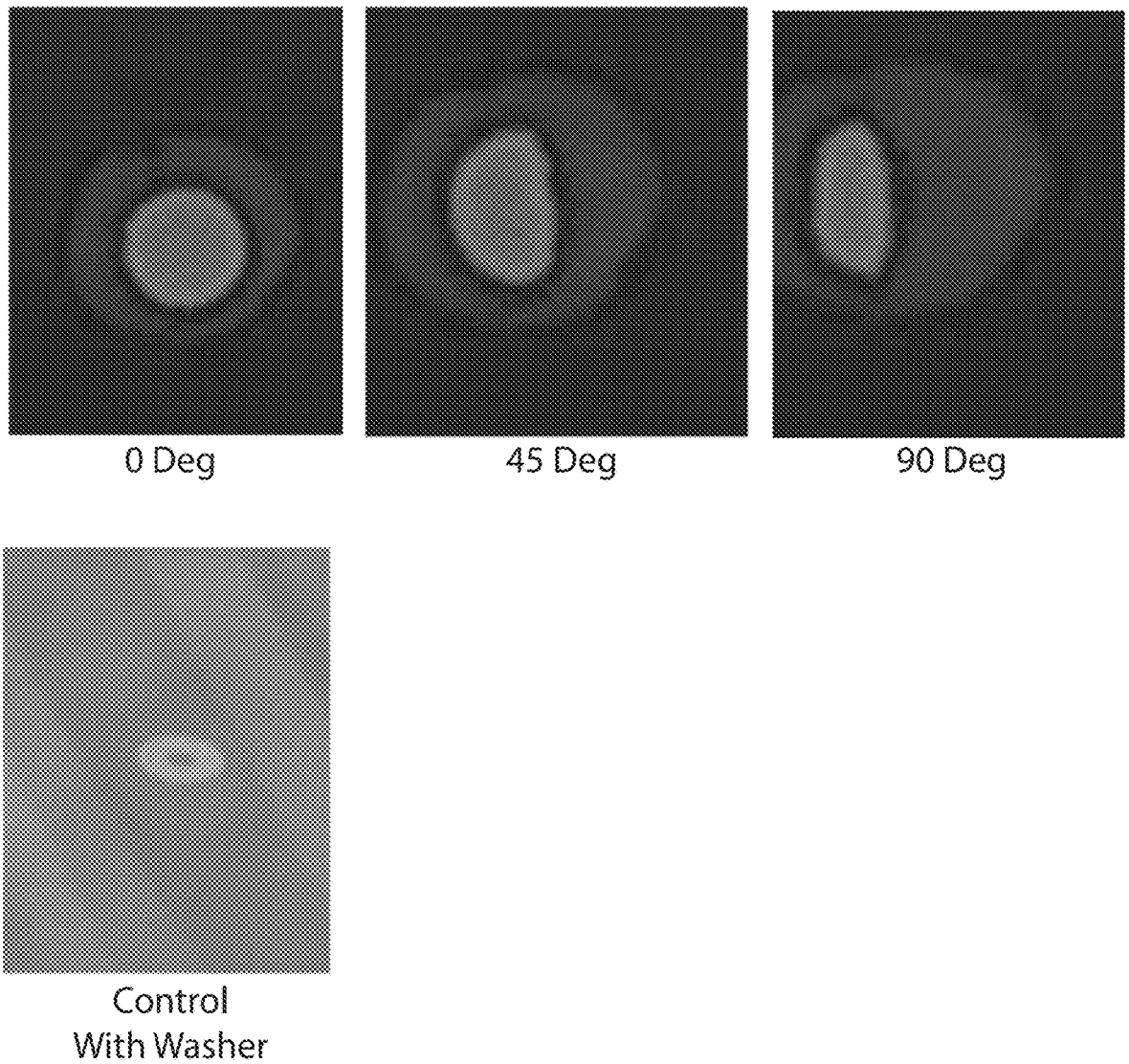
FIG. 13 is a series of x-ray images of an exemplary self-righting article at 0, 45, and 90 degrees of orientation compared to a control (washer), according to one set of embodiments.

A solid shape that is created by rotating a smooth curve defined by the around the y axis (Example: FIG. 7). The shape is made out of a biocompatible polymer (ex. PCL, PLA, PEG) in all areas with positive y values and a biocompatible ceramic (ex. Hydroxyapatite) or metal (ex. Stainless steel, field's metal) in all areas with negative y values. The ratio of the densities of the two materials should be between 6:1 and 16:1. The article can be scaled to any length, but the points in the FIG. 7 describe an object that can fit within a capsule (FIG. 8) such as a 000 capsule.

This shape has been tested against an ellipsoid and a sphere with the same volumes and similar dimension for its righting ability. The articles were tested under a high speed camera at 1000 FPS in several different liquids, including water, oil and gastric fluid, as well as on different surfaces, including plastic and porcine stomach tissue. The results (FIGS. 9-12) showed that the article had faster righting times overall, as well as faster righting times at angles close to the stable orientation. Since the article is most likely to start close to its stable orientation, this makes the article better than the other shapes.

The articles were also tested for their ability to stay righted by being placed on a tilting mixer. The mixer was set to tilt 15 degrees in each direction at 50 rpm. The article never left its stable orientation, while the sphere tilted 18 degrees from its optimal orientation and the ellipsoid tilted 31 degrees from its optimal orientation (FIGS. 13-16)

The article was also placed into a suspended full pig stomach in vitro using a plastic tube as an artificial esophagus and compared how many times it landed in the correct orientation when compared to a sphere made out of only PCL. Out of 60 trials for each of the articles done in water filled, oil filled or empty stomachs, it was found that the article having a shape as in FIG. 7 landed in the correct orientation every time while the sphere landed in the correct orientation only 25% of the time.

Figure 14:
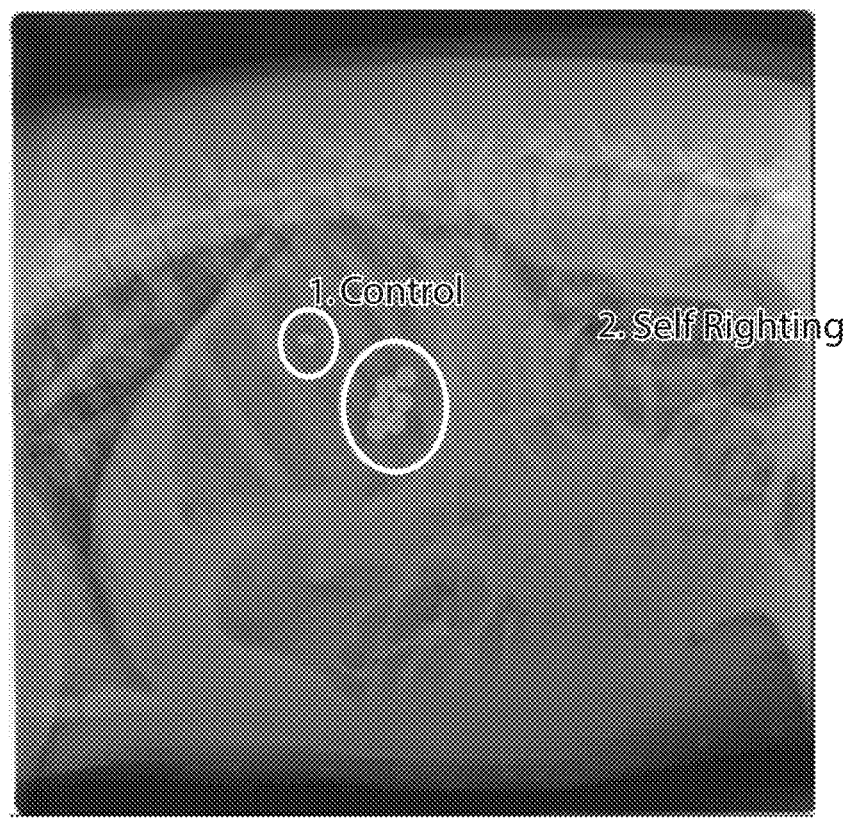
FIG. 14 is an x-ray photograph of an exemplary series of self-righting articles in the GI of a pig, according to one set of embodiments
Figure 15:
FIG. 15 is an endoscopy of an exemplary self-righting article in the GI of a pig, according to one set of embodiments.
Figure 16:
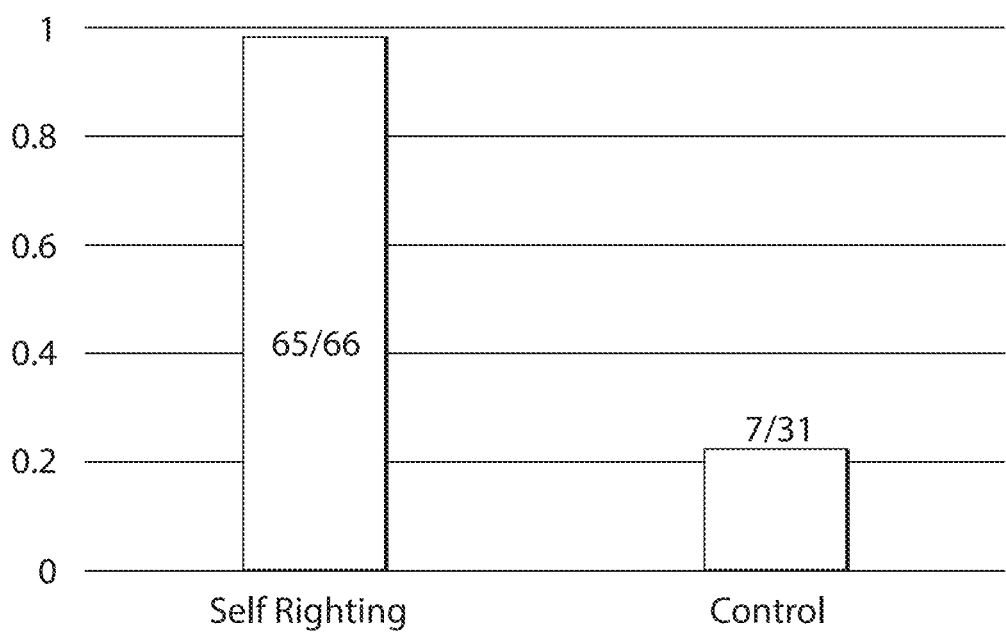
FIG. 16 is a plot of the fraction of articles righted, according to one set of embodiments.
Figure 17:
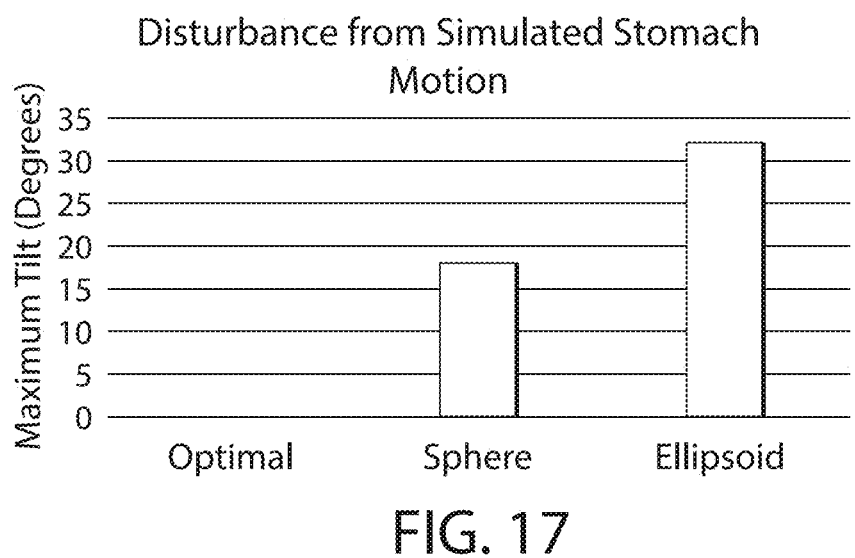
FIG. 17 is a plot of maximum tilt versus shape, according to one set of embodiments.
Figure 18:
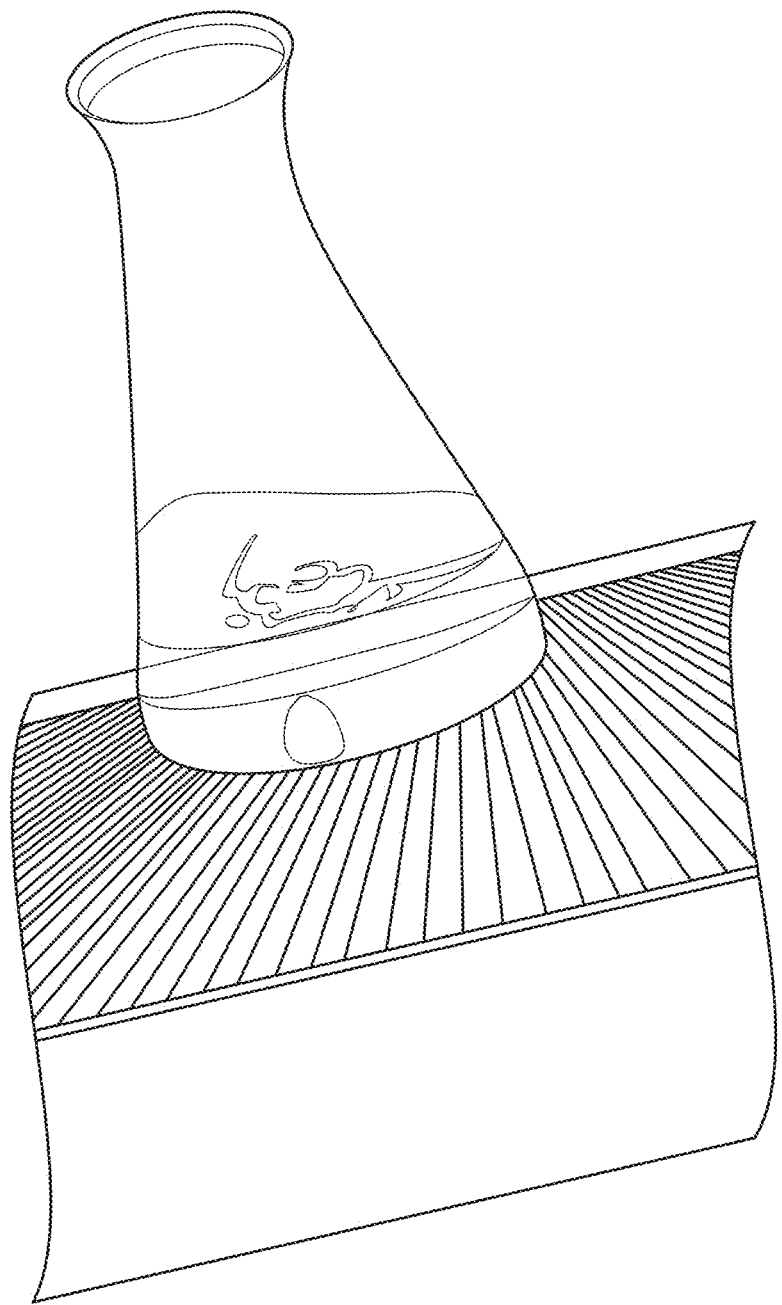
FIG. 18 is a photograph of a maximum tilt testing apparatus, according to one set of embodiments.

Additionally, a similar experiment was performed in vivo. 6 self-righting articles and 6 articles that did not self-right but were the same shape were fed to a sedated pig via a gastric tube. The pigs were then shaken vigorously to simulate walking. After shaking the pigs, they were placed under x-ray and counted the number of articles that remained in the correct orientation. These articles were identified by placing a piece of metal inside of them (FIG. 14). The self-righting articles already had a half sphere of metal on their lower half, which displayed as a full circle under x-ray when self-righted and as a waning moon when not self-righted. A circular washer was placed in the control articles and showed as a full circle when self-righted or as a warped oval when not righted. 65/66 self-righting trials showed the correct orientation after shaking, while only 7/31 control articles showed the correct orientation.

Example 3

Figure 19:
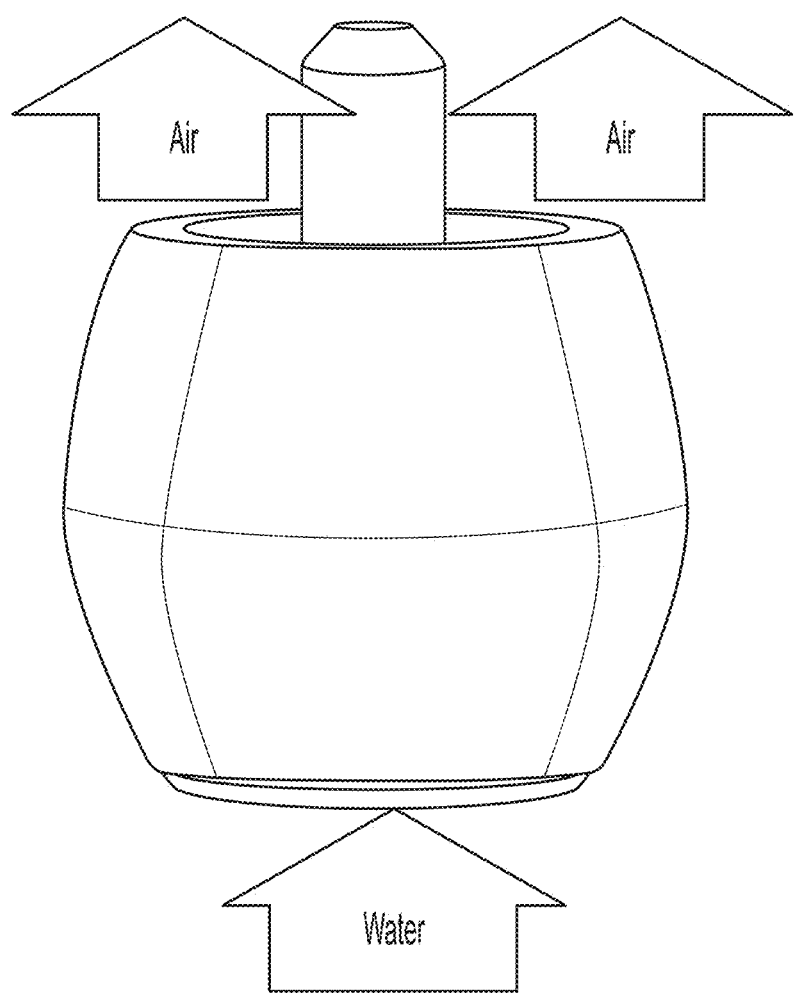
FIG. 19 is a photograph of an exemplary self-righting article comprising air/water vents, according to one set of embodiments.

An object with similar shape to that described in Example 2, but with holes, vents and slits built into the article. Such holes and slits can be used to allow fluid to enter the system or could be used to store articles within the system (FIG. 19). These slits can also be used to hollow out the article to keep the density ratios to reasonable values that can be realized using available materials. For example, by hollowing out the top section of an article, a higher density material can be used to fill in the remaining top areas; higher density materials are allowed, because the only constraints on the article are the outer shape and the center of mass. When making holes, the article should try to remain axisymmetric, or as close to axisymmetric as possible.

Such examples of these holes and slits include but are not limited to the following:

1. A cylinder with a radius less than the radius of the article that is centered at the y axis.
2. A conic section that is centered about the y axis which allows the radius to change as the radius of the system changes.
3. A vertical straight cut with a given width from the top or bottom of the system.
4. Any other sort of cut to the article which maintains the overall integrity of the system.

Example 4

An object with similar shape to that described in Examples 2 and 3, but with a drug delivery article built into the system. This article could be a drug loaded solid or hollow needle. It could be a hollow needle connected to a reservoir, or it could be a series of needles that are loaded or coated with a drug. Other drug delivery articles such as patches are possible as well.

In the example of needles, the needles could either be housed inside or outside of the system. When housed outside the system, they could be connected via an adhesive or embedded within the mold of the article. When housed inside the system, it could be housed within a hollowed out hole in the article.

The needle puncture could be passively actuated from the gravitational force of the article. In this implementation, the weight of the article could push the needles into the tissue.

Example 5

An object with similar shape to that described in Examples 2-4 but with a piece of electronics built into the system.

By adding a piece of electronics to the article in combination with the anchor, the article could be used as a gastro retentive mechanism for electronics. The sensor could have access to the tissue wall or the inside of the GI tract due to the directionality of the article. For example, a pH sensor attached to the bottom of the article would be able to read the pH of the stomach wall area or the inside stomach area depending on its placement on the system.

Example 6

Figure 20:
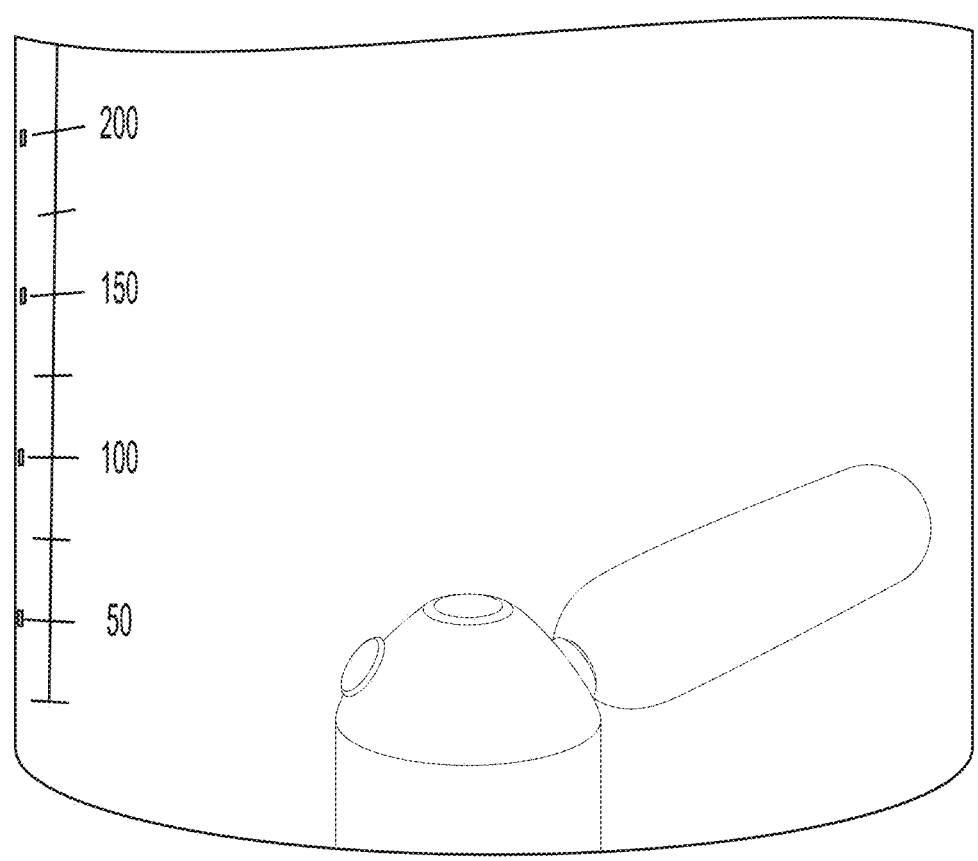
FIG. 20 is a photograph of an exemplary self-righting article comprising a magnetic portion, attached to a magnetic object, according to one set of embodiments.

An object with similar shape to that described in Examples 2-4 but with the ability to attach other articles to the system remotely (FIG. 20).

By adding an attractive and/or adhesive force to the walls of the system, a patient could be able to swallow other capsules filled with new articles or with drugs and have them aggregate together at the system. Such forces could be generated by a magnet, an adhesive, a vacuum or any number of other mechanisms.

For example, a magnet could be attached to the wall of the system as well as the wall of an electronic sensor. The patient could first swallow the self-righting system and have it anchor to the tissue wall as described in example 4. Then the patient could take a separate capsule containing an electronic sensor. The magnetic force generated between the two articles from the placed magnets would allow the two systems to attach. Because the self-righting system is anchored to the tissue wall, the electronic sensor will be able to remain in the stomach as well, even though it does not have any gastro retentive properties. This system could allow for any sort of article to become gastro retentive.

Example 7—Self-Actuating Article

Figure 22:
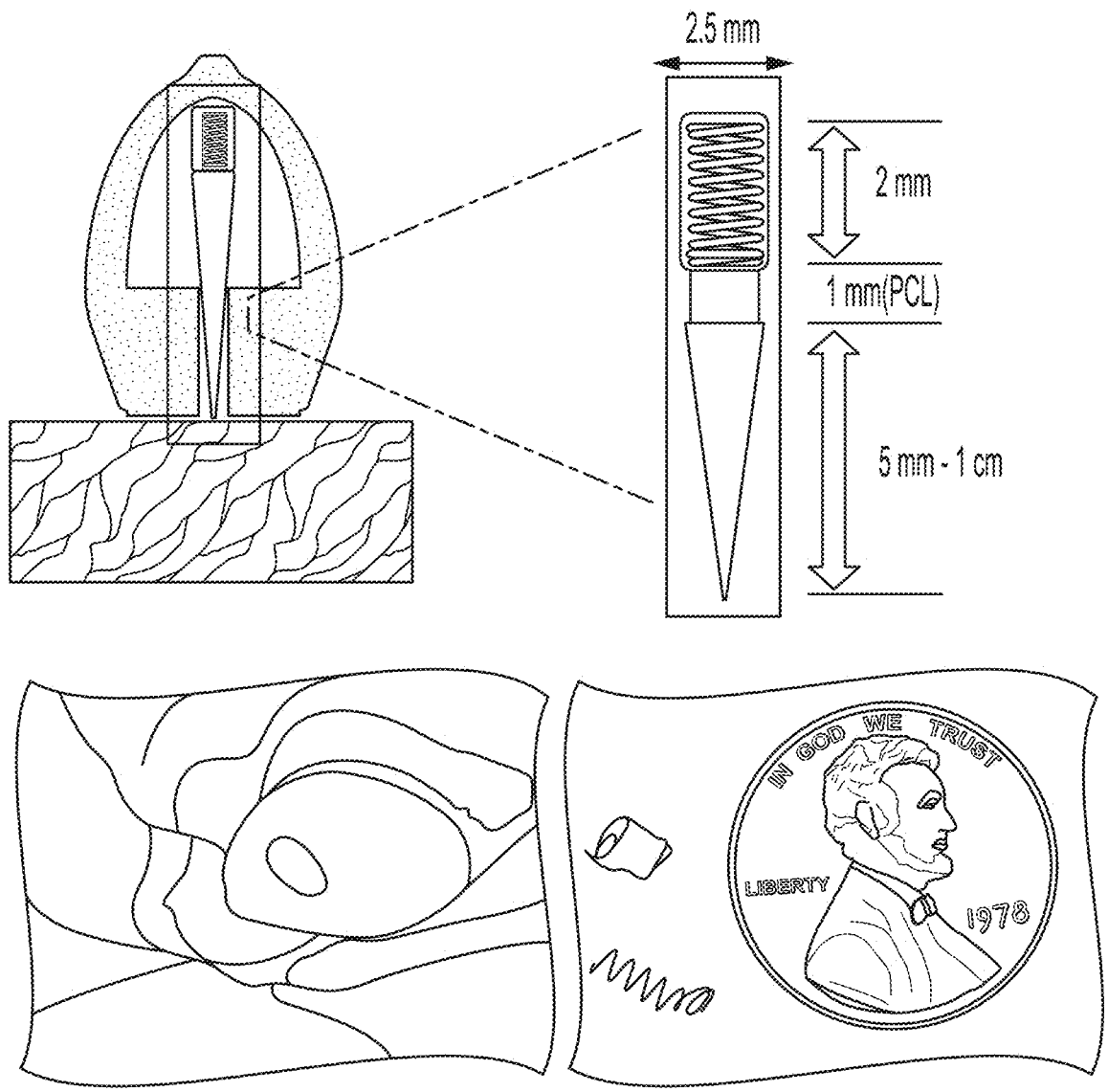
FIG. 22 is a schematic of an exemplary self-actuating article, according to one set of embodiments, a photograph of the article in vivo, and a photograph of the article as compared to an uncompressed spring, according to one set of embodiments.

The device could be actuated actively. This could include mechanisms such as shape memory nitinol, expanding elastomers, or compressed springs. The compressed spring could be immobilized in a solid biodegradable and biocompatible polymer or a sugar (ex. Sucrose, maltose), a mechanism which has been shown to work in vivo (FIG. 22). These mechanisms could then be housed within the hollowed out sections of the article or outside the article. Ways of anchoring the device to the system article but are not limited to magnets, tying knots, and applying adhesives.

Figure 23:
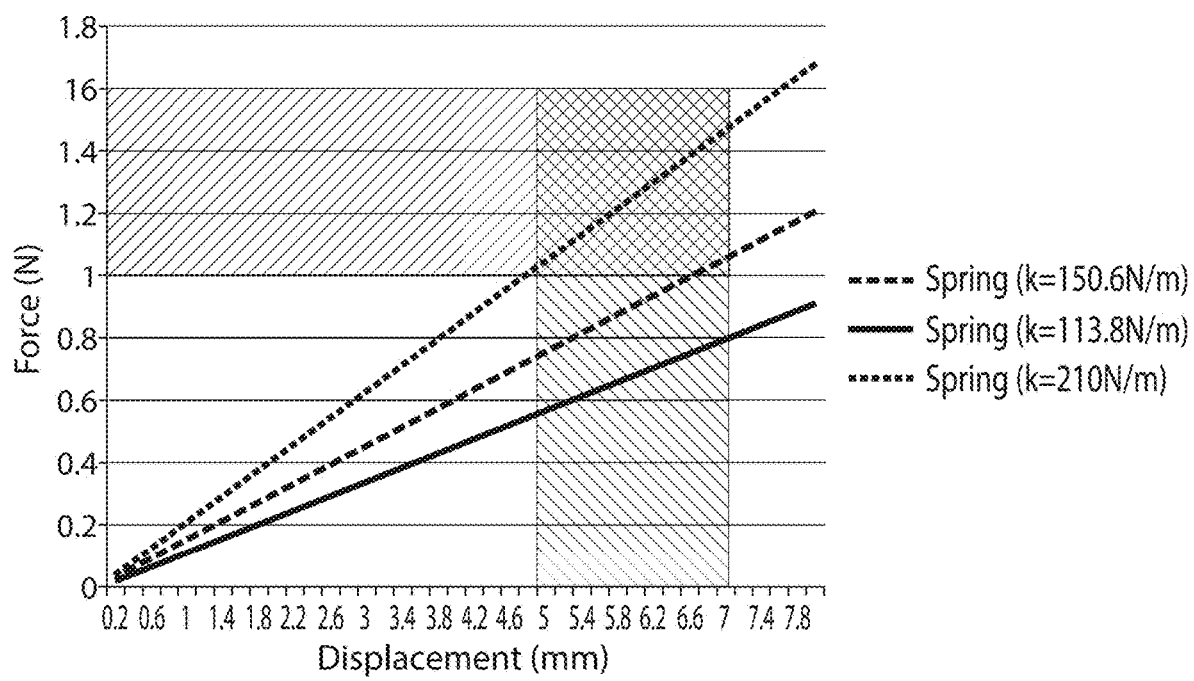
FIG. 23 is a plot of force versus displacement for various spring constants, according to one set of embodiments.

Delving further into the spring example, it may be desirable that the needle enter into the sub-mucosal layer of the GI tract in order to deliver drug, e.g., the needle should penetrate at least 1 mm into the tissue. If the needle penetrates more than 5 mm into the tissue, then the patient will risk perforation. For this reason, the spring may be compressed between 1-5 mm. Also, while the amount of force required to penetrate the GI tissue is generally low, on the order of 1-10 mN, it may take about 100 mN of force to enter into the muscular layer of the stomach in between the mucosal and sub-mucosal layer. In some cases, the spring will contain enough force when compressed that it will push on the tissue with a force of 100 mN plus a safety factor of 3×-10×. This means that the spring could, in some cases, have a spring constant of around 100-250 N/m (FIG. 23).

Additionally, the compressed spring may be encased in a material that can hold such a force. The material may also be brittle, such that e.g., the spring to break out of the material all at once. A brittle material such as (crystallized) sugar will generally crack quickly and completely once it experiences a given stress. Caramelized sucrose generally fractures under 0.1 Mpa of stress. If the compressed spring exerts 1 N of force on the sucrose coating it, then the sucrose coating may be at least 3.56 mm in diameter to contain the spring. Any more caramelized sucrose added to the coating acts could be used as a timing mechanism for the device (e.g., without wishing to be bound by theory—the thickness of the coating may be at least proportional to the time required to degrade the coating).

Figure 24:
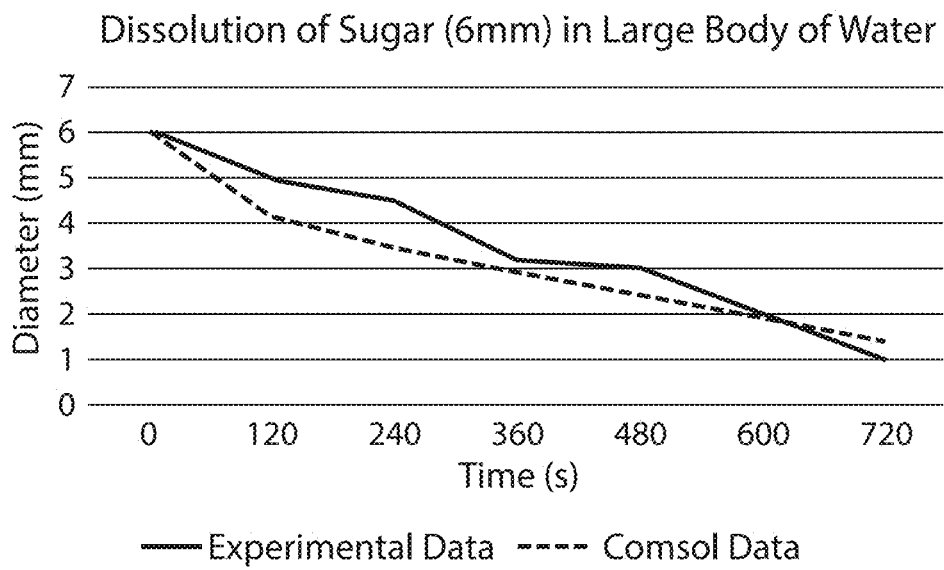
FIG. 24 is a plot of diameter versus time for sugar dissolution, according to one set of embodiments.
Figure 25:
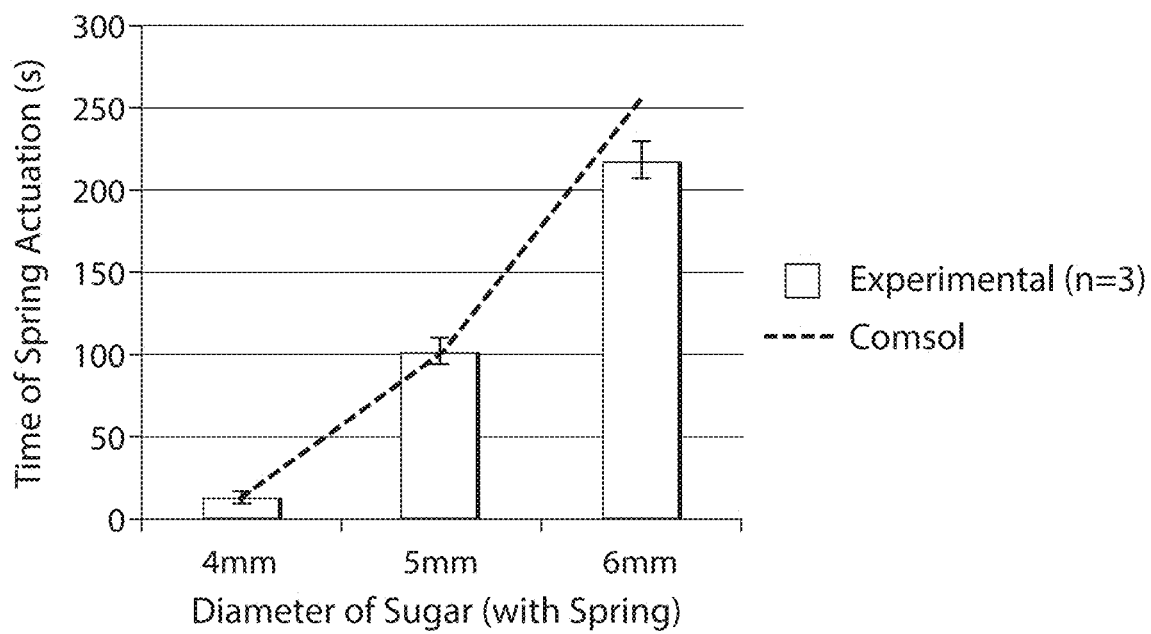
FIG. 25 is a plot of spring actuation time versus diameter, according to one set of embodiments.

Using modeling software that runs a diffusion mass transfer problem with an interface balance, it was determined that the actuation could be delayed between 1-4 minutes once the sucrose coated spring was dissolved in water by coating the spring with between 4-6 mm of sucrose. This was confirmed by experiment (FIGS. 24-25). A delay of at least 20 seconds was shown to be sufficient such that the actuation occurs in the stomach instead of in the mouth or esophagus.

In order to make sure that liquid reaches the sucrose to start this dissolution process, vents may be added to the top and bottom of the device to allow for fluid flow. These vents allow e.g., a way for the air trapped inside to escape. They may also be hydroscopic to allow for water to easily pass though.

Figure 26:
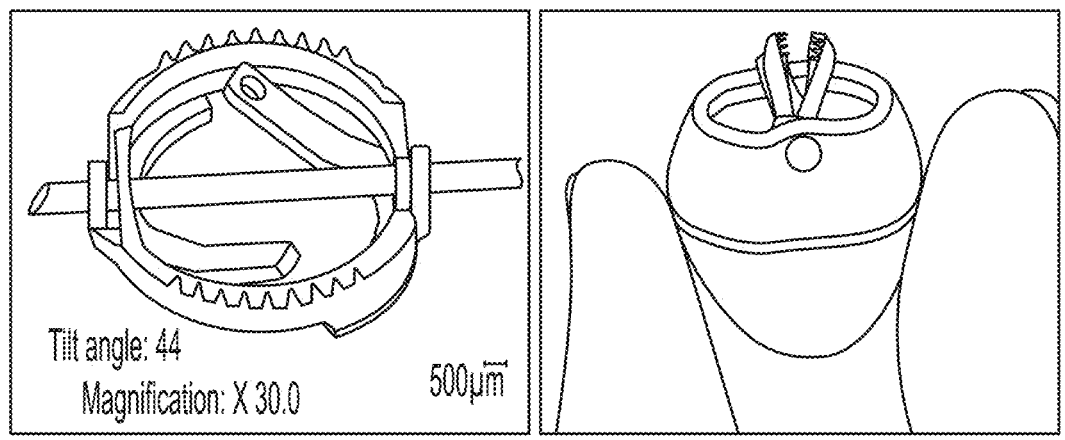
FIG. 26 is a photograph and diagram of an exemplary tissue interfacing component (e.g., biopsy punch) associated with a spring, according to one set of embodiments.
Figure 26:
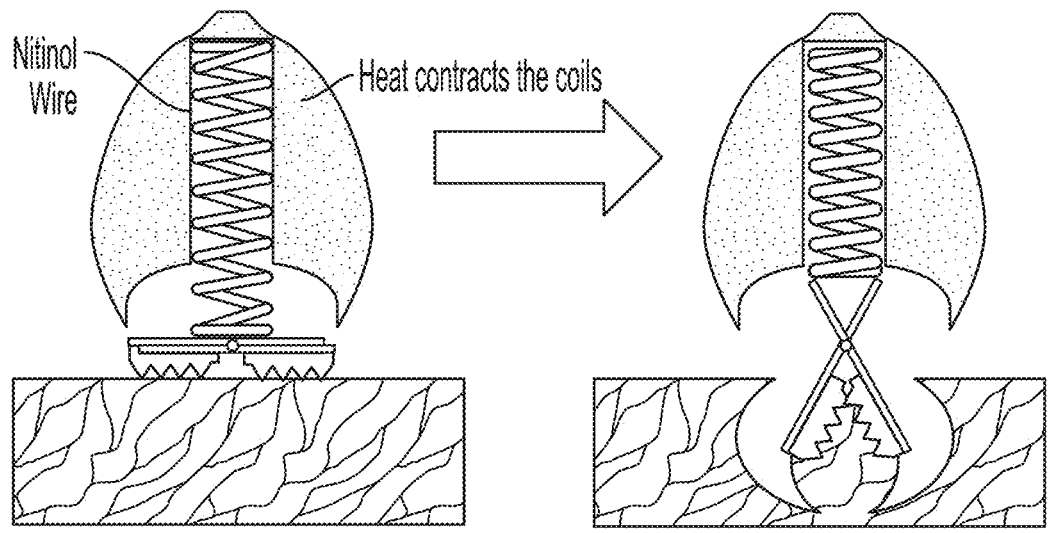

In some cases, an anchoring device will allow the system to attach itself via physical or chemical means to the tissue wall of the GI tract. Such a device could include a barbed or hooked needle, a mucoadhesive patch, a trapping and closing mechanism (FIG. 26), vacuum suction, or any number of other mechanisms. The anchoring device could be located on the bottom of the device to ensure that it is facing the tissue wall.

Figure 27:
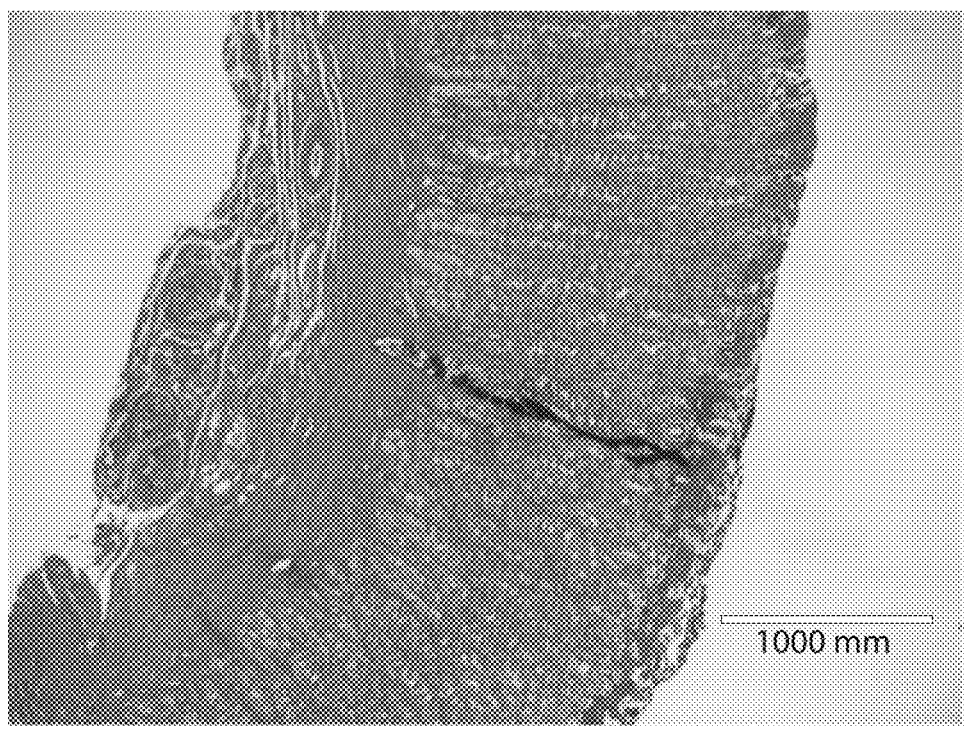
FIG. 27 is a histology of a needle inserted into tissue in vitro from a spring associated article, reaching the muscle layer of the stomach tissue, according to one set of embodiments.

If the anchoring device uses hooks, such as the hooked needle, then it could reach the muscular layer of the tissue in between the mucosal and submucosal layers. FIG. 27 shows a histology slide of a piece of stomach tissue penetrated by the device penetrating to the muscular layer of interest. This penetrate was created by using a sugar coated spring like the ones described above that was compressed 6 mm and had a spring constant of 210 N/m.

Example 8—High API Loading

A solid dissolving needle (e.g., the tissue interfacing component) containing a high concentration of API (e.g., solid therapeutic agent) and a binder (e.g., support material) was formed. This API can consist of anything from a small molecule to a peptide drug to a vaccine. The fabrication of the needle used one or both of the following to create: heat and pressure. Pressure can be applied via a pill press, a hydraulic press, centrifugation, or any other way to provide a large amount of force. Forces applied are between 1-3 metric tons over 100 cm$^2$ but they can be higher without damage to the API and they can be lower if enough heat is applied. Heat is provided either convectively by a heat gun, oven or similar device or conductively to the melting temperature of the binder used. In the examples below, PEG was used due to its relatively low melting point and relatively high level of plasticity. Heat and pressure can be used consecutively or concurrently to force the mixture of powdered API and binder into an in plane or an out of plane mold described in the examples below.

A dissolvable tissue-interfacing component that contained a binder and a solid API loaded at double digit percentages is described. This tissue-interfacing component (e.g., needle) can be applied to the skin, the GI tract, or any other area of the body. In some cases, the needle uses a powdered form of the API. These needles were created by applying pressure and/or adding heat to a powdered mixture, which is a different method from traditional dissolving needles which are pulled or solvent casted, although such a method may be used. Such a needle can be added to an actuator in order to be given enough force to enter the body.

The GI tract offers an incredible opportunity for such a needle formulation. Because the walls of certain areas of the GI tract are generally thick and have an enormous surface area, these needles could be lengthened and expanded to hold an even larger amount of drug when compared to a microneedle. For example, a formulation using an 80% loading of insulin by weight allows one milligram of API delivery in a needle with a diameter of less than 600 μm and a length of 3.3 mm. Such a needle could be delivered to the stomach without the risk of perforation. In addition, less than one hundred conical needles with a length of a mm and a base diameter of 450 μm could deliver the same dosage of API to the slightly thinner small intestine without the risk of perforation.

Example 9

Figure 29:
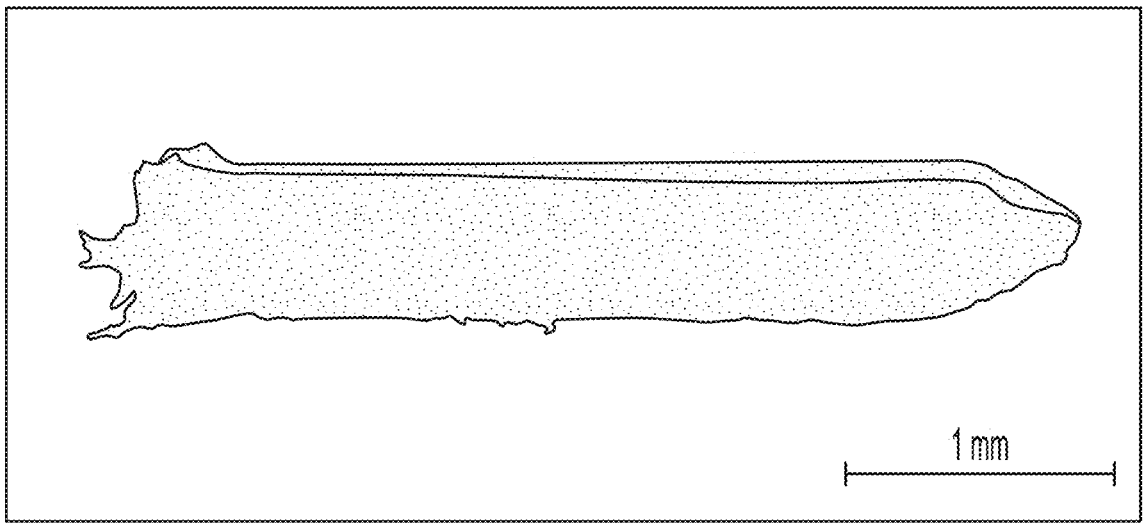
FIG. 29 is photograph of an in plane needle made with 80% BSA and 20% PEG 200 k w/w exposed to 3 metric tons of pressure at 100° C. for 2 min, according to one set of embodiments.
Figure 30:
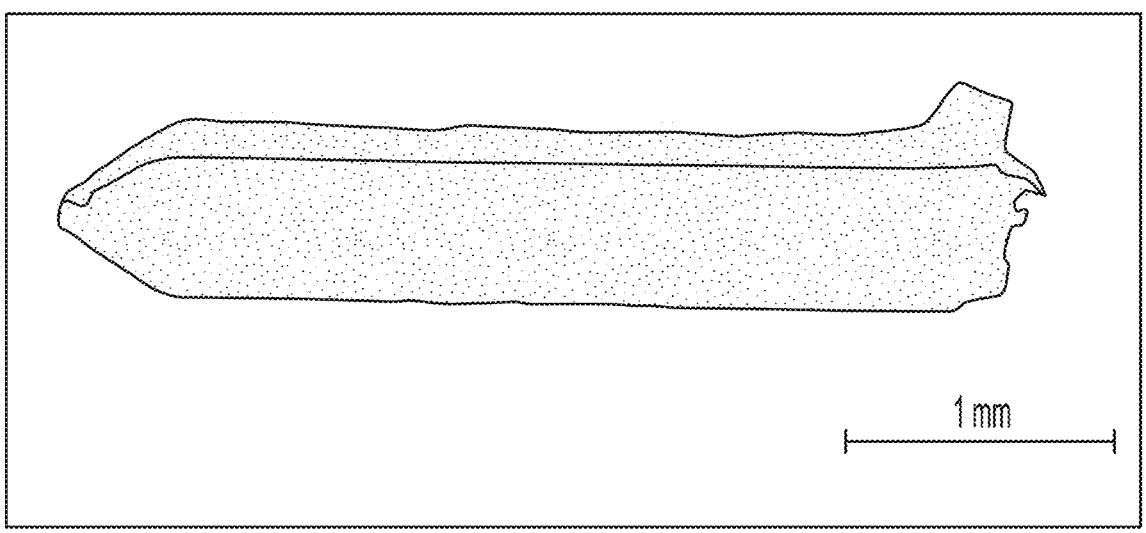
FIG. 30 is a photograph of an in plane needle made with 80% Human Insulin and 20% PEG 200 k w/w exposed to 3 metric tons of pressure at 100° C. for 2 min, according to one set of embodiments.

An In-Plane mold was used to create a needle with a projected two dimensional design. The needle can be up to 2 mm in diameter or greater, although a larger needle will hinder penetration. The needle can be up to a centimeter in length as well. It can be blunt or have a tip angle. It is possible to create an in plane mold using a laser with a small focal diameter, and the tip radius is only limited by this measurement. Larger molecular weight proteins or proteins that are less likely to aggregate such as BSA may use a greater amount of binder. However, needles with a tip radius of 40 micrometers using 100% insulin can also be created. The amount of binder used may help, in some cases, to control the dose of the API given as well as the integrity of the needle. When a 20-30 w/w percentage of binder was added to the mixture, then no issues with binding were observed. Needles with the following dimension (510 um×510 um×3.3 mm) in an 80% API/20% PEG 200 k formulation for both insulin and BSA (FIGS. 29-30).

Figure 31:
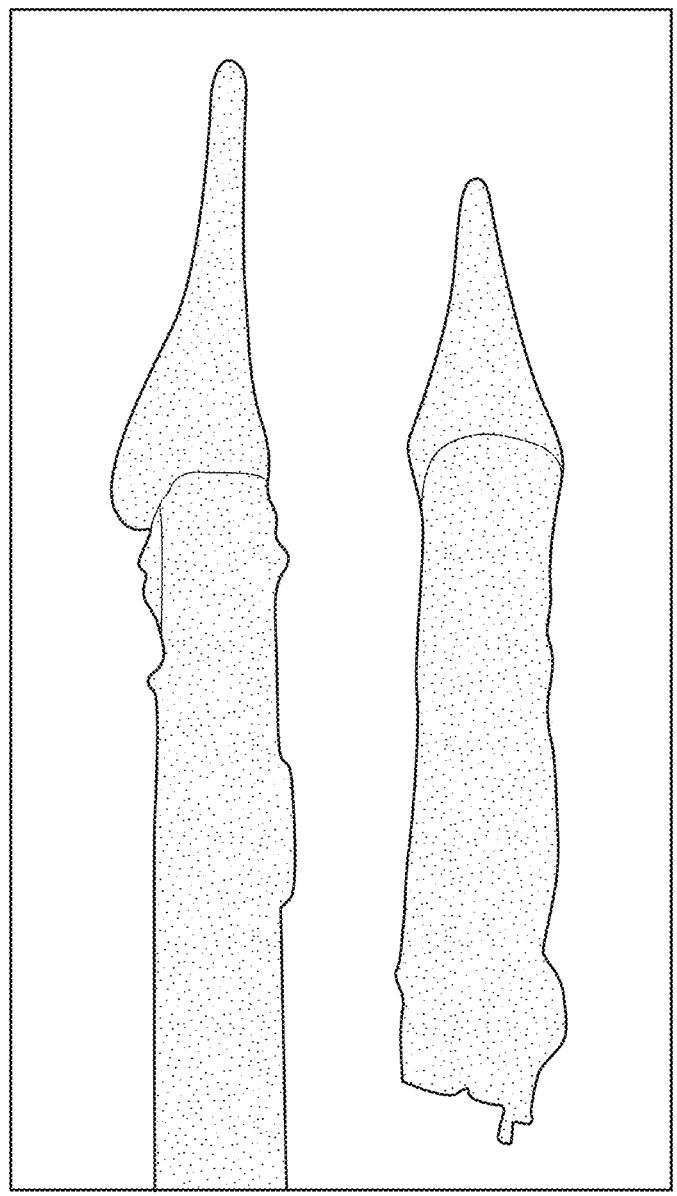
FIG. 31 is a photograph of an in plane needle, the made with 80% Human Insulin and 20% PEG 200 k w/w exposed to 2 metric tons of pressure at 100° C. for 2 min, tips are created by dip coating in maltose, according to one set of embodiments.

A needle can also be made with 2 parts, one containing API and the other containing no API. This allows the creation of a needle where only the tip contains drug. Previous literature has shown that when needles penetrate they create a crater in the penetrated tissue hindering the needle from entering fully. Loading drug at the tip helps to make sure that the entirety of the API dose is delivered. This type of needle can be created by creating a partition above the needle mold and loading only binder on one side and API+Binder on the other side. Because both the formulations contain the same binder, the two sides will fuse to create one needle either under pressure or heat (FIG. 31).

Figure 32:
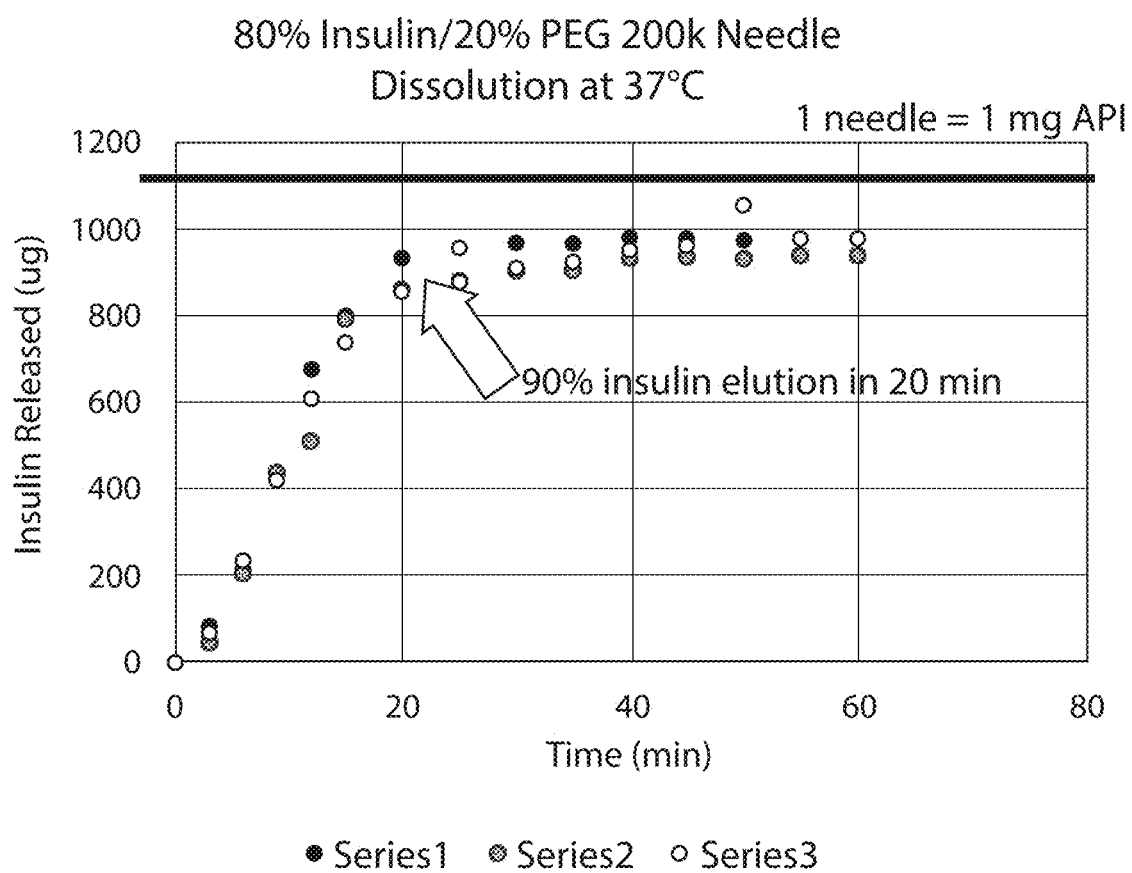
FIG. 32 is a plot of insulin release versus time for components having a relatively high loading of API, according to one set of embodiments.
Figure 33:
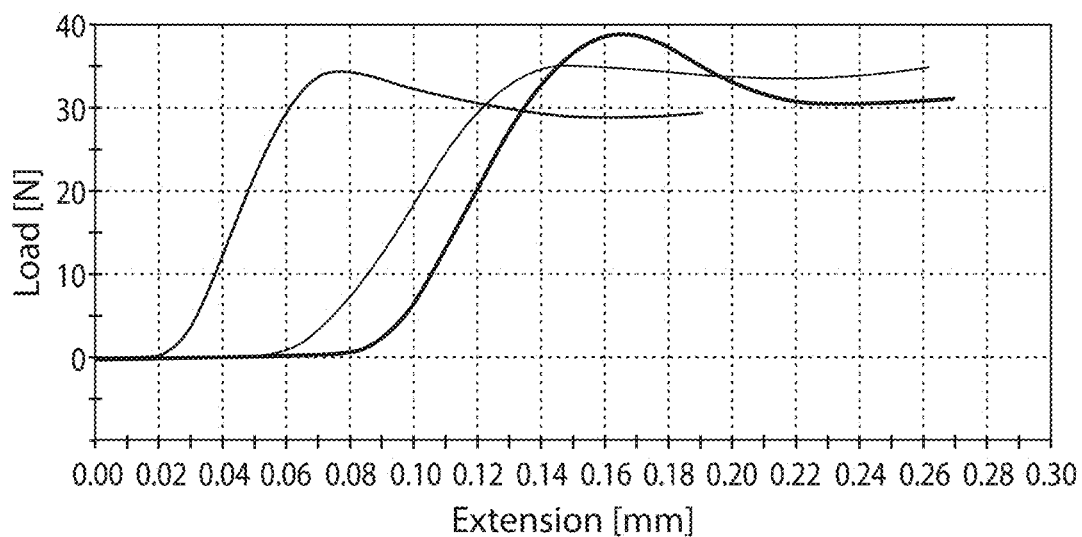
FIG. 33 is a plot of load versus extension (lateral load) for various components having a relatively high loading of API, according to one set of embodiments.
Figure 34:
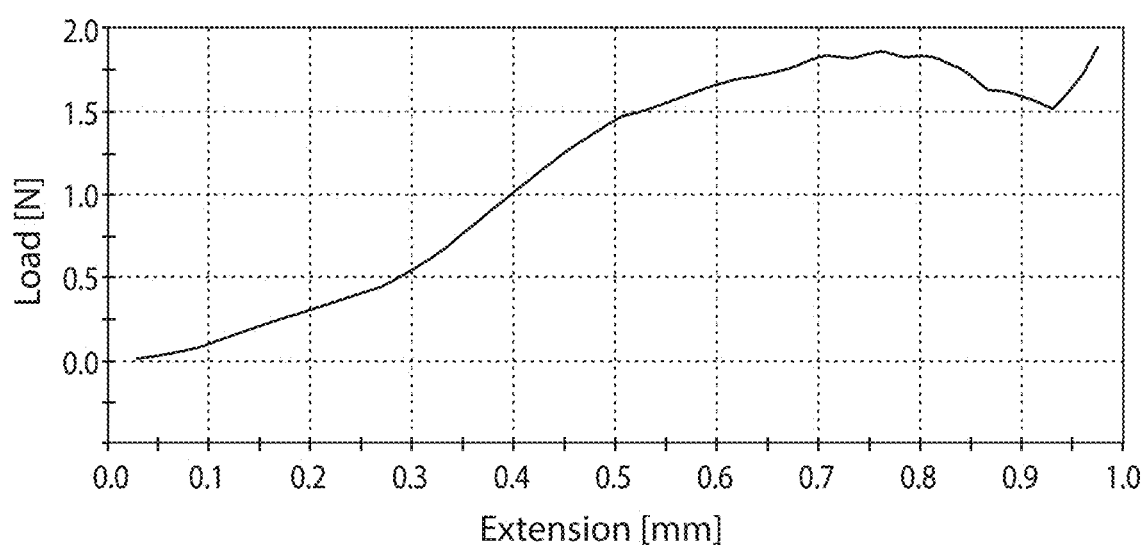
FIG. 34 is a plot of load versus extension (axial load) for various components having a relatively high loading of API, according to one set of embodiments.
Figure 35:
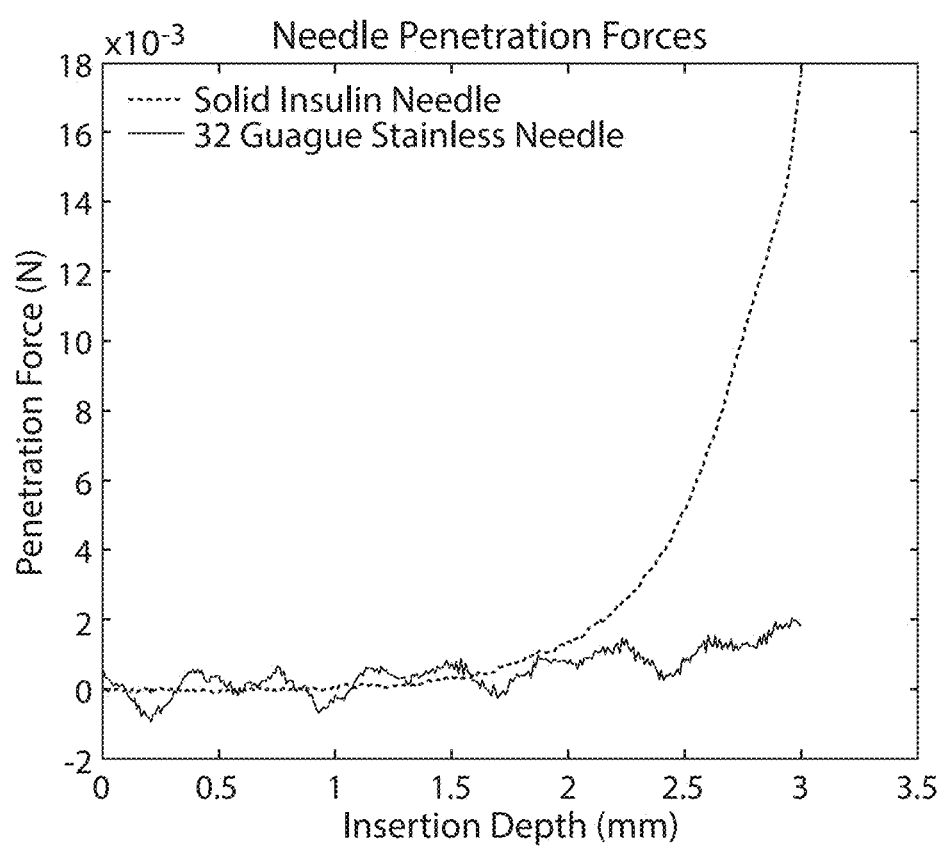
FIG. 35 is a plot of penetration force versus insertion depth for an exemplary component having a relatively high loading of API loading as compared to a 32 gauge stainless needle, according to one set of embodiments.

The high loaded insulin needles were shown to dissolve quickly in PBS at 37° C., within 20 minutes (FIG. 32). The dissolution profiles of the three needles also show the uniformity in drug loading in each of the needles. Additionally, these needles have been tested for their strength using an Instron machine to conduct a crush test. The needles perform with a profile similar to a ductile material. This makes sense since a large percentage of the needle is made of PEG (FIGS. 33-34). Finally, penetration force for these needles were tested in a human stomach. It was found that the needles fully penetrated with 18 mN of force (FIG. 35).

Example 10

An Out-of-Plane mold can create needles with a three dimension shape. This mold is created by first using a 3D printer to fabricate a solid positive mold. Such a printer can create a tip radius of around 1 micron. This positive mold is then coated with a thin, 10 um layer of chromium and another 200 um layer of copper using an evaporator to create a metallic shell with small grain sizes to keep retain the tip sharpness found in the printed prototypes. Next, to generate a negative mold, several millimeters of nickel are electroplated on top of the copper layer. The resulting nickel mold is then separated from the positive mold, planarized and smoothed down to allow for an even distribution of force.

Figure 36:
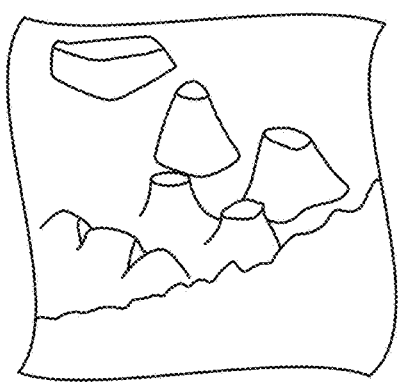
FIG. 36 is a photograph of a component having a relatively high API loading (e.g., needle protrusion on a base plate) made with 83% Human Insulin, 5% HPMC, 2% Magnesium Stearate and 10% PEG 35 k w/w exposed to 3 metric tons of pressure at 100° C. for 2 min, according to one set of embodiments.
Figure 36:
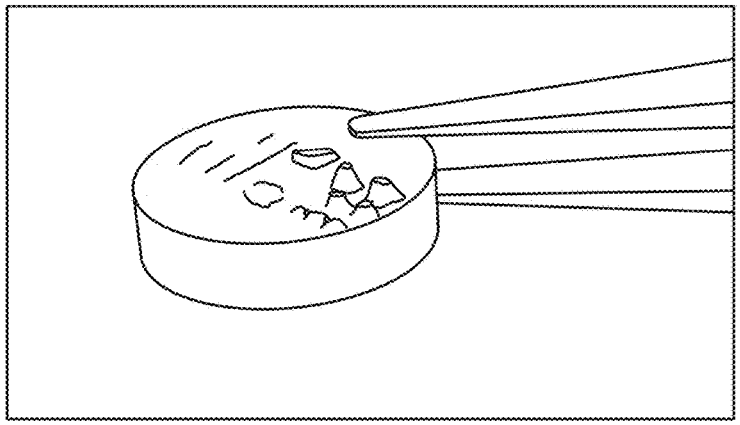
Figure 37:
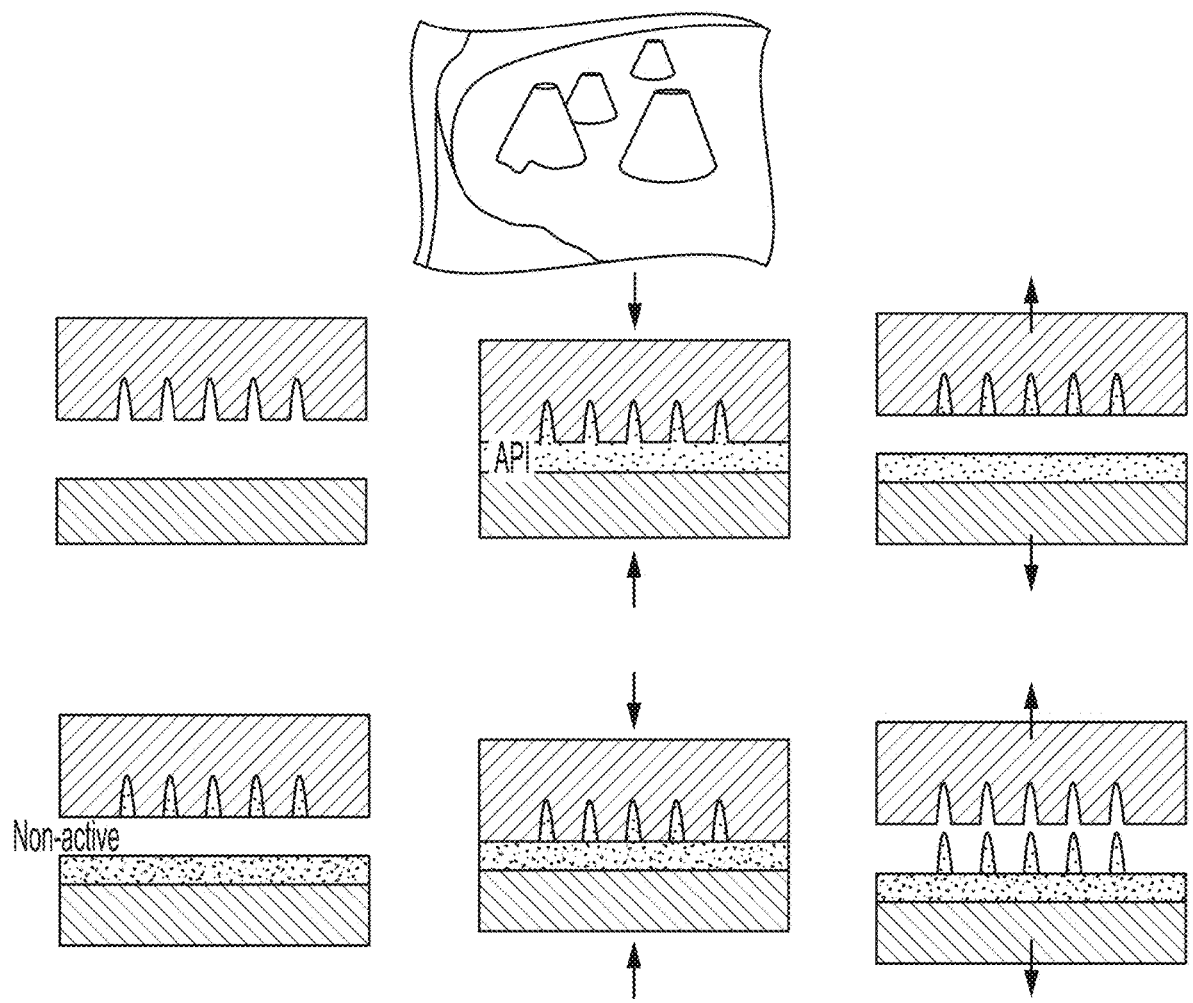
FIG. 37 is a schematic diagram of a method for fabricating a component having a relatively high API loading (e.g., needles) with a non API base plate, the needle protrusion on a base plate made with 85% Human Insulin, 5% HPMC and 10% PEG 35 k w/w exposed to 3 metric tons of pressure at 100° C. for 2 min, according to one set of embodiments.
Figure 38:
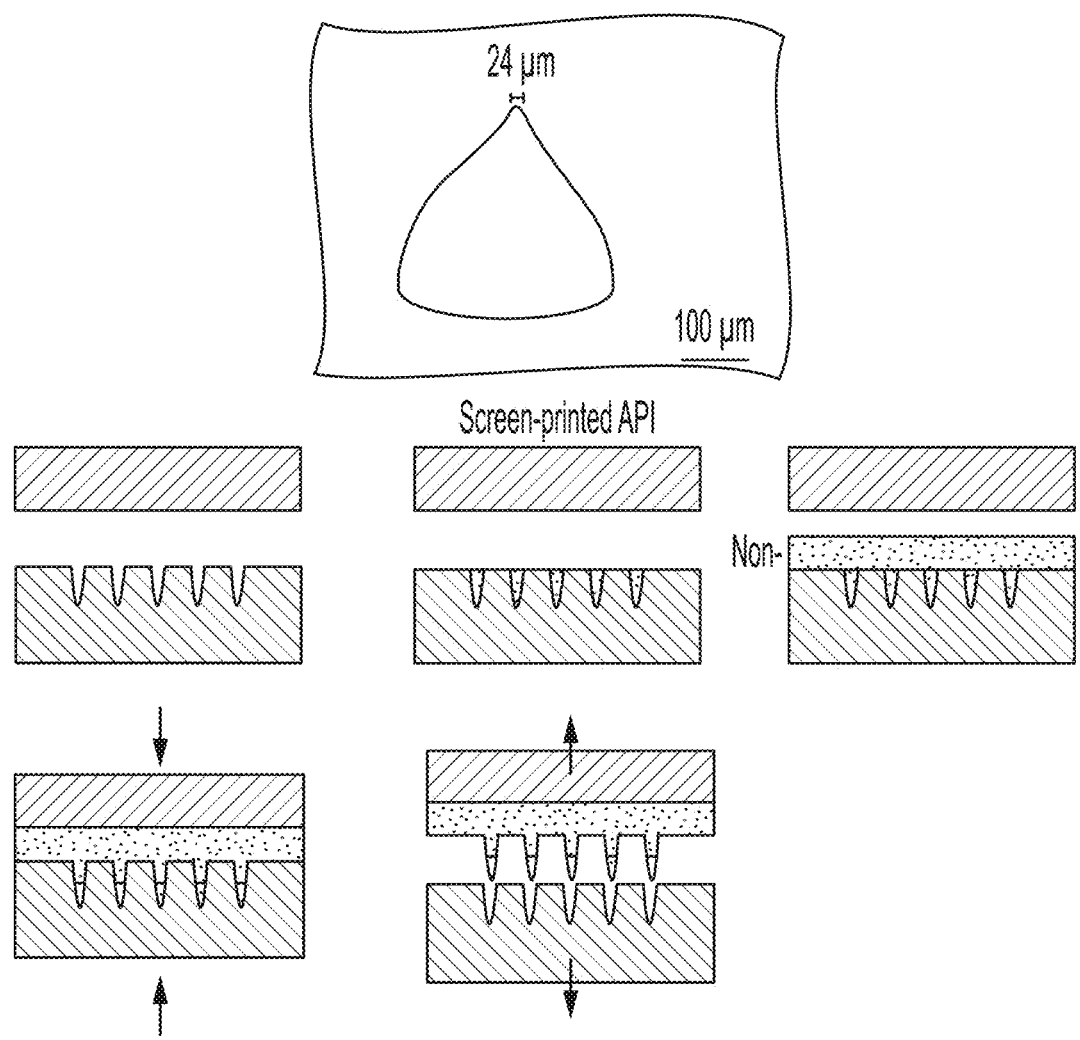
FIG. 38 is a schematic diagram of a method for fabricating a component (e.g., a needle tip) having a relatively high API loading with a non API base plate and needle base. A needle protrusion on a base plate made with 85% Human Insulin, 5% HPMC and 10% PEG 35 k w/w exposed to 3 metric tons of pressure at 100° C. for 2 min, according to one set of embodiments.

Needles were created by compressing a powder into the molds in one of the following methods:

1. The powder is filled on top of the mold and compressed creating a needle and a base made entirely of one formulation (FIG. 36).
2. The powder is filled on top of the mold and compressed creating a needle and a base made entirely of one formulation. The base plate is then separated leaving the needles inside of the mold. The mold is then repressed using a formulation without API. The entire pressed device is removed leaving needles with an API formulation connected to a base plate with no API (FIG. 37).
3. API formulation is loosely packed into the holes of the mold. Then a formulation without API is placed on top of the API formulation. The entire device is pressed at once, leaving an API formulation in the needle tips and a formulation with no API in the needle base and in the base plate (FIG. 38).

Figure 39:
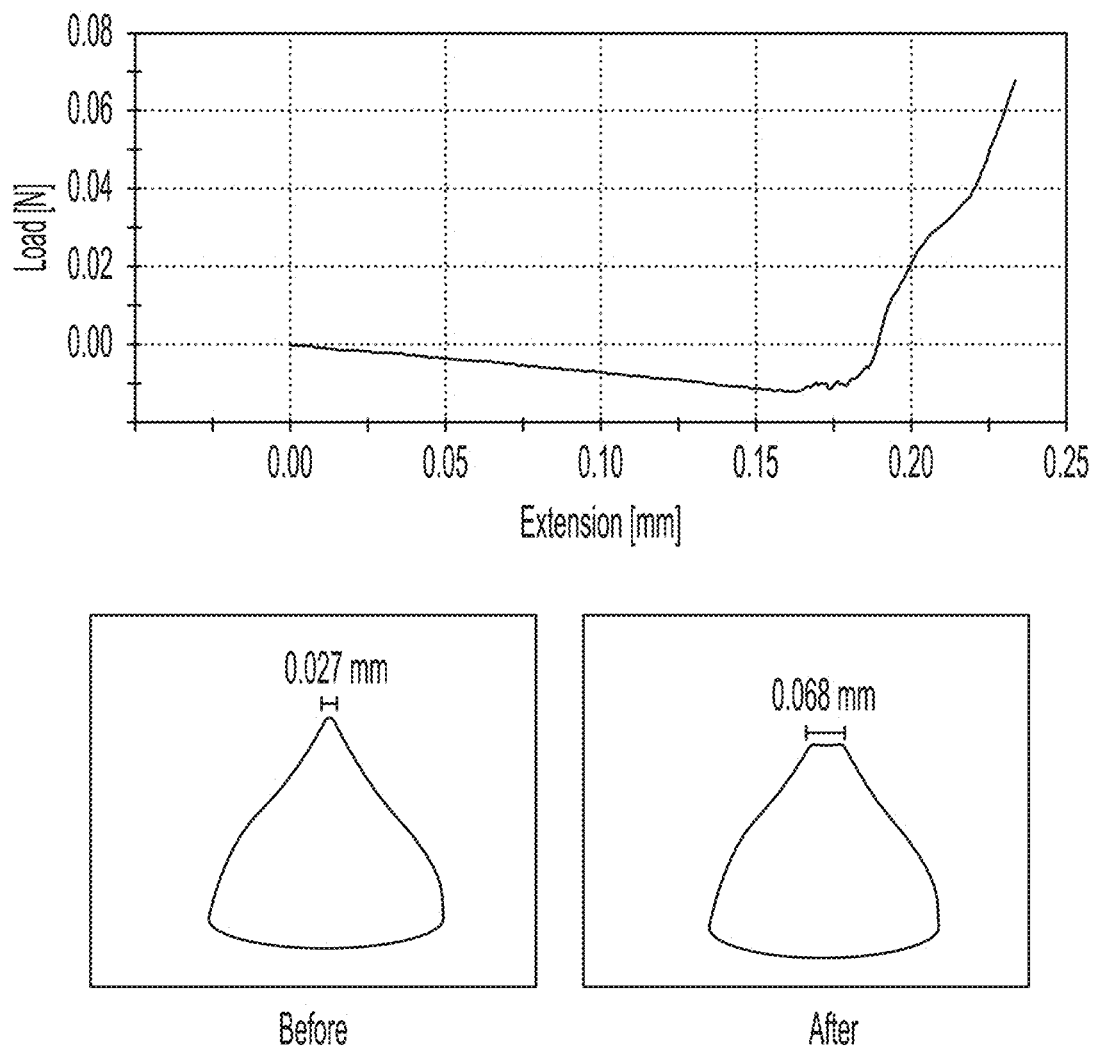
FIG. 39 is a plot of axial loading of a component having a relatively high API loading (e.g., a microneedle), according to one set of embodiments.

These needles have a strong integrity, as shown through axial load tests on an Instron machine. The needles from method 3 began with a tip radius under 10 um and after 0.06 N of force top the tip had a tip radius of 34 um (FIG. 39).

Example 11

Figure 40A:
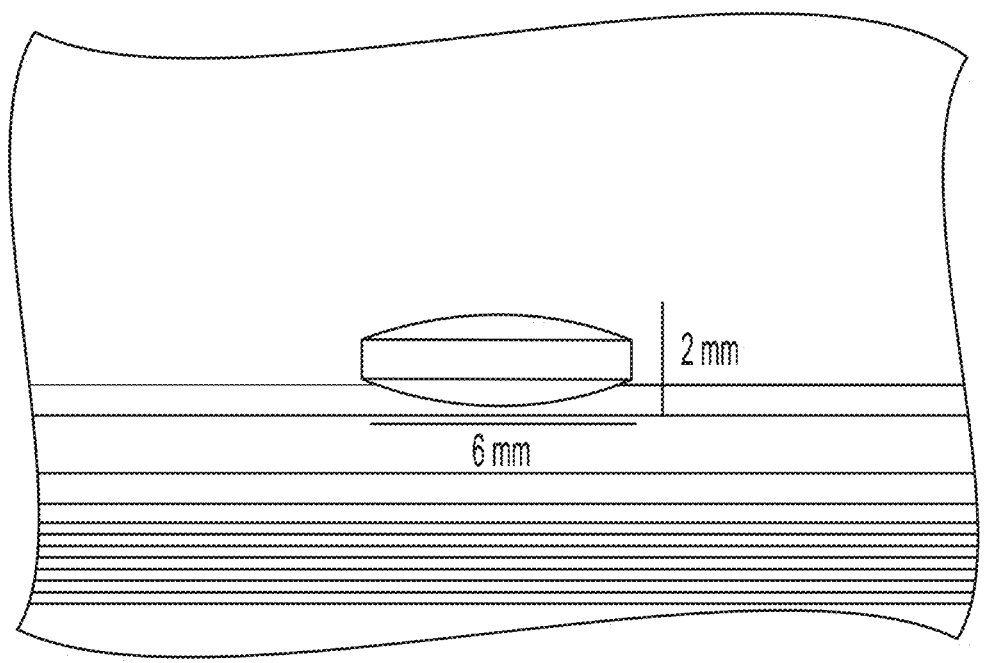
FIG. 40A is a photograph of an exemplary tissue-interfacing component comprising 95 wt % API, according to one set of embodiments.
Figure 40B:
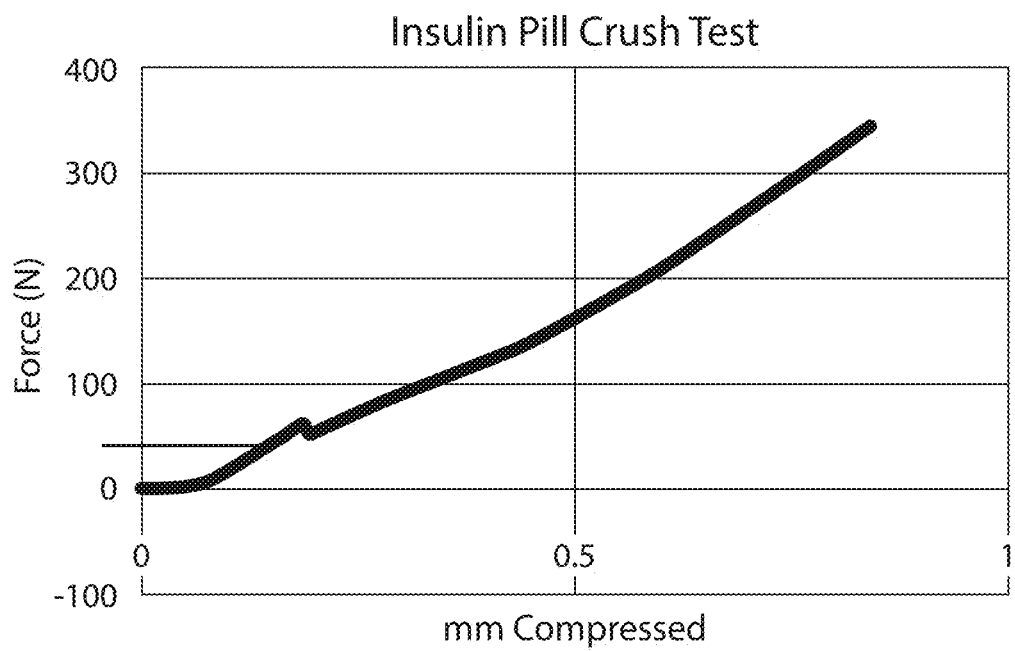
FIGS. 40B-40C are compression tests of the tissue-interfacing component in FIG. 11A.
Figure 40C:
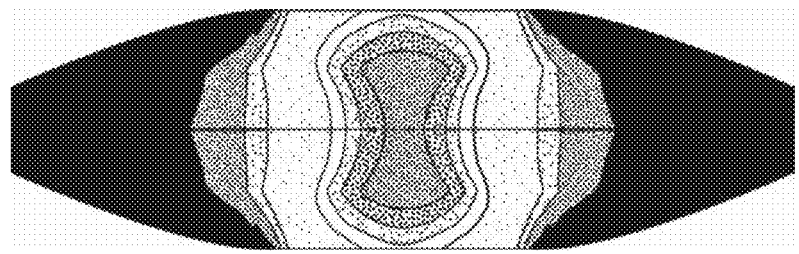

This example demonstrates the formation of a tissue-interfacing component comprising 95 wt % insulin (e.g., the API) and 5 wt % Hydroxypropyl Methylcellulose (HPMC) (e.g., the binder material). The insulin and HPMC were pressed together using a pressure of >1 MPa, as described herein. A photograph of the component is shown in FIG. 40A. The component was shown to withstand a force of >62.7 N (FIGS. 40B-40C) before cracking.

A tissue-interfacing component comprising 100 wt % insulin was also formed.

Figure 40D:
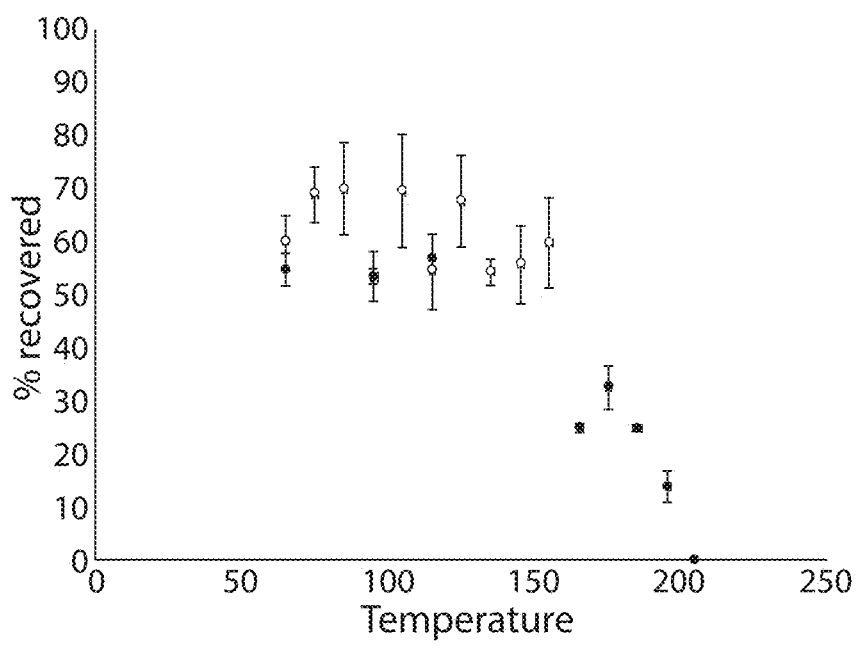
FIG. 40D is a plot of percent insulin recovery versus temperature for a tissue-interfacing component, according to one set of embodiments.
Figure 40E:
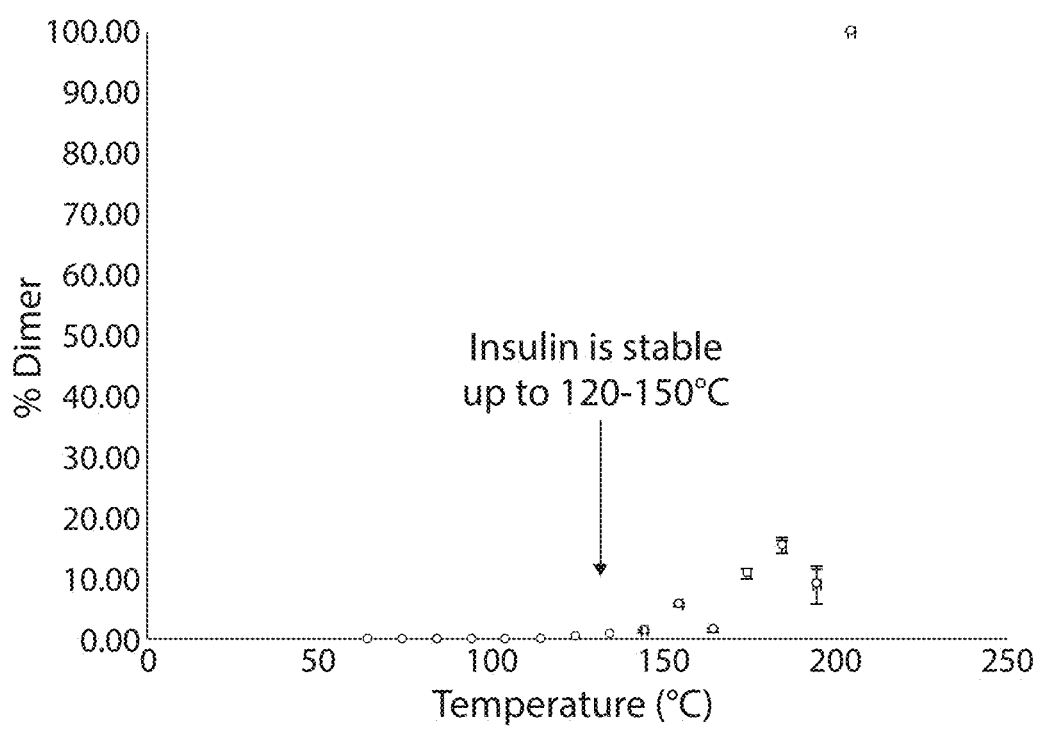
FIG. 40E is a plot of percent insulin dimer formation versus temperature, according to one set of embodiments.

Another tissue-interfacing component was produced using insulin as the API extruded with PCL. The percentage of insulin recovered was quantified and is shown in FIG. 40D. Insulin dimer formation was also tested, demonstrating that the insulin was stable to temperatures of up to 120° C.-150° C. (FIG. 40E).

Example 12

The following example demonstrates the formation of tissue-interfacing components comprising a plurality of microneedles having a high loading of API.

Figure 41:
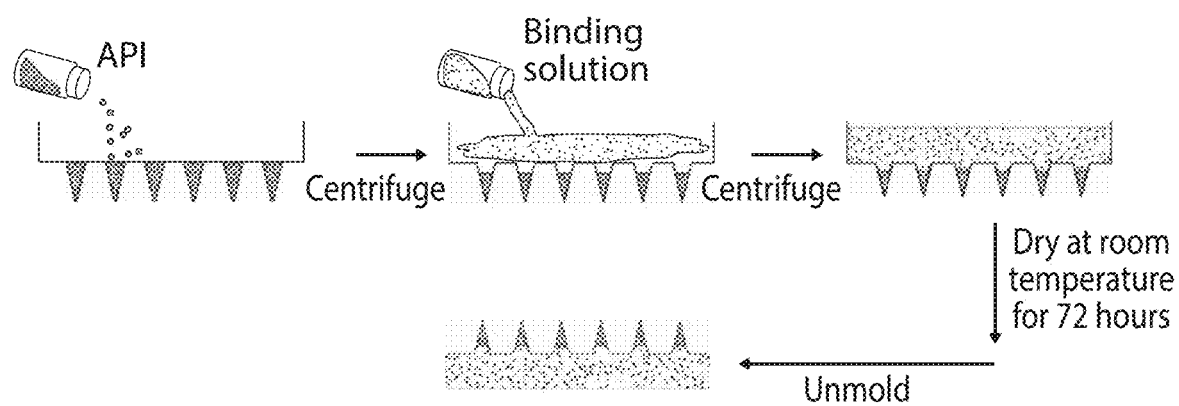
FIG. 41 is a schematic diagram of an exemplary method for fabricating a component having a plurality of microneedles and a relatively high API loading, according to one set of embodiments.

Briefly, as illustrated in FIG. 41, the API was cast in the molds, being pressed into the microneedle cavities. The molds were then centrifuged to force the API into the tip of the microneedle cavities. In some cases, a binder was added into the mold. The molds were again centrifuged to force the binder into the microneedle cavities. The microneedles were left to dry for 1-3 days. The microneedles were removed from the mold and were ready to use. In some cases, the microneedles comprised at least 1 mg of API.

Figure 42A:
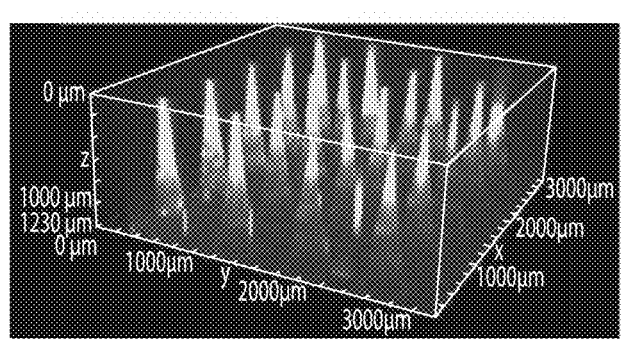
FIGS. 42A-42B are confocal microscopy images of exemplary components loading with FITC-dextran, according to one set of embodiments.
Figure 42B:
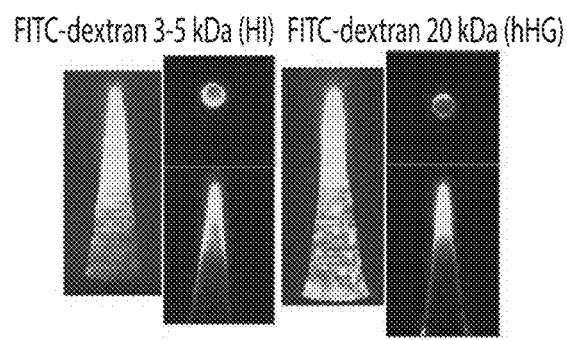

To visualize the distribution of API in the microneedles, FITC-dextran having a molecular weight of 3-5 kDa (e.g., similar to that of insulin) and a molecular weight of 20-22 kDa (e.g., similar to that of some human growth hormone) was used in the methods outlined above in place of the API, and then imaged using confocal microscopy. FIGS. 42A-42B show the distribution of the FITC-dextran in the microneedles. In some cases, the FITC-dextran was most visibly concentrated in the upper third to upper two-thirds of the microneedles (e.g., at the tip).

Microneedles were also prepared with insulin as the API, as described above. All the microneedle patches were imaged prior to the application to the buccal space of swine. Microneedle patches were inserted for different times 5, 15 and 30 seconds into the different areas of the buccal space (tongue, sublingual, cheek, lip and palate) of a swine, in vivo (under anaesthesia). Microneedle patches were tested as control (labelled Control (30 s) in FIG. 43 and these were just placed on top of the surface of the tissue (e.g., so that any potential degradation will be related to the moisture of the surface of placement instead of degradation occurring inside the tissue). All microneedle patches were imaged again post application.

Figure 43:
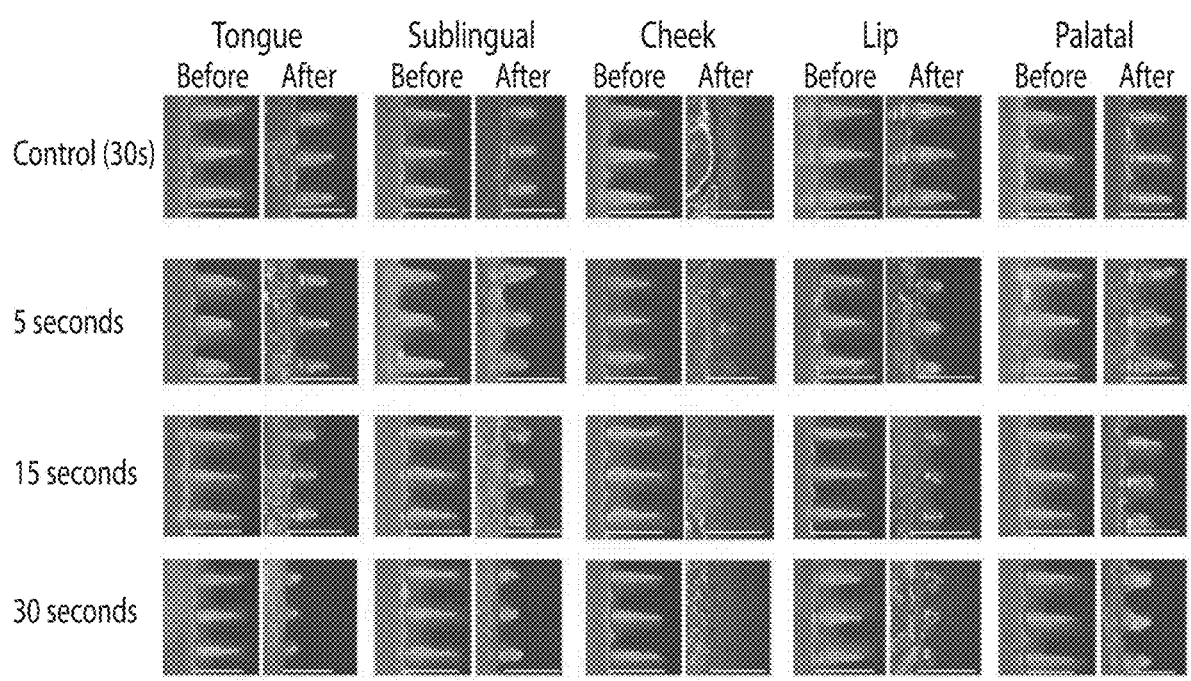
FIG. 43 shows the dissolution of a tissue interfacing component comprising a plurality of microneedles and a relatively high loading of API after administration to various tissues, according to one set of embodiments.

FIG. 43 shows the dissolution of the microneedles on the tongue, sublingual, cheek, lip and palatal tissue in swine over 30 seconds. The experiment demonstrates that, in some cases, the microneedles can dissolve and deliver the API to the tissue in less than 30 seconds and, in some cases, less than 15 seconds or less than 5 seconds.

Figure 44:
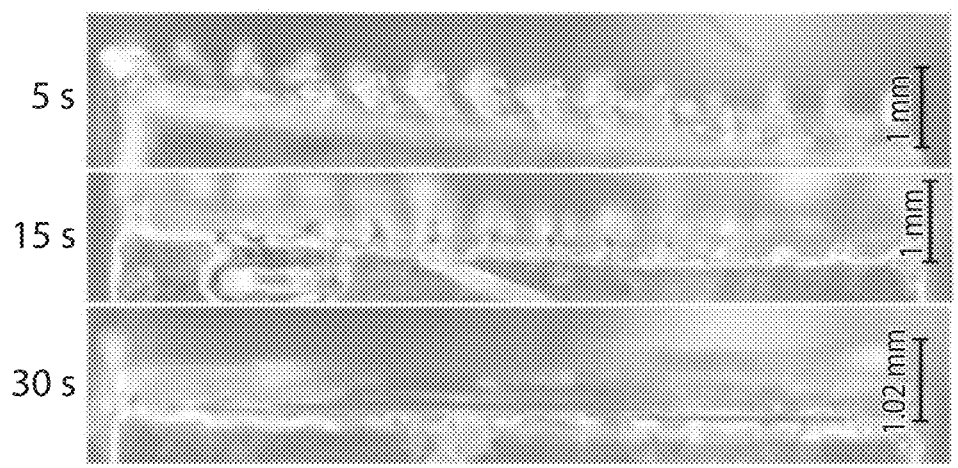
FIG. 44 shows the dissolution of a tissue interfacing component comprising a plurality of microneedles and a relatively high loading of API after administration to human cheek tissue ex vivo, according to one set of embodiments.

Microneedles were again prepared with insulin as the API, as described in Example 5. Here, microneedle patches were inserted in ex vivo human tissue (e.g., human cheek) for different times 5, 15 and 30 seconds. FIG. 44 shows the dissolution of the microneedles over time.

Example 13

The following example demonstrates the in vivo dissolution of microneedles loaded with API at a location internal to a subject.

Microneedles were prepared with insulin as the API, as described in Example 12. Microneedle patches were inserted into the different areas of the buccal space (tongue, sublingual, cheek, lip and palate) and small intestine (SI) in swine, in vivo (under anaesthesia). Blood samples were collected at set times (0, 2.5, 5, 7.5, 10, 15, 20, 25, 30, 35, 40, 45, 50, 55, 60, 70, 80, 90, 100, 110, 120, 135, 150, 165, 180, 210 and 240 min) from where insulin concentration was quantified. FIGS. 45-46 show the plot of blood concentration of insulin after microneedle application to the small intestine (FIG. 45) and palatal tissues (FIG. 46) for various loading of API (1.4 mg, 1.6 mg, 2.01 mg, 2.42 mg, and 3.56 mg).

Figure 47:
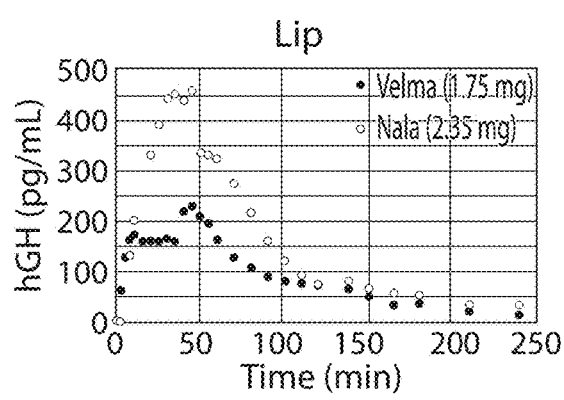
FIG. 47 is a plot of blood concentration of human growth hormone versus time after application of a tissue interfacing component comprising a plurality of microneedles and a relatively high loading of human growth hormone to the lip of swine, according to one set of embodiments.
Figure 48:
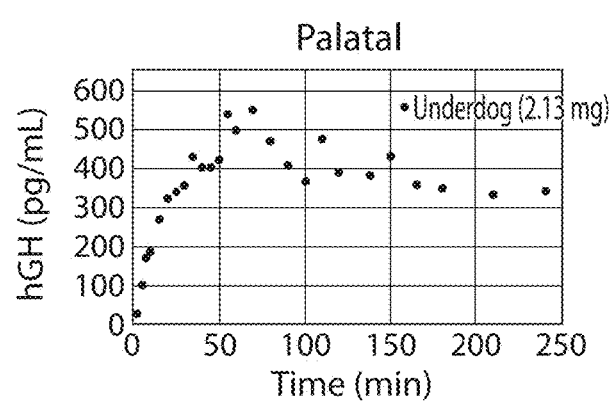
FIG. 48 is a plot of blood concentration of human growth hormone versus time after application of a tissue interfacing component comprising a plurality of microneedles and a relatively high loading of human growth hormone to the palatal tissue of swine, according to one set of embodiments.

Microneedles were also prepared with human growth hormone (hGH) as the API, as described in Example 12. Microneedle patches were inserted into the different areas of the buccal space (tongue, sublingual, cheek, lip and palate) and small intestine (SI) in swine, in vivo (under anaesthesia). Blood samples were collected at set times (0, 2.5, 5, 7.5, 10, 15, 20, 25, 30, 35, 40, 45, 50, 55, 60, 70, 80, 90, 100, 110, 120, 135, 150, 165, 180, 210 and 240 min) from where hGH concentration was quantified. FIGS. 47-48 show the plot of blood concentration of hGH after microneedle application to the lip (FIG. 47) and palatal (FIG. 48) for various loading of API (1.75 mg, 2.35 mg, 2.13 mg).

Figure 49:
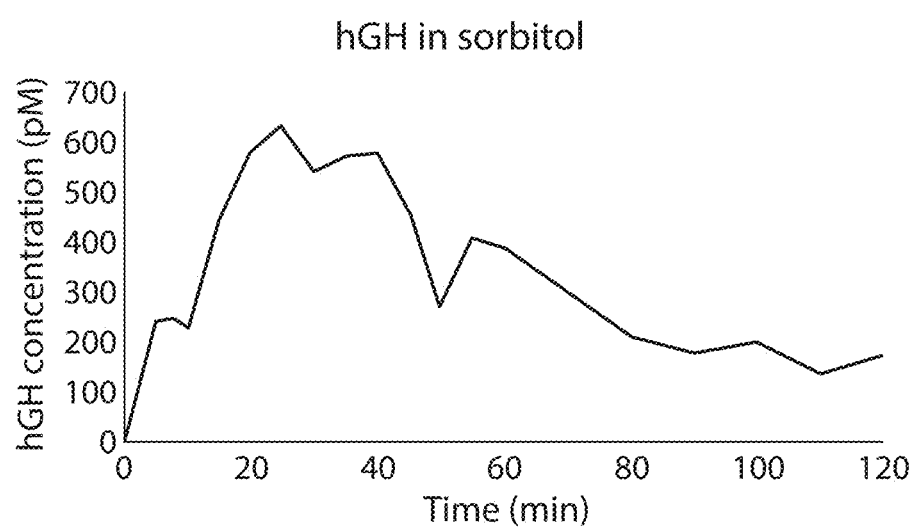
FIG. 49 is a plot of blood concentration of human growth hormone versus time after application of a tissue interfacing component comprising a plurality of microneedles and a relatively high loading of human growth hormone to the lip of swine, according to one set of embodiments.

Microneedles were also prepared with hGH using sorbitol (e.g., a sugar) as a binder. FIG. 49 shows a plot of blood concentration of hGH after microneedle application to the lip of swine in vivo.

Example 14

The following example demonstrates the formation of tissue interfacing components comprising high loading of monoclonal antibodies.

Figure 50:
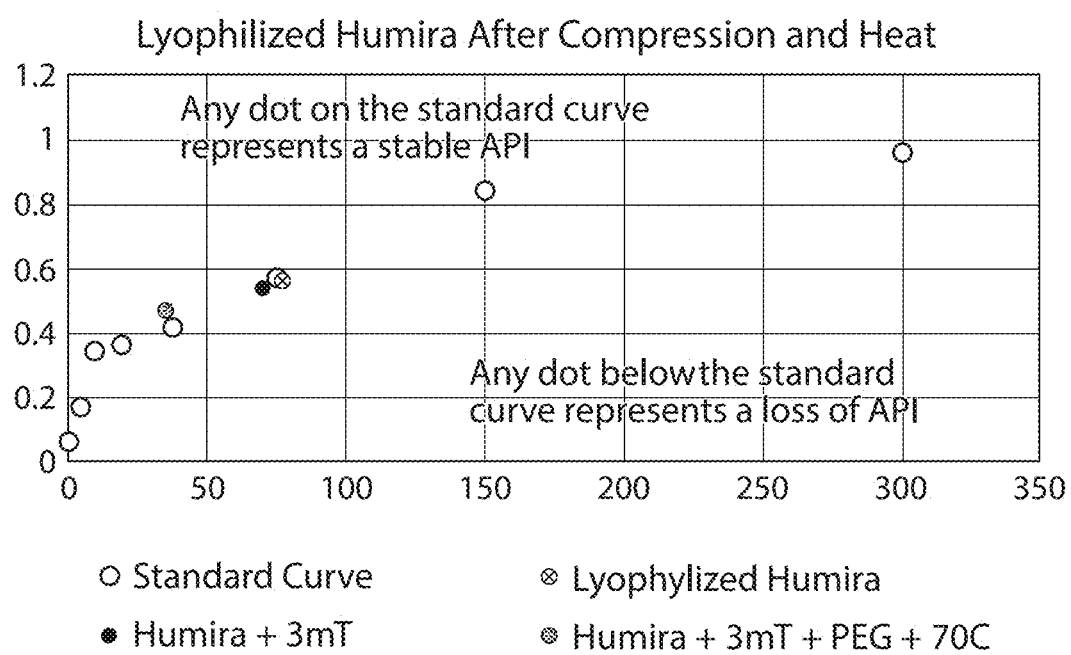
FIG. 50 is a plot of activity of adalimumab before and after exposure to relative high pressure and relative high temperature, according to one set of embodiments.

A dose of adalimumab was freeze dried and subjected to relatively high pressure (up to 3 mT) and/or relatively high heat (up to 70° C.). PEG 200K was used as a binder. An ELISA assay was performed to confirm antibody activity. FIG. 50 shows a plot of the activity of lyophilized adalimumab after exposed to high pressure and high heat.

Prophetic Exemplary Embodiments

1. An article with the capacity for encapsulation that possesses the ability to quickly orient itself towards the tissue wall of the GI tract.
   a. Wherein the shape of the article may be described by the curve in FIG. 7 rotated about the y axis.
   b. Wherein the article is made of a biodegradable and biocompatible polymer (ex PCL) or metal (ex Stainless Steel), or combination thereof.
   c. Wherein there are 2 distinct sections of the article defined by the x axis in FIG. 7 made out of materials with different densities with a density ratio of 6-16:1.
2. The article according to embodiment 1 wherein the article can be hollowed out in a manner to retain self-righting capabilities with holes or vents such as cylinders, conic sections, rectangular sections, or other geometric shapes.
3. The article according to embodiment 1 wherein the article can hold a drug delivery system made out of a needle (hollow or sold) or patch and an actuation mechanism.
   a. Wherein the actuation mechanism can be shape memory nitinol.
   b. Wherein the actuation mechanism can be a compressed spring.
   c. Wherein the actuation mechanism can be gravity.
   d. Wherein the actuation mechanism can be expanding materials.
   e. Wherein the needle can be attached to a drug reservoir.
   f. Wherein the needle can be made of the drug formulation.
   g. Wherein the needle can house the drug formulation.
4. The article according to embodiment 3b wherein the spring has a spring constant between 100-250 N/m, is compressed 1-5 mm, and is coated in 3.6-6 mm of caramelized sucrose.
5. The article according to embodiment 1 wherein the article can be connected to an anchoring system to maintain gastric retention.
   a. Wherein the anchoring mechanism is a hooked needle.
   b. Wherein the anchoring mechanism is a bear trap mechanism.
   c. Wherein the anchoring mechanism is a mucoadhesive patch.
   d. Wherein the anchoring mechanism is vacuum suction.
6. The article according to embodiment 1 wherein the article can attach to other ingested capsules via a magnet, a chemical adhesive, a vacuum force, or another attractive force.
7. The article according to embodiment 1 wherein the article can be connected to an electronic system such as a sensor.
   a. Wherein the electronic system is housed within the article
   b. Wherein the electronic system is taken in another capsule and then attaches to the self-righting system.
8. A device having an actuation mechanism.
   a. Wherein the actuation mechanism can be shape memory nitinol.
   b. Wherein the actuation mechanism can be a compressed spring.
   c. Wherein the actuation mechanism can be gravity.
   d. Wherein the actuation mechanism can be expanding materials.
   e. Wherein the needle can be attached to a drug reservoir.
   f. Wherein the needle can be made of the drug formulation.
   g. Wherein the needle can house the drug formulation.
9. The device according to embodiment 8b wherein the spring has a spring constant between 100-250 N/m, is compressed 1-5 mm, and is coated in 3.6-6 mm of caramelized sucrose.
10. The device according to embodiment 8 wherein the device can be connected to an anchoring system to maintain gastric retention.
    a. Wherein the anchoring mechanism is a hooked needle.
    b. Wherein the anchoring mechanism is a bear trap mechanism.
    c. Wherein the anchoring mechanism is a mucoadhesive patch.
    d. Wherein the anchoring mechanism is vacuum suction.
11. A pressed and/or heated formulation of powdered API and binder with an API loading of >10% w/w that is molded into a penetrable object.
    a. A penetrating object that is a microneedle, with a height of 0.3-1.5 mm and a base diameter of 200 um-700 um.
    b. A penetrating object that is shaped to a traditional needle, with a diameter of up to 1.5 mm and a length of up to 10 cm.
    c. A penetrating object that is shaped like a projectile with a diameter of up to 2 mm in any direction.
12. A penetrating shape where the API with binder is concentrated in the top portion of the object, and the bottom portion of the object is only binder.
13. A penetrating shape made from pressing powder that possesses the structural integrity to penetrate through GI tissue.
14. A penetrating shape made from pressing powder that possesses the structural integrity to penetrate through skin.
15. A penetrating shape where a tip is created out of another brittle material such as a sugar.
16. A penetrating shape where a tip is created by cutting and milling the existing tip of the shape.
17. A penetrating shape created by pressing the API and binder into an in plane mold.
18. A penetrating shape created by pressing the API and binder into an out of plane mold.
19. A penetrating shape created by pressing the API and binder inside of a pill press.
20. A pressed and/or heated formulation of powdered API and binder where the binder is a PEG with a molecular weight between 5 thousand and 1 million
21. A pressed and/or heated formulation of powdered API and binder where the API is Insulin or another peptide.
22. A pressed and/or heated formulation of powdered API and binder where the API is a nucleic acid.
23. A pressed and/or heated formulation of powdered API, a binder and an antiadherent where the antiadherent is chosen from waxes, oils and stearates, for example magnesium stearate, sodium stearyl fumarate and alike.

Example 15—Anchoring Mechanism

The following example demonstrates the formation and use of anchoring mechanisms associated with the systems described herein.

Figure 51:
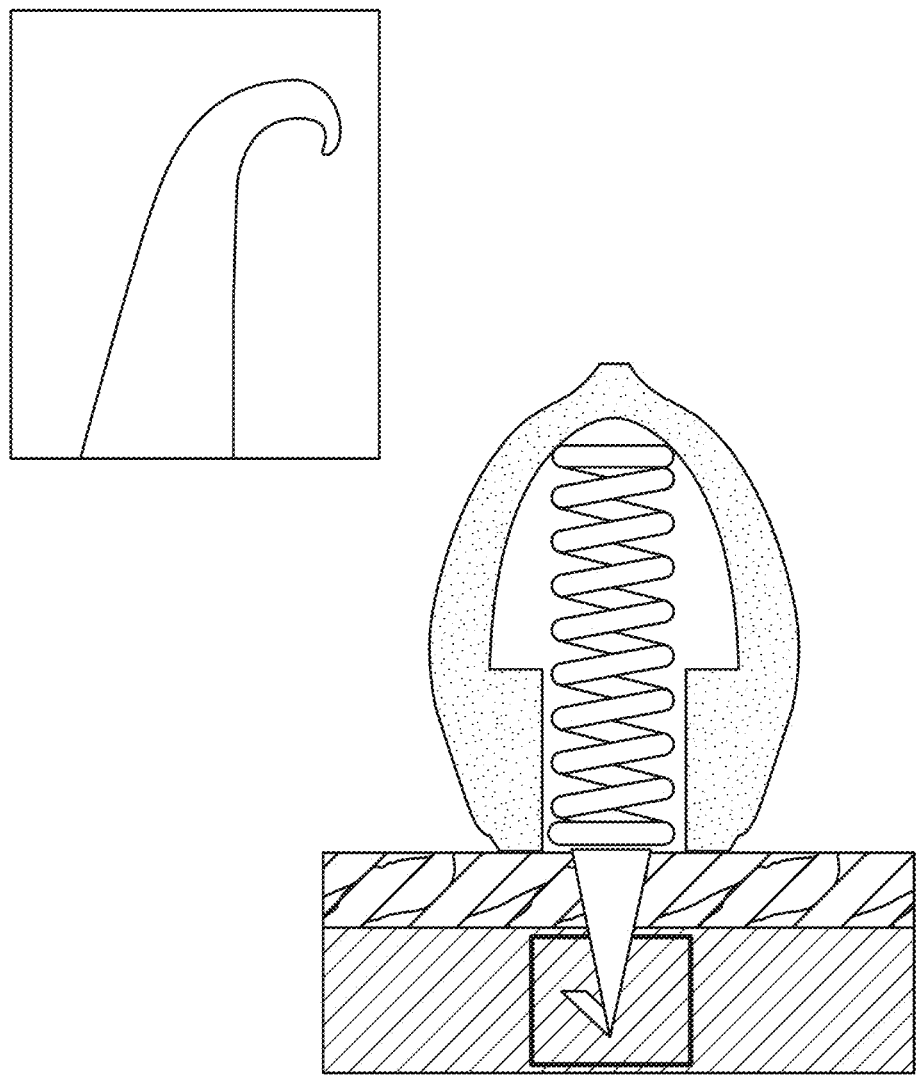
FIG. 51 is a schematic diagram of the self-righting system that is used for tissue localization and ejecting a hooked micropost (i.e. hook). An example of a hooked 32-gauge stainless steel needle is shown on the left, according to one set of embodiments.
Figure 53:
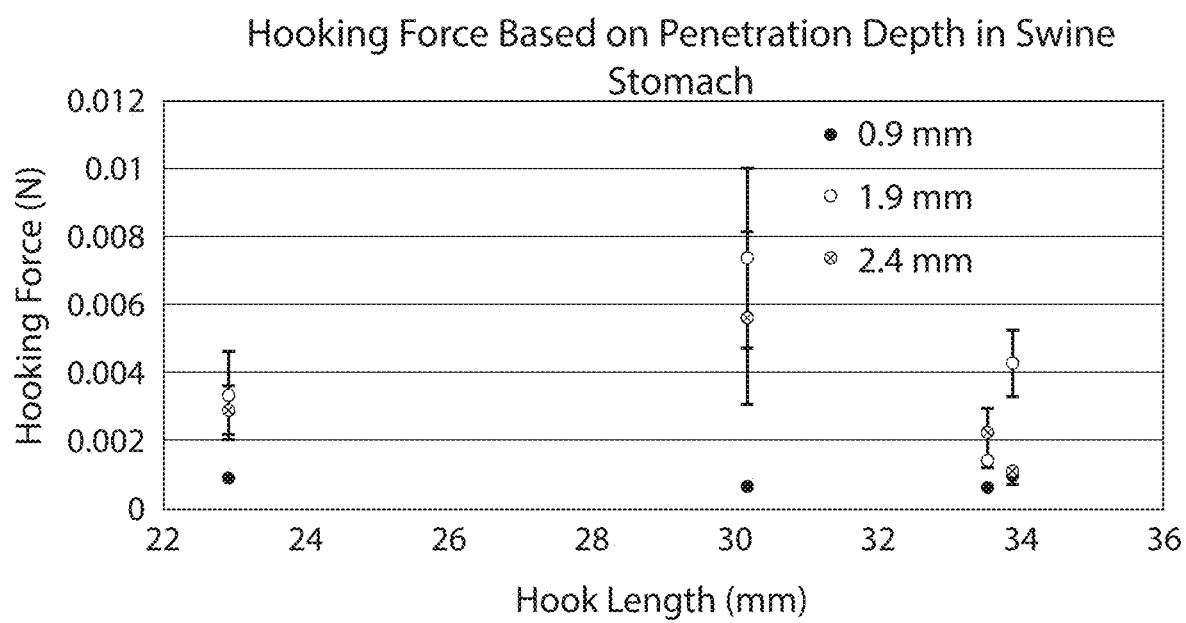
FIG. 53 is a plot of hooking force based on penetration of swine stomach tissue using hooked microposts, according to one set of embodiments.
Figure 54:
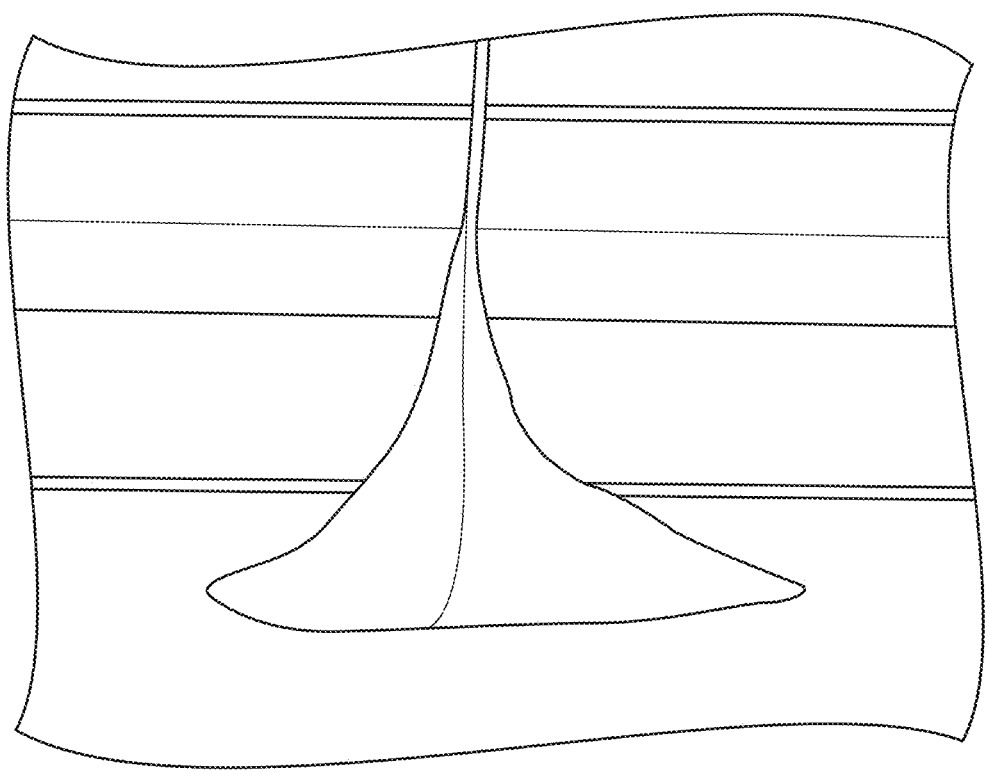
FIG. 54 is a photograph of a hooked micropost that has attached itself to the muscle fibers of swine stomach tissue.
Figure 55:
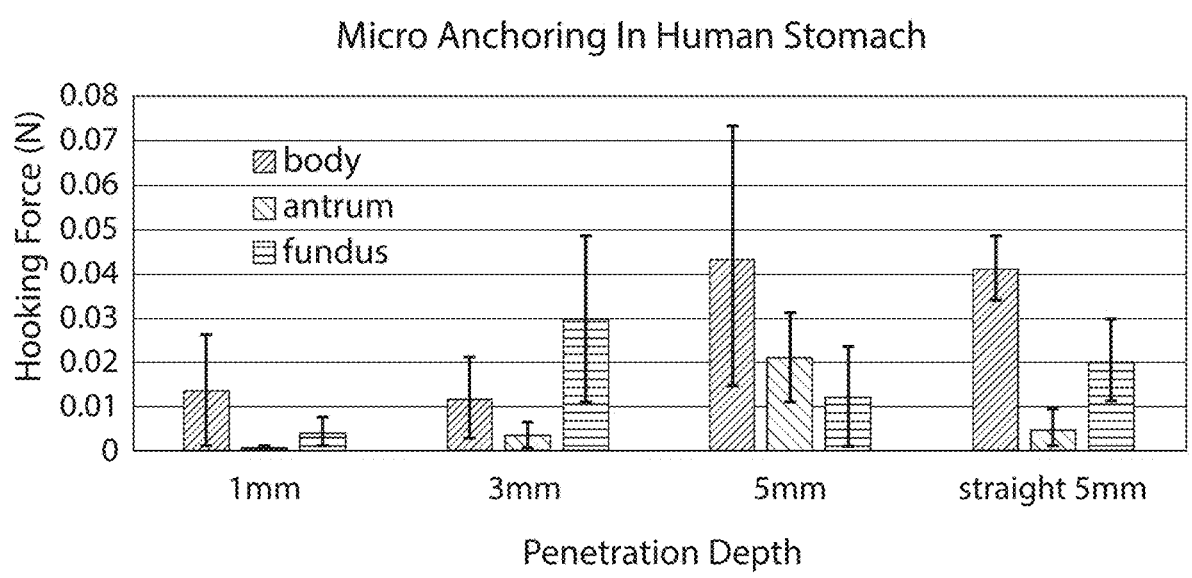
FIG. 55 is a plot of hooking force based on penetration of human stomach tissue using hooked microposts, according to one set of embodiments.
Figure 56:
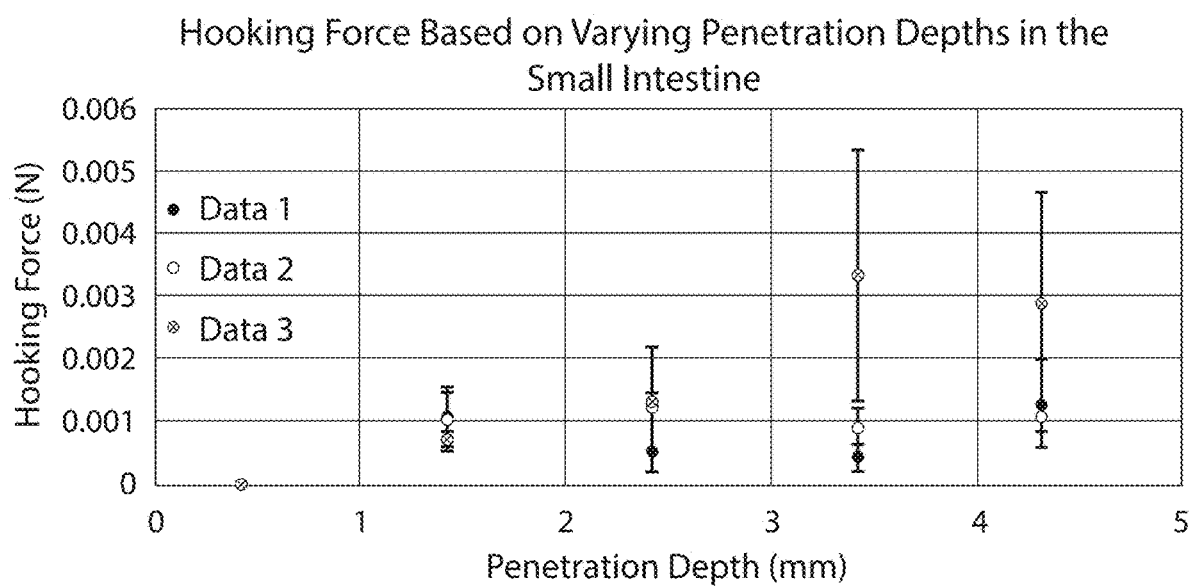
FIG. 56 is a plot of hooking force based on penetration of swine small intestinal tissue using hooked microposts, according to one set of embodiments.
Figure 57:
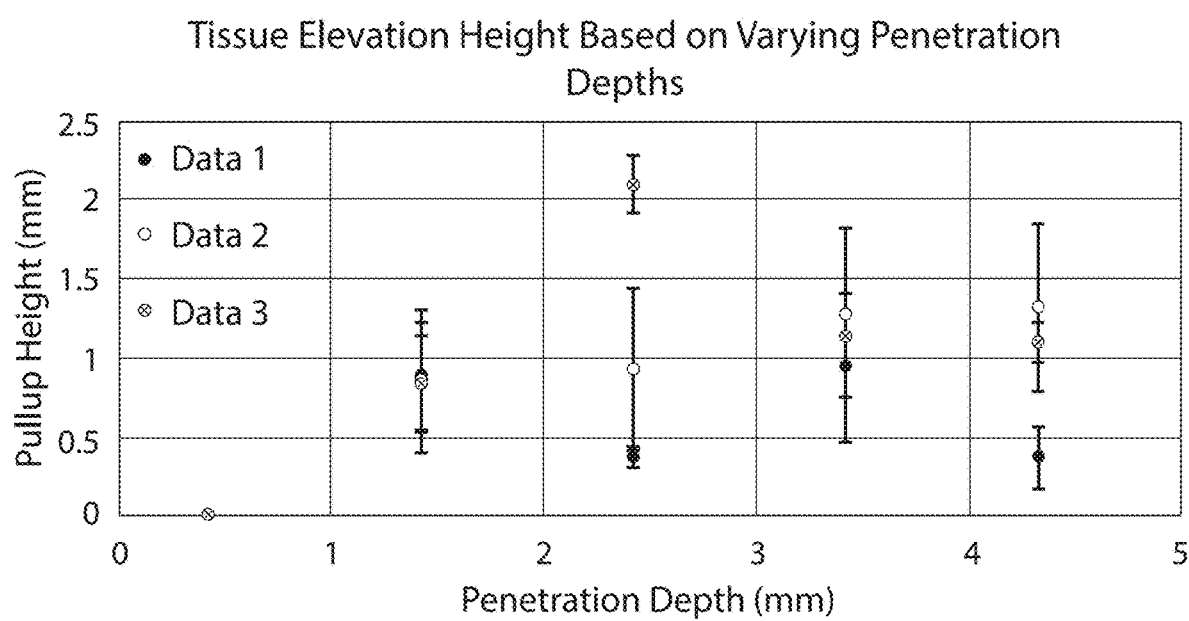
FIG. 57 is a plot of pullup height based on penetration of swine small intestinal tissue using hooked microposts, according to one set of embodiments.
Figure 58:
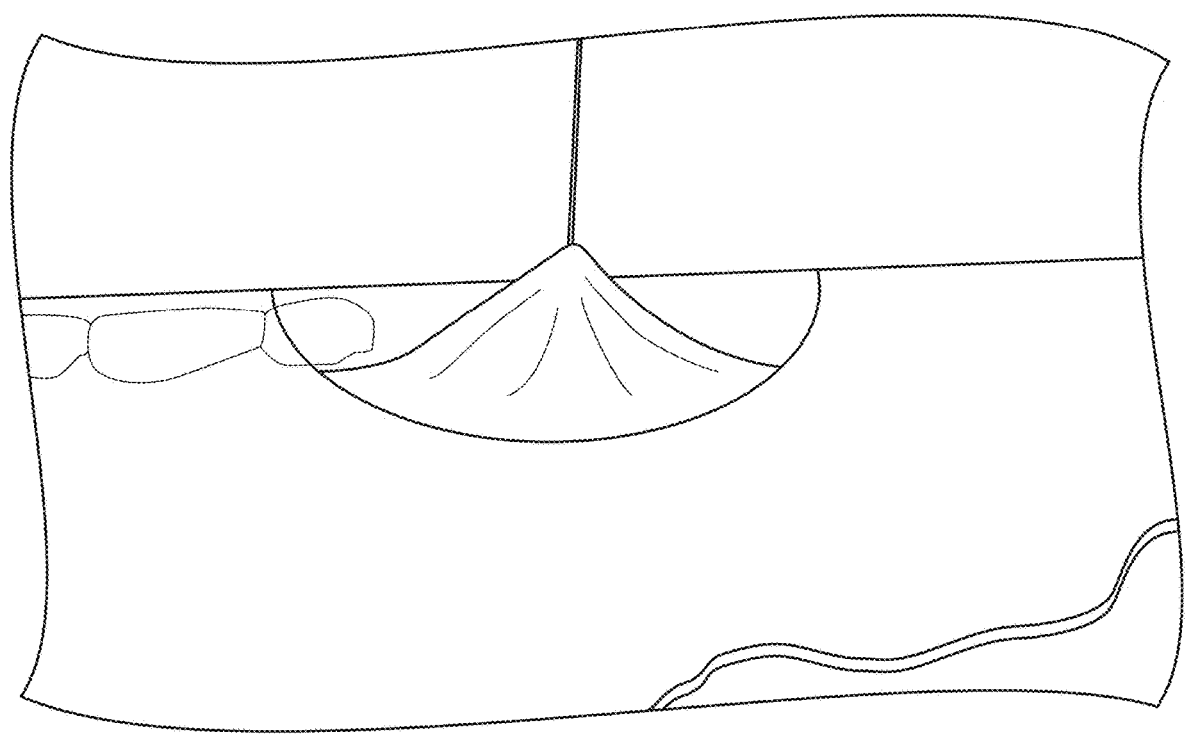
FIG. 58 is a photograph of a hooked micropost that has attached itself to swine small intestinal tissue, according to one set of embodiments.

This addendum to the disclosure discusses ways that hooked needles can be used to anchor a device onto the tissue wall of the GI tract. Needles can be propelled into the GI tract from a self orienting device via a loaded spring mechanism (FIG. 51). There are optimal ways to place the needles so that the device can retain with greater strength in the stomach including: penetration depth (FIG. 52)) and hook size (FIG. 53)). For example, a 32 gauge needle needs to displace the tissue at least 1.9 mm in order to actually penetrate the stomach lining. This means that the device, in some cases, expels the needle this distance to create a hooking effect. If the device expels the needle even further, then it will continue to penetrate the tissue further and it will maintain its hooking hold on the tissue. The hook size refers to the length of the bend at the very tip of the needle. While needles are usually sharpened to a fine point, the needles were purposefully bend this point to create a hook at the end. As this hook becomes larger, the penetration force for the needle increases. A 30 um hook showed a length that balances the penetration force with the amount of tissue hooked into. As seen in FIG. 54), the hook grabs onto the stomach tissue and provides a vertical retention force for the device. This retention force specifically helps the device resist expulsion due to peristaltic movements. The same experiments were performed on a human stomach as well with a 30 um hooked needle, and the devices were shown to hook onto the tissue (FIG. 55). Human stomachs required slightly greater insertion depths compared to pig stomachs. Hooking was also shown to occur in swine small intestine as well (FIGS. 56-58).

Figure 59:
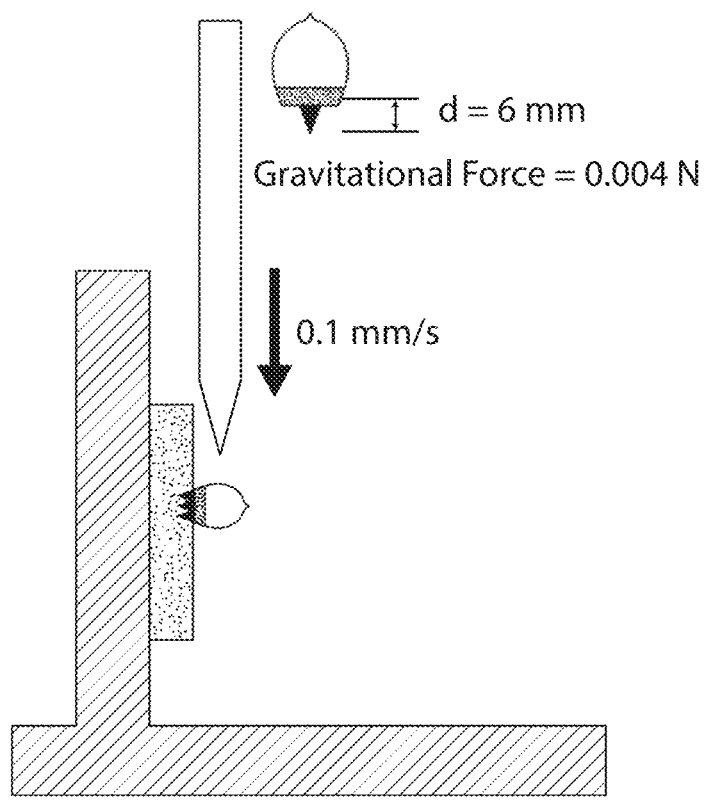
FIG. 59 is a schematic diagram of a model of horizontal tissue retention test. A probe presses down on a device anchored to the tissue via needles and records the force required to dislodge the device, according to one set of embodiments.
Figure 60:
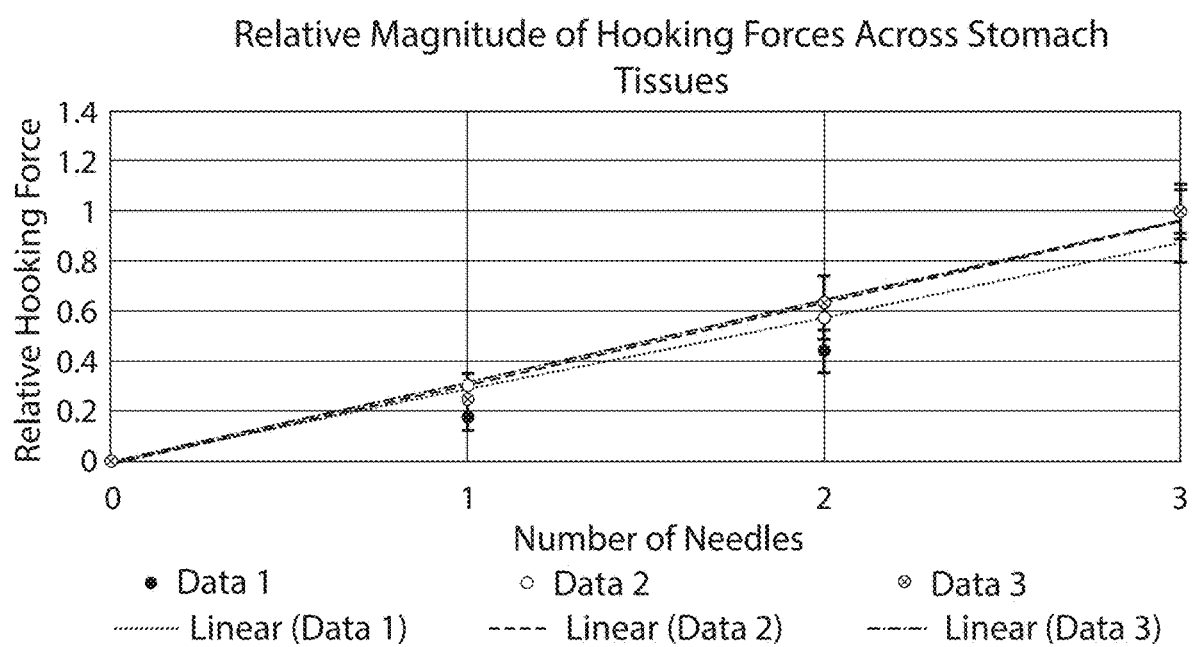
FIG. 60 is a plot of the force required to dislodge a self-righting system and increases linearly with the number of needles inserted into the swine gastric tissue, according to one set of embodiments.
Figure 61:
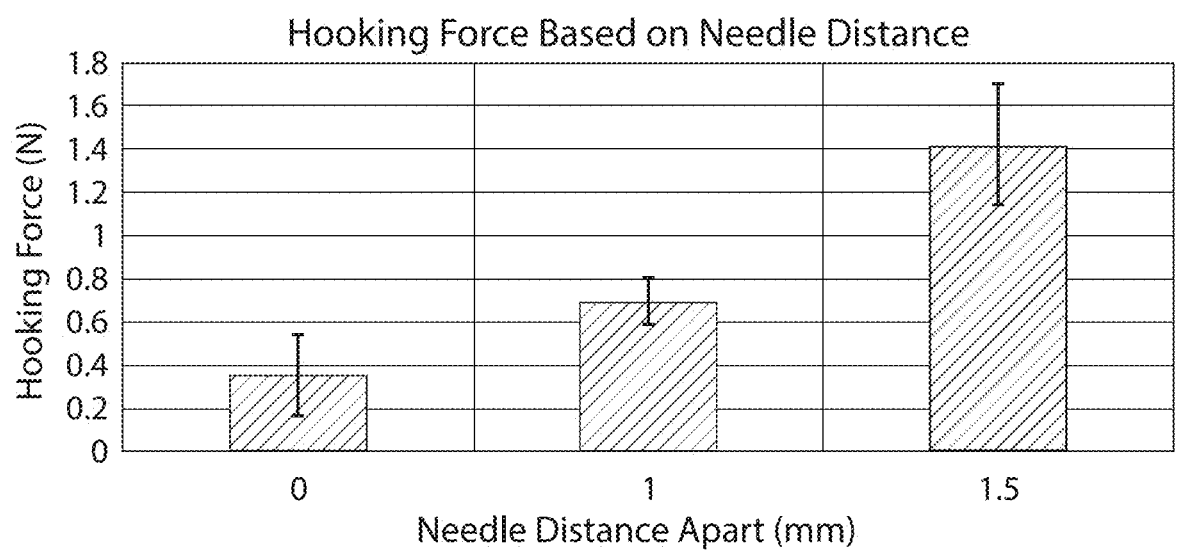
FIG. 61 is a plot of the force required to dislodge a self-righting system from swine stomach tissue versus needle distance, according to one set of embodiments.
Figure 62:
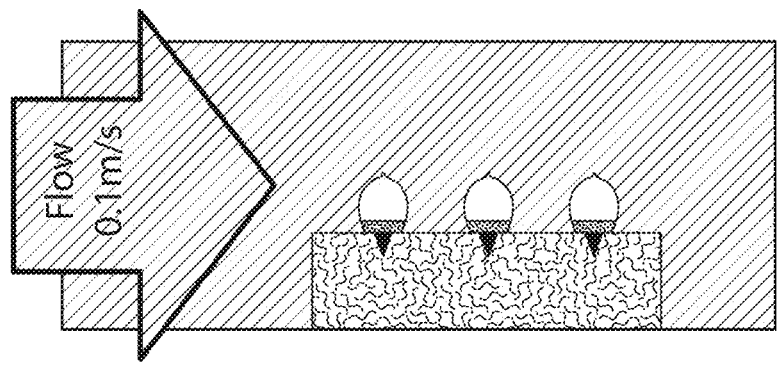
FIG. 62 is a schematic diagram demonstrating design of in-vitro experiment where self-orienting devices are anchored to swine stomach tissue while experiencing pulsatile flow, according to one set of embodiments.
Figure 63:
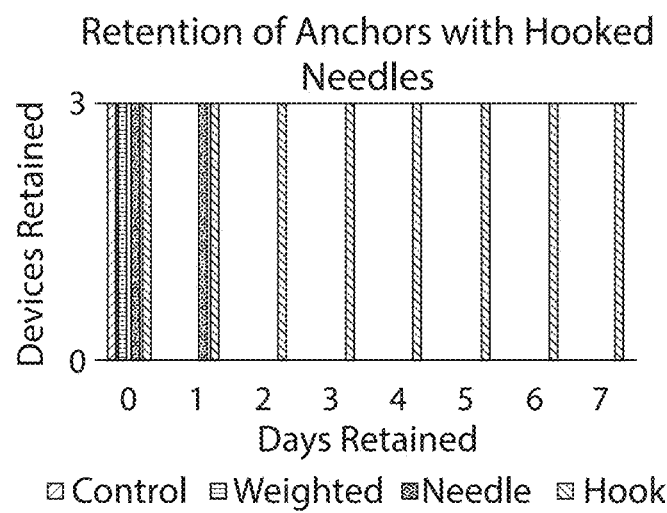
FIG. 63 is a plot demonstrating that the three devices with hooked microposts retained their position for an entire week, as opposed to comparative systems that were dislodged in under two days, according to one set of embodiments.
Figure 64:
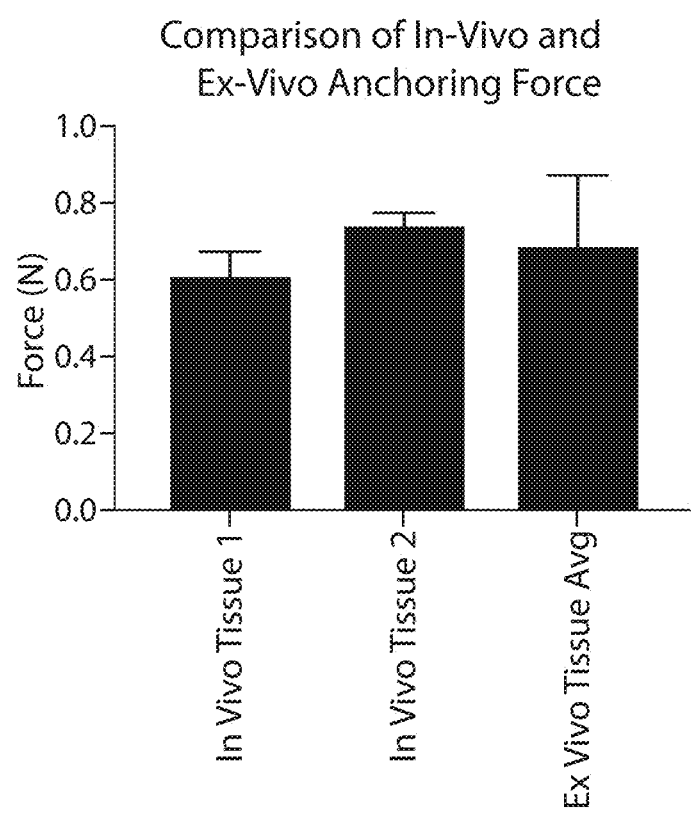
FIG. 64 is a plot of anchoring force versus in-vivo and ex-vivo swine stomachs. The ex-vivo measurement reflects studies using three separate tissue samples from different stomachs, according to one set of embodiments.
Figure 65A:
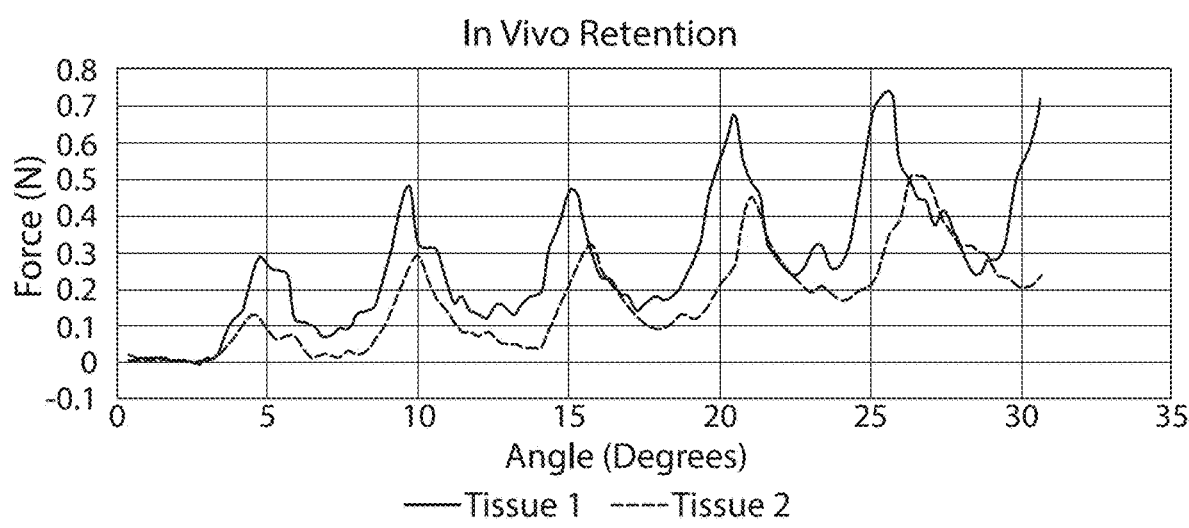
FIG. 65A is a plot demonstrating in-vivo using a swine model that as an anchored self-orienting device encounters a force that is parallel to the stomach tissue, it can retain its position while being rotated up to 30 degrees and experiencing between 0.5N-0.75N of force (the peaks and valleys correspond to the animal's breathing), according to one set of embodiments.

While the hooks on the tips of the needles provide a method to anchor the device to the tissue and provide a vertical retention force, the major forces in the stomach act perpendicular to the stomach lining and come from fluid flow. To test this, the system was inserted into a piece of tissue and pressed down with a probe at a constant force to determine the horizontal retention force of the device (FIG. 59). By inserting more needles into the tissue, the relative horizontal retention force increased linearly with each additional needle (FIG. 60). As the needles are further apart from each other, they also provide greater retention force (FIG. 61). The needle anchoring device had the ability to withstand forces from fluid flow as well as probes. FIGS. 62-63. show an in vitro setup that models the fluid flow in the stomach. Devices were attached to a piece of tissue suspended perpendicular to the ground and exposed to a pulsatile flow of 0.1 m/s for a week. Each device only had one needle anchoring it to the tissue. Devices with straight needles held onto the tissue for one day, while devices with hooked needles held onto the tissue for an entire week. The horizontal tissue test was also performed in live pig models as well (FIG. 64, FIG. 65A). These experiments, performed in two different animals, demonstrated that the devices retained with an equal amount of force in vivo and ex vivo. On average, the devices possessed a retention for of between 0.6-0.8N and could be rotated 30 degrees before they dislodged from the tissue.

Figure 66:
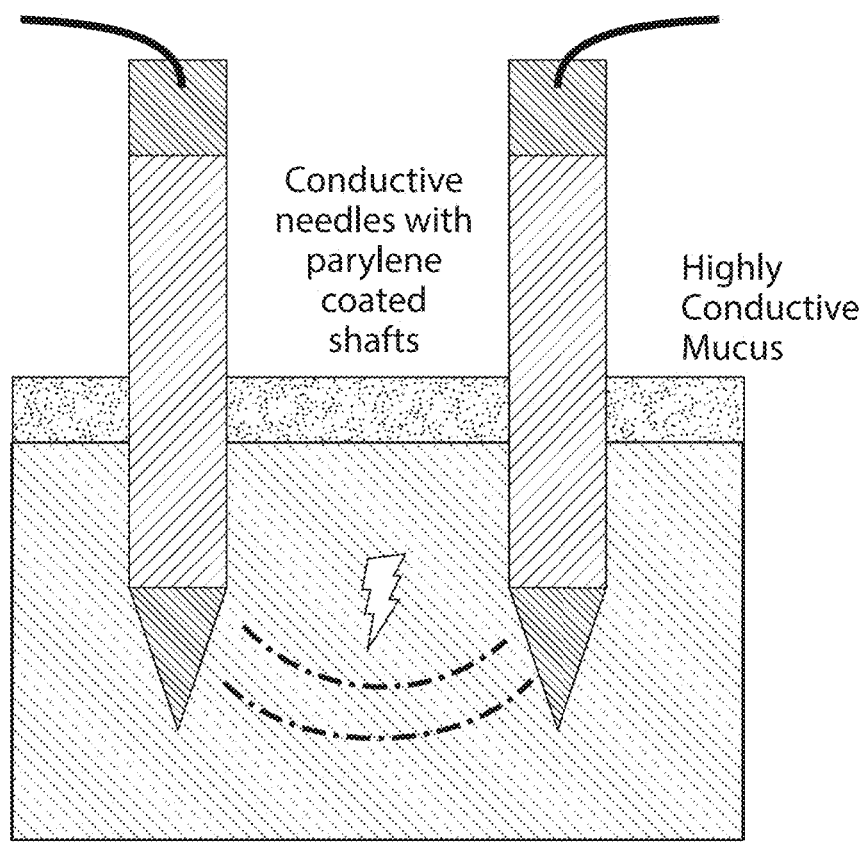
FIG. 66 is a schematic diagram demonstrating how parylene-coated electrical probes may bypass the mucus and conduct electricity through the tissue (e.g., without the coating, the electricity would flow through the lower resistance mucus and not stimulate the tissue), according to one set of embodiments.
Figure 67:
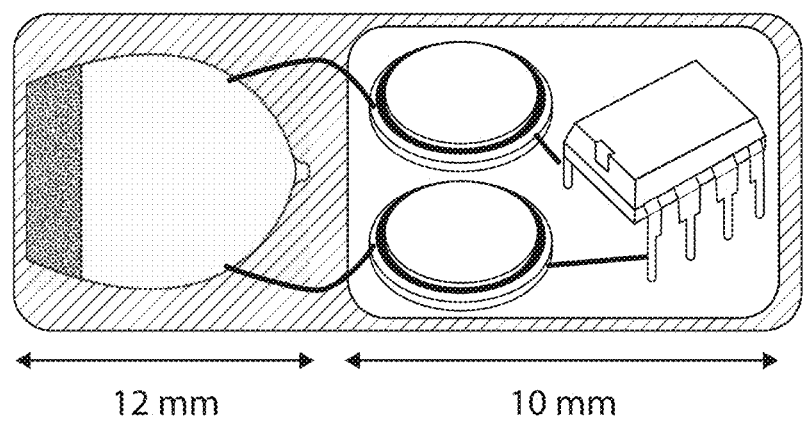
FIG. 67 is a schematic diagram demonstrating an electrical stimulation pill, including the self-orienting device containing two probes, as well as an electrical power source and a programmable microcontroller that are encapsulated in an insulating shell (e.g. PDMS), according to one set of embodiments.
Figure 68:
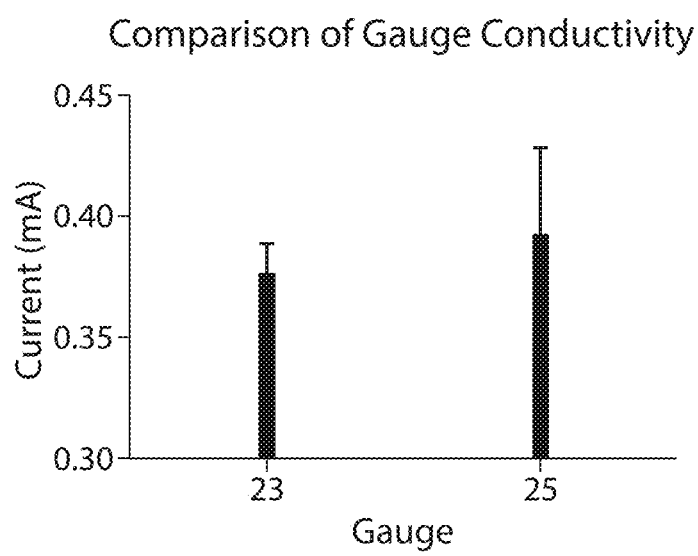
FIG. 68 is a plot demonstrating that current does not significantly change as the radius increases of the tissue-stimulating, electrical probes when powered by two silver oxide batteries (1.55V, 6.8 mm coin cell), according to one set of embodiments.
Figure 69:
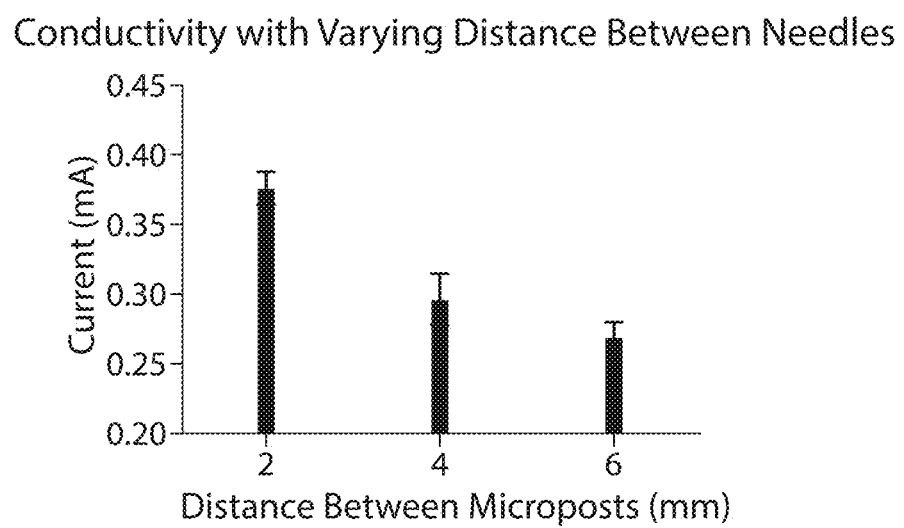
FIG. 69 is a plot demonstrating that current decreases as the distance increases between tissue-stimulating, electrical probes when powered by two silver oxide batteries (1.55V, 6.8 mm coin cell), according to one set of embodiments.
Figure 70A:
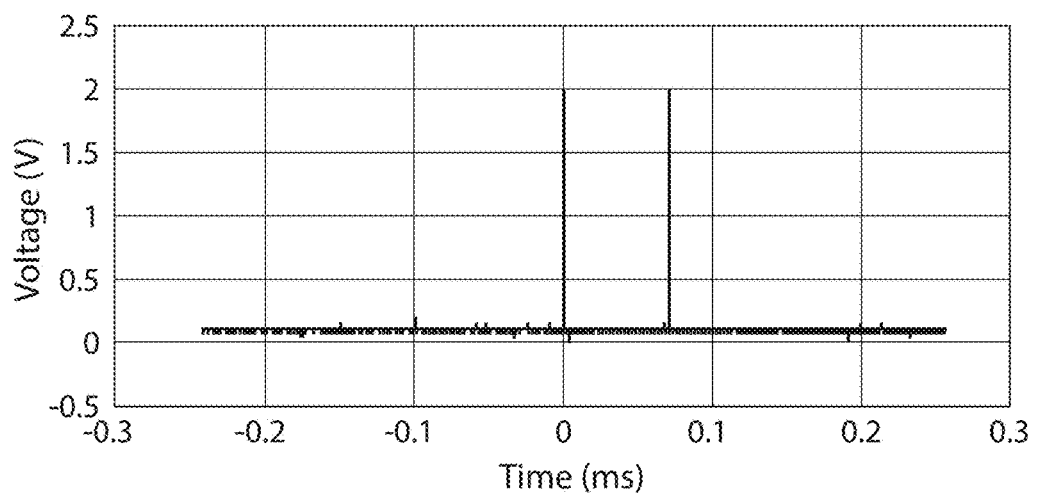
FIGS. 70A-70B is a plot showing electrical probes, powered by a voltage generator, provide pulsatile stimulation through the tissue, as measured by an oscilloscope (FIG. 70A) which can be compared to the background voltage measured within the tissue (FIG. 70B), according to one set of embodiments.
Figure 70B:
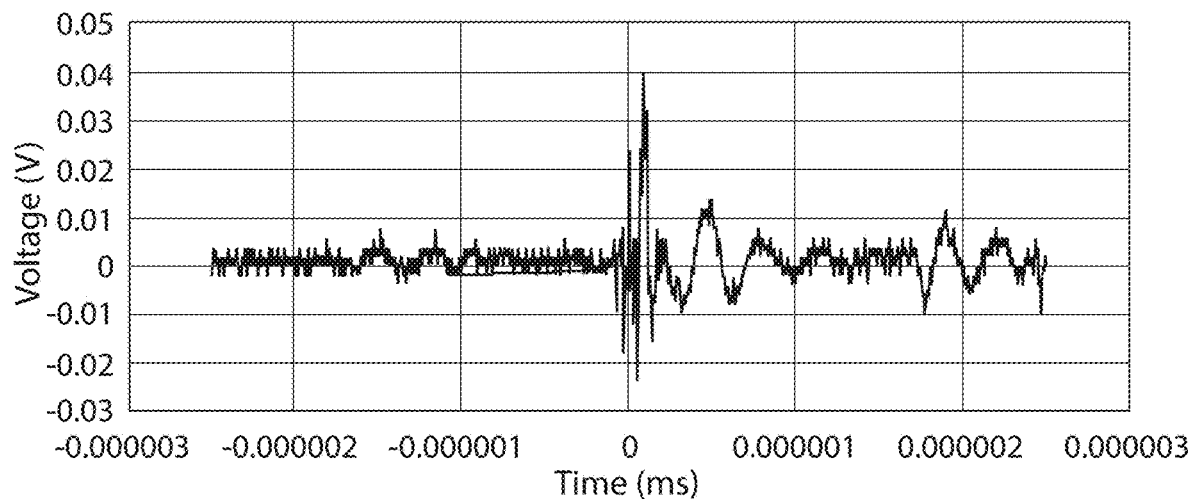
Figure 71A:
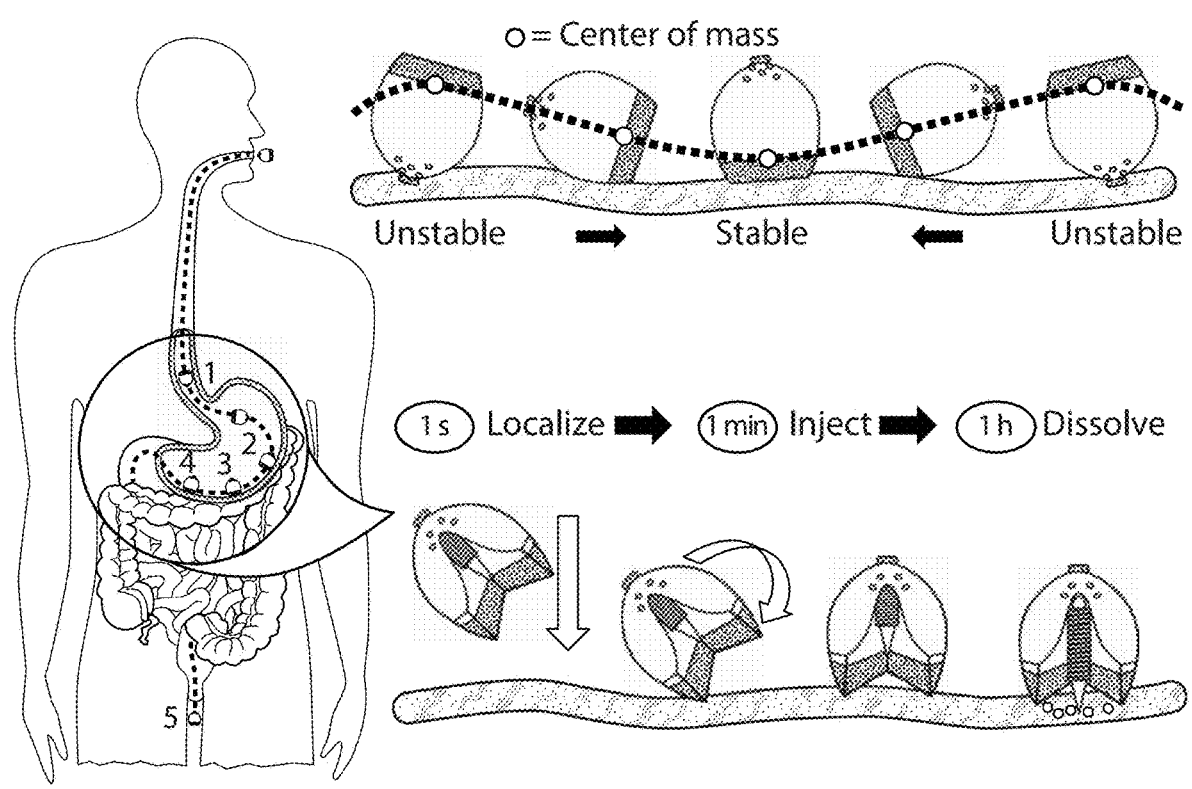
FIGS. 71A-71D shows mechanical API localization and injection for oral gastric delivery.
Figure 71B:
Figure 71C:
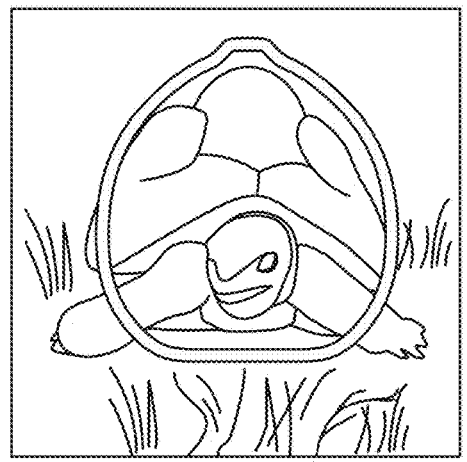
Figure 71D:
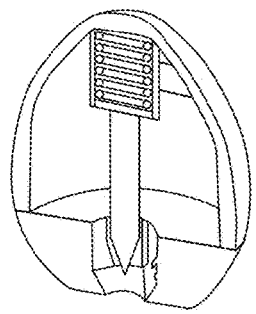

Because the GI tract contains a thick layer of highly conductive mucus on top of its tissue, the shaft of the needles were coated with a 5 um layer of parylene for insulation. Only the base and the tip of the needle were conductive, allowing for the electricity to flow through the tissue rather than the mucus (FIG. 66). The full system consists of a power source, a self actuating device with needle probes, and a microcontroller to regulate the pulses providing the stimulation (FIG. 67). The electrical components must be insulated to prevent a short circuit. All of these components fit easily inside of a 000 capsule. FIG. 68 and FIG. 69 show the effects of changing the probe size as well as changing the probe distance with a fixed power source. The distance between the probes greatly affects the resistance of the completed circuit and therefore changes the amount of current that passes through the system when the voltage is fixed. Changing the probe size surprisingly did not affect the current very much, and this is likely due to the fact that the major factor in the circuit is the tissue and not the probes. FIG. 70A demonstrates the voltage measurements from circuit created by the final device implanted into the tissue wall. The background noise, shown in FIG. 70B is negligible compared to the power produced by the circuit. Using a microcontroller, pulses of electricity were programed into the circuit. This circuit was created by using the paralyene coated needles and attaching them to a self actuating system connected to a constant voltage source and inserting these probes into the tissue wall. While the self righting/self actuating system contains a metal bottom, this bottom was coated in parylene to insulate it. These graphs demonstrate that the device can indeed deliver a programed electrical current into the tissue wall of the GI tract.

Hooked needles possess a few possible safety concerns. First, they must not perforate the tissue. The stomach tissue is about 5 mm thick and the small intestine is about 1-1.5 mm thick. Both of these tissues are malleable, and needles can displace them a greater distance than their depth before they are perforated. For a small intestine, a needle can displace tissue 5.9 mm+−1.1 mm in a sample size of tissues from 3 different pigs for a total of n=15. The lowest value recorded was 4.5 mm. For the stomach it is difficult to displace the tissue an entire centimeter, but if it is done slowly, then it still will not perforate the tissue. For safety's sake, it is ideal to keep the needles the thickness of the tissue, especially if the needles are penetrating quickly.

Needles may also be non-degradable or degrade very slowly in order to provide Gastro-retentive capabilities. This provides the possibility for needles to be left in the tissue for extended periods of time. However, the tissues in the GI tract renew very quickly, so the needles will be forced out of the tissue in time. As long as the needles remained attached to the device, it will be possible to retrieve them using a retrieval protocol as well. For example, a device could be removed via an endoscopy, or it could attach to another swallowed device such as an adhesive hydrogel using host/guest interactions.

Finally, if needles are separated from the device or when the device detaches from the tissue, then the device must pass safely through the GI tract. It has been noted in literature that sharp objects one dimensional objects less than 1 cm in length do not pose a risk for perforation. Generally, if the needles are smaller than 1 cm in length then there is little risk for perforation. However, the ideal length for safety and perforation may depend, in some cases, on the type of tissue, type of subject (e.g., animal, human), and location of the tissue and may, in some cases, be greater than 1 cm.

Prophetic Example

1. A device that uses hooks to latch onto the tissue walls of the GI tract
2. Hooks used are between 10-250 um long with the optimal being around 30 um
3. Hooks are penetrated into the tissue between 1-3 mm
4. Hooks are spaced at least 1.5 mm apart
5. Hooks are non-degradable
6. Needles containing hooks are less than 1 cm in length
7. More than 1 hook can be used per device.
8. Hooks provide vertical retention forces
9. Inserted objects provide horizontal retention forces 10. Metal needles can be used for electrical stimulation
11. Circuit can be made from 1 device with 2 needle probes or two devices each with one needle probe.
12. The whole device setup can fit inside of a 000 capsule and be ingested.
13. The retention of the device is temporary as the stomach lining sloughs off.

In humans, as well as in several animals like pigs, the stomach lies at the end of the esophagus, a long fibromuscular tube that connects to the mouth where food enters the GI tract. The stomach, which is the primary location for food digestion in the human body, is a significant space that offers high residence times of 1-4 hours. To digest the food, the stomach contains gastric acid that creates a low pH environment, as well as many enzymes, such as pepsin, that break it down into amino acids. Through muscular movements, the stomach exerts translational forces on its contents of roughly 0.2 N, which facilitates solution movement. Once food has sufficiently degraded, it passes through the pyloric sphincter into the duodenum to reach the small intestine. To protect itself from the harsh environment within, the interior surface of the stomach has a mucous coating that is 40 to 450 μm thick. Under the mucosa lies the muscularis mucosa, a thin layer composed of smooth muscle fibers. The muscularis mucosa separates the mucosa from the submucosa, which covers the stomach's primary muscle fibers used for contraction.

In order for the needle to penetrate the stomach lining, a system was designed to ensure its placement. Using the theory of a Gomboc, a self-righting shape was previously designed so that the device can invert itself in the gastric acid with the needle facing down. The device itself was made of two different pieces, the heavier bottom piece is made of stainless steel, while the top piece is made out of polycaprolactone (PCL). In the center of the device sits the needle, which is attached to a sugarcoated, condensed spring. Once the sugar dissolves, the spring serves as an auto-injector that ejects the needle from the interior of the device so that it can insert itself into the muscle lining, as shown in FIG. 51. To increase the retention capacity of the needle, a force of 1N was exerted on the needle using an Instron machine to bend its tip, as shown in FIG. 51. This hook at the end of the needle was created to help the needle latch onto the muscle fibers in the distal stomach near the antrum, as shown in FIG. 54.

Figure 52:
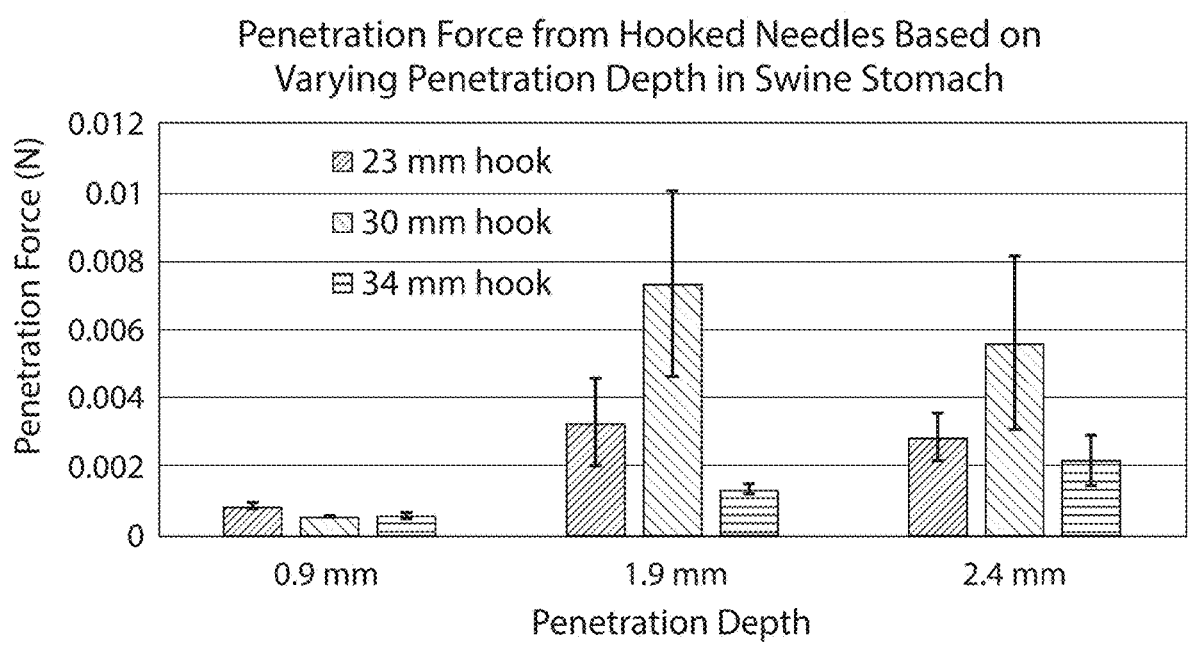
FIG. 52 is a plot of penetration force into swine gastric tissue using hooked microposts, according to one set of embodiments.

To determine the maximum force necessary to dislodge the needle from the stomach lining, an ex-vivo model was created using swine tissue since the pig's gastrointestinal tract has been shown to be a good model of its human counterpart. In order to confirm this, a preliminary ex-vivo experiment was performed. To do so, a 10 cm by 10 cm section of tissue was dissected from the stomach of a Yorkshire pig. The swine tissue was then fixed between two acrylic plates, with the interior surface of the stomach facing up under the plate containing an approximate 3 cm diameter hole in its center. These plates were then placed on the Instron machine comprised of a moving arm containing a force sensor that is accurate up to 0.1 mN. On this arm of the Instron, a stainless steel hooked needle adhered to a screw was secured in place. To determine the force necessary to penetrate the tissue, the Instron arm was lowered at a constant rate of 0.1 mm/sec until it reached 5 mm of depth while the device recorded the hooking force required to be exerted to reach that layer. This experiment was then repeated using tissue from a human cadaver stomach. As shown in FIG. 52 and FIG. 55, the human stomach exhibited very similar properties and produced almost equivalent results compared to the porcine trials.

With pig tissue shown to be a strong model for its human counterpart, a similar experiment was conducted to determine the ideal depth of penetration to maximize the retention force. To determine the ideal depth of penetration to maximize the retention force, the Instron arm was lowered at a constant rate of 0.1 mm/sec until it reached 1 mm, 3 mm, or 5 mm of penetration into the tissue. In this experiment, the Instron recorded the hooking force required to be exerted in order to reach that layer of penetration, as shown in FIG. 56.

In order to verify these measurements, as well as determine which layer of tissue maximized the hooking force, the needles were dyed with a surgical dye before use. Once the experiments were completed, the tissue was fixed to paraffin. The needle puncture site was found by sectioning the tissue by making parallel lateral cuts every 10 microns. Once it was located, the site was analyzed under an inverted microscope to determine the penetration depth. These histology findings also confirmed that the needle had latched onto the muscle fibers in the mucosal musculae layer under the mucous in the stomach lining.

Lastly, to determine the force required to dislodge a needle anchored in the stomach lining, a similar experiment was conducted. A stainless steel hooked needle that was adhered to a screw was attached to the moving arm of the Instron. This arm was then lowered at a constant rate of 0.1 mm/sec until the needle penetrated 2.5 mm into fixed, fresh porcine tissue. Once this distance was reached, the arm was raised at a constant rate of 0.1 mm/sec until the needle detached from the tissue. Through this experiment, the Instron recorded the penetration depth and the force exerted to remove the needle from the tissue. This experiment was repeated several times, and the average forces required to penetrate the tissue and dislodge the needle were found to be on average 3.86 mN and 10 mN respectively.

With the determined force required to dislodge an anchored needle in the stomach lining, as well as confirmation that porcine tissue exhibits similar properties to that of the human stomach, a computational model was created to determine the ability of a self righting device with a hooked needle to retain its position in the human stomach. In addition, this model determined whether a self righting device with a variable number of ancillary bodies, which could be designed for various applications, would be capable of gastric retention.

According to literature, the characteristic fluid flow in the stomach has been found to be 2-3 mm/sec while its Reynolds number has been determined to be on the order of 0.1 to 30. This Reynolds number signifies that the flow within the stomach is laminar and is dominated by viscous forces. Stokes' law, a derivation of the Navier-Stokes equation modeled for small spherical objects in viscous fluids, can then be used to determine the drag force exerted on the device. This expression is shown in Equation 1, where F is the drag force, r is the radius of the device, v is the velocity of the liquid, and μ is the dynamic viscosity of the liquid.

$$F = 6\pi * r * v * \mu \qquad \text{Equation 1}$$

In order to use this equation, the dynamic viscosity of stomach acid must be found. According to literature, the dynamic viscosity of gastric acid can vary tremendously based on the rheological properties of gastric digesta. If a 10% glucose solution meal is ingested, the gastric contents can be modeled as a Newtonian fluid with a viscosity of $10^{-3}$ Pa·s and density of 1 kg/L. However, some foods have been shown to have viscosities as large as 10 Pa·s. The introduction of even 1% of a more viscous food has been shown to increase the viscosity of gastric acid. As a result, an average dynamic viscosity has been difficult to establish. However, for the purposes of this first-order simulation, an assumption was made that the food digested was glucose-based and therefore the dynamic viscosity is approximately $10^{-3}$ Pa·s.

Using the radius of the self righting device that is attached to the needle of 4 mm, the Stokes' equation presented in Equation 1 can be used to determine the drag force exerted on the device. This drag force is established to be $2.26*10^{-7}$ N, as shown using Equation 2.

$$F=6\pi*0.004\text{ m}*0.003\text{ m/s}*0.001\text{ Pa·s}=2.26*10^{-7}\text{ N} \quad \text{Equation 2}$$

As previously noted, since this force is significantly below the necessary force, as determined through the ex-vivo experiments using the Instron, to dislodge the device, it allows for the ability to attach separate, ancillary bodies to the self-righting device using surgical non-absorbable suture that could be used for a range of applications that shall be discussed in Chapter 4. Utilizing Equation 1 to calculate the drag force on these devices, which would likely have a maximum radius of 4.5 mm to fit comfortably in a 00 capsule, each device's drag force can be found to be $2.54*10^{-7}$ N.

When determining the conditions required to dislodge the needle from the stomach lining, it is also important to consider torque. Utilizing the forces found for the self-righting device and the ancillary bodies, the torque can be calculated using Equation 3, where $\tau$ is torque, r is the moment arm, and F is force.

$$\tau = r \times F \quad \text{Equation 3}$$

Figure 65B:
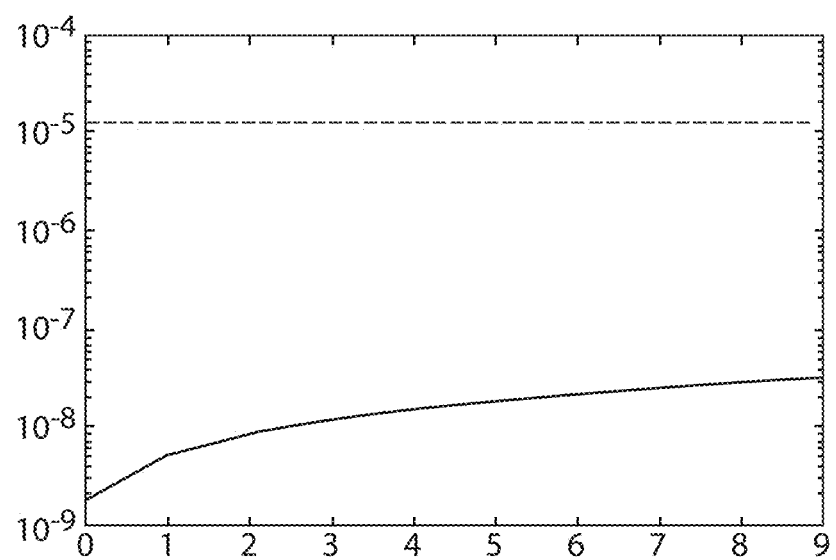
FIG. 65B is a plot showing the relationship between the number of ancillary bodies attached to the self righting device and the drag torque exerted on the system by the gastric acid, according to one set of embodiments.

Using this equation, where the moment arm is the needle's length from the tissue to the bottom of the device (1.25 mm), a plot can then be created. As shown in FIG. 65B, a graph was created to compare the number of ancillary bodies attached to the self-righting device to the torque exerted by the drag force (the dotted red line denotes the maximum torque that can be exerted on the system before the needle is dislodged. This value was determined from the force required to dislodge the needle in the ex-vivo experiments on the Instron, while using the needle's length from the tissue to the bottom of the device of 1.25 mm as the moment arm). However, as shown in this plot, even a device with 9 ancillary bodies would only experience torques several orders of magnitude smaller than what is needed to dislodge it.

From FIG. 65B, it can be determined that the drag torque remains several orders of magnitude smaller than the torque necessary to dislodge the device from the stomach lining. However, as noted earlier, since the dynamic viscosity does not account for food effects, a second model must be created. In the process of chewing, food is mashed into small spherical food boluses that then travel down the esophagus to the stomach. Once these boluses reach the stomach, they mix with gastric acid to form chyme. Using sieving and laser diffraction measurements, studies have shown that across individuals these chewed particles can vary in size based on the texture of the foods ingested. For example, raw vegetables create boluses that are on average larger than 2 mm, whereas more than half of nut particles are less than 1 mm in diameter[26].

Figure 65C:
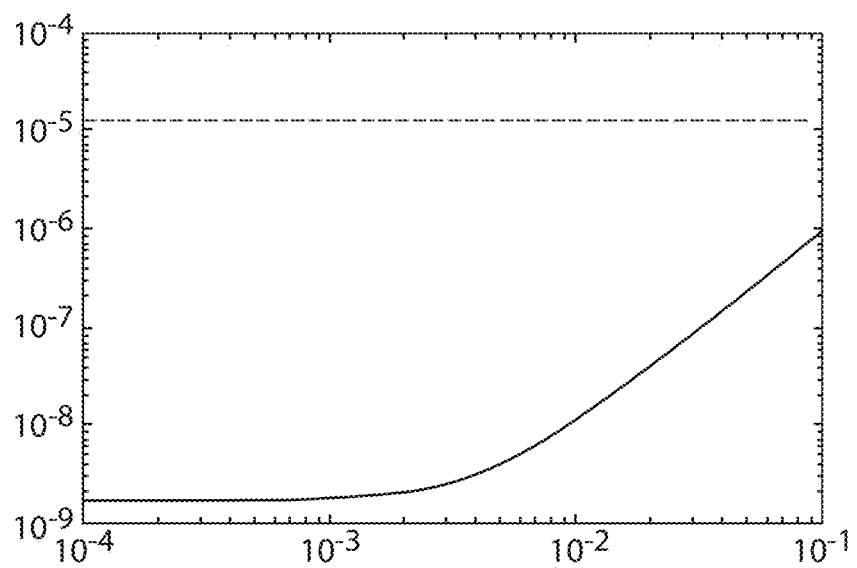
FIG. 65C is a plot comparing the size of the food boluses colliding with the self righting device and the torque exerted on it, according to one set of embodiments.

Because of this large variation in the size of food boluses, a model was created to determine whether they could exert a large enough torque on impact with the self-righting device to dislodge it. It should be noted that this simulation was created with the assumption that no ancillary bodies were attached to the device, however, the needle would have to overcome the torque from the food boluses in addition to its own drag force. To do so, the food density was assumed to be $$1000\ \frac{\text{kg}}{\text{m}^3}$$

and that the boluses would compress on average 50% in a collision with the self-righting device while moving with the gastric acid at 3 mm/s. The lengths of the food boluses considered ranged from 0.1 mm to 100 mm to cover all possible diameters. However, as FIG. 65C shows, even though the torque exerted by the food boluses can increase by an order of magnitude depending on their textures, the torques exerted on the self-righting device would still be far smaller than what would be required to dislodge it (the dotted red line denotes the maximum torque that can be exerted on the system before the needle is dislodged. This value was determined from the force required to dislodge the needle in the ex-vivo experiments on the Instron, while using the needle's length from the tissue to the bottom of the device of 1.25 mm as the moment arm).

With the preliminary measurements for the penetration depth and dislodgement forces determined, in addition to verification using computational simulations that the device could resist the forces present in the stomach, experiments were designed to test its retentive abilities. This chapter will discuss the in-vitro, as well as in-vivo, trials that were necessary to adequately simulate gastric conditions to determine whether the device can resist dislodgement.

In order to test the micropost's ability to retain its position in the stomach lining despite the effects of drag forces from the gastric flow, an in-vitro experiment was designed. To do so, Tygon PVC tubing were connected together to create a closed circuit attached to a water pump. A 10 cm by 10 cm section of tissue was dissected from the stomach of a Yorkshire pig and was fixed to the interior of tubing perpendicular to the ground. 3 self righting devices with hooked needles were then placed on top of this tissue. In addition, 3 self righting devices with unhooked needles, 3 self righting devices with no needle, and 3 spherical objects the same size as the self righting devices were also placed on the tissue as controls. Water was then introduced to the system and the pump was turned on to pump fluid at 0.1 m/s. FIG. 57 illustrates how this experiment was conducted.

The system was run for one week to determine the hooked needle's ability to withstand fluid flow compared to its counterparts. As shown in FIG. 58, while all the controls were dislodged by Day 2, the self-righting device with the hooked needle was able to retain its position for the entire week to verify the computational simulation's results.

With the positive results from the synthetic stomach experiment that confirmed the predictions from the computational simulations, a multi-day in-vivo trial was designed for a swine model. Using an overtube, 4 self-righting devices with hooked needles were placed in a straight line on the right side of the stomach. Another 4 self-righting devices with regular needles were placed in a similar arrangement on the left side of the stomach so that they could be differentiated. On Days #2 and #3, an endoscope was used to monitor whether any of the self-righting devices had moved. However, when the experiment was conducted, all of the devices, whether hooked or unhooked, did not retain their position in the stomach.

There are several potential explanations for why the devices were dislodged in the pig stomach. In order to determine whether the device is not as resilient as the computational models predicted, further experiments must be conducted in-vitro to characterize its retentive ability. The protocols of several of these experiments will be described in Chapter 4. However, the dislodgement may also be due to the differences between the human stomach and the porcine model, such as motility. Unlike humans, which digest food between 1-4 hours in the stomach, pigs can take over 6 hours to pass their meal into the small intestine[27]. In addition, based on observation, pig boluses are much larger than their human counterparts, which would increase the force exerted on the device in a collision. Lastly, pigs eat large portions several times a day to keep their stomachs full, whereas humans exert more moderation in limiting their food intake.

Through ex-vivo experiments on an Instron machine, the force required to penetrate the stomach lining, the depth necessary to ensure maximum retention, and the force required to remove a hooked needle were determined. A couple of computational models were created to utilize this data to verify the self righting device with a hooked needle would be able to retain its position despite the gastric conditions and associated effects it would be subject to. To simulate the drag forces, an in-vitro experiment was conducted to ensure the self-righting device would not be dislodged when exposed to fluid flows. With the positive results from this experiment, an in-vivo trial was conducted using a swine model, however, none of the hooked needles managed to retain their position over the multi-day investigation.

The long-term retention of microposts in the gastric lining could create a number of applications. As previously noted, it would allow for the prolonged delivery of medications that must traditionally be administered daily, such as insulin. It would also offer a viable method for biologic drugs, which traditionally must be injected due to enzymatic degradation in the gastric environment, to be delivered orally.

Such microposts could serve as an anchor in the stomach for other devices that traditionally cannot maintain high residence times in the GI tract. These devices could be attached to the self-righting device using non-absorbable suture and sit in the stomach as ancillary bodies. One potential application could be for Bluetooth low energy for medical monitoring. This technology has created a growing field that promises to help doctors and health workers monitor their patient's condition at home. A small Bluetooth monitor that could fit into a 00 capsule could thus be combined with a long-term needle retentive device to monitor different properties in the stomach, such as pH or temperature changes. Lastly, gastric electrical stimulation has been shown promise in dealing with several clinical problems, such as gastroparesis and obesity. If the ancillary bodies attached to the self-righting device were batteries in a multi-needle system was created, an electrical circuit could be created with the stomach lining that could facilitate this stimulation.

FIG. 51: Diagram of the self-righting system that is used for tissue localization and ejecting a hooked micropost. An example of a hooked 32-gauge stainless steel needle is shown on the left FIG. 52: Penetration of swine gastric tissue using hooked microposts show that 1.9 mm of depth requires the largest penetration force for both 23 mm and 30 mm hooks FIG. 53 Penetration of swine stomach tissue using hooked microposts show that the forces required to dislodge the self-righting system were maximized using 1.9 mm and 2.4 mm hooks when the hooks were 30 mm long FIG. 54: Hooked micropost that has attached itself to the muscle fibers of swine stomach tissue FIG. 55: Penetration of human stomach tissue using hooked microposts show that the forces required to dislodge the self-righting system from the body and antrum tissue were maximized when the penetration depth was 5 mm FIG. 56: Penetration of swine small intestinal tissue using hooked microposts show the forces required to dislodge the self-righting system plateaued after 1.5 mm of penetration FIG. 57: Penetration of swine small intestinal tissue using hooked microposts show that the height to which the tissue could be elevated plateaued following 1.5 mm of penetration FIG. 58: Hooked micropost that has attached itself to swine small intestinal tissue FIG. 59: Model of horizontal tissue retention test. A probe presses down on a device anchored to the tissue via needles and records the force required to dislodge the device.

FIG. 60: The force required to dislodge a self-righting system is shown to increase linearly with the number of needles inserted into the swine gastric tissue FIG. 61: The force required to dislodge a self-righting system from swine stomach tissue is shown to statistically significantly increase when its three needles are spaced farther apart FIGS. 63A-63B: A) Diagram demonstrating design of in-vitro experiment where self-orienting devices are anchored to swine stomach tissue while experiencing pulsatile flow (FIG. 63A). Graph demonstrating that the three devices with hooked microposts retained their position for an entire week, as opposed to other systems that were dislodged in under two days (FIG. 63B).

FIG. 64: Graph demonstrating that there is not a statistically significant difference between the anchoring forces of the self-orienting device to in-vivo and ex-vivo swine stomachs. The ex-vivo measurement reflects studies using three separate tissue samples from different stomachs.

FIG. 65A: Graph demonstrating in-vivo using a swine model that as an anchored self-orienting device encounters a force that is parallel to the stomach tissue, it can retain its position while being rotated up to 30 degrees and experiencing between 0.5N-0.75N of force. The peaks and valleys are a result of the animal's breathing.

FIG. 65B is a plot showing the relationship between the number of ancillary bodies attached to the self righting device and the drag torque exerted on the system by the gastric acid, according to one set of embodiments;

FIG. 65C is a plot comparing the size of the food boluses colliding with the self righting device and the torque exerted on it, according to one set of embodiments;

FIG. 66: Diagram demonstrating how parylene-coated electrical probes bypass the mucus and conduct electricity through the tissue. Without the coating, the electricity would flow through the lower resistance mucus and not stimulate the tissue.

FIG. 67: Diagram demonstrating electrical stimulation pill, including the self-orienting device containing two probes, as well as an electrical power source and a programmable microcontroller that are encapsulated in an insulating shell (e.g. PDMS). This system is connected in a proper electrical circuit using insulated wires. This circuit is completed through the tissue. This entire system can be packaged in a 000 capsule.

FIG. 68: Graph demonstrating that current does not significantly change as the radius increases of the tissue-stimulating, electrical probes when powered by two silver oxide batteries (1.55V, 6.8 mm coin cell).

FIG. 69: Graph demonstrating that current decreases as the distance increases between tissue-stimulating, electrical probes when powered by two silver oxide batteries (1.55V, 6.8 mm coin cell).

FIGS. 70A and 70B: Electrical probes, powered by a voltage generator, provide pulsatile stimulation through the tissue, as measured by an oscilloscope (FIG. 70). This can be compared to the background voltage measured within the tissue (FIG. 70B).

Example 16—Exemplary System (SOMA)

The following example demonstrates the fabrication and design of an exemplary self-righting system, as described herein.

The exemplary system (SOMA)'s self-orienting capability helps ensure that the device is positioned correctly to insert microposts into the tissue wall, and it addresses the safety and efficacy concerns associated with insertion by delivering microposts with force enough to only reach the submucosa, in some embodiments. The stomach's natural biology provides a wide safety margin during the insertion event; it was shown that a micropost would use, in some cases, more than 4 additional Newtons of force to penetrate through the next layer of tissue, the muscularis externa. The SOMA was made from materials tested in both rats and swine for biocompatibility, and its small form factor generally prevents obstruction in the lower GI tract. The SOMA is smaller in volume than the FDA approved daily dosed OROS system (Ø9 mm×15 mm), a non-degradable drug delivery system which provides obstruction rates on the order of 1 in 29 million. When tested in vivo, the SOMA showed no signs of obstruction, did not perforate the tissue, and delivered similar amounts of API over 2 hours as compared to a subcutaneously placed micropost. The unique shape of the SOMA provides an optimized setup for gastric micropost delivery.

Figure 75:
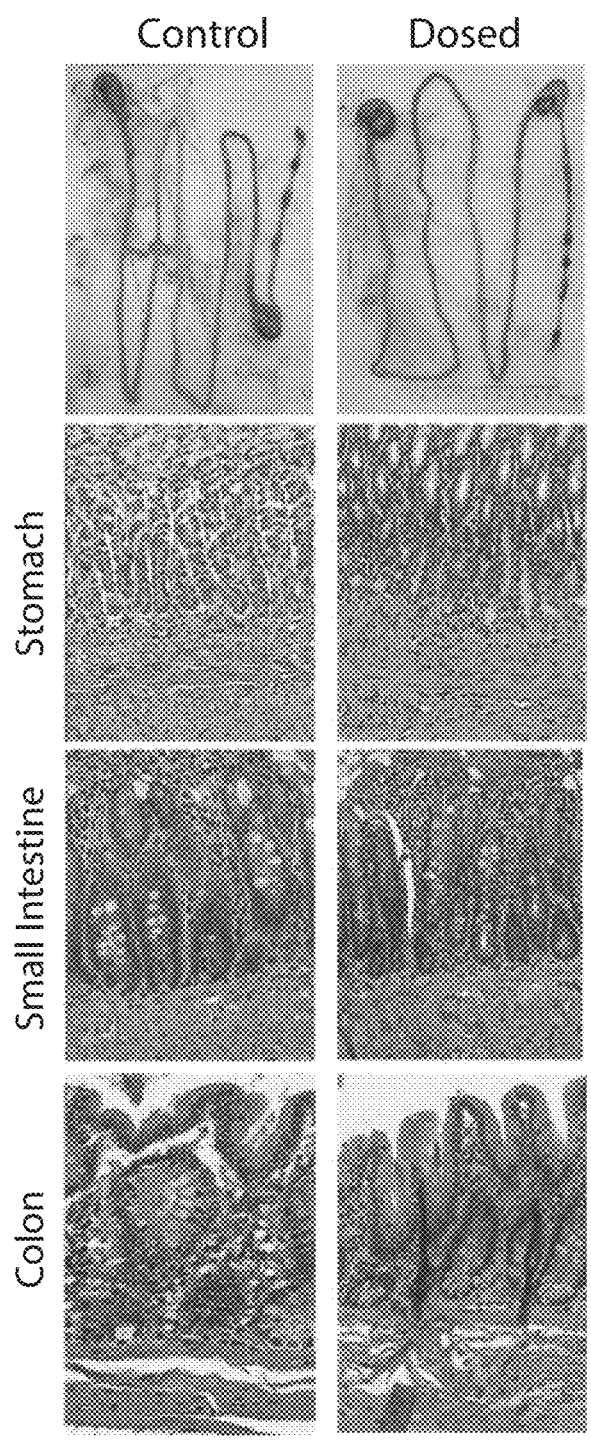
FIG. 75 shows stainless steel toxicity examination for an exemplary system. Histology from the digestive tract of one of six rats fed a single dose of 2000 mg/kg 316 stainless steel particles suspended in 1 mL canola oil via a 15G oral gavage shows no abnormalities when compared to a rat dosed only with 1 mL of canola oil, according to one set of embodiments.

A mono-monostatic body optimized for rapid self-orientation with the capacity to resist external forces (e.g. fluid flow, peristaltic motion, exercise) upon reaching a stable point (FIGS. 71A-71D) was designed. For example, the upper section of a tortoise shell, known as the carapace, has a high curvature to aid in self-orientation, while the lower section, known as the plastron, possesses a lower curvature to increase stability. The tortoise's soft tissue occupies the lower area of the shell, shifting the center of mass towards the plastron and further stabilizing the preferred orientation. Since self-orienting devices generally rely on low centers of mass compared to their centers of volume, a combination of poly-caprolactone (PCL) and 316L stainless steel to produce the density gradient was used. Similarly dense materials such as polypropylene and field's metal function were used interchangeably during the in vitro prototyping process. Because stainless steel is not typically used in oral devices, its oral toxicity was evaluated in rats during both acute and sub-chronic studies. No inflammation or toxicity signs (FIG. 75) were observed, which in line with other studies on stainless steel in the GI space, including ones on dental braces.

Utilizing MATLAB's fmincon function, an axisymmetric shape was designed described by a planar curve C in polar coordinates (r, θ) that minimized the average time required for the object to orient towards the GI tract tissue wall from 36 different angles while maximizing the torque required to tilt the device from its preferred orientation. Theoretical orientation times were computed using Newtonian angular kinematic equations, as described below. As initial guesses for the shape, geometric models of tortoise shells were employed, which combined hyperbolas to represent the carapace and low curvature arcs to represent the plastron. Mimicking the tortoise's mass distribution, the upper portion of the device was hollowed out in the model and used to house the actuation mechanism and API microposts. Additionally the device was scaled to possess a relatively smaller volume.

Figure 72A:
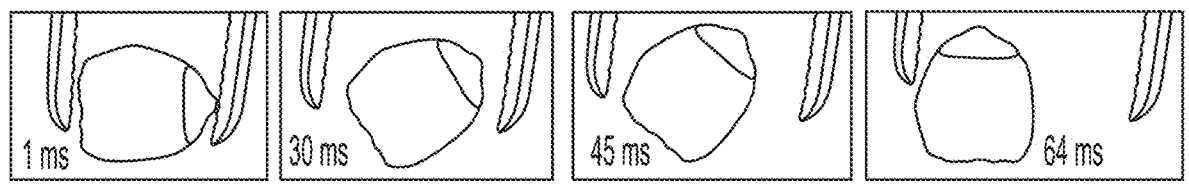
FIGS. 72A-72E shows optimization and self-orientation in vivo of an exemplary system.
Figure 72B:
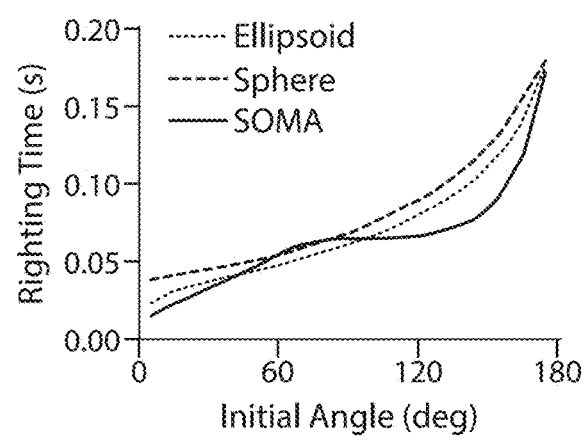
Figure 72C:
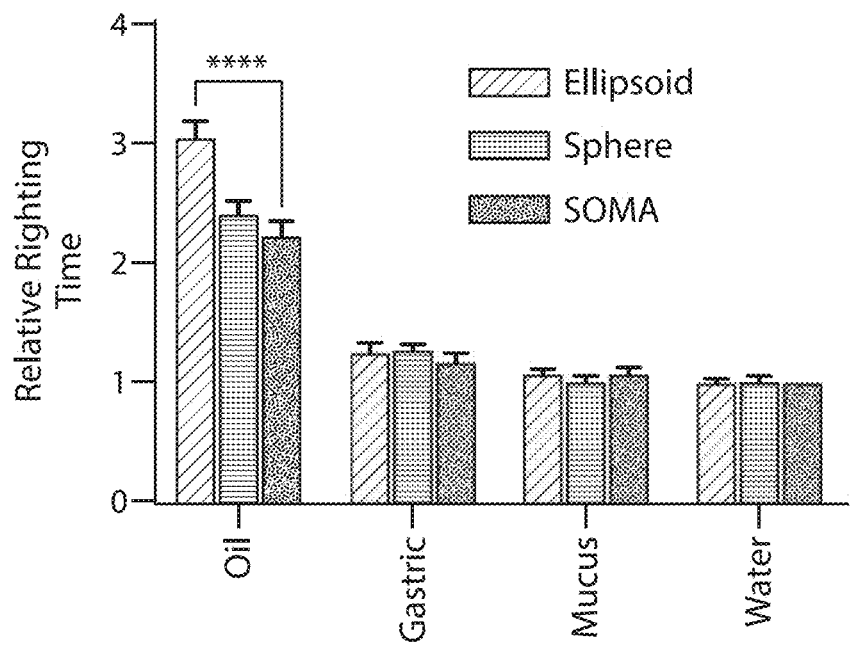
Figure 72D:
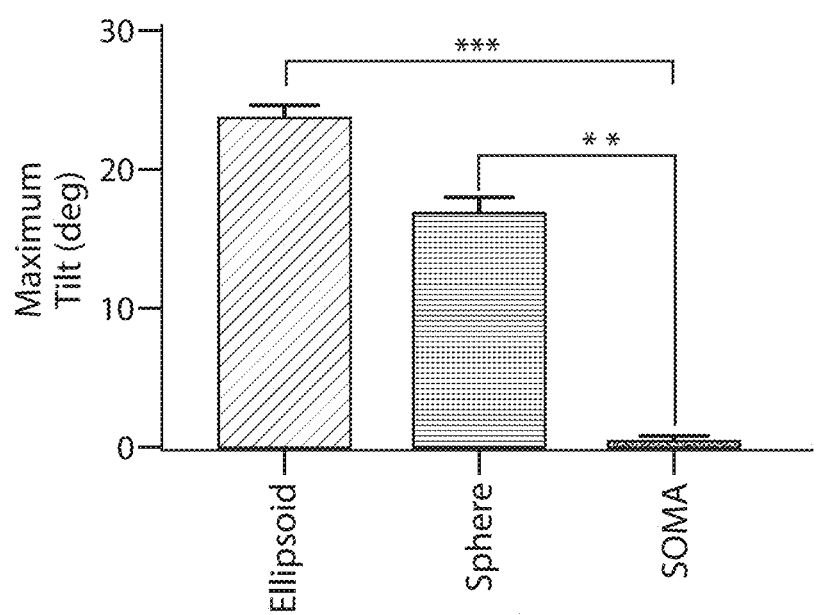

AA fabricated version of the optimized shape was compared to a homo-dense sphere and ellipsoid. Self-orientation and destabilization testing were conducted in vitro with high-speed photography to validate computer modeling (FIG. 2A FIG. 72A). The optimal shape oriented quickest in 69% of all possible orientations and oriented more quickly on average than the other shapes (FIG. 72B). The device reached its preferred orientation in less than 100 ms from over 85% of all starting angles in an idealized environment. When placed in liquids found in the GI tract, such as oil, gastric fluid, mucous and water, the optimized device showed less deceleration due to viscous effects when compared to an ellipsoid (FIG. 72C). The device also showed a strong resilience after orienting to its preferred state when compared to the other shapes, as it did not tilt more than a single degree when exposed to mixing on a tilt shaker at 50 rpm with excursions of +/−15 degrees (FIG. 72D).

Figure 72E:
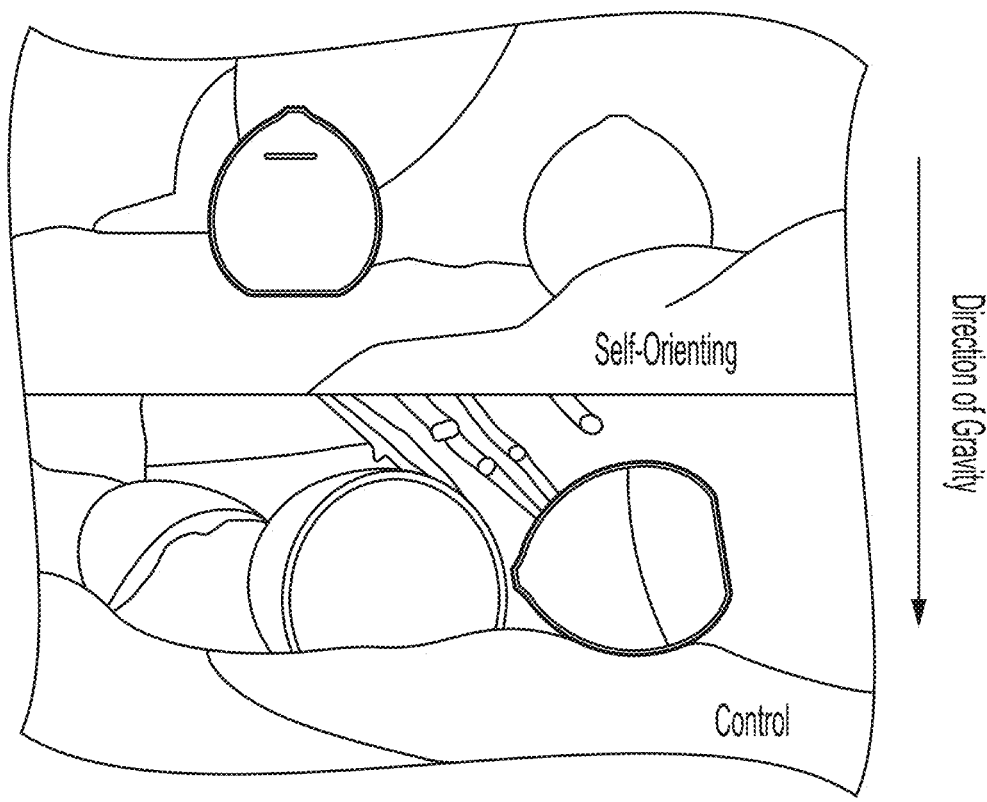
Figure 76:
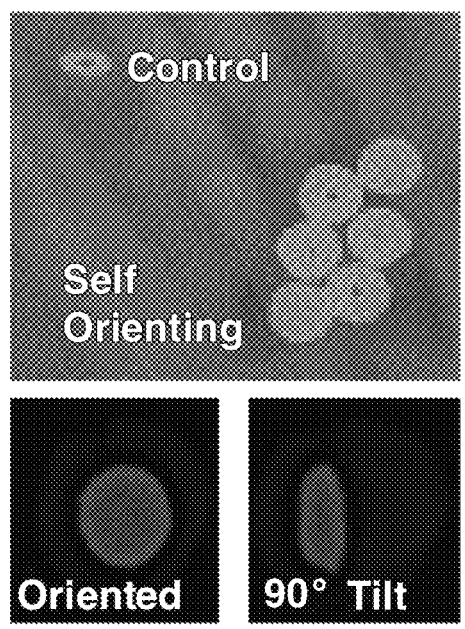
FIG. 76 shows X-ray of SOMA shape in vivo for an exemplary system. Six SOMA devices were fed to a pig along with one control device with the same SOMA shape but a homogeneous density. Due to the circular metal bottom of the SOMA, the devices showed up on an X-ray as a full circle when fully oriented and as a waning circle when unoriented. The control device was also marked with a thin metal washer. The pig was then rotated axially up to 180° as well as tilted in other directions up to 30° to simulated ambulation and extensive motion stress. The pig was then X-rayed. This process was repeated 10 times, and yielded a 100% correction orientation rate for SOMA devices and a 50% orientation rate for control devices, according to one set of embodiments.
Figure 77:
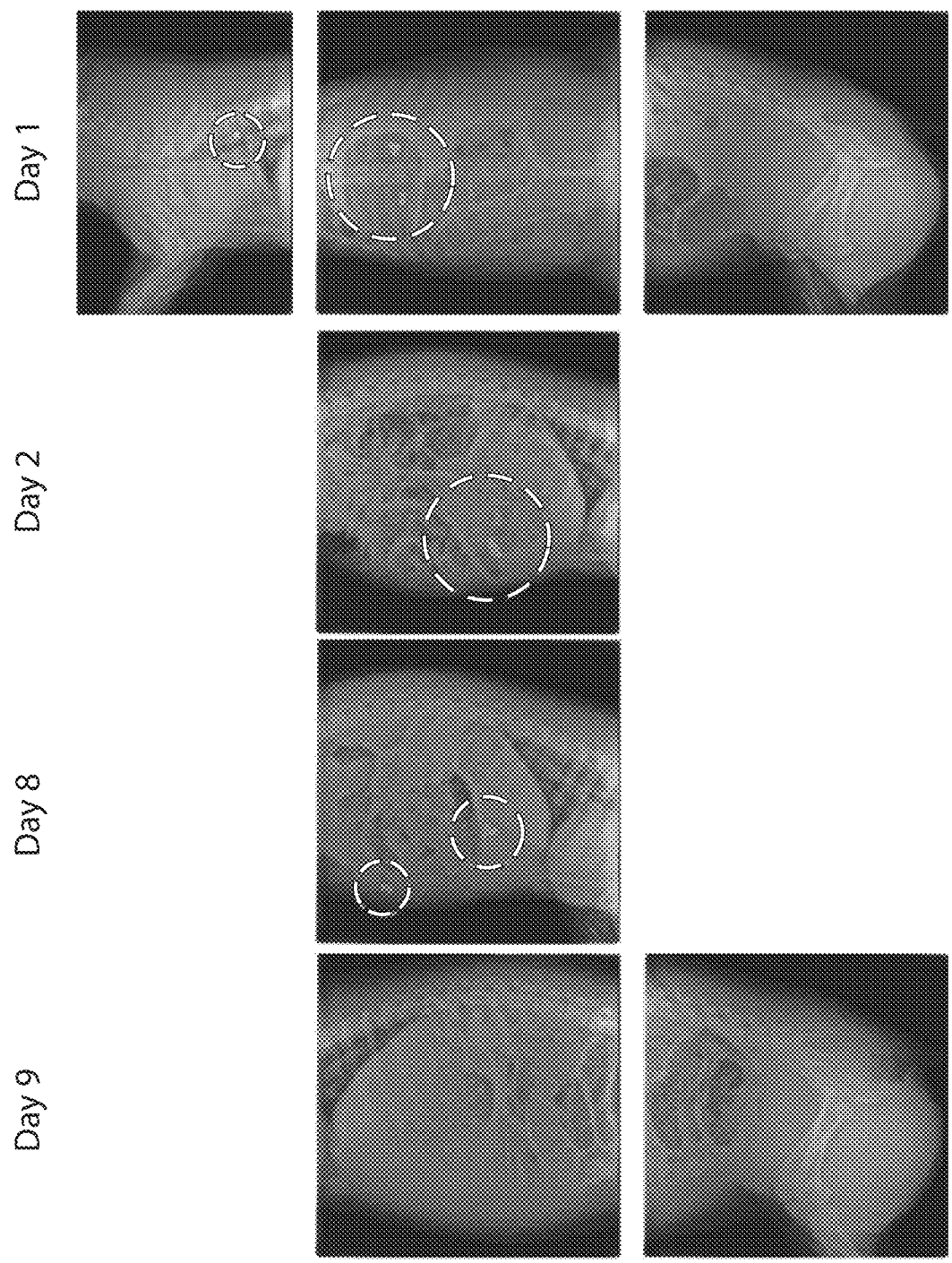
FIG. 77 shows gastro-retentive properties of an exemplary system. Six SOMA devices are shown to pass through a swine's GI tract in 8 days. The SOMA devices spend days 1-7 in the stomach. The day 1 x-ray shows one SOMA device being delivered through the esophagus and 5 soma devices in the stomach. On day 2, all of the SOMA devices are in the stomach, and they remain there until day 7. On day 8, 4 SOMA devices are shown to have moved into the intestines. By day 9, there are no SOMA devices present in the x-rays. This indicates that the SOMAs have passed out of the swine. The pig showed no signs obstruction throughout the experiment, according to one set of embodiments.

After identifying a final shape, it was tested 300 times in an ex vivo experimental setup of a swine stomach as well as 60 times in vivo in fasted animals for self-orienting and persistence of mucosal engagement. In vivo simulated ambulation and extensive motion stress testing via 180 degree rotations and 30 degree tilts of the animal model were conducted. To measure proper device orientation, endoscopy was performed on (FIG. 72E) and x-rays taken of (FIG. 76) the swine following agitation of the abdomen. Optimized devices oriented 100% in each trial, while a control device of the same shape made solely of PCL oriented 50% of the time. No evidence of GI obstruction or other adverse clinical effects were found when 6 SOMA prototypes were dosed to swine at once (FIG. 77). By using a device with the capability of quick and consistent self-orientation in vivo, the drug delivery actuation event occurred generally in the direction of the tissue.

Figure 73A:
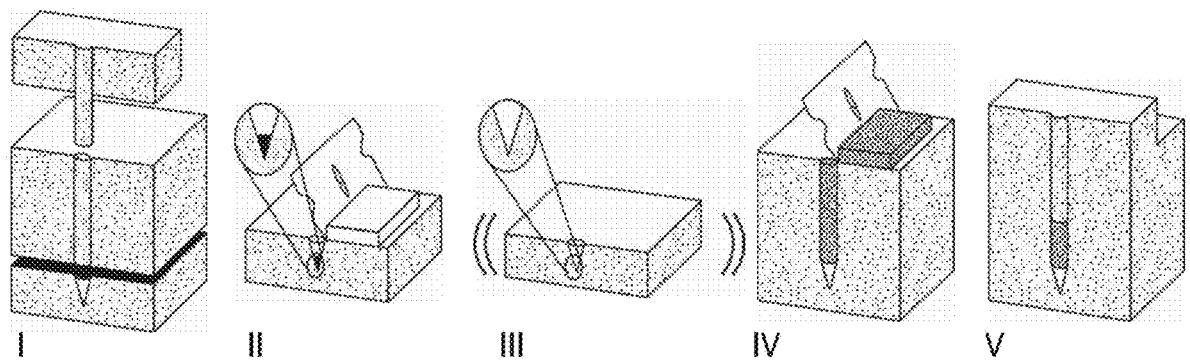

Having created a localization system, fabricated compressed API microposts were fabricated. Compared to liquid or solvent casted formulations, a compressed solid formulation delivered up to 100 times more API per unit volume. By compressing a mixture of 80% human insulin and 20% 200 k molecular weight poly(ethylene) oxide (PEO) under pressures of 550 MPa, 0.5 mg of insulin was loaded into a sharp, conical structure measuring 1.7 mm in height and 1.2 mm in diameter and attached it to a shaft made of degradable biocompatible polymers such as PEO and hydroxypropyl methylcellulose (FIGS. 73A-73B).

Figure 78:
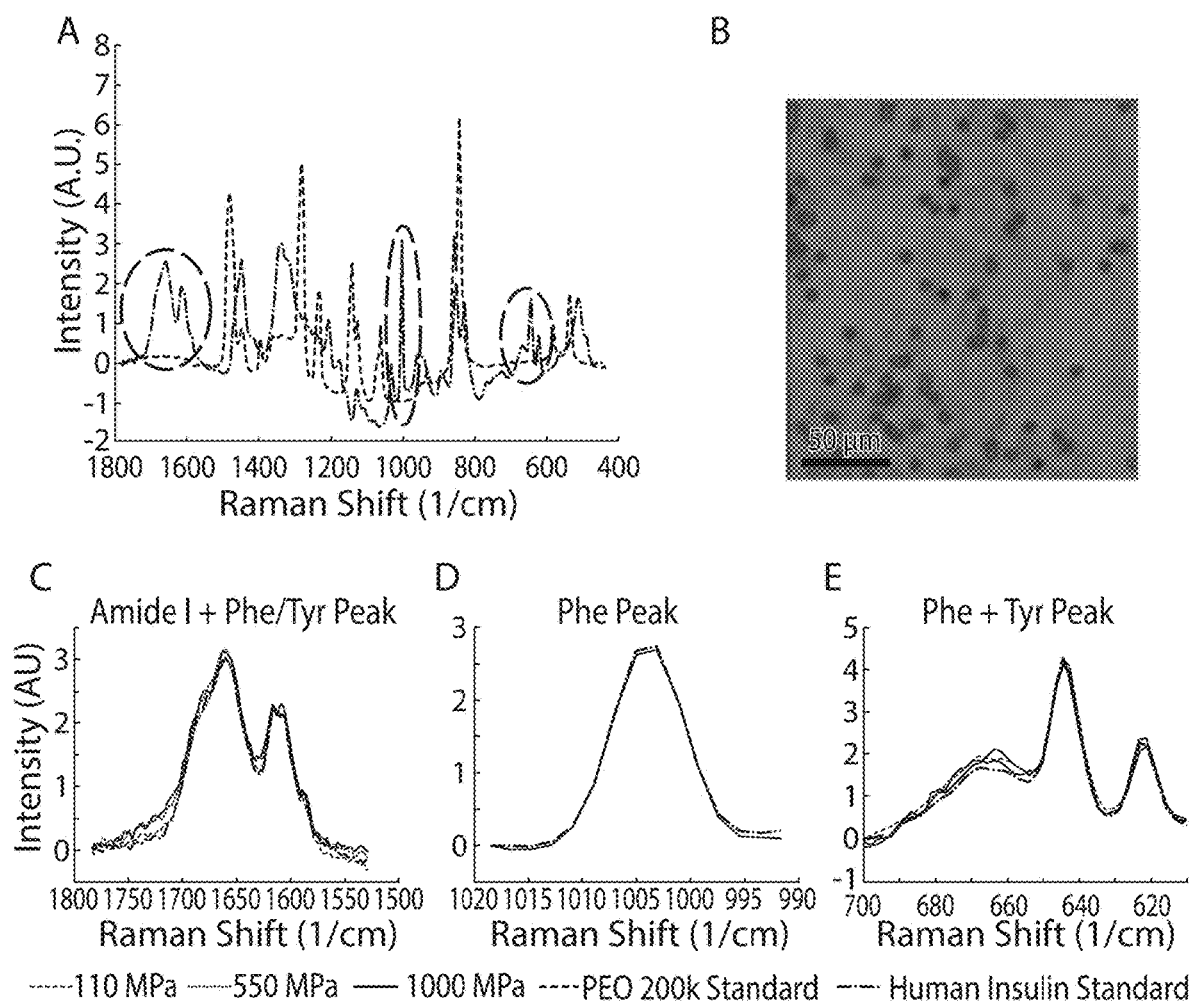
FIG. 78 shows Raman spectroscopy analysis of compressed insulin for an exemplary system. Several microposts were fabricated of compressed insulin and PEO at varying pressures. These API mixtures were analyzed using Raman spectroscopy to determine if any protein folding changes occurred during exposure to high pressures. (A) Standards of human insulin and PEO 200 k. Black circles represent peaks present in the insulin reading that are not present in the PEO reading. These peaks are analyzed in FIG. (C-E). (B) The differences between the two components allowed for an imaging software to generate a visualization of the mixture using built in pre-processing and chemometrics. In this picture, the blue areas contain greater amounts of PEO. The insulin Raman bands overlapped with the PEO bands over all but five bands: (C) The Amide I band occurring at 1660 cm-1; a Tyr peak occurring at 1613 cm-1; (D) a Phenylalanine (Phe) peak occurring at 1003 cm-1; (E) the Phe peak occurring at 622.5 cm-1; and the Tyr peak occurring at 644.3 cm-1. No band shifts or width increases were observed demonstrating that there were no protein folding changes, according to one set of embodiments.
Figure 79:
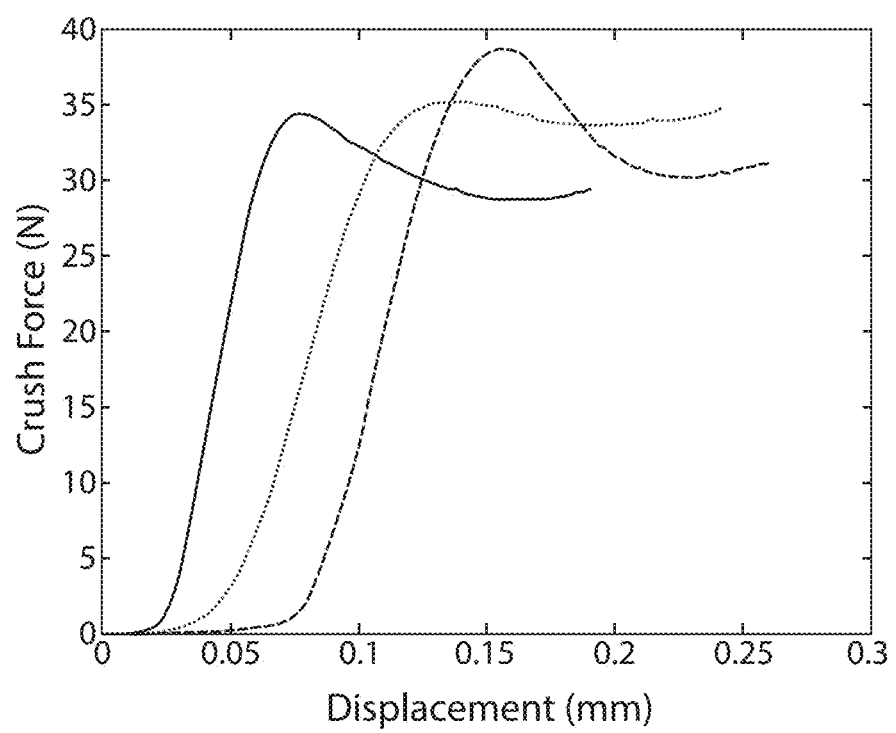
FIG. 79 shows compressed insulin needle crush test for an exemplary system. Cuboid shaped pellets with the dimension of 3.3×0.55×0.55 mm3 were fabricated from the described insulin/PEO 200 k mixture. These pellets, while undergoing a crush test, demonstrated a Young's modulus of 730±30 MPa. This is similar to the Young's modulus of PEO. The ultimate strength of the pellet is 36±2 N, according to one set of embodiments.
Figure 80:
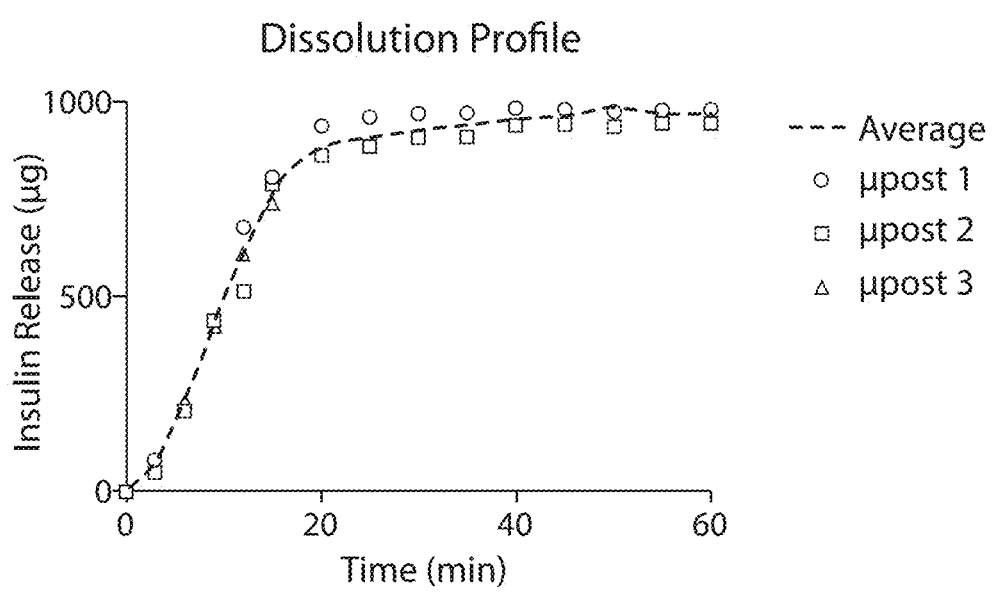
FIG. 80 shows micropost dissolution profile for an exemplary system. microposts containing 80% Human Insulin and 20% PEO 200 k by weight were dissolved in a falcon tube containing 2 mL of PBS at 37° C. shaken on a lab shaker at 50 rpm. 200 μL was sampled every three minutes for the first 15 minutes and every 5 minutes thereafter, and the removed liquid was replaced with fresh PBS. Complete dissolution occurred within 1 h, according to one set of embodiments.
Figure 81A:
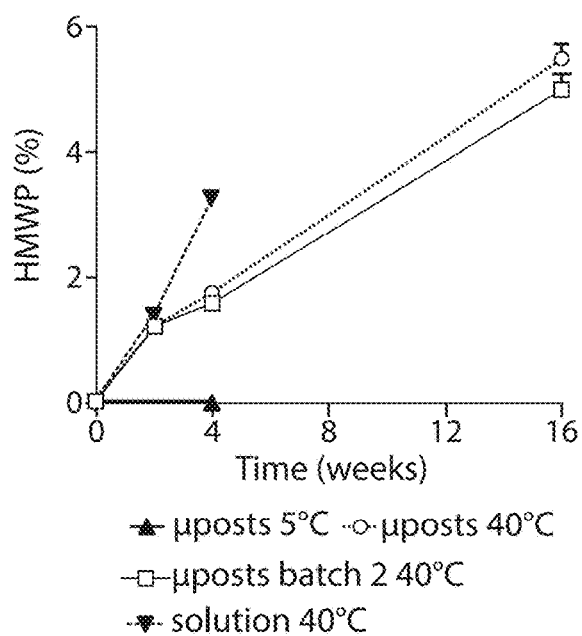
FIG. 81 shows micropost API stability studies for an exemplary system. (A) Insulin purity and (B) high molecular weight protein (HMWP) concentration during 16 weeks of stability testing (n=3, Error Bars=SEM), according to one set of embodiments.
Figure 81B:
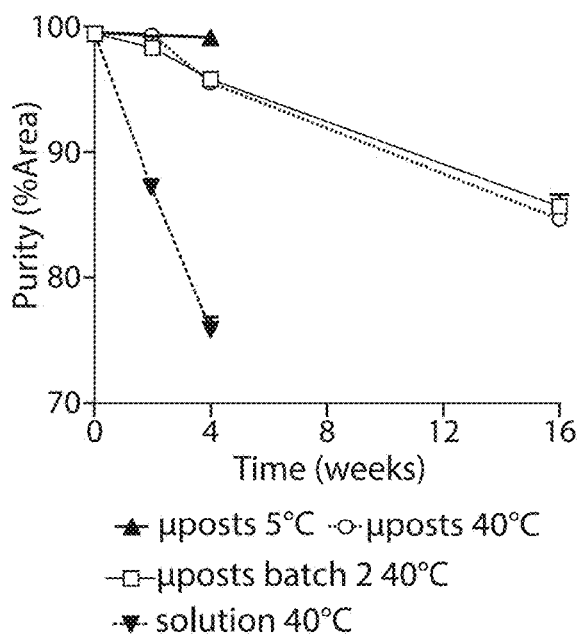

Mechanical and chemical characterization studies ensured the stability of the microposts. Raman spectroscopy of the compressed micropost revealed uniform API distribution throughout the micropost tip and validated the protein structure of the API after high pressure exposure (FIG. 78, Table 1). Compression tests measured a Young's modulus of 730+/−30 MPa, like that of PEO, and an ultimate strength of 20.0+/−0.7 MPa, ensuring micropost integrity in the presence of external force (FIG. 79). Dissolution profiles in vitro demonstrated complete dissolution within 60 minutes (FIG. 80). Stability studies conducted at 40° C. showed that the solid insulin and PEO microposts remained stable in a desiccated environment for 16 weeks, maintaining greater than 80% purity and less than 5% high molecular weight protein (HMWP) formation (FIG. 81). This compares to 4 weeks of stability for a liquid formulation. Using the same compression concept, microposts were fabricated out of 100% insulin, with both the tip and shaft composed entirely of insulin due to the lack of binder. The 100% insulin microposts were utilized in the SOMA to increase the insertion payload.

TABLE 1

| Sample | Amide I Pos/Width | Tyr Pos/Width | Phe Pos/Width | Tyr Pos/Width | Phe Pos/Width |
|---|---|---|---|---|---|
| Standard | 1660/56.1 | 1613/18.5 | 1003.4/7.7 | 644.3/10.0 | 622.5/7.7 |
| 110 MPa | 1660.6/54.8 | 1614.3/16.5 | 1004.9/7.5 | 644.3/10.0 | 623.1/8.1 |
| 550 MPa | 1658.7/59.0 | 1616.3/17.4 | 1003.0/7.0 | 644.3/10.1 | 621.2/6.8 |
| 1000 Mpa | 1658.7/57.1 | 1618.2/18.2 | 1004.9/7.8 | 644.3/8.7 | 621.2/7.4 |

Figure 73D:
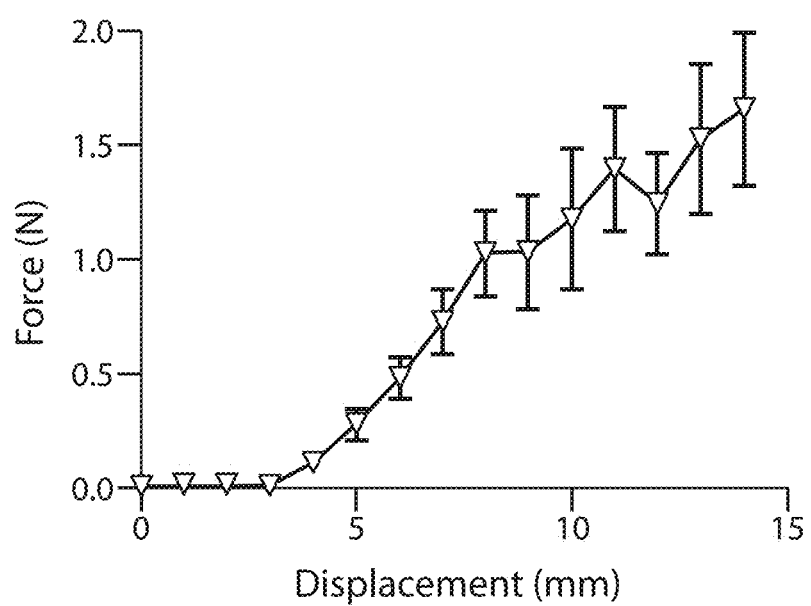
Figure 73E:
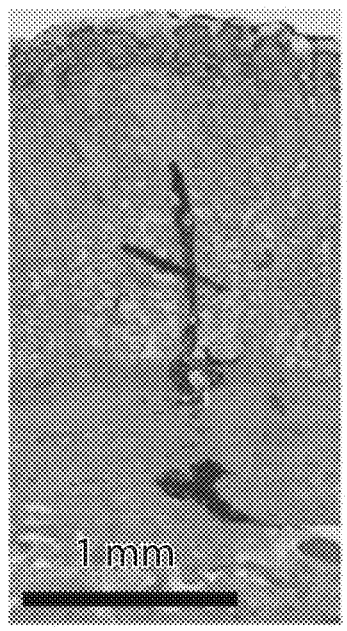

Insertion profiles of insulin microposts into swine gastric tissue in vivo were assessed. The tips were inserted at a rate of 0.2 mm/s using a custom controllable stage (FIG. 82), and generally used generally used a force on the order of 1 N to displace the tissue more than 7 mm (FIG. 73D). Using this measurement as a boundary condition, a time delayed actuation mechanism was implemented into the SOMA with forces capable of inserting drug loaded microposts into stomach tissue without causing perforation. AA spring was used as a source of power because, for example, of its low space requirement and its ability to release energy along one axis near instantaneously. The SOMAs were loaded with stainless steel springs providing 1.7-5 N of force (k=0.1-0.5 N/mm) at full compression. The springs accelerated the microposts for 1 mm and then insert them 5 mm into the tissue. After actuation they remained inside the device. Histology results from the SOMA insertion events were directly compared to ones from an in vivo porcine stomach manually inserted with a dyed Carr-Locke needle (FIG. 73E). Micro computed tomography (CT) imaging established that a spring can propel a barium sulfate loaded micropost from a SOMA into ex vivo swine tissue up to e.g., 2 mm (FIG. 73C). Histology from in situ experiments demonstrated that insulin microposts inserted into the submucosa of swine stomach tissue after being ejected from a SOMA with a 5 N spring (FIGS. 73F and 73H), reaching the same depth as the Carr-Locke needle. In order to ensure a safety margin on insertion force, stainless steel microposts were ejected using 9 N steel springs (k=1.13 N/mm) into ex vivo swine tissue. Even with the additional force and momentum, the stainless steel micropost did not perforate the tissue (FIG. 73G and FIG. 73I).

In order to time the actuation event to occur in the stomach rather than the mouth or esophagus, crystalized sugar and sugar-like materials such as sucrose and isomalt were identified as useful spring encapsulation materials. The brittle nature of the substance allows e.g., for the spring to release completely in a period of 1 ms after the diameter of the coating dissolves to a critical size. Through simulations in COMSOL and in vitro experiments, the ability to tune and release the spring was demonstrated over the time span of 4 minutes with a standard deviation of 11.4 s (FIGS. 83A-83E). The entire spring actuation system easily fit into the hollow portion of the SOMA, while holes placed above the spring allow gastrointestinal fluid to permeate and reach the encapsulation material.

Insulin loaded microposts were administered to swine and blood glucose and insulin levels were measured over the course of 2 h. Delivered intragastrically via the SOMA and subcutaneously via a manual injection, the microposts inserted into the tissue released at a near zero order kinetic rate (FIGS. 74A-74D) (n=5). AA laparotomy and open stomach surgery was also performed to manually place microposts intragastrically, and this delivery method yielded comparable pharmacokinetic uptake to the SOMA (FIGS. 84A-84D). Human insulin levels in the swine plasma stayed within a range of 10-70 pM throughout the sampling period. The manually inserted microposts, fabricated from PEO 200 k and human insulin, as well as the SOMA delivered microposts, produced from 100% human insulin, submerged 280±20 μg of API below the tissue as estimated from weight measurements and histology. All methods of micropost insertion yielded a blood glucose lowering effect, and the microposts inserted intragastrically provided a more pronounced drop compared to subcutaneously dosed microposts. This data was compared to a study which utilized SOMAs designed to localize the microposts to the stomach wall without inserting them into the tissue (n=5). The swine that received the non-inserting SOMAs saw no insulin uptake or blood glucose lowering effects. The near zero order kinetic release rate of the inserted microposts presents the possibility of using them as an implantable drug reservoir, and the ability for these formulations to release API over longer periods of time was rested (FIGS. 84A-84D). The microposts continued to release API in the subcutaneous space over the course of at least 30 h when inserting 1 mg or greater of API (n=6). This could generally enable a reduction in the frequency of dosing.

Micropost

The SOMA generally provides a way to deliver APIs such as insulin orally, and it also shows potential to be used with other APIs. Because some methods of micropost fabrication use high amounts of pressure, delivered molecules should remain active under such a stress. Activity assays on microposts fabricated with lysozyme and glucose-6-phosphate dehydrogenase demonstrate that multiple APIs maintain their activity after the manufacturing process (FIGS. 85A-85D). Additionally, the deliverable dose is constrained by the volume of the micropost which enters into the gastric mucosa. While increasing the depth of penetration and the width of the micropost will allow for a first and second order increase in dose capacity respectively, this may compromise the gastric mucosal barrier and increase the risk of perforation. The SOMA represents a platform with the potential to deliver a broad range of biologic drugs including but not limited to: other protein and nucleic acid based. The drug delivery efficacy achieved with this novel technology suggests that this method could supplant traditional subcutaneous injections for insulin and justifies further evaluation for other biomacromolecules.

Materials and Methods

Dulbecco's Phosphate-Buffered Saline (PBS) was purchased from Gibco by Life Technologies (Woburn, USA).

Human insulin was obtained from Novo Nordisk (Maalov, Denmark). 200,000 molecular weight PEO, 45,000 molecular weight Polycaprolactone (PCL), and sucrose was purchased from Sigma Aldrich (Saint Louis, USA). 301 steel springs were custom fabricated by Madsens Fjedrefabrik (Brondby, Denmark). The three custom fabricated springs possessed the specifications show in Table 2. The 1.7 N spring was purchased from Lee Spring Company (Brooklyn, USA) and is serial #CI008B05S316. Isomalt was purchased from CK Products (Fort Wayne, USA).

TABLE 2

|  | Spring 1 | Spring 2 | Spring 3 |
| --- | --- | --- | --- |
| Diameter (mm) | 2.2 | 2.2 | 2.3 |
| Free Length (mm) | 13.3 | 10.9 | 10.5 |
| Compressed Length(mm) | 1.60 | 1.75 | 2.55 |
| k (N/mm) | 0.19 | 0.55 | 1.1 |
| Coils | 8 | 7 | 7 |
| Wire diameter (mm) | 0.20 | 0.25 | 0.30 |
| Compressed Force (N) | 2.2 | 5 | 9 |

Device Fabrication:

A two part negative mold was designed in Solidworks (Dassault Systemes, Velizy-Villacoublay, France) and printed on a Form 2 3D printer (Formlabs, Somerville, USA) for the Ellipsoid, Sphere and SOMA top portions. Each device was designed to have a weight of 0.77 g with 88% of the weight comprised of stainless steel and the resulting weight comprised of PCL. The PCL top portions were cast into the negative mold in a melted state to form the top section of the device, and the bottom part was created from 316L stainless steel using a milling machine.

The springs were then fixed to the top section of the device using melted PCL, and the drug loaded micropost was attached to the spring again using PCL. Finally, the devices were attached together using PCL.

Before creating the stainless-steel parts, prototype models were made with Field's metal purchased from Alfa Aesar (Haverville, USA). The low melting point of this metal alloy allows for easy device fabrication, and its 7.88 g/cm$^3$ density is similar to that of stainless steel (7.7 g/cm$^3$). These prototypes were used to assess the device in vitro and ex vivo. Stainless steel and PCL devices were used in all in vivo experiments, and were also used in experiments measuring the SOMA's orientation ability in air and water, inside of an excised stomach, and in the presence of motion.

Figure 86:
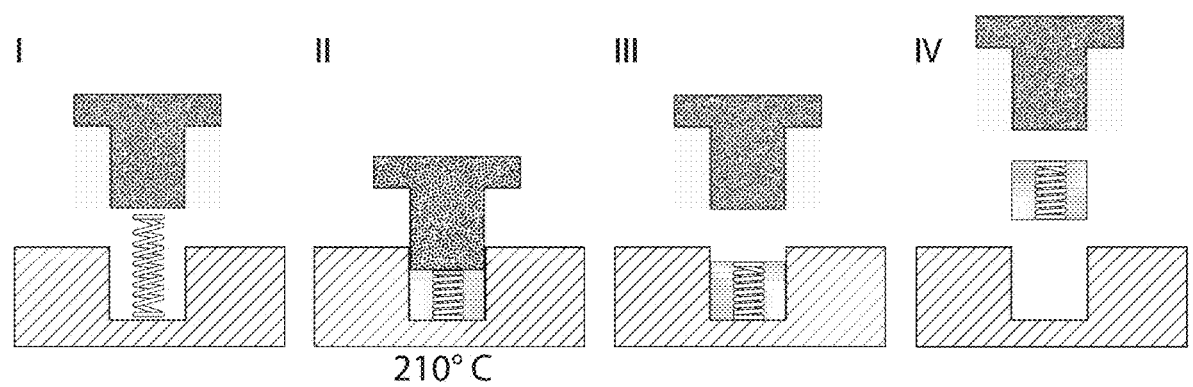
FIG. 86 shows sugar coated spring fabrication work flow for an exemplary system. Sugar coated springs were fabricated in a short four step process. (I) A compression spring was placed in a silicone mold and (II) caramelized sucrose heated to 210° C. for 15 minutes in an oven was poured into the mold. Isomalt was also used. A custom-made plunger compressed the spring into the caramelized sucrose and the mold was left to cool for several minutes. (III) The plunger was then removed and (IV) the sucrose encapsulated spring was pulled out of the mold. The size of the hole in the mold determined the width of the sugar encapsulated spring, according to one set of embodiments.

Sugar Spring Encapsulation:

Sucrose was heated to 210° C. for 15 minutes in a mold made from SYLGARD 184 Elastomer Kit (Dow Chemical, Midland, USA) with holes of three different diameters (4 mm, 5 mm, and 6 mm) (FIG. 86). A spring was placed inside the mold filled with molten sucrose, and caramelized for an additional 5 minutes in the oven. The mold was removed from the oven, and a tailor-made plunger was used to compress the spring into the sucrose, and the sucrose spring was left to cool before being removed from the mold. Isomalt springs were fabricated using the same method, but the material was not caramelized.

Insulin Micropost Fabrication

Insulin microposts were fabricated as described in herein and in FIG. 73A.

Self-Orienting Experiments in Various Fluids

To calculate the righting speeds of the devices, a Vision Research Phantom v7.1 monochrome high-speed-video camera was used (Vision Research, Homewood, USA) recording at 1000 fps. SOMAs made from PCL and Field's metal as well as PCL and 316L stainless steel were released from a 90° angle while submerged inside of a 2×5×10 cm$^3$ clear plastic vessel in one of the following fluids: canola oil (Crisco, Orrville, USA); gastric fluid obtained from a Yorkshire swine and filtered using a 10 µm syringe filter; reconstituted mucin from porcine stomach at 10 mg/mL in 1 M NaOH (Sigma-Aldrich, St. Louis, USA); and tap water (Cambridge, USA). A line was drawn on the axial plane of the device in order to determine the angle in a given frame, and orientation speeds were determined using sequential image analysis in Image J (Open Source). A device was considered oriented when the line drawn was perpendicular to the bottom of the vessel.

Self-Orienting Experiments in Excised Swine Stomach

Swine tissue for ex vivo evaluation was acquired from the Blood Farm Slaughterhouse (West Groton, USA). Swine were euthanized, and fresh tissue was procured and stored on ice. Tissue was tested within 6 hours of euthanasia. To determine the orienting efficiency of devices in a stomach, an intact Yorkshire swine stomach was positioned to hang so that the esophageal sphincter and the pyloric sphincter were elevated above the body of the stomach. A 12.7 cm long and 1.9 cm diameter Tygon tube was then inserted into and clamped against the esophageal sphincter of the stomach to mimic the esophagus. The stomach was then filled with water, and devices were dropped through the tube and into the stomach. Through a window cut on the uppermost section of the stomach (lesser curvature), devices were assessed to determine whether or not the desired side of the device was in contact with the tissue wall. This experiment was performed with SOMA shapes made with just PCL as well as SOMA shapes made with Field's metal and PCL, as well as 316L stainless steel and PCL. Additionally the ellipsoid and the sphere devices were tested as well.

Resistance to Outside Motion Testing

Resistance to outside motion was tested in vitro by submerging devices in water inside of a 500 mL Erlenmeyer flask and recording them while on a tilting shaker using a 15° tilt at 50 rpm. Footage was assessed using Image J on a frame by frame basis and the tilting angle was calculated by determining the maximum angle between the axial plane of the device and the plane of the shaker table over one tilt period.

In Vivo Simulated Walking Test

All animal experiments were approved by and performed in accordance with the Committee on Animal Care at MIT. Female Yorkshire swine were obtained from Tufts University (Medford, USA) for in vivo experiments. Two devices were fed to a swine using an overtube. One device was a SOMA, while another device was of the same shapes as an SOMA but made entirely out of PCL containing a steel washer for X-ray visualization purposes. The swine was moved rostro-caudally and laterally as well as rolled from left lateral side to right lateral side two times. Next the swine was placed back on the table and rolled 180 degrees. Finally, an X-ray was taken to visualize the orientation of the devices. These X-rays were compared to in vitro X-rays where the devices were placed at known angles. Since the stomach of a swine contains different curvatures, a device was considered oriented if it was within 30 degrees of the perpendicular plane of the X-ray (FIG. 76).

Needle Penetration Force Testing In Vivo

Figure 82:
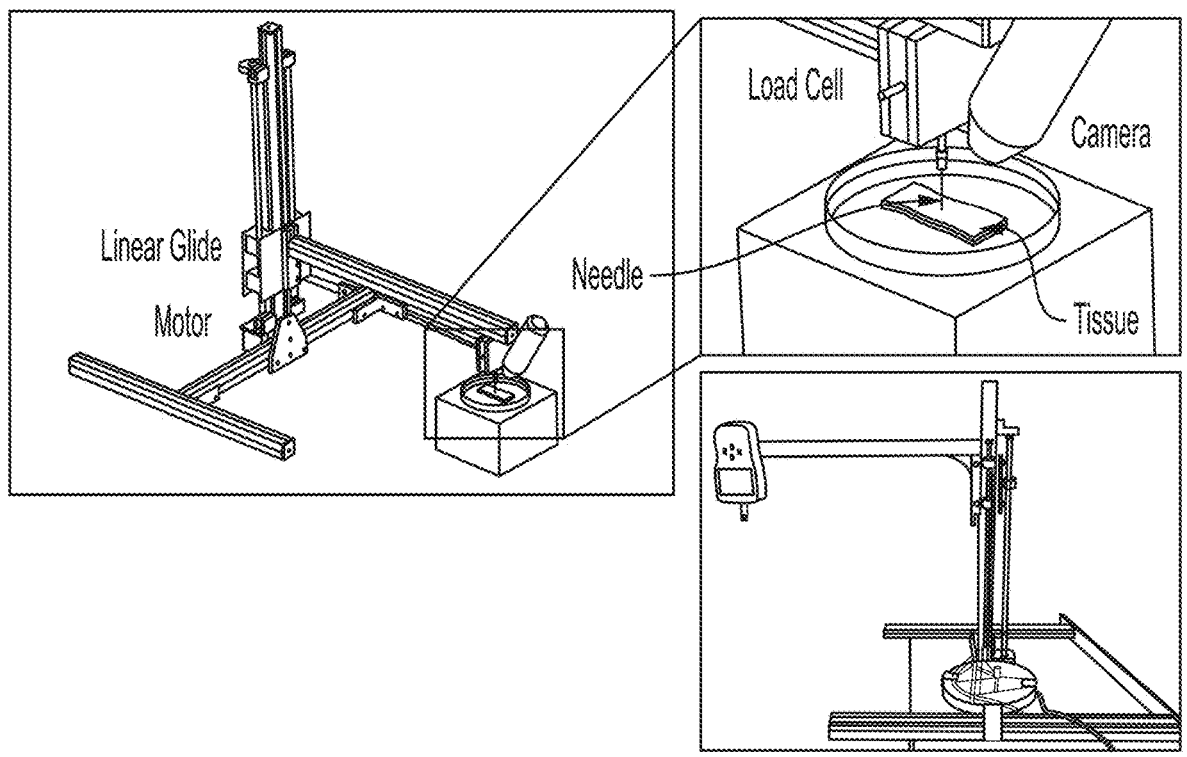
FIG. 82 shows a schematic and a photograph of needle insertion mechanism for an exemplary system. In vivo insertion data and ex vivo insertion data requiring video was acquired using the following device consisting of a linear glide, stepper motor, 0.5 N or 10 N load cell and video camera. The lower right picture shows the 10 N load cell attached to the device. All of the devices were controlled via a custom-made LabView setup, according to one set of embodiments.
Figure 83A:
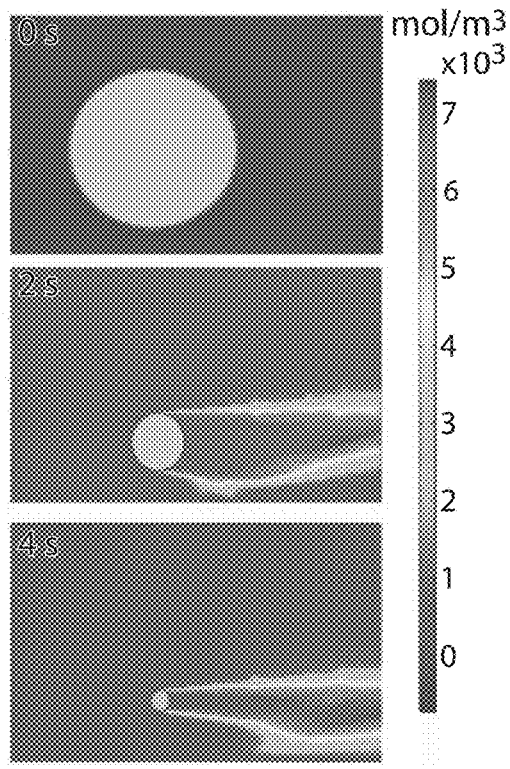
FIGS. 83A-83E shows characterization of sucrose actuation mechanism for an exemplary system. Concentration gradient of sucrose modeled in COMSOL Multiphysics as sucrose cylinder dissolves in an infinite body of (A) water flowing at a velocity of 0.02 m/s and (B) water without convection. The black circle indicates the shrinking boundary of the sugar cylinder, and concentration is shown in units of mol/m3. (C) Rate of dissolution of sucrose cylinder over 4 trials; slope indicates mass transfer coefficient between water and sucrose. (D) The time measured from when a sucrose coated spring is submerged in DI water until it actuates. The bars represent the experimental actuation time (n=3, Error bars=Std. Dev.) and the line represents the time predicted by COMSOL. (E) High speed image of spring popping out of sucrose coating as DI water is dripped on it from above, according to one set of embodiments.
Figure 83B:
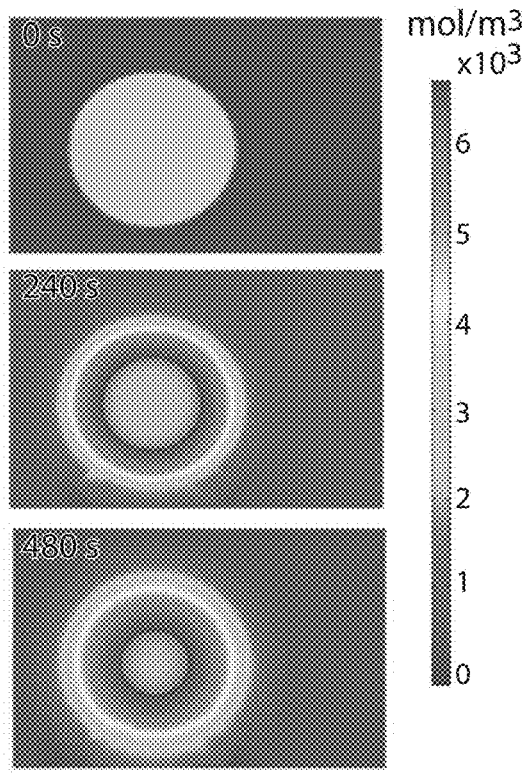
Figure 83C:
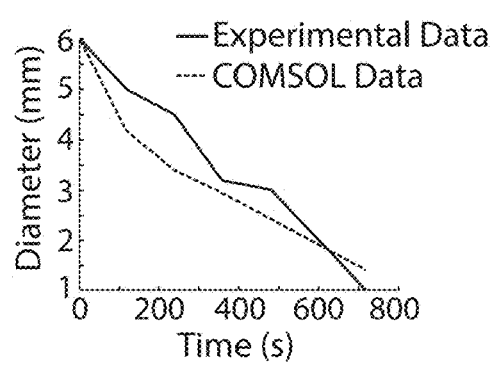
Figure 83D:
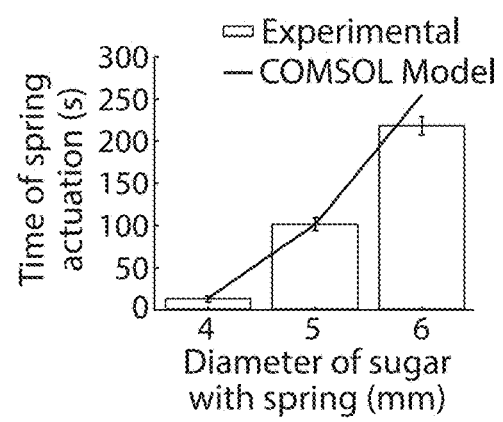
Figure 83E:
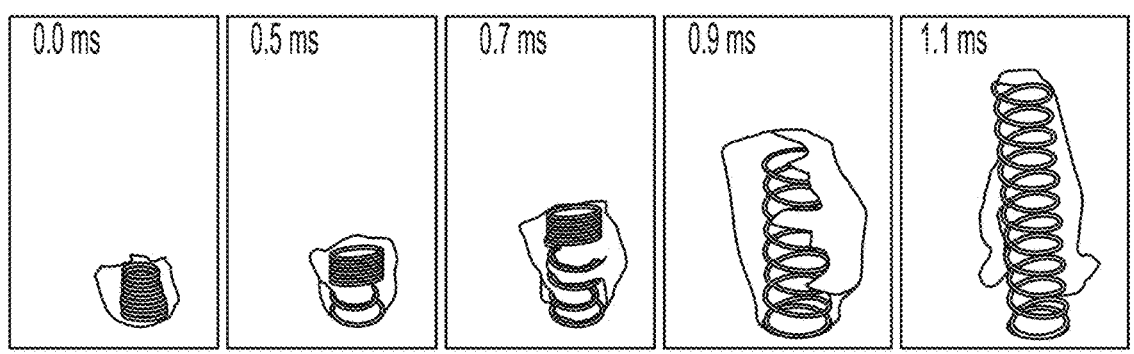
Figure 84A:
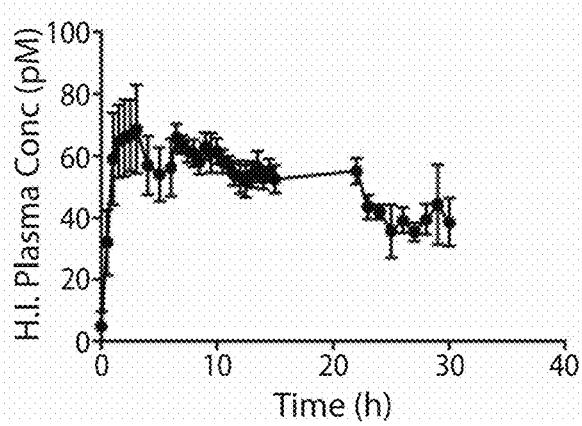
FIGS. 84A-84D shows zero order kinetic release of implantable insulin microposts for an exemplary system. (A) micropost shafts inserted into the subcutaneous (S.C.) space deliver insulin for 30 hours (n=6, Error Bars=SEM). (B) Sustained BG lowering is seen throughout the first 15 h. The swine were fed at hour 22, causing a B.G. spike. These implants do not have a sharp tip and are instead a 1.2 mm in diameter rod that is 1 mm in height. (C) micropost shafts inserted into the intragastric (I.G.) space via a laparotomy and open stomach surgery deliver insulin over 2 hours of sampling (n=5, Error Bars=SEM). (D) Dramatic B.G. lowering is observed, which may be due in part to the surgery, according to one set of embodiments.
Figure 84B:
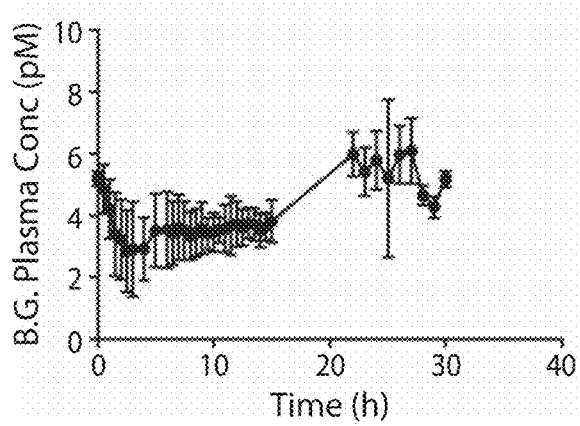
Figure 84C:
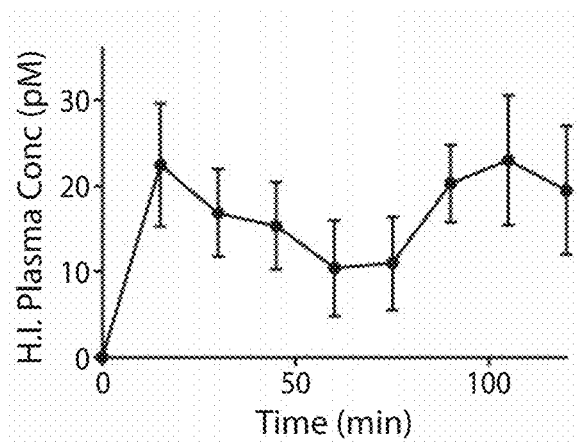
Figure 84D:
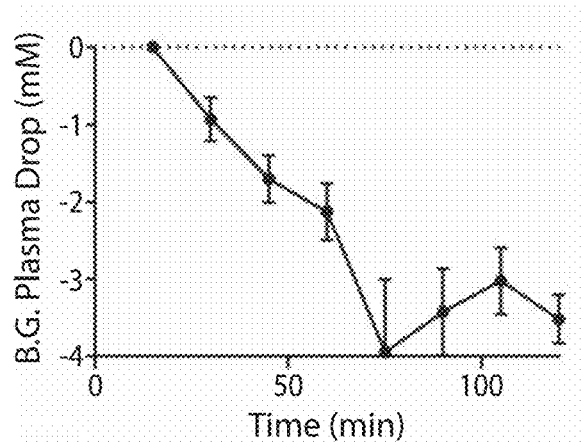
Figure 85A:
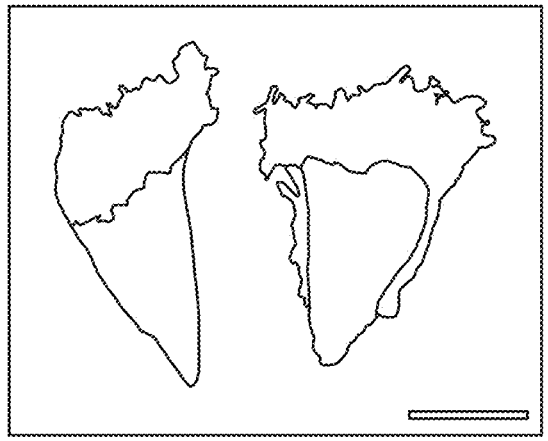
FIGS. 85A-85D shows enzymatic activity assays of fabricated microposts for an exemplary system. micropost tips created with (A) 80% lysosyme and 20% PEO 200 k and (B) 40% glucose-6-phosphate-dehydrogenase and 60% PEO 200 k were dissolved, and (C-D) enzymatic activity assays were performed to ensure that the proteins remained active after the manufacturing process. The control represents uncompressed powder. Scale bar is 1 mm. (Error bar=SEM), according to one set of embodiments.
Figure 85B:
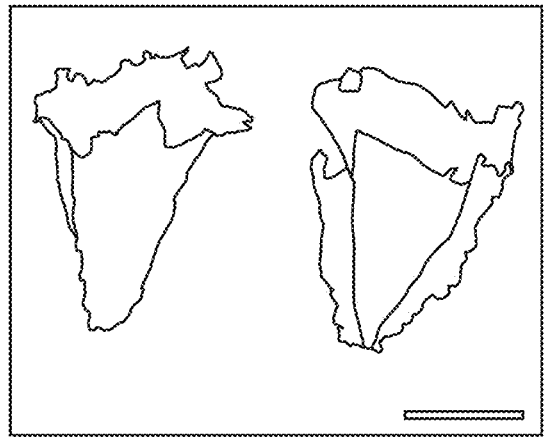
Figure 85C:
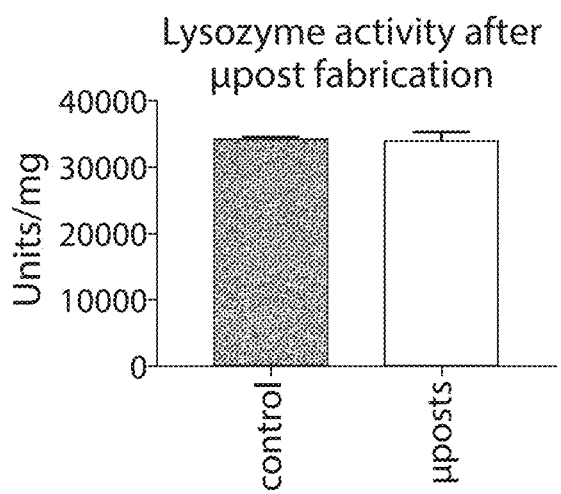
Figure 85D:
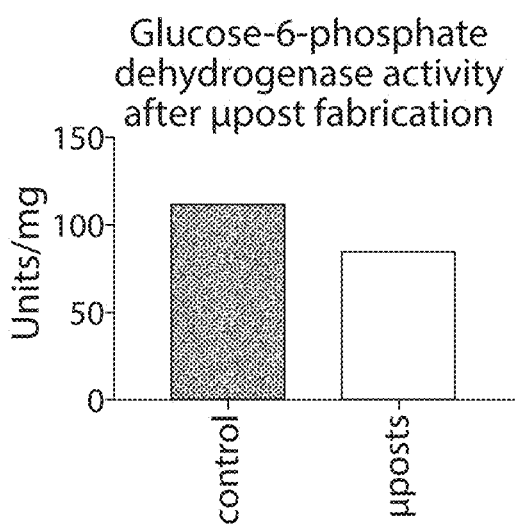

AA specialized stage was constructed to test force insertion profiles in vivo (FIG. 82). This device consisted of a linear that moved downwards towards a piece of tissue at a controlled speed of 0.2 mm/s. A force gauge and a camera was placed on the moving stage. As the needle penetrated the tissue, the force and movie measurements along with the video feed were recorded in LabVIEW. Yorkshire swine were sedated as described in the "In vivo Insulin Delivery Evaluation" methods section. A laparotomy procedure was performed to access the gastric surface mucosa. Gastric tissue was reflected to reveal a working area of at least 7.5×7.5 cm$^2$. The custom apparatus was then positioned above the tissue and used to insert the microposts at 0.2 mm/s. Intraoperative measurements were affected by breathing and determined that the displacement caused by breathing accounted for an extra 3 mm of insertion. This was measured using a ruler and confirmed by comparing the forces on the needles during inhalation and exhalation during the entire insertion process. It was seen that the forces read during exhaled state equaled the forces felt during the inhaled state 3 mm earlier. In vivo force measurements were read by a 10 N force gauge (Shimpo, Cedarhurst USA) with an accuracy of ±0.03 N and a resolution of 0.01 N.

Insulin Micropost In Vitro Dissolution

Three 50 ml-Falcon tubes were filled with 2 mL of PBS and incubated at 37±0.1° C. At the beginning of the test, one insulin micropost tip was submerged in each of the Falcon tubes. A rack containing the tubes was placed in an Innova 44 Shaker Series incubator (New Brunswick Scientific, Edison, USA) set to 37±0.1° C. and 50 rpm.

The tubes were sampled every three minutes until 15 minutes elapsed and then every 5 minutes until 60 minutes elapsed. At each of these times, the test tube rack was removed from the incubator and 200 µL of solution was pipetted into an HPLC vial. Then, 200 µL of PBS at 37±0.1° C. was pipetted back into the tubes. The test tube rack was reinserted into the incubator. A blank reference sample was also collected from a vial of pure PBS incubated at 37±0.1° C.

The HPLC vials were tested in an HPLC machine (Agilent, Santa Clara, USA) to determine the amount of dissolved insulin at a given time using a method retrieved from the following paper with a modification to the run time. Briefly, a 7.8×300 mm$^2$ Insulin HMWP column was utilized and (Waters Corp, Milford, USA) set to room temperature. Elution was performed with a flow rate of 0.5 mL/min for 26 minutes using a mobile phase made from 15% acetic acid (v/v), 20% acetonitrile (v/v), and 0.65 g/L L-arginine all purchased from (Sigma-Aldrich).

Insulin Stability Testing

Insulin micropost tips were placed inside of a desiccated pill container and left inside of a climate controlled room set to 40° C. and 75% relative humidity. An identical batch of micropost tips was placed inside of a climate controlled chamber at 5° C. and 15% relative humidity. Additionally, a liquid formulation of pure insulin dissolved in PBS at a concentration of 4 mg/mL was placed inside of the two climate chambers as well. The samples were left for 0, 2, 4, and 16 weeks. Once removed, dissolution tests were performed on the microposts in addition to a high molecular weight protein (HMWP) analysis, activity testing, and a Raman spectroscopy analysis. The Raman analysis is described in a later section entitled "Raman Spectroscopy", while the HMWP analysis was performed using the HPLC method described in the "in vitro dissolution" section, and the activity testing was performed using a receptor binding assay. In a few words, a scintillation proximity assay (SPA) was performed on the human insulin from the micropost, and the binding receptor affinities were verified by competition of the human insulin from the micropost and [125I] TyrA14-labeled insulin in the SPA. The affinities were analyzed using a four-parameter logistic model and the results compared to untreated human insulin.

Raman Spectroscopy

A DXRxi EM-CCD Raman Imaging microscope (ThermoFisher Scientific, Waltham, USA), was used to image the insulin and PEO compressed mixtures. Samples were exposed to a laser wavelength of 780 nm at a power of 24 mW and a frequency of 200 Hz. The laser beam was focused through a 20× NA 0.40 objective and the scattering collected through same. Rayleigh and anti-Stokes scattering were blocked by an edge filter prior to entrance to a spectrograph configured with a 400 line/mm grating. Areas of 200×200 µm$^2$ were scanned with a scanning step size of 5 µm in each dimension. 300 scans of each section were taken. In order to smooth the data, a principal component analysis was performed to eliminate spectrums with high noise, and a root mean squared analysis was performed to further filter the data. MATLAB's peak finding tools were used to determine the peak location and width of the peaks of interest. Only insulin peaks which did not overlap with the PEO peaks were analyzed, and the results are detailed in FIG. 78.

Enzyme Activity Assays

Micropost tips were fabricated as described above, however, instead of using insulin as an active ingredient, lysozyme from chicken egg was used (Sigma Aldrich) and glucose-6-phosphate dehydrogenase expressed in *E. coli* (G6PD) as the API (Sigma Aldrich). To perform the activity assay on G6PD, an activity assay kit (Sigma Aldrich) was used which measures the amount of oxidized glucose-6-phosphate. 3 micropost tips were fabricated using 40% G6PD and 60% PEO 200 k and dissolved them all together to perform the assay and then compared to G6PD that was not compressed into a micropost tip. Duplicate assays were performed on the dissolved solution.

To measure the activity of lysozyme, the assay provided by Sigma Aldrich was used which measures the amount of lysed *Micrococcus lysodeikticus* cells. Briefly, a 200 unit/mL Lysozyme solution in 50 mM Potassium Phosphate Buffer was added to a 0.015% [w/v] *Micrococcus lysodeikticus* cell suspension in the same buffer. The decrease was recorded in $A_{450}$ over 5 minutes. Nine micropost tips were fabricated from 80% lysozyme and 20% PEO 200 k and dissolved sets of three micropost tips together. Triplicate assays were performed on each dissolved solution for a total of nine tests and the results were compared to the results of a solution made with lysozyme that was not compressed into a micropost tip.

In Vivo Insulin Delivery Evaluation

Figure 87:
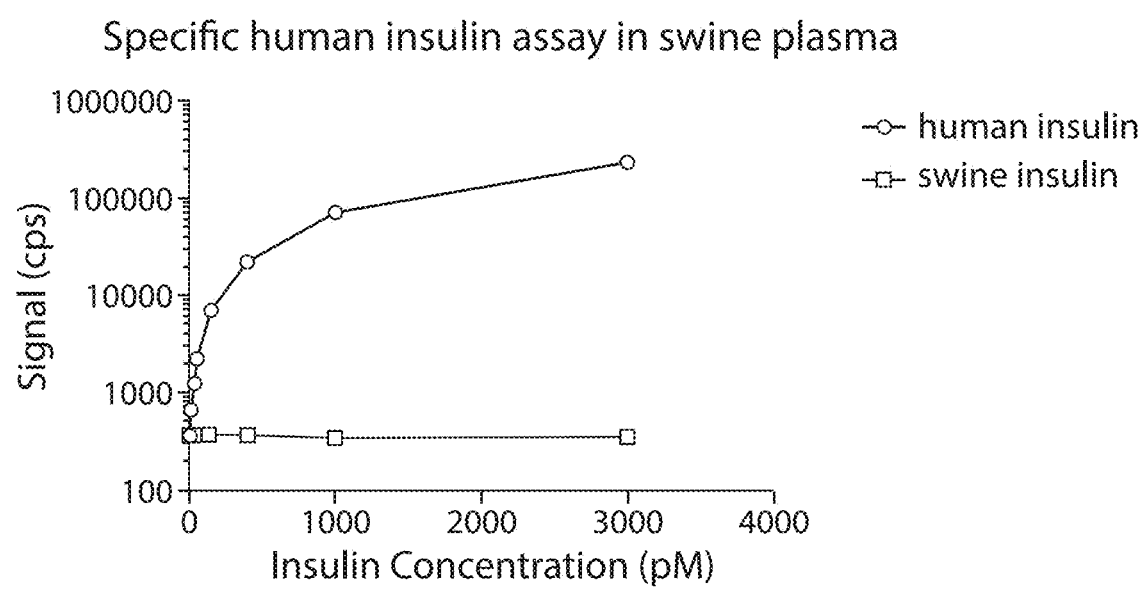
FIG. 87 shows insulin quantification assay for an exemplary system. The ELISA and AlphaLisa experiments utilize a homogeneous bead assay that employs two monoclonal antibodies against human insulin. The assay is specific to human insulin over swine insulin, according to one set of embodiments.

To assess the insulin micropost formulation, the API formulation was administered to a large animal model (female Yorkshire swine, 35 kg to 65 kg) via three separate methods: intragastric injection (I.G.) via the SOMA device; manual I.G.; and subcutaneous injection (S.C.). A swine model was chosen due to the anatomical similarities of the GI tract to humans as well as its wide use in GI tract, device evaluation. No adverse effects were observed during the experiments. To deliver the SOMA devices, the swine were placed on a liquid diet 24 hours before the procedure and fasted the swine overnight. Swine were sedated with intramuscular injection of Telazol (tiletamine/zolazepam) (5 mg/kg), xylazine (2 mg/kg), and atropine (0.05 mg/kg) and if needed supplemental isoflurane (1 to 3% in oxygen) via a face mask. An orogastric tube or overtube was placed with guidance of a gastric endoscopic and remained in the esophagus to ease the passage of the device. SOMA devices were passed through the overtube and placed into the stomach. Although swine were fasted, some swine still possessed food in their stomach during the SOMA delivery. Blood samples collected from SOMA devices which landed on food or did not inject their drug payload after actuation were discarded from the sample. Blood samples were obtained via a central venous line at designated time points, including but not limited to every 10 minutes for the first two hours, every 30 minutes for hours 2-4, and at 6, 12, and 24 hours. Blood samples were immediately tested for glucose levels using a OneTouch Ultra glucose monitor by LifeScan Inc. (Milpitas, USA). Additional blood was collected into Ethylenediaminetetraacetic K3 tubes (Sarstedt, Numbrecht, Germany) and spun down at 2000 Relative Centrifugal Force for 15 minutes. Collected plasma was shipped on dry ice for analysis. Briefly, the homogenous bead assay employed two monoclonal antibodies against human insulin, creating an acceptor-bead, insulin, and donor-bead layering. This generated a signal which was proportional to the concentration of insulin. This test is specific for human insulin and does not detect other endogenous insulins (FIG. 87).

Insulin microposts were delivered subcutaneously by creating a guide hole 3 mm deep in the swine's skin using an 18G needle and placing the micropost into the guide hole. The microposts were delivered via an intragastric injection during a laparotomy procedure in which a 3 cm incision was used to access the gastric mucosa, and a micropost was manually inserted into the gastric surface epithelium. Blood samples and sedation were performed in the same manner as described above.

Figure 73F:
Figure 73G:
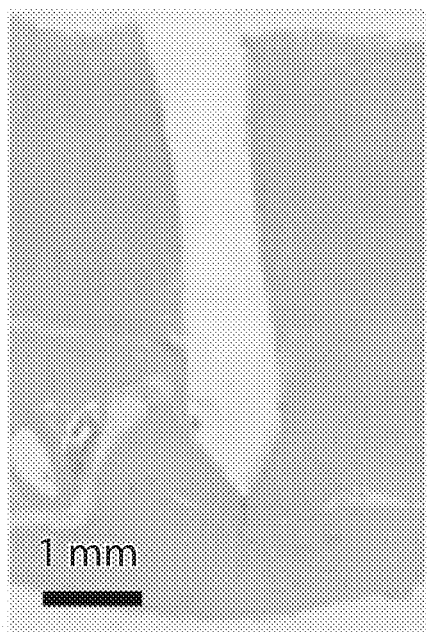
Figure 73H:
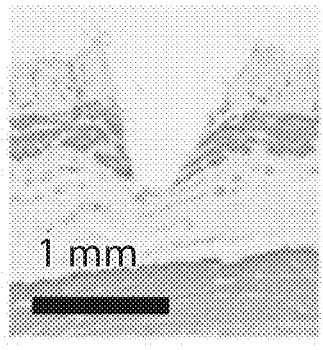
Figure 73I:
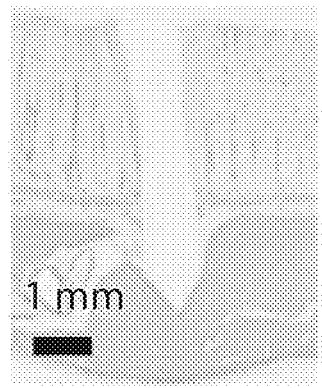
Figure 74A:
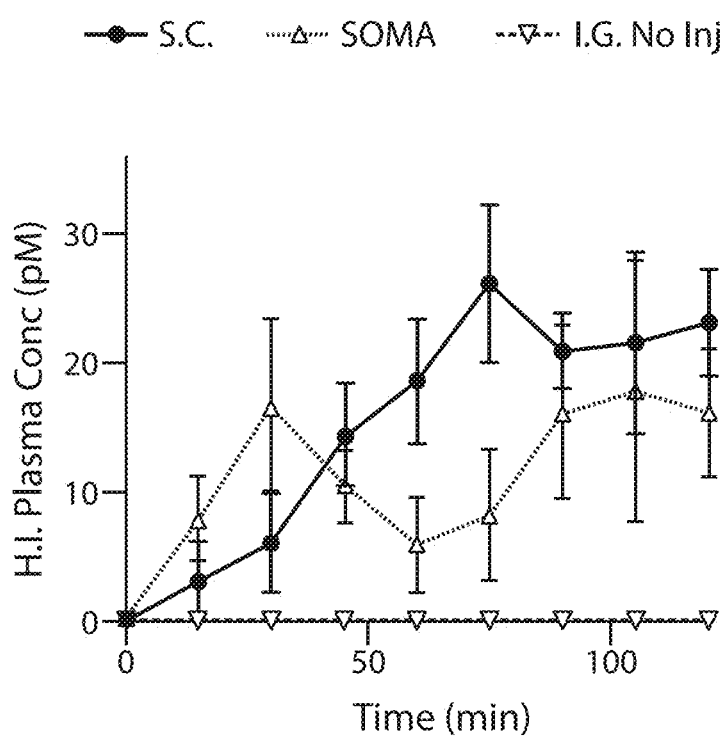
FIGS. 74A-74D show in vivo API micropost delivery and device evaluation for an exemplary system. Blood plasma levels for (FIG. 74A AND FIG. 74B) human insulin and (FIG. 74C AND FIG. 74D) glucose (B.G.) were recorded in swine after injecting a micropost containing human insulin manually subcutaneously (S.C.) or intragastrically (I.G.) via an exemplary system (n=5, Error bars=SEM). These swine are compared to swine dosed with exemplary systems designed to localize the micropost to the tissue wall but not inject it (I.G. no Inj). 280±15 μg of human insulin was submerged underneath the tissue for each injection trial. The manually placed microposts contain 20% PEO 200 k in addition to human insulin. B.G. lowering was measured compared to the 15 minute time point, because anaesthesia caused the BG level to vary dramatically during that time. B.G. lowering was seen during both dosing methods. The I.G. data sets only includes swine with successful fasting without residual food or significant gastric fluid, according to one set of embodiments.
Figure 74B:
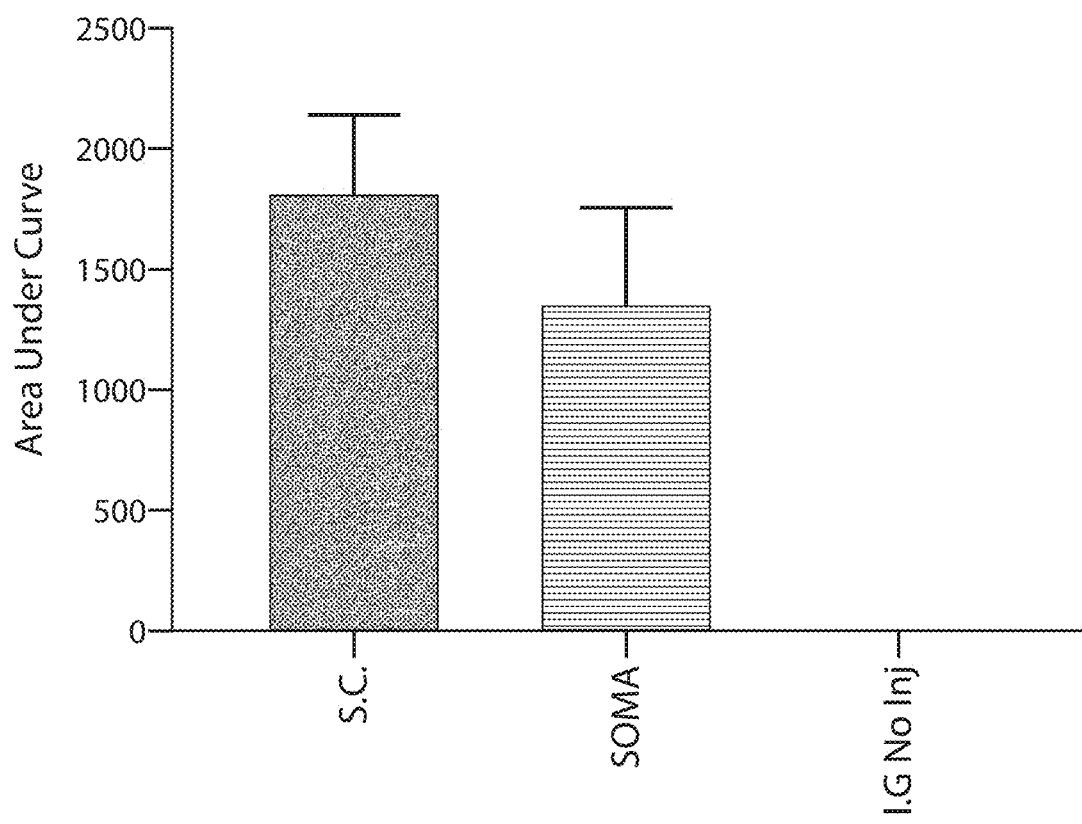
Figure 74C:
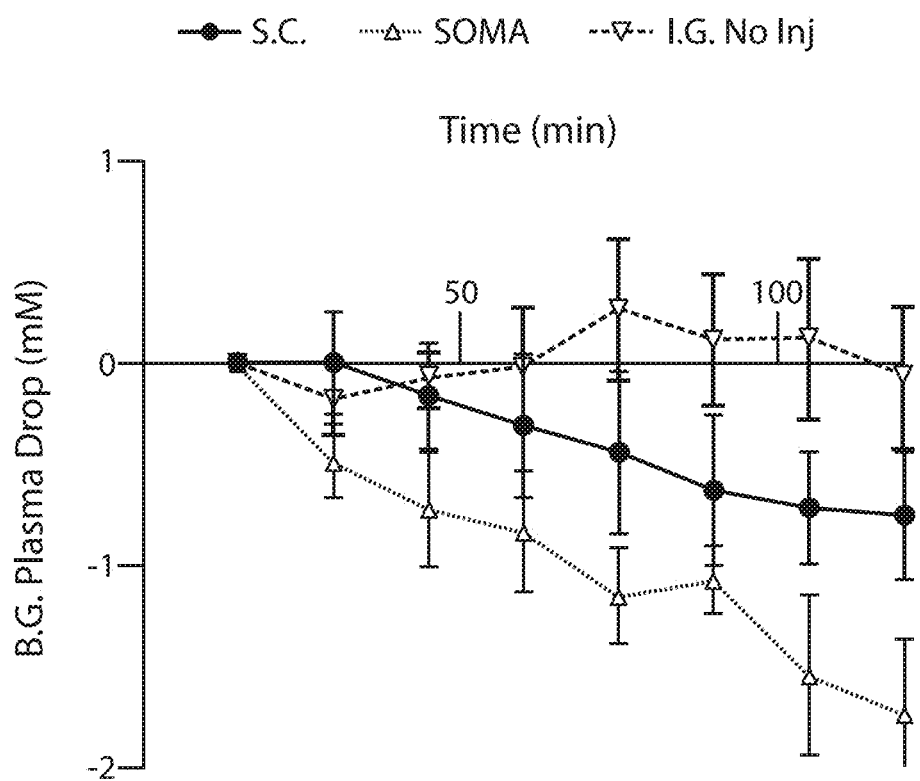
Figure 74D:
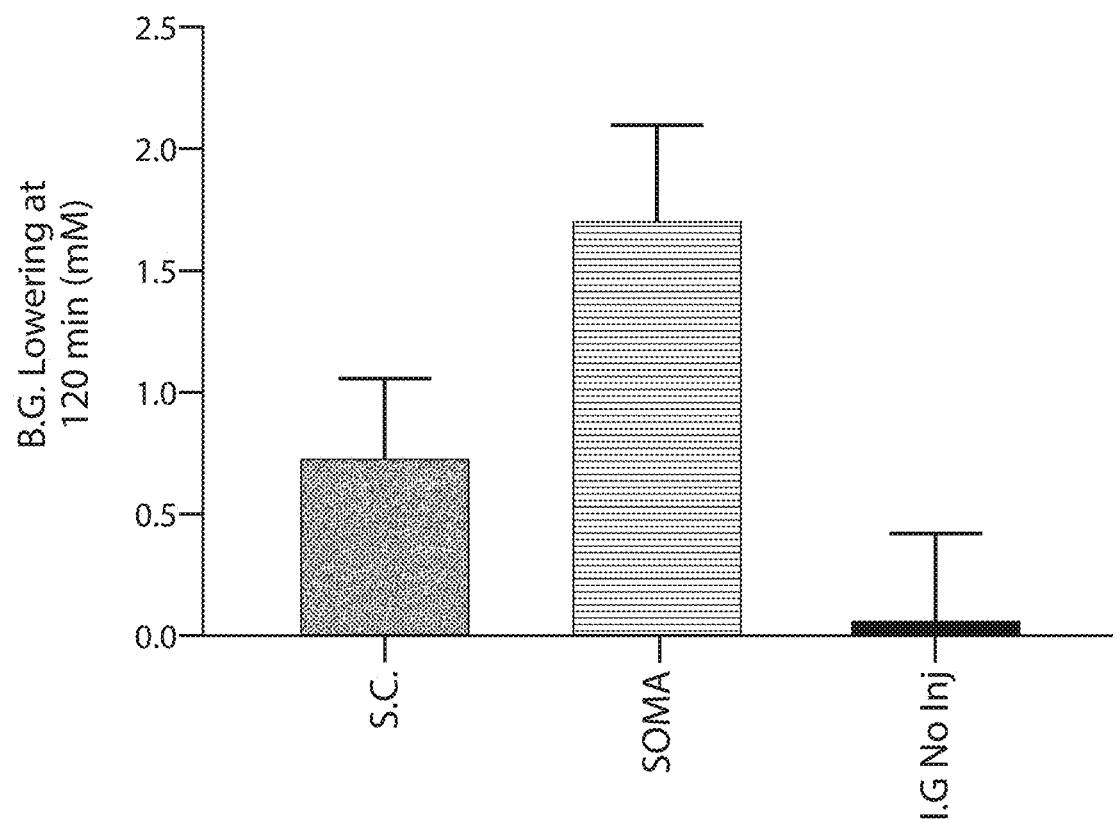

The amount of insulin inserted into the tissue via the SOMA device was estimated using histology results from in situ experiments (FIG. 73F). Because the SOMA microposts shafts and tips were made from 100% human insulin, not all of the API was considered as payload. The micropost insertion depth was evaluated and used to calculate the volume of the micropost which was submerged in the tissue. This volume was then multiplied by the density of the micropost to estimate the amount of API delivered. The amount of human insulin delivered by the manually placed microposts, made from 80% human insulin and 20% PEO 200 k, were assumed to be 100% of the incorporated API because the entire microposts were inserted into the tissue.

In Vivo Retention and Safety Evaluation

Six SOMAs with 32G stainless steel needles permanently fixed protruding 3 mm out of the bottom of the device were placed in the stomach of a swine using an overtube. While these devices were still inside of the stomach, translational swine movements were simulated (to mimic the outside forces as described in the "Simulated Walking Test" methods section) the device might experience while inside of the body. An endoscopy was then performed to check for any bleeding caused by the needles. Daily radiographs were subsequently performed to determine residency time of the devices. X-rays were taken until all devices passed. Additionally, during retention of the devices the animals were evaluated clinically for normal feeding and stooling patterns.

Rat Toxicity Test

Acute Toxicity Study: Three rats (Charles River Labs, Sprague Dawley 400-450 g in weight) were dosed once with 2000 mg/kg of stainless steel particles (McMaster Carr Elmhurst, USA) measuring between 100 and 300 µm in diameter, in 1 mL of soybean soil (Crisco Orrville, USA). These rats were compared to a control group of three rats which were only dosed with 1 mL of soybean oil. After 14 days, both groups were euthanized via an overdose of inhaled carbon dioxide and a necropsy was performed and samples of heart, lung, stomach, small intestine, colon, liver, kidney, spleen, pancreas and bladder were fixed in formalin, stained using H&E and analyzed by a pathologist to determine if any abnormalities were noted.

Sub chronic Study: Six rats (Charles River Labs, Sprague Dawley 330-450 g in weight) were dosed, via oral gavage, with 80 mg/kg of stainless steel particles, measuring between 100 and 300 µm in diameter, in 1 mL of soybean oil five days per week for four weeks. These rats were compared to a control group of six rats which were only dosed with 1 mL of soybean oil for the same frequency and duration. Whole blood samples were taken at days 1, 15, and 26 and tested for traces of chromium and nickel. Urine samples were taken at day 15 to test for traces of chromium and nickel as well. Radiographs of the GI tract were taken using a Faxitron Multifocus (Faxitron, Tucson, USA) at day 8 to confirm passage of the stainless steel. At the end of the study, on day 26, all 12 rats were euthanized via an overdose of inhaled carbon dioxide and a necropsy was performed. Samples of heart, lung, stomach, small intestine, colon, liver, kidney, spleen, pancreas and bladder were fixed in formalin, stained using H&E and analyzed by a pathologist to determine if any abnormalities were noted.

Figure 88:
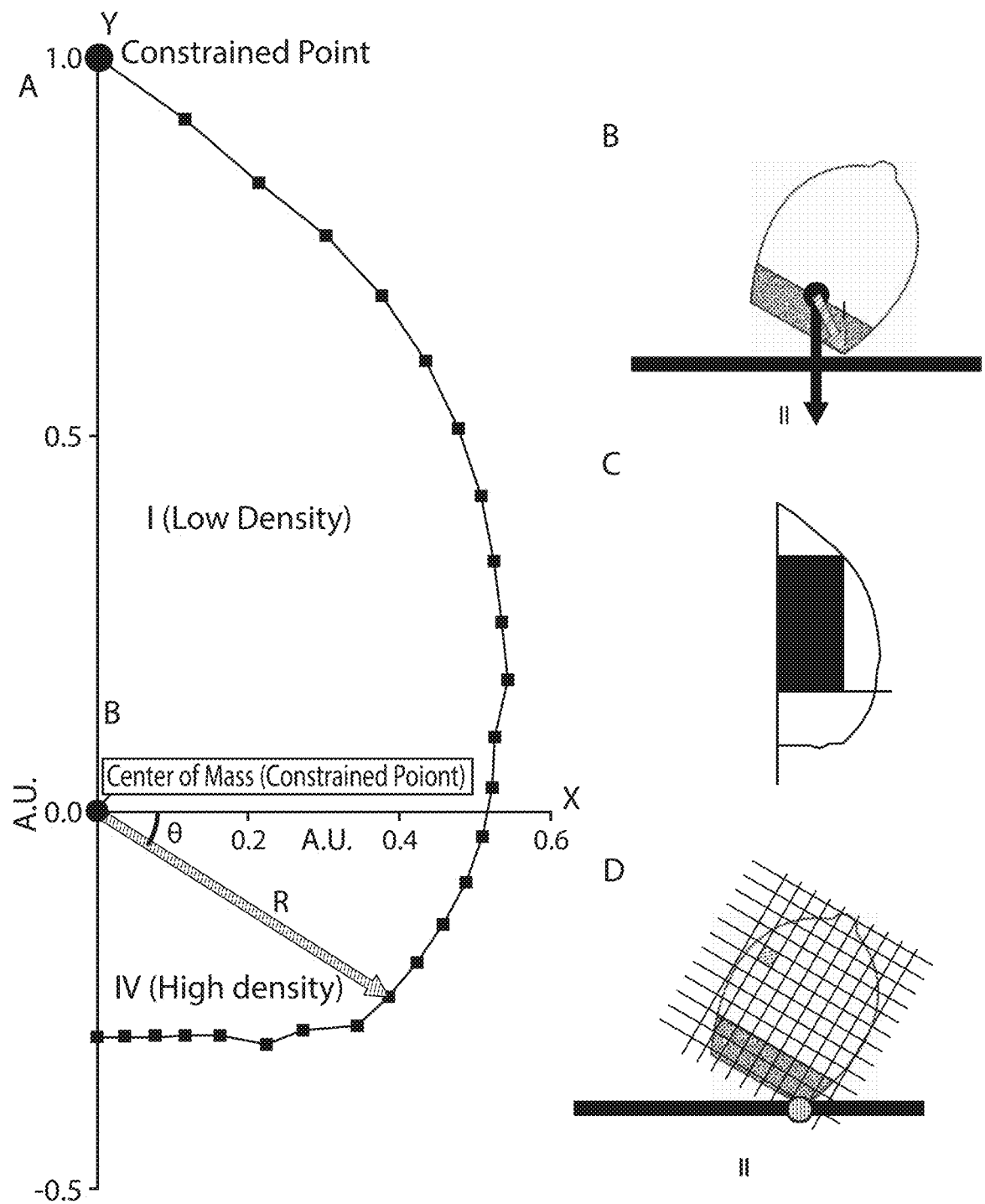
FIG. 88 shows computational results from self-orientating shape optimization for an exemplary system, according to one set of embodiments.

Computational Optimization:

The optimized shape was created by performing a two dimensional curve optimization over a 180 degree plane in quadrants I and IV and revolving the curve about the Y axis. FIG. 88 illustrates the optimized curve as well as the vectors and methods described in this section. The optimization function varied the radius of 25 different points spaced apart at equal angles along a curve drawn in polar coordinates. When reconverted into Cartesian coordinates, the space inside the revolved curve and below the X-Z plane was set to contain high density material (7.7 g/cm$^3$) while space above the X-Z plane and inside the revolved curve was set to contain low density material (1.1 g/cm$^3$). To simulate a hollow top section, a 4 mm in radius cylinder centered about the Y axis, beginning at the X-Z plane and ending at the curve boundary was removed from the top portion of the shape. The mass of the spring and the micropost were incorporated into the model. In order to define a scale for the shape the center of mass was constrained to the origin and the highest possible point to the coordinate [0,1]. The final shape was scaled to fit the size constraints. These constraints matched the requirements of an axisymmetric mono-monostatic shape, so no possible solutions were lost.

The optimization itself utilized Newton's kinematic equations to find a given shape's self-orientation time, t:

$$\Delta\theta = \omega t + \tfrac{1}{2}\alpha t^2 \qquad \text{Equation (1)}$$

$$\alpha = \tau/I \qquad \text{Equation (2)}$$

$$\omega = \omega_0 + \alpha t \qquad \text{Equation (3)}$$

$$I = \int r^2 dM \qquad \text{Equation (4)}$$

$$\tau = d \ast F \ast \sin(\theta) \qquad \text{Equation (5)}$$

where angular acceleration $\alpha$, and angular velocity $\omega$, are determined based on the device's moment of inertia I, and torque $\tau$. The gravitational force F, acted as the external force in the model and was used to calculate the simulated torque applied to the lever arm d, defined as the distance between the device's center of mass and point of contact with the tissue wall.

The angular acceleration of the device at a given orientation, defined by equation 2, determines the orientation speed and varies with torque and moment of inertia. The moment of inertia was calculated along with the total weight of the device by breaking the 3D space up into a 50×50×50 array of equally sized blocks, assigning a density to each block, and performing a summation described in equation 4.

Calculating the torque on the device, required determining both the direction and magnitude of the force and distance vectors as per equation 5. The force vector was the gravitational force on the object starting from the center of mass and pointing in a direction perpendicular to the surface of contact. The distance vector was calculated as the distance between the center of mass and the pivot point of the device on the surface of contact. When determining the pivot point, the greater curvature of the device was taken into account, as areas with concave curvature do not touch the surface.

Sucrose Encapsulation Dissolution Modeling

The radius at which the sucrose encapsulation would propagate a crack was calculated using Griffith's criterion:

$$\sigma_c^2 = \frac{2\gamma E}{\pi a},$$

where $\sigma_c$, is the critical stress applied by the spring, $\gamma$ is the surface energy of the material, E is the Young's modulus of the material, and a is the surface area perpendicular to the applied stress. Because all variables in the equation remain constant aside from the surface area, the dissolution rate defines the time until the cracking event and spring release. The COMSOL models and experimental testing are based on a spring that provides 1N of force. The physical spring was created by cutting a purchased spring into the appropriate size.

COMSOL Multiphysics (Stockholm, Sweden) was used to mathematically model the dissolution of a sucrose cylinder in both still water and water that flowed at 0.02 m/s, similar to that of the human stomach. Fick's law was used to estimate the rate of the diffusion process at the shrinking boundary between the sucrose and the water. Diffusion coefficient of $5.2*10^{-10}$ m²/s, an equilibrium concentration for sucrose in water of 6720 mol/m³, and mass transfer coefficient of $7.8*10^{-4}$ m/s (found experimentally) were used as parameters. The COMSOL model was run at starting sucrose cylinder diameters of 6 mm, 5 mm, and 4 mm, and the time it took for the cylinder to dissolve to a diameter of 1.7 mm was used to predict the actuation timing if a spring had been present in the cylinder.

To calculate the mass transfer coefficient of sucrose in water, sucrose was caramelized at 215° C. for 15 minutes in a PDMS mold with a 6 mm in diameter hole to create a cylindrical shape. The caramelized sucrose cylinder was placed in a 500 mL beaker of water at room temperature, and the diameter of the sucrose was measured every minute. The rate of dissolution was modeled and the slope of the linear fit was determined to be the mass transfer coefficient.

In order to test the dissolution of the sucrose coating on springs, sucrose encapsulated springs were placed in 500 mL beaker of water at room temperature, and the timing of the spring actuation was recorded for 4 mm, 5 mm, and 6 mm diameter sucrose spring, with three trials each.

Example 17—Coating

This example demonstrates the use of various coatings on the systems, described herein.

An Instron was used to compress at 0.1 mm/s for various coatings (PDMS Dip Coating, PDMS Film Coating, PCL Dip Coating, and PCL 3× Dip Coating). The results are summarized in Table 4.

TABLE 4

|  | PDMS Dip Coating (N) | PDMS Film Coating (N) | PCL 1 Dip Coating (N) | PCL 3 dip coating (N) |
|---|---|---|---|---|
| Average | 2.87 | 0.04 | 0.09 | 0.18 |
| Standard Error | 0.75 | 0.01 | 0.01 | 0.03 |

EXEMPLARY EMBODIMENTS

1. An ingestible self-righting article, comprising:
   a first portion having an average density;
   a second portion having an average density different from the average density of the first portion; and
   a payload portion for carrying an agent for release internally of a subject that ingests the article,
   wherein the self-righting article is configured to be encapsulated in a capsule.

2. An ingestible self-righting article, comprising a payload portion for carrying an agent for release internally of a subject that ingests the article, wherein the article has a geometric center, and a center of mass offset from the geometric center such that the article, suspended via an axis passing through the geometric center, with the center of mass offset laterally from the geometric center, experiences an externally applied torque of 0.09*10^-4 Nm or less due to gravity about the axis,
   wherein the self-righting article is configured to be encapsulated in a capsule.

3 A self-righting article, comprising:
   a first portion having an average density;
   a second portion having an average density different than the average density of the first portion; and
   a tissue-interfacing component associated with the self-righting article,
   wherein a ratio of the average density of the first portion to the average density of the second portion is greater than or equal to 2.5:1.

4. A self-righting article as in any preceding embodiment, wherein the self-righting article is a gomboc shape.

5. A self-righting article as in any preceding embodiment, wherein the self-righting article maintains an orientation of 20 degrees or less from vertical when acted on by 0.09*10^-4 Nm or less externally applied torque 6. A self-righting article as in any preceding embodiment, wherein the first portion has an average density of less than or equal to 2 g/mL and greater than or equal to 0.6 g/mL.

7. A self-righting article as in any preceding embodiment, wherein the second portion has an average density of less than 20 g/mL and greater than or equal to 3 g/mL.

8. A self-righting article as in any preceding embodiment, wherein the first portion comprises a first material and the second portion comprises a second material.

9. A self-righting article as in any preceding embodiment, wherein the first material and/or second material is selected from the group consisting of polymers, ceramics, and metals.

10. A self-righting article as in any preceding embodiment, wherein the first material and/or second material is biocompatible.

11. A self-righting article as in any preceding embodiment, wherein the first material and/or the second material are biodegradable.

12. A self-righting article as in any preceding embodiment, wherein the first material is a metal, ceramic, or combinations thereof.

13. A self-righting article as in any preceding embodiment, wherein the metal is selected from the group consisting of stainless steel, iron-carbon alloys, Field's metal, wolfram, molybdemum, gold, zinc, iron, and titanium.

14. A self-righting article as in any preceding embodiment, wherein the ceramic is selected from the group consisting of hydroxyapatite, aluminum oxide, calcium oxide, and tricalcium phosphate, zirconium oxide, silicates, silicon dioxide.

15. A self-righting article as in any preceding embodiment, wherein the second material is a polymer.

16. A self-righting article as in any preceding embodiment, wherein the polymer is selected from the group consisting of polycaprolactone, polylactic acid, polyethylene glycol, polypropylene, polyethylene, polycarbonate, polystyrene, and polyether ether ketone, and polyvinyl alcohol.

17. A self-righting article as in any preceding embodiment, wherein the first material is different from the second material.

18. A self-righting article as in any preceding embodiment, wherein an active pharmaceutical ingredient is disposed in a hollow portion.

19. A self-righting article as in any preceding embodiment, wherein the self-righting article has a self-righting time from 90 degrees in oil of less than or equal to 0.15 seconds, a self-righting time from 90 degrees in gastric fluid of less than or equal to 0.06 seconds, a self-righting time from 90 degrees in mucus of less than or equal to 0.05 seconds 20. A self-righting article as in any preceding embodiment, wherein the self-righting article has a self-righting time from 90 degrees in water of less than or equal to 0.05 seconds.

21. A self-righting article as in any preceding embodiment, wherein the self-righting article comprises one or more vents.

22. A self-righting article as in any preceding embodiment, wherein the self-righting article has a largest cross-sectional dimension of less than or equal to 1.1 cm.

23. A capsule comprising an outer shell and a self-righting article as in any preceding embodiment.

24. A capsule as in embodiment 23, comprising a spring-actuated component.

25. A method of orienting a capsule in a subject, comprising:
   administering, to the subject, a capsule comprising an outer shell and a self-righting article, the self-righting article comprising:
   a first portion having an average density;
   a second portion having an average density different from the average density of the first portion; and
   a tissue interfacing component associated with the self-righting article.

26. A method as in embodiment 25, wherein the self-righting article comprises an active pharmaceutical agent.

27. A method as in embodiment 26, wherein at least a portion of the active pharmaceutical agent is released to a location internal of the subject.

28. A method as in embodiment 25, comprising administering, to the subject, a sensor such that the sensor is associated with the self-righting article.

29. A method of delivering a pharmaceutical agent to a location internal of a subject, comprising:
   administering, to the subject, a capsule comprising an outer shell and a self-righting article, the self-righting article comprising:
      a first portion comprising a first material having a first average density;
      a second portion comprising a second material, having a second average density, different from the first average density; and
      a tissue interfacing component disposed within the self-righting article and associated with an active pharmaceutical agent,
      wherein a ratio of the average density of the first material to the average density of the second material is greater than or equal to 2.5:1,
      wherein the self-righting article is oriented at the location internal of a subject such that the tissue interfacing component punctures a tissue proximate the location internal of the subject; and
      wherein at least a portion of the active pharmaceutical agent is released into the tissue.

30. A self-righting article, comprising:
   a first material and a second material, different than the first material; and
   an active pharmaceutical agent associated with the self-righting article,
   wherein an axis essentially perpendicular to a tissue-engaging surface of the self-righting article is configured to maintain an orientation of 20 degrees or less from vertical when acted on by $0.09*10^{-4}$ Nm or less externally applied torque, and
   wherein a ratio of an average density of the first material to an average density of the second material is greater than or equal to 2.5:1.

31. A self-righting article, comprising:
   at least a first portion having an average density greater than 1 $g/cm^3$,
   wherein the self-righting article has a largest cross-sectional dimension of less than or equal to 1.1 cm, and
   wherein an axis perpendicular to a tissue-engaging surface of the self-righting article is configured to maintain an orientation of 20 degrees or less from vertical when acted on by $0.09*10^{-4}$ Nm or less externally applied torque.

32. A self-righting article, comprising:
   a first portion comprising a first material having a first average density;
   a second portion comprising a second material, having a second average density,
   different from the first average density; and
   wherein the self-righting article has a most stable, lowest-potential-energy physical configuration, and a self-righting time, from 90 degrees offset in any orientation from the most stable configuration, in water of less than or equal to 0.05 seconds, and
   wherein a ratio of average density of the first material to an average density of the second material is greater than or equal to 2.5:1.

33. A self-righting article, comprising:
   at least a first portion having an average density greater than 1 $g/cm^3$,
   wherein the self-righting article has a largest cross-sectional dimension of less than or equal to 1.1 cm, and
   wherein the self-righting article has a self-righting time from 90 degrees in water of less than or equal to 0.05 seconds.

34. A self-righting article, comprising:
   at least a first portion having an average density greater than 1 $g/cm^3$,
   wherein the self-righting article has a self-righting time from 90 degrees in water of less than or equal to 0.05 seconds, wherein a longitudinal axis perpendicular to a tissue-engaging surface of the self-righting article is configured to maintain an orientation of 20 degrees or less from vertical when acted on by 0.09*10^−4 Nm or less externally applied torque, and/or wherein the self-righting article has a rate of obstruction of less than or equal to 1%.

34. An article, comprising:
   an outer shell;
   a spring at least partially encapsulated within the outer shell;
   a support material associated with the spring such that the support material maintains at least a portion of the spring under at least 5% compressive strain under ambient conditions; and
   a tissue interfacing component operably linked to the spring.

35. An article as in any preceding embodiment, wherein the support material at least partially releases the spring under physiological conditions.

36. An article as in any preceding embodiment, wherein the tissue interfacing component comprises a needle, a biopsy component, a hook, a mucoadhesive patch, or combinations thereof.

37. An article as in any preceding embodiment, wherein the article comprises an active pharmaceutical agent.

38. An article as in any preceding embodiment, wherein the article is configured such that at least a portion of the active pharmaceutical agent is released from the article upon at least partial degradation of the support material.

39. An article as in any preceding embodiment, wherein the support material is configured to maintain the spring under compression such that, upon at least partial degradation of the support material, the spring decompresses.

40. An article as in any preceding embodiment, wherein the support material comprises a brittle material.

41. An article as in embodiment 40, wherein the brittle material comprises sugar and/or a polymer.

42. An article as in any preceding embodiment, wherein the support material is a coating having greater than or equal to 3 mm and less than or equal to 6 mm in thickness.

43. An article as in any preceding embodiment, wherein the spring comprises a material selected from the group consisting of nitinol, metals, and polymers.

44. An article as in any preceding embodiment, wherein the spring has a spring constant of greater than or equal to 100 N/m and less than or equal to 20000 N/m.

45. An article as in any preceding embodiment, wherein the spring is compressed by greater than or equal to 1 mm and less than or equal to 5 mm from the uncompressed length of the spring.

46. An article as in any preceding embodiment, wherein the outer shell is a capsule.

47. An article as in any preceding embodiment, wherein the article is associated with a self-righting system.

48. An article as in any preceding embodiment, herein the spring has a mean cross-sectional dimension of greater than or equal to 1 mm and less than or equal to 10 mm.

49. A method, comprising:
   administering, to a subject, an article, the article comprising:
   an outer shell;
   a spring at least partially encapsulated with the outer shell;
   a support material associated with the spring such that the support material maintains at least a portion of the spring under at least 10% compressive strain under ambient conditions; and
   a tissue interfacing component associated with the spring.

50. A method for puncturing a tissue located internally of a subject, comprising:
   administering, to a subject, an article, the article comprising:
   an outer shell;
   a spring at least partially encapsulated by the outer shell;
   a support material associated with the spring such that the support material maintains at least a portion of the spring under at least 10% compressive strain under ambient conditions; and
   a tissue interfacing component associated with the spring;
   wherein at least a portion of the support material is degraded such that the spring extends and/or the tissue interfacing component penetrates a tissue located internal to the subject.

51. A method as in embodiment 50, wherein an active pharmaceutical agent is released during and/or after penetration of the tissue located internal to the subject.

52. A method as in embodiment 51, wherein the self-righting article is oriented such that a longitudinal axis of the tissue interfacing component is orthogonal to the tissue located proximate the self-righting article.

53. An article, comprising:
   a tissue interfacing component and a spring associated with the tissue interfacing component, the spring maintained in an at least partially compressed state by a support material under at least 5% compressive strain,
   wherein the spring is configured to release at least 10% of a stored compressive energy of the spring within 10 minutes of exposing the support material to a fluid.

54. An article as in embodiment 53, comprising a pharmaceutical agent associated with the tissue interfacing component.

55. An article as in embodiment 53 or 54, comprising a self-righting article associated with the tissue interfacing component.

56. A tissue interfacing component, comprising:
   a solid therapeutic agent and a support material,
   wherein the solid therapeutic agent is present in the tissue interfacing component in an amount of greater than or equal to 10 wt % as a function of the total weight of the tissue interfacing component,
   wherein the solid therapeutic agent and support material are distributed substantially homogeneously, and
   wherein the tissue interfacing component is configured to penetrate tissue.

57. A tissue interfacing component as in embodiment 56, comprising a plurality of microneedles comprising the solid therapeutic agent and the support material.

58. A tissue interfacing component as in embodiment 56, comprising a support material associated with the tissue interfacing component.

59. A tissue interfacing component having a tip, and comprising:
   a solid therapeutic agent and a support material associated with the solid therapeutic agent,
   wherein at least a portion of the solid therapeutic agent is associated with one or more tips of the tissue interfacing component, and
   wherein the solid therapeutic agent is present in the tissue interfacing component in an amount of greater than or equal to 10 wt % as a function of the total weight of the tissue interfacing component.

60. A tissue interfacing component as in embodiment 59, comprising a plurality of microneedles comprising the solid therapeutic agent and the support material.

61. A tissue interfacing component as in embodiment 59 or 60, wherein at least a portion of the solid therapeutic agent is present on at least a surface of the tip.

62. A tissue interfacing component as in any one of embodiments 59-61, wherein at least a portion of the tip comprises the solid therapeutic agent.

63. A tissue interfacing component as in embodiment 62, wherein the tip comprises greater than or equal to 70 wt % solid therapeutic agent versus the total weight of the tip.

64. A tissue interfacing component as in embodiment 59 or 60, wherein at least a portion of the support material is present on at least a surface of the tip.

65. A method of forming a tissue interfacing component, comprising:
providing a solid therapeutic agent and a support material; and
compressing, using at least 1 MPa of pressure, and/or heating the solid therapeutic agent and a support material together to form the tissue interfacing component, wherein the tissue interfacing component is configured to penetrate tissue.

66. A method as in embodiment 65, wherein compressing comprises centrifugation of the solid therapeutic agent and the support material.

67. A method as in embodiment 65, wherein compressing comprises using at least 20 MPa of pressure.

68. A tissue interfacing component or method as in any preceding embodiment, wherein the support material is biodegradable.

69. A tissue interfacing component or method as in any preceding embodiment, wherein the support material comprises a polymer.

70. A tissue interfacing component or method as in embodiment 69, wherein the polymer is selected from the group consisting of polyethylene glycol and HPMC.

71. A tissue interfacing component or method as in any preceding embodiment, wherein the solid therapeutic agent is selected from the group consisting of active pharmaceutical ingredients, insulin, nucleic acids, peptides, and antibodies.

72. A tissue interfacing component or method as in any preceding embodiment, wherein the tissue interfacing component comprises a coating.

73. A tissue interfacing component or method as in any preceding embodiment, wherein the coating has a yield strength of greater than or equal to 50 MPa.

74. An article, comprising:
greater than or equal to 80 wt % solid active pharmaceutical agent versus the total article weight,
wherein the article has a Young's elastic modulus of greater than or equal to 100 MPa, and
wherein the article is configured to penetrate at least 1 mm into human gastrointestinal mucosal tissue with a force of less than or equal to 20 mN.

75. A method of forming an article, comprising:
introducing, into a mold, a composition comprising greater than or equal to 80 wt % solid active pharmaceutical agent versus the total weight of the composition;
applying greater than or equal to 1 MPa of pressure to the composition; and
heating the composition to a temperature of at least 70° C. for at least 1 min,
wherein the article is configured to penetrate at least 1 mm into human gastrointestinal mucosal tissue with a force of less than or equal to 20 mN.

76. An article, comprising:
greater than or equal to 80 wt % solid active pharmaceutical agent versus the total article weight,
wherein the article is configured to deliver at least 1 mg of active pharmaceutical agent per square centimeter of a tissue of a subject, and/or
wherein the article comprises greater than or equal to 1 mg of active pharmaceutical agent per square centimeter.

77. An article or method as in any preceding embodiment, wherein the active pharmaceutical agent is cast into a mold to form the article.

78. An article or method as in any preceding embodiment, wherein the mold is centrifuged.

79. An article or method as in any preceding embodiment, further comprising a binder.

80. An article or method as in embodiment 79, wherein the binder comprises sugar such as sorbitol or sucrose, gelatin, polymer such as PVA, PEG, PCL, PVA or PVP, and/or ethanol.

81. An article or method as in any preceding embodiment, wherein the article comprises greater than or equal to 1 mg of active pharmaceutical agent.

82. An article or method as in any preceding embodiment, wherein the active pharmaceutical agent is selected from the group consisting of bacteriophage, DNA, insulin, human growth hormone, monoclonal antibodies, adalimumab, epinephrine, and ondansetron.

83. A self-righting article configured to anchor at a location internal to a subject, comprising:
at least a first portion having an average density greater than 1 g/cm$^3$ wherein a longitudinal axis perpendicular to a tissue-engaging surface of the article is configured to maintain an orientation of 20 degrees or less from vertical when acted on by 0.09*10^-4 Nm or less externally applied torque; and
at least one anchoring mechanism associated with the self-righting article.

84. An article configured to anchor at a location internal to a subject, comprising:
an outer shell;
a spring at least partially encapsulated by the outer shell, the spring maintained in an at least partially compressed state by a support material under at least 5% compressive strain,
at least one anchoring mechanism operably linked to the spring.

85. A method for anchoring an article to a location internal to a subject, comprising:
administering, to the subject, the article, wherein the article comprises at least a first portion having an average density greater than 1 g/cm$^3$ and at least one anchoring mechanism, the article configured to be retained at the location under greater than or equal to 0.6 N of force and/or a change in orientation of greater than or equal to 30 degrees.

86. A method or article as in any preceding embodiment, wherein each anchoring mechanism comprises a hook 87. An article or method as in any preceding embodiment, wherein each anchoring mechanism is a hooked needle 88. An article or method as in any preceding embodiment, wherein each anchoring mechanism is configured to penetrate a tissue at the location internal to the subject at a depth of greater than or equal to 1 mm and less than or equal to 3 mm.

89. An article or method as in any preceding embodiment, wherein the hooks comprise a non-degradable material under physiological conditions.

90. An article or method as in any preceding embodiment, wherein the anchoring mechanism has a length of greater than or equal to 10 microns and less than or equal to 250 microns 91. An article or method as in any preceding embodiment, wherein each anchoring mechanism has a hooking force of greater than or equal to 0.002 N and less than or equal to 1 N 92. An article or method as in any preceding embodiment, wherein the article is configured to be retained at the location under greater than or equal to 0.6 N of transversely applied force.

93. An article or method as in any preceding embodiment, wherein the article is configured to be retained at the location after a change in orientation of greater than or equal to 30 degrees 94. An article or method as in any preceding embodiment, wherein the article comprises two or more anchoring mechanisms spaced at least 1 mm apart.

95. A self-righting article configured for administration to a location internal to a subject, comprising:
    at least a first portion having an average density greater than 1 g/cm3, the self-righting article has a self-righting time from 90 degrees in water of less than or equal to 0.05 second;
    at least two tissue interfacing component comprising a tissue-contacting portion configured for contacting tissue, each tissue-contacting portion comprising an electrically-conductive portion configured for electrical communication with tissue and an insulative portion configured to not be in electrical communication with tissue; and
    a power source in electric communication with the at least two tissue interfacing components.

96. An article configured for administration to at a location internal to a subject, comprising:
    an outer shell;
    a spring at least partially encapsulated by the outer shell, the spring maintained in an at least partially compressed state by a support material under at least 5% compressive strain,
    at least two tissue interfacing components comprising a tissue-contacting portion configured for contacting tissue, each tissue-contacting portion comprising an electrically-conductive portion configured for electrical communication with tissue and an insulative portion configured to not be in electrical communication with tissue; and
    a power source in electric communication with the at least two tissue interfacing components.

97. A method for providing electrical stimulation to a location internal to a subject, comprising:
    administering, to the subject, an article comprising at least one tissue interfacing component disposed within the article, each tissue interfacing component comprising a conductive material;
    releasing the at least one interfacing component from the article;
    inserting the at least one interfacing component into a tissue at the location internal to the subject;
    applying a current generated by a power source in electrical communication with the tissue interfacing components across the two or more tissue interfacing components,
    wherein the article comprises a spring maintained in an at least partially compressed state by a support material under at least 5% compressive strain, each tissue interfacing component operably linked to the spring.

98. A method as in embodiment 97, comprising administering two or more articles to the subject and applying the current across the two articles.

99. An article or method as in any preceding embodiment, wherein the article is configured to be retained at the location internal to subject under greater than or equal to 0.6 N of force and/or a change in orientation of greater than or equal to 30 degrees.

100. A self-righting article, comprising:
    a tissue interfacing component and a spring associated with the tissue interfacing component, the spring maintained by a support material under at least 5% compressive strain,
    wherein the self-righting article has a largest cross-sectional dimension of less than or equal to 1.1 cm, and
    wherein an axis essentially perpendicular to a tissue-engaging surface of the self-righting article is configured to maintain an orientation of 20 degrees or less from vertical when acted on by $0.09*10^{-4}$ Nm or less externally applied torque, and/or
    wherein the self-righting article has a self-righting time from 90 degrees in water of less than or equal to 0.05 seconds.

101. A self-righting article as in embodiment 100, wherein the spring is configured to release at least 10% of a stored compressive energy of the spring within 10 min of exposing the support material to a fluid.

102. A self-righting article as in embodiment 100 or 101, wherein the self-righting article has a self-righting time from 90 degrees in water of less than or equal to 0.05 seconds.

103. An article for delivering a pharmaceutical agent to a subject, comprising:
    a tissue interfacing component; and
    a spring associated with the tissue interfacing component and maintained by a support material under at least 5% compressive strain,
    wherein the tissue interfacing component comprises a solid pharmaceutical agent in an amount of greater than or equal to 110 wt % versus the total tissue interfacing component weight.

104. An article as in embodiment 103, wherein the spring is configured to release at least 90% of a stored compressive energy of the spring within 10 min of exposing the support material to a fluid.

105. An article as in embodiment 103 or 104, wherein the tissue interfacing component is a needle.

106. An article as in any one of embodiments 103-105, wherein the tissue interfacing component has a Young's elastic modulus of greater than or equal to 100 MPa.

107. An article for delivering a pharmaceutical agent to a subject, comprising:
    a tissue interfacing component; and
    a spring associated with the tissue interfacing component,
    wherein the needle comprises a solid pharmaceutical agent in an amount of greater than or equal to 80 wt % versus the total needle weight, and
    wherein the spring is configured to release at least 10% of a stored compressive energy of the spring within 10 min of exposing the support material to a fluid.

108. An article as in embodiment 107, wherein the spring is maintained by a support material under at least 5% compressive strain.

109. A self-righting article, comprising one or more tissue interfacing components associated with the self-righting article,
    wherein the self-righting article has a self-righting time from 90 degrees in water of less than or equal to 0.05 seconds, and wherein the self-righting article is configured such that at least one tissue interfacing component has a longest longitudinal axis oriented within 15 degrees of vertical upon self-righting.

110. A self-righting article, comprising a tissue interfacing component associated with the self-righting article,
wherein the tissue interfacing component comprises a solid pharmaceutical agent in an amount of greater than or equal to 10 wt % versus the total tissue interfacing component weight, and
wherein an axis essentially perpendicular to a tissue-engaging surface of the self-righting article is configured to maintain an orientation of 20 degrees or less from vertical when acted on by 0.09*10^−4 Nm or less externally applied torque.

111. A method of delivering a pharmaceutical agent to a subject, comprising:
administering, to the subject, an article comprising a tissue interfacing component associated with the pharmaceutical agent; and
releasing, at the location internal to the subject, at least a portion of the pharmaceutical agent from the article.
wherein, upon reaching a location internal to the subject, the article:
has a longitudinal axis of the article is configured to orient to about 90 degrees with respect to vertical; and/or
has a longitudinal axis that maintains an orientation of 20 degrees or less from vertical when acted on by 0.09*10^−4 Nm or less externally applied torque; and/or
can penetrate mucosal tissue with certain amount of force; and/or
has a self-righting time from 90 degrees in water of less than or equal to 0.05 seconds; and/or
has an average density greater than 1 g/cm³; and/or
comprises a solid pharmaceutical agent in an amount of greater than or equal to 10 wt % versus the total tissue interfacing component weight; and/or
comprises a spring configured for instantaneous release.

112. A method of collecting a sample from a subject, comprising:
administering, to the subject, an article comprising a spring, a support material, and a biopsy mechanism; and
collecting the sample, via the biopsy mechanism, at a location internal to the subject,
wherein, upon reaching the location internal to the subject an axis essentially perpendicular to a tissue-engaging surface of the self-righting article is configured to maintain an orientation of 20 degrees or less from vertical when acted on by 0.09*10^−4 Nm or less externally applied torque and the spring is configured to release at least 10% of a stored compressive energy of the spring within 0.1 ms of mechanical failure of the support material.

113. A method as in embodiment 112, comprising exposing the tissue interfacing component to a fluid of the subject such that at least a portion of the tissue interfacing component actuates.

114. A self-righting article, comprising
a self-actuating component comprising a spring and a support material adapted to maintain the spring in at least a partially compressed state and structured for at least partial degradation when exposed to a biological fluid; and
a tissue interfacing component associated with an active pharmaceutical agent;
wherein the self-righting article is configured as a monostatic body due to the center of mass of the self-righting article and the shape of the self-righting article.

115. A self-righting article as in embodiment 114, wherein when the self-righting article is at least partially supported by the tissue of the subject, the self-righting article orients in a direction to allow the tissue interfacing component to release at least a portion of the active pharmaceutical agent into the tissue.

116. A self-righting article, comprising:
a first portion having a mass;
a second portion having a mass different from the mass of the first portion;
a self-actuating component;
a tissue interfacing component associated with an active pharmaceutical agent and operably linked to the self-actuating component; and
a tissue engaging surface configured to contact a surface of a tissue internal to a subject;
wherein the self-righting article is configured as a monostatic body due to the center of mass of the self-righting article and the shape of the self-righting article;
wherein when the self-righting article is at least partially supported by the tissue of the subject, the self-righting article orients in a direction to allow the tissue interfacing component to release at least a portion of the active pharmaceutical agent into the tissue.

117. A self-righting article as in embodiment 116, wherein the first portion comprises a first material and the second portion comprises a second material, wherein the first material and the second material are the same.

118. A self-righting article as in embodiment 116, wherein the first portion comprises a first material and the second portion comprises a second material, wherein the first material and the second material are different.

119. A self-righting article, comprising:
a first portion comprising a first material and having a mass;
a second portion comprising a second material and having a mass different from the mass of the first portion;
a self-actuating component;
a tissue interfacing component associated with an active pharmaceutical agent and operably linked to the self-actuating component; and
a tissue engaging surface configured to contact a surface of a tissue located internal to a subject;
wherein the self-righting article has an average density greater than 1 g/cm³;
wherein the self-righting article is configured as a monostatic body due to the center of mass of the self-righting article and the shape of the self-righting article; and
wherein when the self-righting article is at least partially supported by the tissue of the subject, the self-righting article orients in a direction to allow the tissue interfacing component to release at least a portion of the active pharmaceutical agent into the tissue.

120. A self-righting article as in any one of embodiments 116-119, wherein the first material and/or second material is selected from the group consisting of a polymer, a ceramic, a metal, a metal alloy, and combinations thereof.

121. A self-righting article as in embodiment 120, wherein the metal is selected from the group consisting of stainless steel, iron-carbon alloys, Field's metal, wolfram, molybdenum, gold, zinc, iron, and titanium.

122. A self-righting article as in embodiment 120, wherein the ceramic is selected from the group consisting of hydroxyapatite, aluminum oxide, calcium oxide, tricalcium phosphate, zirconium oxide, silicates, and silicon dioxide.

123. A self-righting article as in embodiment 120, wherein the polymer is selected from the group consisting of polycaprolactone, polylactic acid, polyethylene glycol, polypropylene, polyethylene, polycarbonate, polystyrene, and polyether ether ketone, and polyvinyl alcohol.

124. A self-righting article as in any one of embodiments 117-123, wherein the first material is a metal and the second material is a polymer.

125. A self-righting article as in any one of embodiments 117-123, wherein the first material is a polymer and the second material is a metal.

126. A self-righting article as in any one of embodiments 117-125, wherein the self-actuating component comprises a spring and a support material adapted to maintain the spring in at least a partially compressed state, wherein the support material is configured for at least partial degradation in a biological fluid.

127. A self-righting article as in embodiment 126, wherein the spring comprises a spring constant in the range of 100 N/m to 1500 N/m.

128. A self-righting article as in any one of embodiments 115-127, wherein the tissue interfacing component comprises the active pharmaceutical agent.

129. A self-righting article as in embodiment 128, wherein the active pharmaceutical agent is present in the tissue interacting component in an amount greater than or equal to 80 wt % of the total weight of the tissue interfacing component.

130. A self-righting article as in embodiment 128, wherein 100 wt % of the tissue interacting component is the active pharmaceutical agent.

131. A self-righting article as in any one of embodiments 115-130, wherein the self-righting article comprises one or more vents configured such that the self-actuating component is in fluidic communication with an external environment.

132. A self-righting article as in any one of embodiments 115-131, wherein the biological fluid is gastric fluid.

133. A self-righting article as in any one of embodiments 115-132, wherein the shape of the self-righting article is a gomboc shape.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. An ingestible self-righting article, comprising a payload portion for carrying an agent for release internally of a subject that ingests the article, wherein the article has a geometric center, and a center of mass offset from the geometric center such that the article, suspended via an axis passing through the geometric center, with the center of mass offset laterally from the geometric center, experiences an externally applied torque of $0.09*10^{-4}$ Nm or less due to gravity about the axis,
wherein the self-righting article is configured to be encapsulated in a capsule.

2. A self-righting article as in claim 1, wherein the self-righting article is a gomboc shape.

3. A self-righting article as in claim 1, wherein the self-righting article maintains an orientation of 20 degrees or less from vertical when acted on by $0.09*10^{-4}$ Nm or less externally applied torque.

4. A self-righting article as in claim 1, wherein the self-righting article comprises a first portion having an average density of less than or equal to 2 g/mL and greater than or equal to 0.6 g/mL, and a second portion having an average density different from the average density of the first portion.

5. A self-righting article as in claim 4, wherein the second portion has an average density of less than 20 g/mL and greater than or equal to 3 g/mL.

6. A self-righting article as in claim 4, wherein the first portion comprises a first material and the second portion comprises a second material.

7. A self-righting article as in claim 6, wherein the first material and/or second material is selected from the group consisting of polymers, ceramics, and metals.

8. A self-righting article as in claim 6, wherein the first material and/or second material is biocompatible.

9. A self-righting article as in claim 6, wherein the first material and/or the second material are biodegradable.

10. A self-righting article as in claim 6, wherein the first material is a metal, ceramic, or combinations thereof.

11. A self-righting article as in claim 10, wherein the metal is selected from the group consisting of stainless steel, iron-carbon alloys, Field's metal, wolfram, molybdemum, gold, zinc, iron, and titanium.

12. A self-righting article as in claim 10, wherein the ceramic is selected from the group consisting of hydroxyapatite, aluminum oxide, calcium oxide, and tricalcium phosphate, zirconium oxide, silicates, silicon dioxide.

13. A self-righting article as in claim 6, wherein the second material is a polymer.

14. A self-righting article as in claim 13, wherein the polymer is selected from the group consisting of polycaprolactone, polylactic acid, polyethylene glycol, polypropylene, polyethylene, polycarbonate, polystyrene, and polyether ether ketone, and polyvinyl alcohol.

15. A self-righting article as in claim 6, wherein the first material is different from the second material.

16. A self-righting article as in claim 1, wherein an active pharmaceutical ingredient is disposed in a hollow portion.

17. A self-righting article as in claim 1, wherein the self-righting article has a self-righting time from 90 degrees in oil of less than or equal to 0.15 seconds, a self-righting time from 90 degrees in gastric fluid of less than or equal to 0.06 seconds, a self-righting time from 90 degrees in mucus of less than or equal to 0.05 seconds.

18. A self-righting article as in claim 1, wherein the self-righting article has a self-righting time from 90 degrees in water of less than or equal to 0.05 seconds.

19. A self-righting article as in claim 1, wherein the self-righting article comprises one or more vents.

20. A self-righting article as in claim 1, wherein the self-righting article has a largest cross-sectional dimension of less than or equal to 2 cm.

21. A capsule comprising an outer shell and a self-righting article as in claim 1.

22. A capsule as in claim 21, comprising a spring-actuated component.

23. A self-righting article as in claim 1, wherein the self-righting article comprises an outer shell having a monostatic shape.

24. A self-righting article as in claim 1, wherein the self-righting article comprises a self-actuating component comprising a spring and a support material adapted to maintain the spring in at least a partially compressed state and structured for at least partial degradation when exposed to a biological fluid.

25. A self-righting article as in claim 24, wherein the support material maintains at least a portion of the spring under at least 5% compressive strain under ambient conditions.

26. A self-righting article as in claim 24, wherein the self-righting article comprises a tissue interfacing component operably linked to the spring.

27. A self-righting article as in claim 26, wherein the tissue interfacing component comprises a needle, a biopsy component, a hook, or a mucoadhesive patch.

28. A self-righting article as in claim 26, wherein the tissue interfacing component comprises an active pharmaceutical agent.

29. A self-righting article as in claim 26, wherein the tissue interfacing component has a Young's elastic modulus of greater than or equal to 100 MPa.

30. A self-righting article as in claim 26, wherein the needle comprises a solid pharmaceutical agent in an amount of greater than or equal to 10 wt % versus the total needle weight.

31. A self-righting article, comprising:
a first material and a second material, different than the first material; and
an active pharmaceutical agent associated with the self-righting article,
wherein an axis essentially perpendicular to a tissue-engaging surface of the self-righting article is configured to maintain an orientation of 20 degrees or less from vertical when acted on by 0.09*10^−4 Nm or less externally applied torque, and wherein a ratio of an average density of the first material to an average density of the second material is greater than or equal to 2.5:1.

32. A self-righting article as in claim 31, wherein the self-righting article comprises an outer shell having a monostatic shape.

33. A self-righting article as in claim 31, wherein the self-righting article comprises a self-actuating component comprising a spring and a support material adapted to maintain the spring in at least a partially compressed state and structured for at least partial degradation when exposed to a biological fluid.

34. A self-righting article as in claim 33, wherein the support material maintains at least a portion of the spring under at least 5% compressive strain under ambient conditions.

35. A self-righting article as in claim 33, wherein the self-righting article comprises a tissue interfacing component operably linked to the spring.

36. A self-righting article as in claim 35, wherein the tissue interfacing component comprises a needle, a biopsy component, a hook, or a mucoadhesive patch.

37. A self-righting article as in claim 35, wherein the tissue interfacing component comprises an active pharmaceutical agent.

38. A self-righting article as in claim 35, wherein the tissue interfacing component has a Young's elastic modulus of greater than or equal to 100 MPa.

39. A self-righting article as in claim 35, wherein the needle comprises a solid pharmaceutical agent in an amount of greater than or equal to 10 wt % versus the total needle weight.

40. A self-righting article, comprising:
at least a first portion having an average density greater than 1 g/cm$^3$,
wherein the self-righting article has a largest cross-sectional dimension of less than or equal to 1.1 cm, and
wherein an axis perpendicular to a tissue-engaging surface of the self-righting article is configured to maintain an orientation of 20 degrees or less from vertical when acted on by 0.09*10^−4 Nm or less externally applied torque.

41. A self-righting article as in claim 40, wherein the self-righting article comprises an outer shell having a monostatic shape.

42. A self-righting article as in claim 40, wherein the self-righting article comprises a self-actuating component comprising a spring and a support material adapted to maintain the spring in at least a partially compressed state and structured for at least partial degradation when exposed to a biological fluid.

43. A self-righting article as in claim 42, wherein the support material maintains at least a portion of the spring under at least 5% compressive strain under ambient conditions.

44. A self-righting article as in claim 42, wherein the self-righting article comprises a tissue interfacing component operably linked to the spring.

45. A self-righting article as in claim 44, wherein the tissue interfacing component comprises a needle, a biopsy component, a hook, or a mucoadhesive patch.

46. A self-righting article as in claim 44, wherein the tissue interfacing component comprises an active pharmaceutical agent.

47. A self-righting article as in claim 44, wherein the tissue interfacing component has a Young's elastic modulus of greater than or equal to 100 MPa.

48. A self-righting article as in claim 44, wherein the needle comprises a solid pharmaceutical agent in an amount of greater than or equal to 10 wt % versus the total needle weight.

49. A self-righting article, comprising:
at least a first portion having an average density greater than 1 g/cm$^3$,
wherein the self-righting article has a largest cross-sectional dimension of less than or equal to 1.1 cm, and
wherein the self-righting article has a self-righting time from 90 degrees in water of less than or equal to 0.05 seconds.

50. A self-righting article as in claim 49, wherein the self-righting article comprises an outer shell having a monostatic shape.

51. A self-righting article as in claim 49, wherein the self-righting article comprises a self-actuating component comprising a spring and a support material adapted to maintain the spring in at least a partially compressed state and structured for at least partial degradation when exposed to a biological fluid.

52. A self-righting article as in claim 51, wherein the support material maintains at least a portion of the spring under at least 5% compressive strain under ambient conditions.

53. A self-righting article as in claim 51, wherein the self-righting article comprises a tissue interfacing component operably linked to the spring.

54. A self-righting article as in claim 53, wherein the tissue interfacing component comprises a needle, a biopsy component, a hook, or a mucoadhesive patch.

55. A self-righting article as in claim 53, wherein the tissue interfacing component comprises an active pharmaceutical agent.

56. A self-righting article as in claim 53, wherein the tissue interfacing component has a Young's elastic modulus of greater than or equal to 100 MPa.

57. A self-righting article as in claim 53, wherein the needle comprises a solid pharmaceutical agent in an amount of greater than or equal to 10 wt % versus the total needle weight.

58. A self-righting article, comprising:
- at least a first portion having an average density greater than 1 g/cm$^3$,
- wherein the self-righting article has a self-righting time from 90 degrees in water of less than or equal to 0.05 seconds,
- wherein a longitudinal axis perpendicular to a tissue-engaging surface of the self-righting article is configured to maintain an orientation of 20 degrees or less from vertical when acted on by 0.09*10^−4 Nm or less externally applied torque, and/or
- wherein the self-righting article has a rate of obstruction of less than or equal to 1%.

59. A self-righting article as in claim 58, wherein the self-righting article comprises an outer shell having a monostatic shape.

60. A self-righting article as in claim 58, wherein the self-righting article comprises a self-actuating component comprising a spring and a support material adapted to maintain the spring in at least a partially compressed state and structured for at least partial degradation when exposed to a biological fluid.

61. A self-righting article as in claim 60, wherein the support material maintains at least a portion of the spring under at least 5% compressive strain under ambient conditions.

62. A self-righting article as in claim 60, wherein the self-righting article comprises a tissue interfacing component operably linked to the spring.

63. A self-righting article as in claim 62, wherein the tissue interfacing component comprises a needle, a biopsy component, a hook, or a mucoadhesive patch.

64. A self-righting article as in claim 62, wherein the tissue interfacing component comprises an active pharmaceutical agent.

65. A self-righting article as in claim 62, wherein the tissue interfacing component has a Young's elastic modulus of greater than or equal to 100 MPa.

66. A self-righting article as in claim 62, wherein the needle comprises a solid pharmaceutical agent in an amount of greater than or equal to 10 wt % versus the total needle weight.

* * * * *